US008426408B2

(12) United States Patent
Curtin et al.

(10) Patent No.: US 8,426,408 B2
(45) Date of Patent: Apr. 23, 2013

(54) PYRIMIDINE INHIBITORS OF KINASES

(75) Inventors: Michael Curtin, Pleasant Prairie, WI (US); Michael R. Michaelides, Libertyville, IL (US); Howard Robin Heyman, Deerfield, IL (US); Robin Frey, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 211 days.

(21) Appl. No.: 12/796,751

(22) Filed: Jun. 9, 2010

(65) Prior Publication Data
US 2010/0317680 A1 Dec. 16, 2010

Related U.S. Application Data

(60) Provisional application No. 61/185,758, filed on Jun. 10, 2009.

(51) Int. Cl.
C07D 403/12 (2006.01)
A61K 31/506 (2006.01)

(52) U.S. Cl.
USPC .......... 514/235.8; 514/252.19; 514/275; 544/122; 544/295; 544/324

(58) Field of Classification Search .......... 544/122, 544/295, 324; 514/235.8, 252.19, 275
See application file for complete search history.

(56) References Cited

U.S. PATENT DOCUMENTS

| | | | |
|---|---|---|---|
| 5,374,301 A | 12/1994 | Gregory et al. | |
| 5,980,623 A | 11/1999 | Hiraoka et al. | |
| 6,015,455 A | 1/2000 | Yano et al. | |
| 6,048,390 A | 4/2000 | Yano et al. | |
| 6,117,996 A | 9/2000 | Lowe et al. | |
| 6,531,491 B1 | 3/2003 | Kania et al. | |
| 6,534,524 B1 | 3/2003 | Kania et al. | |
| 6,602,871 B2 | 8/2003 | Lam et al. | |
| 6,884,890 B2 | 4/2005 | Kania et al. | |
| 6,891,044 B2 | 5/2005 | Kania et al. | |
| 7,141,581 B2 | 11/2006 | Bender et al. | |
| 7,141,587 B2 | 11/2006 | Kania et al. | |
| 2004/0171634 A1 | 9/2004 | Kania et al. | |
| 2004/0220248 A1 | 11/2004 | Kania et al. | |
| 2005/0038097 A1 | 2/2005 | Bender et al. | |
| 2005/0124662 A1 | 6/2005 | Kania et al. | |
| 2006/0178378 A1 | 8/2006 | Dai et al. | |
| 2008/0132504 A1* | 6/2008 | Garcia-Echeverria et al. | 514/235.8 |
| 2008/0207876 A1 | 8/2008 | Betley et al. | |

FOREIGN PATENT DOCUMENTS

| | | |
|---|---|---|
| EP | 1903045 A1 | 3/2008 |
| GB | 2275479 A | 8/1994 |
| JP | 7238245 A | 9/1995 |
| JP | 8113744 A | 5/1996 |
| JP | 11029729 A | 2/1999 |
| WO | WO9710887 A1 | 3/1997 |
| WO | WO0039108 A1 | 7/2000 |
| WO | WO2006055831 A2 | 5/2006 |
| WO | WO2006131768 A2 | 12/2006 |
| WO | WO2008147831 A1 | 12/2008 |

OTHER PUBLICATIONS

Johnson et al., Relationships between drug activity in NCI preclinical in vitro and in vivo models and early clinical trials, British Journal of Cancer (2001) 64(10): 1424-1431.*
Caravajal et al., Aurora Kinases: New Targets for Cancer Therapy, Clin Cancer Res 2006:12(23), pp. 6869-6875, Dec. 1, 2006.*
Gura, Systems for identifying New Drugs Are Often Faulty, Cancer Models, Science, vol. 278, No. 5340, pp. 1041-1042, Nov. 1997.*
Simone, Oncology: Introduction, Cecil Textbook of Medicine, 20th Edition, vol. 1, pp. 1004-1010, 1996.*
Rogers et al., PubMed Abstract (J Cell Biol. 157(2):219-29, Epub) Apr. 2002.*
Tanaka et al., PubMed Abstract (Cell 108(3):317-29) Feb. 2002.*
Araki K., et al., "High expression of Aurora-B/Aurora and Ipll-like midbody-associated protein (AIM-1) in astrocytomas", J Neurooncol., 2004, 67 (1-2), 53-64.
Bischoff J. R., et al., "A homologue of Drosophila aurora kinase is oncogenic and amplified in human colorectal cancers", EMBO J., 1998, 17 (11), 3052-3065.
Bodvarsdottir S. K., et al., "Aurora-A amplification associated with BRCA2 mutation in breast tumours", Cancer Lett., 2007, 248 (1), 96-102.
Chen J., et al., "Association between Aurora-A kinase polymorphisms and age of onset of hereditary nonpolyposis colorectal cancer in a Caucasian population", Mol Carcinog., 2007, 46 (4), 249-256.
Chieffi P., et al., "Aurora B expression directly correlates with prostate cancer malignancy and influence prostate cell proliferation", Prostate, 2006, 66 (3), 326-333.
Comperat E., et al., "Aurora-A/STK-15 is a predictive factor for recurrent behaviour in non-invasive bladder carcinoma: a study of 128 cases of non-invasive neoplasms", Virchows Arch., 2007, 450 (4), 419-424.
Cox D. G., et al., "Polymorphisms of the AURKA (STK15/Aurora Kinase) Gene and Breast Cancer Risk ", Cancer Causes Control, 2006, 17 (1), 81-83.

(Continued)

Primary Examiner — Deepak Rao
(74) Attorney, Agent, or Firm — Susan L. Steele

(57) ABSTRACT

The present invention relates to compounds of formula (I) or pharmaceutical acceptable salts,

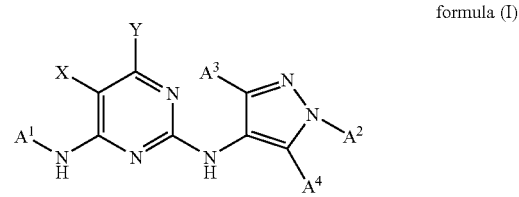

formula (I)

wherein $A^1$, $A^2$, $A^3$, $A^4$, X and Y are defined in the description. The present invention relates also to methods of making said compounds, and compositions containing said compounds which are useful for inhibiting kinases such as aurora and KDR.

14 Claims, No Drawings

OTHER PUBLICATIONS

Dimitrov S., et al., "Endothelial apoptotic activity of angiocidin is dependent on its polyubiquitin binding activity", Br J Cancer., 2005, 93 (6), 662-669.

Ellis Lee M., et al, "VEGF-targeted therapy: mechanisms of anti-tumour activity", nature reviews cancer, 2008, 8, Macmillan Publishers Limited., 579-591.

Ewart-Toland A., et al., "Aurora-A/STK15 T+91A is a general low penetrance cancer susceptibility gene: a meta-analysis of multiple cancer types", Carcinogenesis, 2005, 26 (8), 1368-1373.

Ewart-Toland A., et al., "Identification of Stk6/STK15 as a candidate low-penetrance tumor-susceptibility gene in mouse and human", Nat Genet., 2003, 34 (4), 403-412.

Fraizer G. C., et al., "Aurora-A/STK15/BTAK enhances chromosomal instability in bladder cancer cells", Int J Oncol., 2004, 25 (6), 1631-1639.

Gu J., et al., "Polymorphisms of STK15 (Aurora-A) gene and lung cancer risk in Caucasians", Carcinogenesis, 2007, 28 (2), 350-355.

Hienonen T., et al., "Preferential amplification of AURKA 91A (11e31) in familial colorectal cancers", Int J Cancer, 2006, 118 (2), 505-508.

Hoque A., et al., "Loss of aurora A/STK15/BTAK overexpression correlates with transition of in situ to invasive ductal carcinoma of the breast", Cancer Epidemiol Biomarkers Prev., 2003, 12 (2), 1518-1522.

Jeng Y. M., et al., "Overexpression and amplification of Aurora-A in hepatocellular carcinoma", Clin Cancer Res, 2004, 10 (6), 2065-2071.

Ju H., et al., "Functional polymorphism 57Val>Ile of aurora kinase A associated with increased risk of gastric cancer progression", Cancer Lett., 2006, 242 (2), 273-279.

Keen N., et al., "Aurora-kinase inhibitors as anticancer agents", Nat Rev Cancer, 2004, 4(12), 927-936.

Kimura M. T., et al., "Two functional coding single nucleotide polymorphisms in STK15 (Aurora-A) coordinately increase esophageal cancer risk", Cancer Res., 2005, 65 (9), 3548-3554.

Klein A., et al., "Overexpression and amplification of STK15 in human gliomas", Int J Oncol., 2004, 25 (6), 1789-1794.

Kolb et al., "Tyrosine kinase assays adapted to homogeneous time-resolved fluorescence", Drug Discovery Today, 1998, 3 (7), 333-342.

Kurahashi T., et al., "Significance of Aurora-A expression in renal cell carcinoma", Urol Oncol, 2007, 25 (2), 128-133.

Landen C. N., et al, "Overexpression of the centrosomal protein Aurora-A kinase is associated with poor prognosis in epithelial ovarian cancer patients", Clin Cancer Res., 2007, 13 (14), 4098-4104.

Lassmann S., et al., "Predictive value of Aurora-A/STK15 expression for late stage epithelial ovarian cancer patients treated by adjuvant chemotherapy", Clin Cancer Res., 2007, 13 (14), 4083-4091.

Li D., et al., "Overexpression of oncogenic STK15/BTAK/Aurora A kinase in human pancreatic cancer", Clin Cancer Res., 2003, 9 (3), 991-997.

Lin Yong-Shiang, et al, "Gene Expression Profiles of the Aurora Family Kinases ", Gene Expression, 2006, 13, cognizent, 15-26.

Lo Y. L., et al., "Breast cancer risk associated with genotypic polymorphism of the mitosis-regulating gene Aurora-A/STK15/BTAK.", Int J Cancer, 2005, 115 (2), 276-283.

Mathis G.,, "HTRF(R) Technology", J Biomol Screen, 1999, 4 (6), 309-314.

Miyoshi Y., et al., "Association of centrosomal kinase STK15/BTAK mRNA expression with chromosomal instability in human breast cancers", Int J Cancer, 2001, 92 (3), 370-373.

Moreno-Bueno G., et al., "Differential gene expression profile in endometrioid and nonendometrioid endometrial carcinoma: STK15 is frequently overexpressed and amplified in nonendometrioid carcinomas", Cancer Res., 2003, 63 (18), 5697-5702.

Neben K., et al., "Microarray-based screening for molecular markers in medulloblastoma revealed STK15 as independent predictor for survival", Cancer Res., 2004, 64 (9), 3103-3111.

Nishida N., et al., "High copy amplification of the Aurora-A gene is associated with chromosomal instability phenotype in human colorectal cancers", Cancer Biol Ther., 2007, 6 (4), 525-533.

PCT International search report for application No. PCT/US2010/37801 mailed on Apr. 8, 2010, 12 pages.

Oi G., et al., "Aurora-B expression and its correlation with cell proliferation and metastasis in oral cancer", Virchows Arch., 2007, 450 (3), 297-302.

Reichardt W., et al., "The putative serine/threonine kinase gene STK15 on chromosome 20q13.2 is amplified in human gliomas", Oncol Rep, 2003, 10 (5), 1275-1279.

Reiter R., et al., "Aurora kinase a messenger RNA overexpression is correlated with tumor progression and shortened survival in head and neck squamous cell carcinoma", Clin Cancer Res., 2006, 12 (17), 5136-5141.

Royce M. E., et al., "STK15/Aurora-A expression in primary breast tumors is correlated with nuclear grade but not with prognosis", Cancer, 2004, 100 (1), 12-19.

Sen S., et al., "A putative serine/threonine kinase encoding gene BTAK on chromosome 20q13 is amplified and overexpressed in human breast cancer cell lines", Oncogene., 1997, 14 (18), 2195-2200.

Sen S., et al., "Amplification/overexpression of a mitotic kinase gene in human bladder cancer", J Natl Cancer Inst., 2002, 94 (17), 1320-1329.

Smith S. L., et al., "Overexpression of aurora B kinase (AURKB) in primary non-small cell lung carcinoma is frequent, generally driven from one allele, and correlates with the level of genetic instability", Br J Cancer., 2005, 93 (6), 719-729.

Sorrentino R., et al., "Aurora B overexpression associates with the thyroid carcinoma undifferentiated phenotype and is required for thyroid carcinoma cell proliferation", J Clin Endocrinol Metab., 2005, 90 (2), 928-935.

Tanaka T., et al., "Centrosomal kinase AIK1 is overexpressed in invasive ductal carcinoma of the breast", Cancer Res., 1999, 59 (9), 2041-2044.

Tatsuka M., et al., "Overexpression of Aurora-A potentiates HRAS-mediated oncogenic transformation and is implicated in oral carcinogenesis", Oncogene, 2005, 24 (6), 1122-1127.

Tchatchou S., et al., "Aurora kinases A and B and familial breast cancer risk", Cancer Lett., 2007, 247 (2), 266-272.

Tong T., et al., "Overexpression of Aurora-A contributes to malignant development of human esophageal squamous cell carcinoma", Cancer Res., 2004, 10 (21), 7304-7310.

Vidarsdottir L., et al., "Breast cancer risk associated with AURKA 91T—>A polymorphism in relation to BRCA mutations", Cancer Lett, 2007, 250 (2), 206-212.

Vischioni B., et al., "Frequent overexpression of aurora B kinase, a novel drug target, in non-small cell lung carcinoma patients", Mol Cancer Ther., 2006, 5 (11), 2905-2913.

Xu H. T., et al., "Expression of serine threonine kinase 15 is associated with poor differentiation in lung squamous cell carcinoma and adenocarcinoma", Pathol Int., 2006, 56 (7), 375-380.

Yang S. B., et al., "Amplification and overexpression of Aurora-A in esophageal squamous cell carcinoma", Oncol Rep., 2007, 17 (5), 1083-1088.

Zeng W. F., et al., "Aurora B expression correlates with aggressive behaviour in glioblastoma multiforme", J Clin Pathol., 2007, 60 (2), 218-221.

Zhonghua Zhong Liu et al., Chin J Oncol , 2005, 27 (3).

Zhonghua Zhong Liu et al., Natl J Med China , 2003, 83 (4).

Zhu J., et al., "Aurka amplification, chromosome instability, and centrosome abnormality in human pancreatic carcinoma cells", Cancer Genet Cytogenet., 2005, 159 (1), 10-17.

Curtin M., et al., "Novel Pyrimidines as Potent Inhibitors of the Aurora Kinases," Dec. 2010, Poster.

Curtin M.L., et al., "Pyrazole Diaminopyrimidines as Dual Inhibitors of KDR and Aurora B Kinases," Bioorganic & Medicinal Chemistry Letters, 2012, vol. 22 (14), pp. 4750-4755.

* cited by examiner

PYRIMIDINE INHIBITORS OF KINASES

This application claims priority to U.S. Provisional Application Ser. No. 61/185,758 filed Jun. 10, 2009, which is incorporated by reference in its entirety.

REFERENCE TO A SEQUENCE LISTING

This application contains a Sequence Listing in computer readable form, which is incorporated herein by reference.

BACKGROUND OF THE INVENTION

Mitosis is a process by which a complete copy of a duplicated genome is segregated by the microtubule spindle apparatus into two daughter cells. Aurora-kinases, key mitotic regulators required for genome stability, have been found to be overexpressed in human tumors. There is therefore an existing need in the therapeutic arts for compounds which inhibit Aurora-kinases, compositions comprising the inhibitors and methods of treating diseases during which Aurora-kinases are unregulated or overexpressed.

The reversible phosphorylation of proteins is one of the primary biochemical mechanisms mediating eukaryotic cell signaling. This reaction is catalyzed by protein kinases that transfer the g-phosphate group of ATP to hydroxyl groups on target proteins. 518 such enzymes exist in the human genome of which ~90 selectively catalyze the phosphorylation of tyrosine hydroxyl groups Cytosolic tyrosine kinases reside intracellularly whereas receptor tyrosine kinases (RTKs) possess both extracellular and intracellular domains and function as membrane spanning cell surface receptors. As such, RTKs mediate the cellular responses to environmental signals and facilitate a broad range of cellular processes including proliferation, migration and survival.
RTK signaling pathways are normally highly regulated, yet their over-activation has been shown to promote the growth, survival and metastasis of cancer cells. Dysregulated RTK signaling occurs through gene over-expression or mutation and has been correlated with the progression of various human cancers.

The VEGF receptor (VEGFR) family consists of three RTKs, KDR (kinase insert domain-containing receptor; VEGFR2), FLT1 (Fms-like tyrosine kinase; VEGFR1), and FLT4 (VEGFR3). These receptors mediate the biological function of the vascular endothelial growth factors (VEGF-A, -B, -C, -D, -E and placenta growth factor (PlGF)), a family of homodimeric glycoproteins that bind the VEGF receptors with varying affinities.

KDR is the major mediator of the mitogenic, angiogenic and permeability-enhancing effects of VEGF-A, hereafter referred to as VEGF. Many different cell types are able to produce VEGF, yet its biological activity is limited predominately to the vasculature by way of the endothelial cell-selective expression of KDR. Not surprisingly, the VEGF/KDR axis is a primary mediator of angiogenesis, the means by which new blood vessels are formed from preexisting vessels.

FLT1 binds VEGF, VEGF-B and placental growth factor. FLT1 is expressed on the surface of smooth muscle cells, monocytes and hematopoietic stems cells in addition to endothelial cells. Activation of FLT1 signaling results in the mobilization of marrow-derived endothelial progenitor cells that are recruited to tumors where they contribute to new blood vessel formation.

FLT4 mediates the signaling of VEGF-C and VEGF-D, which mediate formation of tumor-associated lymphatic vessels (lymphangiogenesis). Lymphatic vessels are one of the routes by which cancer cells disseminate from solid tumors during metastasis. The PDGF receptor (PDGFR) family consists of five RTK's, PDGFR-a and -b, CSF1R, KIT, and FLT3.

The a and b isoforms of the platelet-derived growth factor (PDGF) receptors occur as homodimers or a/b heterodimers and are found most commonly on the surface of fibroblasts and smooth muscle cells. PDGFR-b contributes to tumor angiogenesis through the proliferation and migration of pericytes, the peri-endothelial cells that associate with and stabilize immature blood vessels. In gliomas, autocrine PDGFR stimulation, brought about by the co-expression of PDGF and PDGF receptors, mediates tumor cell proliferation and survival.

CSF-1R is encoded by the cellular homolog of the retroviral oncogene v-fms and is a major regulator of macrophage development. Macrophages are frequent components of tumor stroma and have been shown to modify the extracellular matrix in a manner beneficial to tumor growth and metastasis.

KIT is expressed by hematopoietic progenitor cells, mast cells, germ cells and by pacemaker cells in the gut (interstitial cells of Cajal). It contributes to tumor progression by two general mechanisms namely autocrine stimulation by its ligand, stem cell factor (SCF), and through mutations that result in ligand-independent kinase activity.

FLT3 is normally expressed on hematopoietic stem cells where its interaction with FLT3 ligand (FL) stimulates stem cell survival, proliferation and differentiation. In addition to being over-expressed in various leukemia cells, FLT3 is frequently mutated in hematological malignancies with approximately one-third of patients with acute myeloid leukemia (AML) harboring activating mutations.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

The present invention has numerous embodiments. One embodiment of this invention, therefore, pertains to compounds that have formula (I)

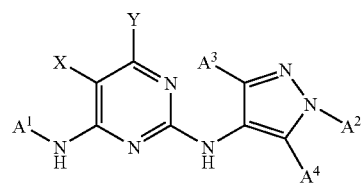

formula (I)

wherein $A^1$, $A^2$, $A^3$, $A^4$, X and Y are as defined below and subsets therein.

Also provided are pharmaceutically acceptable compositions, comprising a therapeutically effective amount of a compound of formula (I), and a pharmaceutically acceptable salt in combination with a pharmaceutically suitable carrier.

One embodiment is directed a method of treating cancer in a mammal comprising administering thereto a therapeutically acceptable amount of a compound or pharmaceutically acceptable salt of formula (I). Yet another embodiment pertains to a method of decreasing tumor volume in a mammal comprising administering thereto a therapeutically acceptable amount of a compound or pharmaceutically acceptable salt of formula (I).

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer in a mammal, the methods comprising administering thereto a therapeutically effective amount of a compound having formula (I), with or without also administering radiotherapy thereto.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

ABBREVIATIONS AND DEFINITIONS

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$—", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—$NH_2$.

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-$NH_2$.

The term "alkyloxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-$NH_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-5-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—$NH_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl(azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "KDR" means kinase insert domain receptor (a type III receptor tyrosine kinase) and is also known as FLK1, VEGFR, VEGFR2, and CD309.

The term "VEGFR" means vascular endothelial growth factor receptor.

The term "PDGFR" means platelet-derived growth factor receptor.

Compounds

Suitable groups for $A^1$, X, Y, $A^2$, $A^3$, and $A^4$ in compounds of Formula (I) are independently selected. The described embodiments of the present invention may be combined. Such combination is contemplated and within the scope of the present invention. For example, it is contemplated that embodiments for any of $A^1$, X, Y, $A^2$, $A^3$, and $A^4$ can be combined with embodiments defined for any other of $A^1$, X, Y, $A^2$, $A^3$, and $A^4$.

In one aspect, the present invention provides compounds of formula (I)

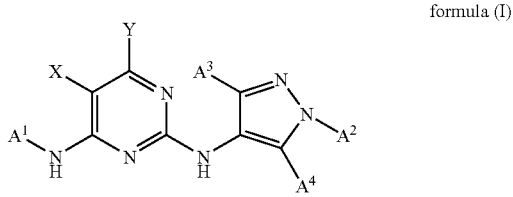

formula (I)

wherein $A^1$ is aryl, heteroaryl, heterocycloalkyl, heterocycloalkenyl, cycloalkyl, cycloalkenyl, bridged cycloalkyl, bridged cycloalkenyl, and bridged heterocycloalkyl, wherein $A^1$ is optionally substituted with 1, 2, or 3 $R^1$;

$R^1$, at each occurrence, is independently halogen, cyano, nitro, $-C_{1-4}$-alkyl, $-C_3$-$C_8$-cycloalkyl, $-C_{3-8}$-heterocycloalkyl, $-OH$, $-OC_{1-4}$-alkyl, $-OC_{1-4}$-haloalkyl, $-C(O)OH$, $-C(O)OR^a$, $-C(O)NH_2$, $-C(O)NHR^a$, $-C(O)N(R^a)_2$, $-SO_2NH_2$, $-SO_2NR^a$, or $-SO_2N(R^a)_2$, wherein the $R^1$—$C_{1-4}$-alkyl is optionally substituted with halogen, $-OH$, $-OC_{1-4}$-alkyl, or $-C_{3-8}$-heterocycloalkyl, and wherein the $R^1$—$C_3$-$C_8$-cycloalkyl and $-C_{3-8}$-heterocycloalkyl are each independently optionally substituted with halogen, $-OH$, or $-C_{1-4}$-alkyl;

$R^a$, at each occurrence, is independently selected from the group consisting of $-C_{1-4}$-alkyl, $-C_{3-8}$-cycloalkyl, $-C_{3-8}$-heterocycloalkyl, $-C_{1-4}$-haloalkyl, $-C_{1-4}$-alkylamino, and $-C_{1-4}$-alkylhydroxy;

X and Y are each independently H, F, Cl, Br, nitro, $-CF_3$, $-CF_2CF_3$, $-OCF_3$, $-OCF_2CF_3$, $-C(O)NH_2$, $-CH_3$, $-CH_2CH_3$, $-OCH_3$, or $-OCH_2CH_3$;

$A^2$ is H, $R^2$, or $R^3$;

$R^2$ is $-C_{1-6}$-alkyl, $-C_{2-6}$-alkenyl, or $-C_{2-6}$-alkynyl, wherein $R^2$ is optionally substituted with 1, 2, 3, or 4 substituents selected from the group consisting of $R^4$, halogen, cyano, nitro, $-OR^b$, $-C(O)R^b$, $-C(O)OR^b$, $-OC(O)R^b$, $-NR^cR^d$, $-NR^cC(O)R^b$, $-NHC(O)NHR^c$, $-C(O)NR^cR^d$, $NR^cSO_2R^b$, $-SR^b$, $-S(O)R^b$, $-SO_2R^b$, $-SO_2NR^cR^d$, $-CF_3$, $-CF_2CF_3$, $-OCF_3$, and $-OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, $-C_{1-6}$-alkyl, $-C_{2-6}$-alkenyl, $-C_{2-6}$-alkynyl, halogen, cyano, nitro, $-OR^e$, $-C(O)R^e$, $-C(O)OR^e$, $-OC(O)R^e$, $-NR^fR^g$, $-NR^fC(O)R^e$, $-NHC(O)NHR^f$, $-C(O)NR^fR^g$, $-NR^fSO_2R^e$, $-SR^e$, $-S(O)R^e$, $-SO_2R^e$, $-OC(O)OR^e$, $-SO_2NR^fNR^g$, $-CF_3$, $-CF_2CF_3$, $-OCF_3$, and $-OCF_2CF_3$, wherein the alkyl, alkenyl, and alkynyl substituents are optionally substituted with one or more substituents selected from the group consisting of aryl, heterocyclyl, cycloalkyl, halogen, cyano, $-OR^e$, $-C(O)R^e$, $-C(O)OR^e$, $-OC(O)R^e$, $-NR^fR^g$, $-NR^fC(O)R^e$, $-NHC(O)NHR^f$ and $-C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of $-C_{1-6}$-alkyl, $-C_{2-6}$-alkenyl, $-C_{2-6}$-alkynyl, halogen, cyano, nitro, $-OR^e$, $-C(O)R^e$, $-C(O)OR^e$, $-OC(O)R^e$, $-NR^fR^g$, $-NR^fC(O)R^e$, $-NHC(O)NHR^f$, $-C(O)NR^fR^g$, $-NR^fSO_2R^e$, $-SR^e$, $-S(O)R^e$, $-SO_2R^e$, $-OC(O)OR^e$, $-SO_2NR^fNR^g$, $-CF_3$, $-CF_2CF_3$, $-OCF_3$, and $-OCF_2CF_3$, wherein the alkyl, alkenyl, and alkynyl substituents are optionally substituted with one or more substituents selected from the group consisting of aryl, heterocyclyl, cycloalkyl, halogen, cyano, $-OR^e$, $-C(O)R^e$, $-C(O)OR^e$, $-OC(O)R^e$, $-NR^fR^g$, $-NR^fC(O)R^e$, $-NHC(O)NHR^f$ and $-C(O)NR^fR^g$;

$A^3$ and $A^4$ are each independently H or $-C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, $-OC_{1-4}$-alkyl, $-C(O)OC_{1-4}$ alkyl, $-OC(O)C_{1-4}$-alkyl, $-NHC(O)C_{1-4}$-alkyl, and $-C(O)NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, $-OC_{1-4}$-alkyl, $-C(O)OC_{1-4}$ alkyl, $-OC(O)C_{1-4}$-alkyl, $-NHC(O)C_{1-4}$-alkyl, and $-C(O)NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, $-OC_{1-4}$-alkyl, $-C(O)OC_{1-4}$-alkyl, $-OC(O)C_{1-4}$-alkyl, $-NHC(O)C_{1-4}$-alkyl, $-N(C_{1-4}$-alkyl$)_2$, and $-C(O)NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, $-OC_{1-4}$-alkyl, $-C(O)OC_{1-4}$-alkyl, $-OC(O)C_{1-4}$-alkyl, $-NHC(O)C_{1-4}$-alkyl, and $-C(O)NHC_{1-4}$-alkyl, wherein $C_{1-4}$-alkyl is an unsubstituted branched or straight chain alkyl group; or a pharmaceutically acceptable salt thereof.

In one embodiment of formula (I), is $A^1$ is aryl, heteroaryl, cycloalkyl, cycloalkenyl, bridged cycloalkyl, bridged cycloalkenyl, or bridged heterocycloalkyl. In another embodiment of formula (I), $A^1$ is heteroaryl, cycloalkyl, cycloalkenyl, bridged cycloalkyl, bridged cycloalkenyl, or bridged heterocycloalkyl. In another embodiment of formula (I), $A^1$ is $C_{4-6}$ cycloalkyl, $C_{7-8}$ bridged cycloalkyl, or $C_{7-8}$ bridged cycloalkenyl.

In one embodiment of formula (I), $A^1$ is selected from the group consisting of

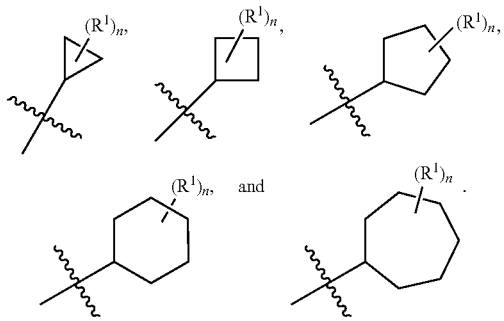

wherein n is 0, 1, 2, or 3 and $R^1$ is as described in formula (I). In another embodiment of formula (I), $A^1$ is selected from the group consisting of

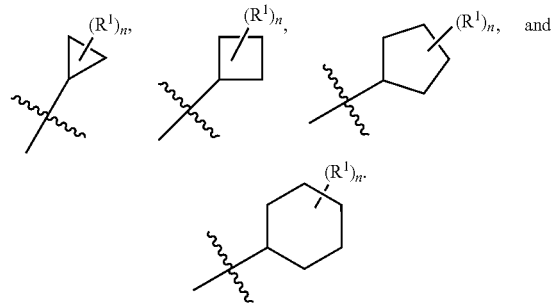

wherein n is 0, 1, 2, or 3 and $R^1$ is as described in formula (I).

In one embodiment of formula (I), $A^1$ is selected from the group consisting of

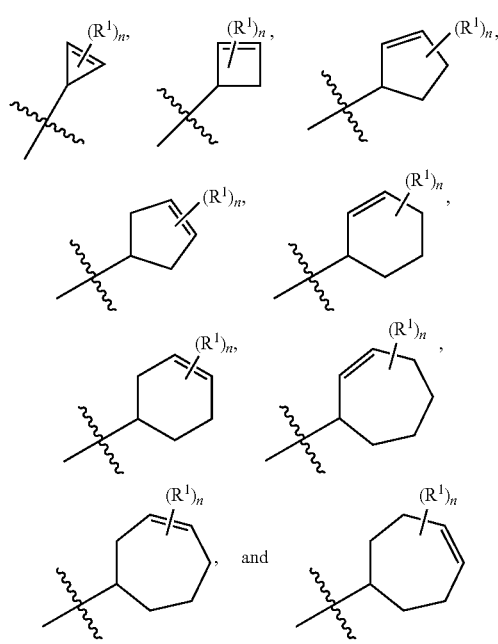

wherein n is 0, 1, 2, or 3, and $R^1$ is as described in formula (I). In another formula (I), $A^1$ is

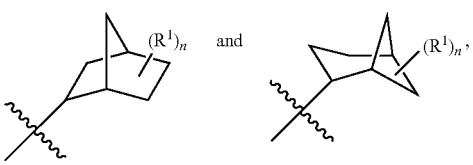

wherein n is 0, 1, 2, or 3, and $R^1$ is as described in formula (I).

In one embodiment of formula (I), $A^1$ is selected from the group consisting of

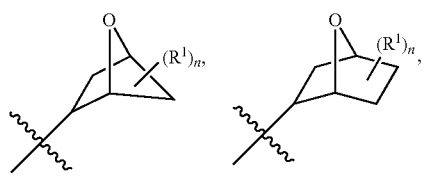

wherein n is 0, 1, 2, or 3, and $R^1$ is as described in formula (I). In another embodiment of formula (I), $A^1$ is selected from the group consisting of

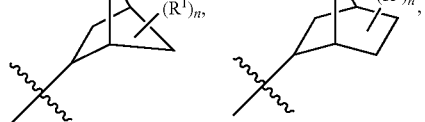

wherein n is 0, 1, 2, or 3, and $R^1$ is as described in formula (I).

In one embodiment of formula (I), $A^1$ is selected from the group consisting of

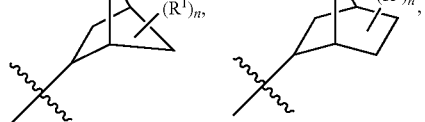

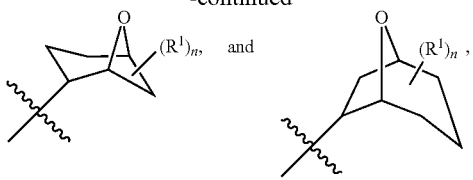

wherein n is 0, 1, 2, or 3, and $R^1$ is as described in formula (I).

In one embodiment of formula (I), $A^1$ is selected from the group consisting of

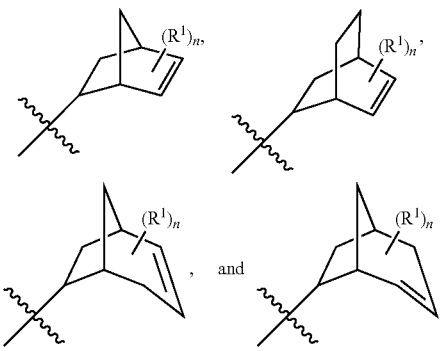

wherein n is 0, 1, or 2, and $R^1$ is as described in formula (I). In another embodiment of formula (I), $A^1$ is

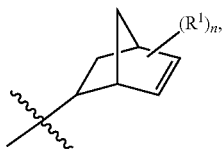

wherein n is 0, 1, 2, or 3, and $R^1$ is as described in formula (I).

In one embodiment of formula (I), $A^1$ is selected from the group consisting of

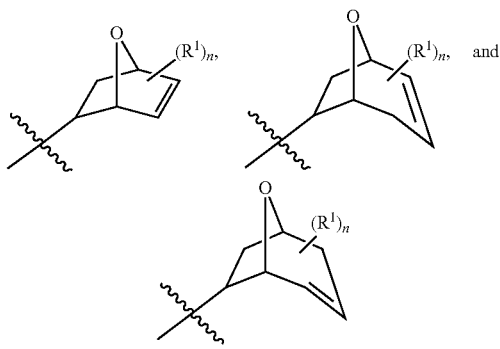

wherein n is 0, 1, or 2, and $R^1$ is as described in formula (I).

In one embodiment of formula (I), $A^1$ is aryl. In another embodiment of formula (I), $A^1$ is phenyl.

In one embodiment of formula (I), $A^1$ is heteroaryl. In another embodiment of formula (I), $A^1$ is pyridyl, pyrazyl, pyrimidinyl, pyridazinyl, 1,3,5-, 1,2,4- or 1,2,3-triazinyl; imidazyl, indazolyl, furanyl, thiophenyl, pyrazolyl, oxazolyl, isoxazolyl, thiazolyl, 1,2,3-, 1,2,4-, 1,2,5-, or 1,3,4-oxadiaz- olyl, isothiazolyl; benzimidazolyl, benzothiofuranyl, benzisoxazolyl, benzoxazolyl, purinyl, anthranilyl; benzopyranyl, quinolinyl, isoquinolinyl, cinnolinyl, quinazolinyl, or benzoxazinyl. In another embodiment of formula (I), $A^1$ is

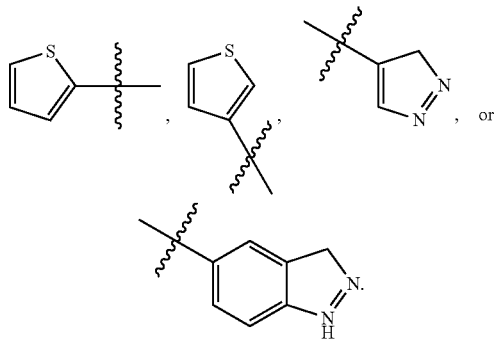

In one embodiment of formula (I), $A^1$ is unsubstituted.

In one embodiment of formula (I), $A^1$ is substituted with 1, 2, or 3 $R^1$, wherein $R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —$OC_{1-4}$-haloalkyl, —C(O)OH, —C(O)$OR^a$, —C(O)$NH_2$, —C(O)$NHR^a$, —C(O)N($R^a$)$_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl; and wherein $R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-haloalkyl, —$C_{1-4}$-alkylamino, and —$C_{1-4}$-alkylhydroxy;

In another embodiment of formula (I), $A^1$ is substituted with 1, 2, or 3 $R^1$, wherein $R^1$, at each occurrence, is independently —$C_{1-4}$-alkyl, —$C_3$-$C_8$-cycloalkyl, —$C_{3-8}$-heterocycloalkyl, —$OC_{1-4}$-alkyl, —C(O)$OR^a$, —C(O)$NH_2$, or —C(O)$NHR^a$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl; and wherein $R^a$ is —$C_{1-4}$-alkyl.

In another embodiment of formula (I), $A^1$ is substituted with 1, 2, or 3 $R^1$, wherein $R^1$ is selected from the group consisting of —C(O)$NH_2$, —C(O)$NHCH_3$, —C(O)$NHCH_2CH_3$, —C(O)$OCH_3$, or —C(O)$OCH_2CH_3$.

In one embodiment of formula (I), X and Y are both H. In another embodiment of formula (I), Y is H, and X is F, Cl, or Br. In another embodiment of formula (I), Y is $CH_3$, and X is F, Cl, or Br. In another embodiment of formula (I), Y is H, and X is F, Cl, Br, —$NO_2$, —$CF_3$, —C(O)$NH_2$, —$CH_3$, or —$OCH_3$.

In one embodiment of formula (I), $A^2$ is H. In another embodiment of formula (I), $A^2$ is $R^2$ or $R^3$. In another embodiment of formula (I), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^c$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$. In another embodiment of formula (I), $A^2$ is $R^2$, and $R^2$ is —$C_{1-6}$-alkyl, wherein —$C_{1-6}$-alkyl is unsubstituted. In another embodiment of formula (I), $A^2$ is $R^2$, and $R^2$ is —$C_{1-3}$-alkyl, wherein —$C_{1-3}$-alkyl is unsubstituted. In another embodiment of formula (I), $A^2$ is —$CH_3$, —$CH_2CH_3$, or —$CH(CH_3)_2$. In another embodiment of formula (I), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$. In another embodiment of formula (I), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$, wherein $R^4$ is independently cycloalkyl, aryl, or heterocycloalkyl, $R^4$ is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (I), $A^2$ is —$CH_3$, —$CH_2CH_3$, —$CH(CH_3)_2$, —$CH_2CF_3$, —$CH_2CH_2OH$, —$CH_2C(O)OH$, —$CH_2C(O)NH_2$, —$CH_2CH_2OCH_3$, —$CH_2CH(CH_3)OH$, —$CH_2CH(OH)CH_2CH_3$, —$CH_2CH_2SO_2CH_3$, —$CH_2C(O)NHCH_3$, —$CH_2CH_2N(CH_3)_2$, —$CH_2C(O)N(CH_3)_2$, —$CH_2CH_2CH(CH_3)_2$, —$CH_2C(O)OCH(CH_3)_2$, —$CH_2CH_2OCH_2CH_2OCH_3$, or —$CH_2CH_2N(CH_3)_2$.

In one embodiment of formula (I), $R^3$ is cycloalkyl, aryl, or heterocycloalkyl, optionally substituted with 1 or 2 substituents selected from the group consisting of —$C_{1-6}$-alkyl, halogen, —$OR^e$, and —$C(O)R^e$. In another embodiment of formula (I), $R^3$ is —$C_{3-8}$-cycloalkyl. In another embodiment of formula (I), $R^3$ is —$C_{3-6}$-cycloalkyl. In another embodiment of formula (I), $R^3$ is —$C_4$-cycloalkyl.

In another embodiment of formula (I), $R^3$ is aryl. In another embodiment of formula (I), $R^3$ is phenyl or naphthyl, which is unsubstituted. In another embodiment of formula (I), $R^3$ is phenyl or naphthyl, which is optionally substituted with 1 or 2 substituents selected from the group consisting of —$C_{1-6}$-alkyl, halogen, —$OR^e$, and —$C(O)R^e$. In another embodiment of formula (I), $R^3$ is phenyl, which is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (I), $R^3$ is heterocycloalkyl. In another embodiment of formula (I), $R^3$ is heterocycloalkyl, which is unsubstituted. In another embodiment of formula (I), $R^3$ is heterocycloalkyl, optionally substituted with 1 or 2 substituents selected from the group consisting of —$C_{1-6}$-alkyl, halogen, —$OR^e$, and —$C(O)R^e$. In another embodiment of formula (I), $R^3$ is azetidinyl, pyrrolidinyl, morpholinyl, piperidinyl, tetrahydrofuranyl, or piperazinyl. In another embodiment of formula (I), $R^3$ is azetidinyl, pyrrolidinyl, morpholinyl, piperidinyl, tetrahydrofuranyl, or piperazinyl, which are unsubstituted. In another embodiment of formula (I), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, halogen, —$OR^e$, and —$C(O)R^e$. In another embodiment of formula (I), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$. In another embodiment of formula (I), $R^3$ is azetidinyl, pyrrolidinyl, piperidinyl, or tetrahydrofuranyl. In another embodiment of formula (I), $R^3$ is azetidinyl, pyrrolidinyl, piperidinyl, or tetrahydrofuranyl, which are unsubstituted. In another embodiment of formula (I), $R^3$ is azetidinyl, pyrrolidinyl, piperidinyl, or tetrahydrofuranyl, which are optionally substituted with 1 or 2 substituents selected from the group consisting of —$C_{1-6}$-alkyl, halogen, —$OR^e$, and —$C(O)R^e$. In another embodiment of formula (I), $R^3$ is azetidinyl, pyrrolidinyl, piperidinyl, or tetrahydrofuranyl which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$.

In one embodiment of formula (I), $A^3$ is H. In another embodiment of formula (I), $A^3$ is —$C_{1-6}$-alkyl. In another embodiment of formula (I), $A^3$ is methyl.

In one embodiment of formula (I), $A^4$ is H. In another embodiment of formula (I), $A^4$ is —$C_{1-6}$-alkyl. In another embodiment of formula (I), $A^4$ is methyl.

In one embodiment of formula (I), $A^3$ is H, and $A^4$ is H. In one embodiment of formula (I), $A^3$ is H, and $A^4$ is methyl. In one embodiment of formula (I), $A^3$ is methyl, and $A^4$ is H.

Another aspect of the invention provides compounds of formula (II), wherein $R^1$, X, Y, $A^2$, $A^3$ and $A^4$ are as defined generally and in subsets above, n is 0, 1, 2, or 3, and $A^{1A}$ is cycloalkyl.

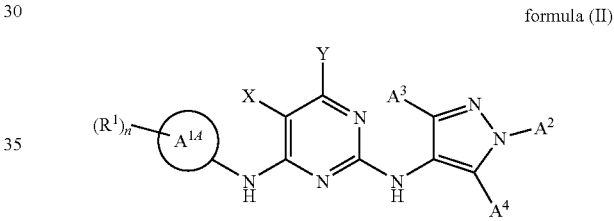

formula (II)

In another aspect, the present invention provides compounds of formula (II) wherein $A^{1A}$ is cycloalkyl;

n is 0, 1, 2, or 3;

$R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —$C(O)OH$, —$C(O)OR^a$, —$C(O)NH_2$, —$C(O)NHR^a$, —$C(O)N(R^a)_2$, —$SO_2NH_2$, —$SO_2NR^a$, or —$SO_2N(R^a)_8$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —$C(O)NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, —$N(C_{1-4}$-alkyl)$_2$, and —$C(O)NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group; or a pharmaceutically acceptable salt In one embodiment of formula (II), $A^{1A}$ is selected from the group consisting of

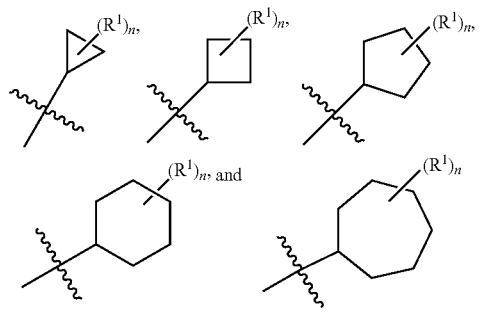

wherein n is 0, 1, 2, or 3 and $R^1$ is as described in formula (I). In another embodiment of formula (I), $A^{1A}$ is selected from the group consisting of

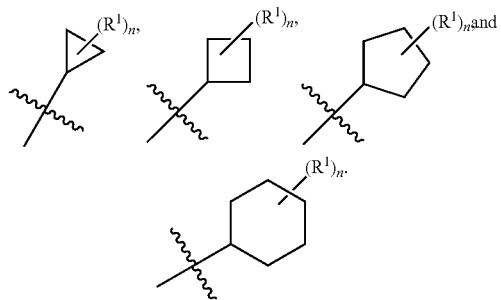

wherein n is 0, 1, 2, or 3 and $R^1$ is as described in formula (I).

In one embodiment of formula (II), n is 1, 2, or 3, wherein $R^1$ is selected from the group consisting of $R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —$OC_{1-4}$-haloalkyl, —$C(O)OH$, —$C(O)OR^a$, —$C(O)NH_2$, —$C(O)NHR^a$, —$C(O)N(R^a)_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl; and where $R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-haloalkyl, —$C_{1-4}$-alkylamino, and —$C_{1-4}$-alkylhydroxy; In another embodiment of formula (II), n is 1, and $R^1$ is —$C(O)NH_2$, —$C(O)NHCH_3$, —$C(O)NHCH_2CH_3$, —$C(O)OCH_3$, or —$C(O)OCH_2CH_3$.

In one embodiment of formula (II), X and Y are both H. In another embodiment of formula (II), Y is H, and X is F, Cl, or Br. In another embodiment of formula (II), Y is $CH_3$, and X is F, Cl, or Br. In another embodiment of formula (II), Y is H, and X is F, Cl, Br, —$NO_2$, —$CF_3$, —$C(O)NH_2$, —$CH_3$, or, —$OCH_3$.

In one embodiment of formula (II), $A^2$ is H. In another embodiment of formula (II), $A^2$ is $R^2$ or $R^3$. In another embodiment of formula (II), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —S(O)$R^b$, —SO$_2$$R^b$, —SO$_2$N$R^c$$R^d$, —CF$_3$, —CF$_2$CF$_3$, —OCF$_3$, and —OCF$_2$CF$_3$. In another embodiment of formula (II), $A^2$ is $R^2$, and $R^2$ is —C$_{1-6}$-alkyl, wherein —C$_{1-6}$-alkyl is unsubstituted. In another embodiment of formula (II), $A^2$ is $R^2$, and $R^2$ is —C$_{1-3}$-alkyl, wherein —C$_{1-3}$-alkyl is unsubstituted. In another embodiment of formula (II), $A^2$ is —CH$_3$, —CH$_2$CH$_3$, or —CH(CH$_3$)$_2$. In another embodiment of formula (II), $A^2$ is $R^2$, and $R^2$ is —C$_{1-6}$-alkyl, wherein $R^2$ is substituted with 1 or 2 substituents selected from the group consisting of $R^4$, —O$R^b$, —C(O)O$R^b$, —N$R^c$$R^d$, —C(O)N$R^c$$R^d$, —SO$_2$$R^b$, and —CF$_3$. In another embodiment of formula (II), $A^2$ is $R^2$, and $R^2$ is —C$_{1-6}$-alkyl, wherein $R^2$ is substituted with 1 or 2 substituents selected from the group consisting of $R^4$, —O$R^b$, —C(O)O$R^b$, —N$R^c$$R^d$, —C(O)N$R^c$$R^d$, —SO$_2$$R^b$, and —CF$_3$, wherein $R^4$ is independently cycloalkyl, aryl, or heterocycloalkyl, $R^4$ is optionally substituted with 1 or 2 substituents selected from the group consisting of —C$_{1-6}$-alkyl, halogen, —O$R^e$, and —C(O)$R^e$, $R^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (II), $A^2$ is —CH$_3$, —CH$_2$CH$_3$, —CH(CH$_3$)$_2$, —CH$_2$CF$_3$, —CH$_2$CH$_2$OH, —CH$_2$C(O)OH, —CH$_2$C(O)NH$_2$, —CH$_2$CH$_2$OCH$_3$, —CH$_2$CH(CH$_3$)OH, —CH$_2$CH(OH)CH$_2$CH$_3$, —CH$_2$CH$_2$SO$_2$CH$_3$, —CH$_2$C(O)NHCH$_3$, —CH$_2$CH$_2$N(CH$_3$)$_2$, —CH$_2$C(O)N(CH$_3$)$_2$, —CH$_2$CH$_2$CH(CH$_3$)$_2$, —CH$_2$C(O)OCH(CH$_3$)$_2$, —CH$_2$CH$_2$OCH$_2$CH$_2$OCH$_3$, or —CH$_2$CH$_2$N(CH$_3$)$_2$.

In one embodiment of formula (II), $R^3$ is cycloalkyl, aryl, or heterocycloalkyl, optionally substituted with 1 or 2 substituents selected from the group consisting of —C$_{1-6}$-alkyl, halogen, —O$R^e$, and —C(O)$R^e$. In another embodiment of formula (II), $R^3$ is —C$_{3-8}$-cycloalkyl. In another embodiment of formula (II), $R^3$ is —C$_{3-6}$-cycloalkyl. In another embodiment of formula (II), $R^3$ is —C$_4$-cycloalkyl.

In another embodiment of formula (II), $R^3$ is aryl. In another embodiment of formula (II), $R^3$ is phenyl or naphthyl, which is unsubstituted. In another embodiment of formula (II), $R^3$ is phenyl or naphthyl, which is optionally substituted with 1 or 2 substituents selected from the group consisting of —C$_{1-6}$-alkyl, halogen, —O$R^e$, and —C(O)$R^e$. In another embodiment of formula (II), $R^3$ is phenyl, which is optionally substituted with 1 or 2 substituents selected from the group consisting of —C$_{1-6}$-alkyl, halogen, —O$R^e$, and —C(O)$R^e$, $R^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (II), $R^3$ is heterocycloalkyl. In another embodiment of formula (II), $R^3$ is heterocycloalkyl, which is unsubstituted. In another embodiment of formula (II), $R^3$ is heterocycloalkyl, optionally substituted with 1 or 2 substituents selected from the group consisting of —C$_{1-6}$-alkyl, halogen, —O$R^e$, and —C(O)$R^e$. In another embodiment of formula (II), $R^3$ is azetidinyl, pyrrolidinyl, morpholinyl, piperidinyl, tetrahydrofuranyl, or piperazinyl. In another embodiment of formula (II), $R^3$ is azetidinyl, pyrrolidinyl, morpholinyl, piperidinyl, tetrahydrofuranyl, or piperazinyl, which are unsubstituted. In another embodiment of formula (II), $R^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, halogen, —O$R^e$, and —C(O)$R^e$. In another embodiment of formula (II), $R^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$. In another embodiment of formula (II), $R^3$ is azetidinyl, pyrrolidinyl, piperidinyl, or tetrahydrofuranyl. In another embodiment of formula (II), $R^3$ is azetidinyl, pyrrolidinyl, piperidinyl, or tetrahydrofuranyl, which are unsubstituted. In another embodiment of formula (II), $R^3$ is azetidinyl, pyrrolidinyl, piperidinyl, or tetrahydrofuranyl, which are optionally substituted with 1 or 2 substituents selected from the group consisting of —C$_{1-6}$-alkyl, halogen, —O$R^e$, and —C(O)$R^e$. In another embodiment of formula (II), $R^3$ is azetidinyl, pyrrolidinyl, piperidinyl, or tetrahydrofuranyl which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$.

In one embodiment of formula (II), $A^3$ is H. In another embodiment of formula (II), $A^3$ is —C$_{1-6}$-alkyl. In another embodiment of formula (II), $A^3$ is methyl.

In one embodiment of formula (II), $A^4$ is H. In another embodiment of formula (II), $A^4$ is —C$_{1-6}$-alkyl. In another embodiment of formula (II), $A^4$ is methyl.

In one embodiment of formula (II), $A^3$ is H, and $A^4$ is H. In one embodiment of formula (II), $A^3$ is H, and $A^4$ is methyl. In one embodiment of formula (II), $A^3$ is methyl, and $A^4$ is H.

Another aspect of the invention provides compounds of formula (IIa), (IIb), (IIc), (IId), (IIe), and (IIf), wherein $R^1$, X, Y, $A^2$, $A^3$ and $A^4$ are as defined generally and in subsets above.

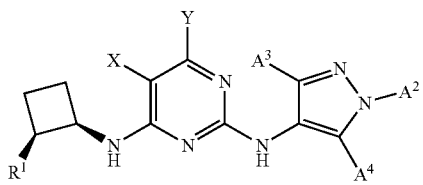

formula (IIa)

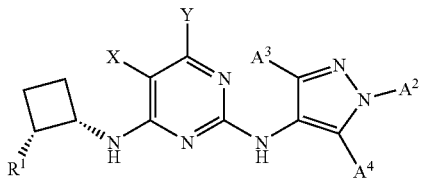

formula (IIb)

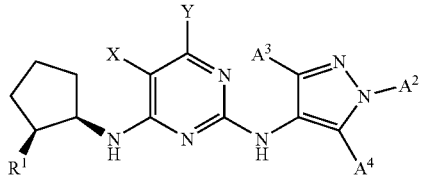

formula (IIc)

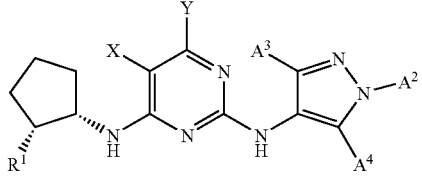

formula (IId)

-continued

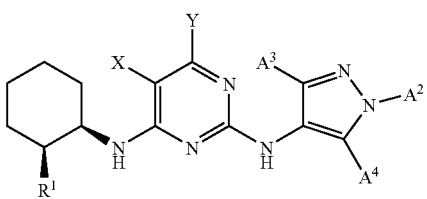

formula (IIe)

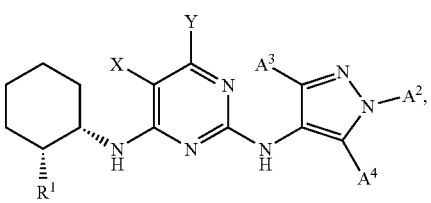

formula (IIf)

Another aspect of the invention provides compounds of formula (IIIa) and (IIIb), wherein $R^1$, X, Y, $A^2$, $A^3$, and $A^4$ are as defined generally and in subsets above.

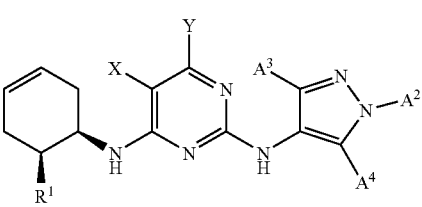

formula (IIIa)

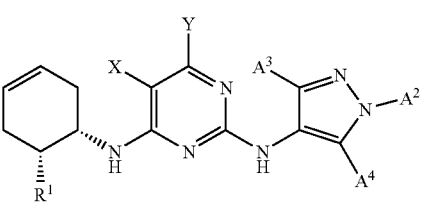

formula (IIIb)

In another aspect, the present invention provides compounds of formula (IIIa) and (IIIb), wherein $R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —C(O)OH, —C(O)$OR^a$, —C(O)$NH_2$, —C(O)$NHR^a$, —C(O)N($R^a$)$_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-haloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —C(O)$NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^c$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)NH$C_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)NH$C_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, —N($C_{1-4}$-alkyl)$_2$, and —C(O)NH$C_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)NH$C_{1-4}$-alkyl, wherein $C_{1-4}$-alkyl is an unsubstituted branched or straight chain alkyl group; or a pharmaceutically acceptable salt thereof.

In one embodiment of formula (IIIa) and (IIIb), $R^1$ is —C(O)NH$_2$, —C(O)NHCH$_3$, —C(O)NHCH$_2$CH$_3$, —C(O)OCH$_3$, or —C(O)OCH$_2$CH$_3$.

In one embodiment of formula (IIIa) and (IIIb), X and Y are both H. In another embodiment of formula (IIIa) and (IIIb), Y is H, and X is F, Cl, or Br. In another embodiment of formula (IIIa) and (IIIb), Y is CH$_3$, and X is F, Cl, or Br. In another embodiment of formula (IIIa) and (IIIb), Y is H, and X is F, Cl, Br, —NO$_2$, —CF$_3$, —C(O)NH$_2$, —CH$_3$, or, —OCH$_3$.

In one embodiment of formula (IIIa) and (IIIb), $A^2$ is H. In another embodiment of formula (IIIa) and (IIIb), $A^2$ is $R^2$ or $R^3$. In another embodiment of formula (IIIa) and (IIIb), $A^2$ is $R^2$, and $R^2$ is —C$_{1-6}$-alkyl, —C$_{2-6}$-alkenyl, or —C$_{2-6}$-alkynyl, wherein $R^2$ is optionally substituted with 1, 2, 3, or 4 substituents selected from the group consisting of $R^4$, halogen, cyano, nitro, —OR$^b$, —C(O)R$^b$, —C(O)OR$^b$, —OC(O)R$^b$, —NR$^c$R$^d$, —NR$^c$C(O)R$^b$, —NHC(O)NHR$^c$, —C(O)NR$^c$R$^d$, NR$^c$SO$_2$R$^b$, —SR$^b$, —S(O)R$^b$, —SO$_2$R$^b$, —SO$_2$NR$^c$R$^d$, —CF$_3$, —CF$_2$CF$_3$, —OCF$_3$, and —OCF$_2$CF$_3$. In another embodiment of formula (IIIa) and (IIIb), $A^2$ is $R^2$, and $R^2$ is —C$_{1-6}$-alkyl, wherein —C$_{1-6}$-alkyl is unsubstituted. In another embodiment of formula (IIIa) and (IIIb), $A^2$ is $R^2$, and $R^2$ is —C$_{1-3}$-alkyl, wherein —C$_{1-3}$-alkyl is unsubstituted. In another embodiment of formula (IIIa) and (IIIb), $A^2$ is —CH$_3$, —CH$_2$CH$_3$, or —CH(CH$_3$)$_2$. In another embodiment of formula (IIIa) and (IIIb), $A^2$ is $R^2$, and $R^2$ is —C$_{1-6}$-alkyl, wherein $R^2$ is substituted with 1 or 2 substituents selected from the group consisting of $R^4$, —OR$^b$, —C(O)OR$^b$, —NR$^c$R$^d$, —C(O)NR$^c$R$^d$, —SO$_2$R$^b$, and —CF$_3$. In another embodiment of formula (IIIa) and (IIIb), $A^2$ is $R^2$, and $R^2$ is —C$_{1-6}$-alkyl, wherein $R^2$ is substituted with 1 or 2 substituents selected from the group consisting of $R^4$, —OR$^b$, —C(O)OR$^b$, —NR$^c$R$^d$, —C(O)NR$^c$R$^d$, —SO$_2$R$^b$, and —CF$_3$, wherein $R^4$ is independently cycloalkyl, aryl, or heterocycloalkyl, $R^4$ is optionally substituted with 1 or 2 substituents selected from the group consisting of —C$_{1-6}$-alkyl, halogen, —OR$^e$, and —C(O)R$^e$, R$^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (IIIa) and (IIIb), $A^2$ is —CH$_3$, —CH$_2$CH$_3$, —CH(CH$_3$)$_2$, —CH$_2$CF$_3$, —CH$_2$CH$_2$OH, —CH$_2$C(O)OH, —CH$_2$C(O)NH$_2$, —CH$_2$CH$_2$OCH$_3$, —CH$_2$CH(CH$_3$)OH, —CH$_2$CH(OH)CH$_2$CH$_3$, —CH$_2$CH$_2$SO$_2$CH$_3$, —CH$_2$C(O)NHCH$_3$, —CH$_2$CH$_2$N(CH$_3$)$_2$, —CH$_2$C(O)N(CH$_3$)$_2$, —CH$_2$CH$_2$CH(CH$_3$)$_2$, —CH$_2$C(O)OCH(CH$_3$)$_2$, —CH$_2$CH$_2$OCH$_2$CH$_2$OCH$_3$, or —CH$_2$CH$_2$N(CH$_3$)$_2$.

In one embodiment of formula (IIIa) and (IIIb), $R^3$ is cycloalkyl, aryl, or heterocycloalkyl, optionally substituted with 1 or 2 substituents selected from the group consisting of —C$_{1-6}$-alkyl, halogen, —OR$^e$, and —C(O)R$^e$. In another embodiment of formula (IIIa) and (IIIb), $R^3$ is —C$_{3-8}$-cycloalkyl. In another embodiment of formula (IIIa) and (IIIb), $R^3$ is —C$_{3-6}$-cycloalkyl. In another embodiment of formula (IIIa) and (IIIb), $R^3$ is —C$_4$-cycloalkyl.

In another embodiment of formula (IIIa) and (IIIb), $R^3$ is aryl. In another embodiment of formula (IIIa) and (IIIb), $R^3$ is phenyl, which is unsubstituted. In another embodiment of formula (IIIa) and (IIIb), $R^3$ is phenyl, which is optionally substituted with 1 or 2 substituents selected from the group consisting of —C$_{1-6}$-alkyl, halogen, —OR$^e$, and —C(O)R$^e$. In another embodiment of formula (IIIa) and (IIIb), $R^3$ is phenyl, which is optionally substituted with 1 or 2 substituents selected from the group consisting of —C$_{1-6}$-alkyl, halogen, —OR$^e$, and —C(O)R$^e$, R$^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (IIIa) and (IIIb), $R^3$ is heterocycloalkyl. In another embodiment of formula (IIIa) and (IIIb), $R^3$ is heterocycloalkyl, which is unsubstituted. In another embodiment of formula (IIIa) and (IIIb), $R^3$ is heterocycloalkyl, optionally substituted with 1 or 2 substituents selected from the group consisting of —C$_{1-6}$-alkyl, halogen, —OR$^e$, and —C(O)R$^e$. In another embodiment of formula (IIIa) and (IIIb), $R^3$ is azetidinyl, pyrrolidinyl, morpholinyl, piperidinyl, tetrahydrofuranyl, or piperazinyl. In another embodiment of formula (IIIa) and (IIIb), $R^3$ is azetidinyl, pyrrolidinyl, morpholinyl, piperidinyl, tetrahydrofuranyl, or piperazinyl, which are unsubstituted. In another embodiment of formula (IIIa) and (IIIb), $R^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, halogen, —OR$^e$, and —C(O)R$^e$. In another embodiment of formula (IIIa) and (IIIb), $R^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$. In another embodiment of formula (IIIa) and (IIIb), $R^3$ is azetidinyl, pyrrolidinyl, piperidinyl, or tetrahydrofuranyl. In another embodiment of formula (IIIa) and (IIIb), $R^3$ is azetidinyl, pyrrolidinyl, piperidinyl, or tetrahydrofuranyl, which are unsubstituted. In another embodiment of formula (IIIa) and (IIIb), $R^3$ is azetidinyl, pyrrolidinyl, piperidinyl, or tetrahydrofuranyl, which are optionally substituted with 1 or 2 substituents selected from the group consisting of —C$_{1-6}$-alkyl, halogen, —OR$^e$, and —C(O)R$^e$. In another embodiment of formula (IIIa) and (IIIb), $R^3$ is azetidinyl, pyrrolidinyl, piperidinyl, or tetrahydrofuranyl which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$.

In one embodiment of formula (IIIa) and (IIIb), $A^3$ is H. In another embodiment of formula (IIIa) and (IIIb), $A^3$ is —C$_{1-6}$-alkyl. In another embodiment of formula (IIIa) and (IIIb), $A^3$ is methyl.

In one embodiment of formula (IIIa) and (IIIb), $A^4$ is H. In another embodiment of formula (IIIa) and (IIIb), $A^4$ is —C$_{1-6}$-alkyl. In another embodiment of formula (IIIa) and (IIIb), $A^4$ is methyl.

In one embodiment of formula (IIIa) and (IIIb), $A^3$ is H, and $A^4$ is H. In another embodiment of formula (IIIa) and (IIIb), $A^3$ is H, and $A^4$ is methyl. In another embodiment of formula (IIIa) and (IIIb), $A^3$ is methyl, and $A^4$ is H.

Another aspect of the invention provides compounds of formula (IV), wherein $R^1$, X, Y, $A^2$, $A^3$, and $A^4$ are as defined generally and in subsets above, n is 0, 1, 2, or 3, and $A^{1B}$ is heteroaryl or aryl.

formula (IV)

In another aspect, the present invention provides compounds of formula (IV) wherein $A^{1B}$ is heteroaryl or aryl;

n is 0, 1, 2, or 3;

$R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —$OC_{1-4}$-haloalkyl, —C(O)OH, —C(O)$OR^a$, —C(O)$NH_2$, —C(O)$NHR^a$, —C(O)N($R^a$)$_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-haloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —C(O)$NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^c$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$ alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$ alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, —N($C_{1-4}$-alkyl)$_2$, and —C(O)$NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group; or a pharmaceutically acceptable salt.

In one embodiment of formula (IV), $A^{1B}$ is heteroaryl. In another embodiment of formula (IV), $A^{1B}$ is pyridyl, pyrazyl, pyrimidinyl, pyridazinyl, 1,3,5-, 1,2,4- or 1,2,3-triazinyl; imidazyl, indazolyl, furanyl, thiophenyl, pyrazolyl, oxazolyl, isoxazolyl, thiazolyl, 1,2,3-, 1,2,4-, 1,2,5-, or 1,3,4-oxadiazolyl, isothiazolyl; benzimidazolyl, benzothiofuranyl, benzisoxazolyl, benzoxazolyl, purinyl, anthranilyl; benzopyranyl, quinolinyl, isoquinolinyl, cinnolinyl, quinazolinyl, or benzoxazinyl. In another embodiment of formula (IV), $A^{1B}$ is

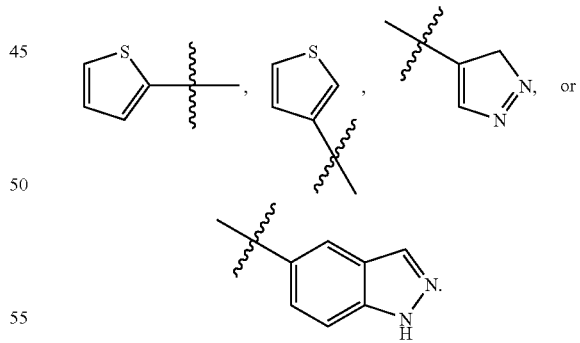

In one embodiment of formula (IV), n is 1 or 2, and $R^1$ is —C(O)$NH_2$, —C(O)$NHCH_3$, —C(O)$NHCH_2CH_3$, —C(O)$OCH_3$, —C(O)$OCH_2CH_3$, or —$C_{1-4}$-alkyl. In another embodiment of formula (IV), $A^1$ is unsubstituted.

In another embodiment of formula (IV), $A^{1B}$ is phenyl, n is 1 or 2, and $R^1$ is, at each occurrence, is independently —$C_{1-4}$-alkyl, —$C_3$-$C_8$-cycloalkyl, or —$C_{3-8}$-heterocycloalkyl, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$- heterocycloalkyl are each independently optionally substituted with halogen, —OH, or —$C_{1-4}$-alkyl.

In one embodiment of formula (IV), X and Y are both H. In another embodiment of formula (IV), Y is H, and X is F, Cl, or Br. In another embodiment of formula (IV), Y is $CH_3$, and X is F, Cl, or Br. In another embodiment of formula (IV), Y is H, and X is F, Cl, Br, —$NO_2$, —$CF_3$, —$C(O)NH_2$, —$CH_3$, or, —$OCH_3$.

In one embodiment of formula (IV), $A^2$ is H. In another embodiment of formula (IV), $A^2$ is $R^2$ or $R^3$. In another embodiment of formula (IV), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$. In another embodiment of formula (IV), $A^2$ is $R^2$, and $R^2$ is —$C_{1-6}$-alkyl, wherein —$C_{1-6}$-alkyl is unsubstituted. In another embodiment of formula (IV), $A^2$ is $R^2$, and $R^2$ is —$C_{1-3}$-alkyl, wherein —$C_{1-3}$-alkyl is unsubstituted. In another embodiment of formula (IV), $A^2$ is —$CH_3$, —$CH_2CH_3$, or —$CH(CH_3)_2$. In another embodiment of formula (IV), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$. In another embodiment of formula (IV), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$, wherein $R^4$ is independently cycloalkyl, aryl, or heterocycloalkyl, $R^4$ is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (IV), $A^2$ is —$CH_3$, —$CH_2CH_3$, —$CH(CH_3)_2$, —$CH_2CF_3$, —$CH_2CH_2OH$, —$CH_2C(O)OH$, —$CH_2C(O)NH_2$, —$CH_2CH_2OCH_3$, —$CH_2CH(CH_3)OH$, —$CH_2CH(OH)CH_2CH_3$, —$CH_2CH_2SO_2CH_3$, —$CH_2C(O)NHCH_3$, —$CH_2CH_2N(CH_3)_2$, —$CH_2C(O)N(CH_3)_2$, —$CH_2CH_2CH(CH_3)_2$, —$CH_2C(O)OCH(CH_3)_2$, —$CH_2CH_2OCH_2CH_2OCH_3$, or —$CH_2CH_2N(CH_3)_2$.

In one embodiment of formula (IV), $R^3$ is cycloalkyl, aryl, or heterocycloalkyl, optionally substituted with 1 or 2 substituents selected from the group consisting of —$C_{1-6}$-alkyl, halogen, —$OR^e$, and —$C(O)R^e$. In another embodiment of formula (IV), $R^3$ is —$C_{3-8}$-cycloalkyl. In another embodiment of formula (IV), $R^3$ is —$C_{3-6}$-cycloalkyl. In another embodiment of formula (II), $R^3$ is —$C_4$-cycloalkyl.

In another embodiment of formula (IV), $R^3$ is aryl. In another embodiment of formula (IV), $R^3$ is phenyl, which is unsubstituted. In another embodiment of formula (IV), $R^3$ is phenyl, which is optionally substituted with 1 or 2 substituents selected from the group consisting of —$C_{1-6}$-alkyl, halogen, —$OR^e$, and —$C(O)R^e$. In another embodiment of formula (IV), $R^3$ is phenyl, which is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (IV), $R^3$ is heterocycloalkyl. In another embodiment of formula (IV), $R^3$ is heterocycloalkyl, which is unsubstituted. In another embodiment of formula (IV), $R^3$ is heterocycloalkyl, optionally substituted with 1 or 2 substituents selected from the group consisting of —$C_{1-6}$-alkyl, halogen, —$OR^e$, and —$C(O)R^e$. In another embodiment of formula (IV), $R^3$ is azetidinyl, pyrrolidinyl, morpholinyl, piperidinyl, tetrahydrofuranyl, or piperazinyl. In another embodiment of formula (IV), $R^3$ is azetidinyl, pyrrolidinyl, morpholinyl, piperidinyl, tetrahydrofuranyl, or piperazinyl, which are unsubstituted. In another embodiment of formula (IV), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, halogen, —$OR^e$, and —$C(O)R^e$. In another embodiment of formula (IV), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$. In another embodiment of formula (IV), $R^3$ is azetidinyl, pyrrolidinyl, piperidinyl, or tetrahydrofuranyl. In another embodiment of formula (IV), $R^3$ is azetidinyl, pyrrolidinyl, piperidinyl, or tetrahydrofuranyl, which are unsubstituted. In another embodiment of formula (IV), $R^3$ is azetidinyl, pyrrolidinyl, piperidinyl, or tetrahydrofuranyl, which are optionally substituted with 1 or 2 substituents selected from the group consisting of —$C_{1-6}$-alkyl, halogen, —$OR^e$, and —$C(O)R^e$. In another embodiment of formula (IV), $R^3$ is azetidinyl, pyrrolidinyl, piperidinyl, or tetrahydrofuranyl which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$.

In one embodiment of formula (IV), $A^3$ is H. In another embodiment of formula (IV), $A^3$ is —$C_{1-6}$-alkyl. In another embodiment of formula (IV), $A^3$ is methyl.

In one embodiment of formula (IV), $A^4$ is H. In another embodiment of formula (IV), $A^4$ is —$C_{1-6}$-alkyl. In another embodiment of formula (IV), $A^4$ is methyl.

In one embodiment of formula (IV), $A^3$ is H, and $A^4$ is H. In one embodiment of formula (II), $A^3$ is H, and $A^4$ is methyl. In one embodiment of formula (IV), $A^3$ is methyl, and $A^4$ is H.

Another aspect of the invention provides compounds of formula (Va) and formula (Vb), wherein X, Y, $R^1$, $A^2$, $A^3$, and $A^4$ are as defined generally and in subsets above, and each $R^{1a}$ is H or —$C_{1-4}$-alkyl.

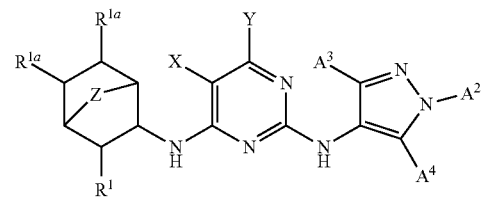

formula (Va)

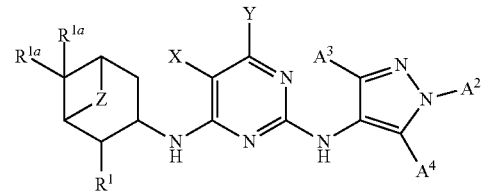

formula (Vb)

Z is CH or O;

$R^1$, at each occurrence, is independently halogen, cyano, nitro, —$C_{1-4}$-alkyl, —$C_{3}$-$C_{8}$-cycloalkyl, —$C_{3-8}$-heterocycloalkyl, —OH, —$OC_{1-4}$-alkyl, —$OC_{1-4}$-haloalkyl, —C(O)OH, —C(O)$OR^a$, —C(O)$NH_2$, —C(O)$NHR^a$, —C(O)N($R^a$)$_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-haloalkyl, —$C_{1-4}$-alkylamino, and —$C_{1-4}$-alkylhydroxy;

$R^{1a}$ is H or —$C_{1-4}$-alkyl;

X and Y are each independently H, F, Cl, Br, —$NO_2$, —$CF_3$, —$CF_2CF_3$, —$OCF_3$, —$OCF_2CF_3$, —C(O)$NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^c$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, —N($C_{1-4}$-alkyl)$_2$, and —C(O)$NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group; or a pharmaceutically acceptable salt In one embodiment of formula (Va) and (Vb), $R^1$ is —C(O)$NH_2$, —C(O)$NHCH_3$, —C(O)$NHCH_2CH_3$, —C(O)$OCH_3$, or —C(O)$OCH_2CH_3$.

In one embodiment of formula (Va) and (Vb), each $R^{1a}$ is H or —$C_{1-4}$-alkyl. In another embodiment of formula (Va) and (Vb), each $R^{1a}$ is H. In another embodiment of formula (Va) and (Vb), each $R^{1a}$ is —$C_{1-4}$-alkyl. In another embodiment of formula (Va) and (Vb), one $R^{1a}$ is —$C_{1-4}$-alkyl, and the other is H. In another embodiment of formula (Va) and (Vb), each $R^{1a}$ is —$CH_3$.

In one embodiment of formula (Va) and (Vb), X and Y are both H. In another embodiment of formula (Va) and (Vb), Y is H, and X is F, Cl, or Br. In another embodiment of formula (Va) and (Vb), Y is $CH_3$, and X is F, Cl, or Br. In another embodiment of formula (Va) and (Vb), Y is H, and X is F, Cl, Br, —$NO_2$, —$CF_3$, —C(O)$NH_2$, —$CH_3$, or, —$OCH_3$.

In one embodiment of formula (Va) and (Vb), $A^2$ is H. In another embodiment of formula (Va) and (Vb), $A^2$ is $R^2$ or $R^3$. In another embodiment of formula (Va) and (Vb), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^c$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$. In another embodiment of formula (Va) and (Vb), $A^2$ is $R^2$, and $R^2$ is —$C_{1-6}$-alkyl, wherein —$C_{1-6}$-alkyl is unsubstituted. In another embodiment of formula (Va) and (Vb), $A^2$ is $R^2$, and $R^2$ is —$C_{1-3}$-alkyl, wherein —$C_{1-3}$-alkyl is unsubstituted. In another embodiment of formula (Va) and (Vb), $A^2$ is —$CH_3$, —$CH_2CH_3$, or —CH($CH_3$)$_2$. In another embodiment of formula (Va) and (Vb), $A^2$ is $R^2$, and $R^2$ is —$C_{1-6}$-alkyl, wherein $R^2$ is substituted with 1 or 2 substituents selected from the group consisting of $R^4$, —$OR^b$, —C(O)$OR^b$, —$NR^cR^d$, —C(O)$NR^cR^d$, —$SO_2R^b$, and —$CF_3$. In another embodiment of formula (Va) and (Vb), $A^2$ is $R^2$, and $R^2$ is —$C_{1-6}$-alkyl, wherein $R^2$ is substituted with 1 or 2 substituents selected from the group consisting of $R^4$, —$OR^b$, —C(O)

$OR^b$, $-NR^cR^d$, $-C(O)NR^cR^d$, $-SO_2R^b$, and $-CF_3$, wherein $R^4$ is independently cycloalkyl, aryl, or heterocycloalkyl, $R^4$ is optionally substituted with 1 or 2 substituents selected from the group consisting of $-C_{1-6}$-alkyl, halogen, $-OR^e$, and $-C(O)R^e$, $R^e$ is $C_{1-6}$-alkyl, and wherein the $C_{1-6}$-alkyl is optionally substituted with one or more substituents selected from the group consisting of $-NHC(O)C_{1-4}$-alkyl, and $-N(C_{1-4}\text{-alkyl})_2$.

In another embodiment of formula (Va) and (Vb), $A^2$ is $-CH_3$, $-CH_2CH_3$, $-CH(CH_3)_2$, $-CH_2CF_3$, $-CH_2CH_2OH$, $-CH_2C(O)OH$, $-CH_2C(O)NH_2$, $-CH_2CH_2OCH_3$, $-CH_2CH(CH_3)OH$, $-CH_2CH(OH)CH_2CH_3$, $-CH_2CH_2SO_2CH_3$, $-CH_2C(O)NHCH_3$, $-CH_2CH_2N(CH_3)_2$, $-CH_2C(O)N(CH_3)_2$, $-CH_2CH_2CH(CH_3)_2$, $-CH_2C(O)OCH(CH_3)_2$, $-CH_2CH_2OCH_2OCH_3$, or $-CH_2CH_2N(CH_3)_2$.

In one embodiment of formula (Va) and (Vb), $R^3$ is cycloalkyl, aryl, or heterocycloalkyl, optionally substituted with 1 or 2 substituents selected from the group consisting of $-C_{1-6}$-alkyl, halogen, $-OR^e$, and $-C(O)R^e$. In another embodiment of formula (Va) and (Vb), $R^3$ is $-C_{3-8}$-cycloalkyl. In another embodiment of formula (Va) and (Vb), $R^3$ is $-C_{3-6}$-cycloalkyl. In another embodiment of formula (II), $R^3$ is $-C_4$-cycloalkyl.

In another embodiment of formula (Va) and (Vb), $R^3$ is aryl. In another embodiment of formula (Va) and (Vb), $R^3$ is phenyl, which is unsubstituted. In another embodiment of formula (Va) and (Vb), $R^3$ is phenyl, which is optionally substituted with 1 or 2 substituents selected from the group consisting of $-C_{1-6}$-alkyl, halogen, $-OR^e$, and $-C(O)R^e$. In another embodiment of formula (Va) and (Vb), $R^3$ is phenyl, which is optionally substituted with 1 or 2 substituents selected from the group consisting of $-C_{1-6}$-alkyl, halogen, $-OR^e$, and $-C(O)R^e$, $R^e$ is $C_{1-6}$-alkyl, and wherein the $C_{1-6}$-alkyl is optionally substituted with one or more substituents selected from the group consisting of $-NHC(O)C_{1-4}$-alkyl, and $-N(C_{1-4}\text{-alkyl})_2$.

In another embodiment of formula (Va) and (Vb), $R^3$ is heterocycloalkyl. In another embodiment of formula (Va) and (Vb), $R^3$ is heterocycloalkyl, which is unsubstituted. In another embodiment of formula (Va) and (Vb), $R^3$ is heterocycloalkyl, optionally substituted with 1 or 2 substituents selected from the group consisting of $-C_{1-6}$-alkyl, halogen, $-OR^e$, and $-C(O)R^e$. In another embodiment of formula (Va) and (Vb), $R^3$ is azetidinyl, pyrrolidinyl, morpholinyl, piperidinyl, tetrahydrofuranyl, or piperazinyl. In another embodiment of formula (Va) and (Vb), $R^3$ is azetidinyl, pyrrolidinyl, morpholinyl, piperidinyl, tetrahydrofuranyl, or piperazinyl, which are unsubstituted. In another embodiment of formula (Va) and (Vb), $R^3$ is azetidinyl, pyrrolidinyl, morpholinyl, piperidinyl, tetrahydrofuranyl, or piperazinyl, which are optionally substituted with 1 or 2 substituents selected from the group consisting of $-C_{1-6}$-alkyl, halogen, $-OR^e$, and $-C(O)R^e$. In another embodiment of formula (Va) and (Vb), $R^3$ is azetidinyl, pyrrolidinyl, morpholinyl, piperidinyl, tetrahydrofuranyl, or piperazinyl, which are optionally substituted with 1 or 2 substituents selected from the group consisting of $-C_{1-6}$-alkyl, $C(O)CH_3$, $C(O)CH_2N(CH_3)_2$, and $C(O)CH_2NHC(O)CH_3$. In another embodiment of formula (Va) and (Vb), $R^3$ is azetidinyl, pyrrolidinyl, piperidinyl, or tetrahydrofuranyl. In another embodiment of formula (Va) and (Vb), $R^3$ is azetidinyl, pyrrolidinyl, piperidinyl, or tetrahydrofuranyl, which are unsubstituted. In another embodiment of formula (Va) and (Vb), $R^3$ is azetidinyl, pyrrolidinyl, piperidinyl, or tetrahydrofuranyl, which are optionally substituted with 1 or 2 substituents selected from the group consisting of $-C_{1-6}$-alkyl, halogen, $-OR^e$, and $-C(O)R^e$. In another embodiment of formula (Va) and (Vb), $R^3$ is azetidinyl, pyrrolidinyl, piperidinyl, or tetrahydrofuranyl which are optionally substituted with 1 or 2 substituents selected from the group consisting of $-C_{1-6}$-alkyl, C(O)CH_3, $C(O)CH_2N(CH_3)_2$, and $C(O)CH_2NHC(O)CH_3$.

In one embodiment of formula (Va) and (Vb), $A^3$ is H. In another embodiment of formula (Va) and (Vb), $A^3$ is $-C_{1-6}$-alkyl. In another embodiment of formula (Va) and (Vb), $A^3$ is methyl.

In one embodiment of formula (Va) and (Vb), $A^4$ is H. In another embodiment of formula (Va) and (Vb), $A^4$ is $-C_{1-6}$-alkyl. In another embodiment of formula (Va) and (Vb), $A^4$ is methyl.

In one embodiment of formula (Va) and (Vb), $A^3$ is H, and $A^4$ is H. In one embodiment of formula (II), $A^3$ is H, and $A^4$ is methyl. In one embodiment of formula (Va) and (Vb), $A^3$ is methyl, and $A^4$ is H.

In one embodiment of formula (Va) and (Vb), Z is CH or O. In another embodiment of formula (Va) and (Vb), Z is CH. In another embodiment of formula (Va) and (Vb), Z is O.

Another aspect of the invention provides compounds of formula (VIa) and formula (VIb), wherein each $R^1$, $R^{1a}$, X, Y, $A^2$, $A^3$, and $A^4$ are as defined generally and in subsets above.

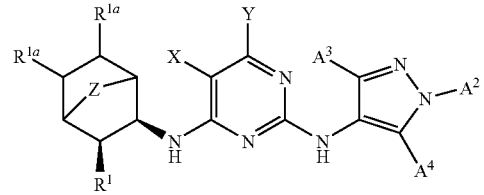

formula (VIa)

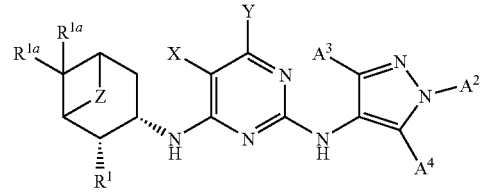

formula (VIb)

Z is CH or O;

$R^1$, at each occurrence, is independently halogen, cyano, nitro, $-C_{1-4}$-alkyl, $-C_3-C_8$-cycloalkyl, $-C_{3-8}$-heterocycloalkyl, $-OH$, $-OC_{1-4}$-alkyl, $-C(O)OH$, $-C(O)OR^a$, $-C(O)NH_2$, $-C(O)NHR^a$, $-C(O)N(R^a)_2$, $-SO_2NH_2$, $-SO_2NR^a$, or $-SO_2N(R^a)_2$, wherein the $R^1$—$C_{1-4}$-alkyl is optionally substituted with halogen, $-OH$, $-OC_{1-4}$-alkyl, or $-C_{3-8}$-heterocycloalkyl, and wherein the $R^1$—$C_3$-$C_8$-cycloalkyl and $-C_{3-8}$-heterocycloalkyl are each independently optionally substituted with halogen, $-OH$, or $-C_{1-4}$-alkyl;

$R^a$, at each occurrence, is independently selected from the group consisting of $-C_{1-4}$-alkyl, $-C_{3-8}$-cycloalkyl, $-C_{3-8}$-heterocycloalkyl, $-C_{1-4}$-alkylamino, and $-C_{1-4}$-alkylhydroxy;

$R^{1a}$ is H or $-C_{1-4}$-alkyl;

X and Y are each independently H, F, Cl, Br, $-NO_2$, $-CF_3$, $-CF_2CF_3$, $-OCF_3$, $-OCF_2CF_3$, $-C(O)NH_2$, $-CH_3$, $-CH_2CH_3$, $-OCH_3$, or $-OCH_2CH_3$;

$A^2$ is H, $R^2$, or $R^3$;

$R^2$ is $-C_{1-6}$-alkyl, $-C_{2-6}$-alkenyl, or $-C_{2-6}$-alkynyl, wherein $R^2$ is optionally substituted with 1, 2, 3, or 4 substituents selected from the group consisting of $R^4$, halogen, cyano, nitro, $-OR^b$, $-C(O)R^b$, $-C(O)OR^b$, $-OC(O)R^b$, $-NR^c$ $R^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, —$N(C_{1-4}$-alkyl$)_2$, and —$C(O)NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group; or a pharmaceutically acceptable salt.

In one embodiment of formula (Va) and (Vb), $R^1$ is —$C(O)NH_2$, —$C(O)NHCH_3$, —$C(O)NHCH_2CH_3$, —$C(O)OCH_3$, or —$C(O)OCH_2CH_3$.

In one embodiment of formula (VIa) and (VIb), each $R^{1a}$ is H or —$C_{1-4}$-alkyl. In another embodiment of formula (VIa) and (VIb), each $R^{1a}$ is H. In another embodiment of formula (VIa) and (VIb), each $R^{1a}$ is —$C_{1-4}$-alkyl. In another embodiment of formula (VIa) and (VIb), one $R^{1a}$ is —$C_{1-4}$-alkyl, and the other is H. In another embodiment of formula (VIa) and (VIb), each $R^{1a}$ is —$CH_3$.

In one embodiment of formula (VIa) and (VIb), X and Y are both H. In another embodiment of formula (VIa) and (VIb), Y is H, and X is F, Cl, or Br. In another embodiment of formula (VIa) and (VIb), Y is $CH_3$, and X is F, Cl, or Br. In another embodiment of formula (VIa) and (VIb), Y is H, and X is F, Cl, Br, —$NO_2$, —$CF_3$, —$C(O)NH_2$, —$CH_3$, or, —$OCH_3$.

In one embodiment of formula (VIa) and (VIb), $A^2$ is H. In another embodiment of formula (VIa) and (VIb), $A^2$ is $R^2$ or $R^3$. In another embodiment of formula (VIa) and (VIb), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$. In another embodiment of formula (VIa) and (VIb), $A^2$ is $R^2$, and $R^2$ is —$C_{1-6}$-alkyl, wherein —$C_{1-6}$-alkyl is unsubstituted. In another embodiment of formula (VIa) and (VIb), $A^2$ is $R^2$, and $R^2$ is —$C_{1-3}$-alkyl, wherein —$C_{1-3}$-alkyl is unsubstituted. In another embodiment of formula (VIa) and (Vb), $A^2$ is —$CH_3$, —$CH_2CH_3$, or —$CH(CH_3)_2$. In another embodiment of formula (VIa) and (VIb), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$. In another embodiment of formula (VIa) and (VIb), $A^2$ is $R^2$, and $R^2$ is $C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$, wherein $R^4$ is independently cycloalkyl, aryl, or heterocycloalkyl, $R^4$ is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (VIa) and (VIb), $A^2$ is —$CH_3$, —$CH_2CH_3$, —$CH(CH_3)_2$, —$CH_2CF_3$, —$CH_2CH_2OH$, —$CH_2C(O)OH$, —$CH_2C(O)NH_2$, —$CH_2CH_2OCH_3$, —$CH_2CH(CH_3)OH$, —$CH_2CH(OH)CH_2CH_3$, —$CH_2CH_2SO_2CH_3$, —$CH_2C(O)NHCH_3$, —$CH_2CH_2N(CH_3)_2$, —$CH_2C(O)N(CH_3)_2$, —$CH_2CH_2CH(CH_3)_2$, —$CH_2C(O)OCH(CH_3)_2$, —$CH_2CH_2OCH_2CH_2OCH_3$, or —$CH_2CH_2N(CH_3)_2$.

In one embodiment of formula (VIa) and (VIb), $R^3$ is cycloalkyl, aryl, or heterocycloalkyl, optionally substituted with 1 or 2 substituents selected from the group consisting of —$C_{1-6}$-alkyl, halogen, —$OR^e$, and —$C(O)R^e$. In another embodiment of formula (VIa) and (VIb), $R^3$ is —$C_{3-8}$-cycloalkyl. In another embodiment of formula (VIa) and (VIb), $R^3$ is —$C_{3-6}$-cycloalkyl. In another embodiment of formula (VI), $R^3$ is —$C_4$-cycloalkyl.

In another embodiment of formula (VIa) and (VIb), $R^3$ is aryl. In another embodiment of formula (VIa) and (VIb), $R^3$ is phenyl, which is unsubstituted. In another embodiment of formula (VIa) and (VIb), $R^3$ is phenyl, which is optionally substituted with 1 or 2 substituents selected from the group consisting of —$C_{1-6}$-alkyl, halogen, —$OR^e$, and —$C(O)R^e$. In another embodiment of formula (VIa) and (VIb), $R^3$ is phenyl, which is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (VIa) and (VIb), $R^3$ is heterocycloalkyl. In another embodiment of formula (VIa) and (VIb), $R^3$ is heterocycloalkyl, which is unsubstituted. In another embodiment of formula (VIa) and (VIb), $R^3$ is heterocycloalkyl, optionally substituted with 1 or 2 substituents selected from the group consisting of —$C_{1-6}$-alkyl, halogen, —$OR^e$, and —$C(O)R^e$. In another embodiment of formula (VIa) and (VIb), $R^3$ is azetidinyl, pyrrolidinyl, morpholinyl, piperidinyl, tetrahydrofuranyl, or piperazinyl. In another embodiment of formula (VIa) and (VIb), $R^3$ is azetidinyl, pyrrolidinyl, morpholinyl, piperidinyl, tetrahydrofuranyl, or piperazinyl, which are unsubstituted. In another embodiment of formula (VIa) and (VIb), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, halogen, —$OR^e$, and —$C(O)R^e$. In another embodiment of formula (VIa) and (VIb), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$. In another embodiment of formula (Va) and (Vb), $R^3$ is azetidinyl, pyrrolidinyl, piperidinyl, or tetrahydrofuranyl. In another embodiment of formula (VIa) and (VIb), $R^3$ is azetidinyl, pyrrolidinyl, piperidinyl, or tetrahydrofuranyl, which are unsubstituted. In another embodiment of formula (VIa) and (VIb), $R^3$ is azetidinyl, pyrrolidinyl, piperidinyl, or tetrahydrofuranyl, which are optionally substituted with 1 or 2 substituents selected from the group consisting of —$C_{1-6}$-alkyl, halogen, —$OR^e$, and —$C(O)R^e$. In another embodiment of formula (VIa) and (VIb), $R^3$ is azetidinyl, pyrrolidinyl, piperidinyl, or tetrahydrofuranyl which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$.

In one embodiment of formula (VIa) and (VIb), $A^3$ is H. In another embodiment of formula (VIa) and (VIb), $A^3$ is —$C_{1-6}$-alkyl. In another embodiment of formula (VIa) and (VIb), $A^3$ is methyl.

In one embodiment of formula (VIa) and (VIb), $A^4$ is H. In another embodiment of formula (VIa) and (VIb), $A^4$ is —$C_{1-6}$-alkyl. In another embodiment of formula (VIa) and (VIb), $A^4$ is methyl.

In one embodiment of formula (VIa) and (VIb), $A^3$ is H, and $A^4$ is H. In one embodiment of formula (VI), $A^3$ is H, and $A^4$ is methyl. In one embodiment of formula (VIa) and (VIb), $A^3$ is methyl, and $A^4$ is H.

In one embodiment of formula (VIa) and (VIb), Z is CH or O. In another embodiment of formula (VIa) and (VIb), Z is CH. In another embodiment of formula (VIa) and (VIb), Z is O.

Another aspect of the invention provides compounds of formula (VII), wherein each $R^1$, X, Y, $A^2$, $A^3$, and $A^4$ are as defined generally and in subsets above, and each $R^{1a}$ is H or —$C_{1-4}$-alkyl.

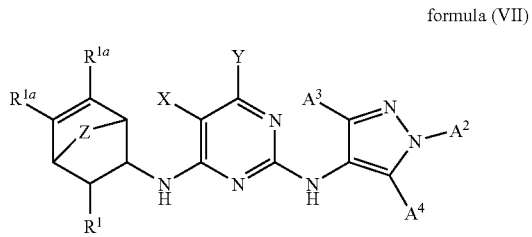

formula (VII)

In another aspect, the present invention provides compounds of formula (VII)

Z is CH or O;

$R^1$, at each occurrence, is independently halogen, cyano, nitro, —$C_{1-4}$-alkyl, —$C_{3-8}$-cycloalkyl, —$C_{3-8}$-heterocycloalkyl, —OH, —$OC_{1-4}$-alkyl, —C(O)OH, —$C(O)OR^a$, —$C(O)NH_2$, —$C(O)NHR^a$, —$C(O)N(R^a)_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_{3-8}$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —$C(O)NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —OC(O)$R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fR^g$, —$CF_3$, —$CF_2CF_3$, —$OCF_3$, and —OCF$_2$CF$_3$, wherein the alkyl, alkenyl, and alkynyl substituents are optionally substituted with one or more substituents selected from the group consisting of aryl, heterocyclyl, cycloalkyl, halogen, cyano, —OR$^e$, —C(O)R$^e$, —C(O)OR$^e$, —OC(O)R$^e$, —NR$^f$R$^g$, —NR$^f$C(O)R$^e$, —NHC(O)NHR$^f$ and —C(O)NR$^f$R$^g$;

A$^3$ and A$^4$ are each independently H or —C$_{1-6}$-alkyl;

R$^b$, at each occurrence, is independently selected from the group consisting of hydrogen, C$_{1-6}$ alkyl, C$_{3-8}$ cycloalkyl, phenyl, and benzyl, wherein the C$_{1-6}$ alkyl, C$_{3-8}$ cycloalkyl, phenyl, or benzyl are optionally substituted with one or more substituents selected from the group consisting of halogen, cyano, nitro, hydroxy, amino, —OC$_{1-4}$-alkyl, —C(O)OC$_{1-4}$-alkyl, —OC(O)C$_{1-4}$-alkyl, —NHC(O)C$_{1-4}$-alkyl, and —C(O)NHC$_{1-4}$-alkyl, wherein C$_{1-4}$-alkyl is an unsubstituted branched or straight chain alkyl group;

R$^c$ and R$^d$, at each occurrence, are independently selected from the group consisting of hydrogen, C$_{1-6}$ alkyl, C$_{3-8}$ cycloalkyl, phenyl, and benzyl, wherein the C$_{1-6}$ alkyl, C$_{3-8}$ cycloalkyl, phenyl, or benzyl are optionally substituted with one or more substituents selected from the group consisting of halogen, cyano, nitro, hydroxy, amino, —OC$_{1-4}$-alkyl, —C(O)OC$_{1-4}$-alkyl, —OC(O)C$_{1-4}$-alkyl, —NHC(O)C$_{1-4}$-alkyl, and —C(O)NHC$_{1-4}$-alkyl, wherein C$_{1-4}$-alkyl is an unsubstituted branched or straight chain alkyl group;

R$^e$, at each occurrence, is independently selected from the group consisting of hydrogen, C$_{1-6}$ alkyl, C$_{3-8}$ cycloalkyl, phenyl, and benzyl, wherein the C$_{1-6}$ alkyl, C$_{3-8}$ cycloalkyl, phenyl, or benzyl are optionally substituted with one or more substituents selected from the group consisting of halogen, cyano, nitro, hydroxy, amino, —OC$_{1-4}$-alkyl, —C(O)OC$_{1-4}$-alkyl, —OC(O)C$_{1-4}$-alkyl, —NHC(O)C$_{1-4}$-alkyl, —N(C$_{1-4}$-alkyl)$_2$, and —C(O)NHC$_{1-4}$-alkyl, wherein C$_{1-4}$-alkyl is an unsubstituted branched or straight chain alkyl group; and R$^f$ and R$^g$, at each occurrence, are independently selected from the group consisting of hydrogen, C$_{1-6}$ alkyl, C$_{3-8}$ cycloalkyl, phenyl, and benzyl, wherein the C$_{1-6}$ alkyl, C$_{3-8}$ cycloalkyl, phenyl, or benzyl are optionally substituted with one or more substituents selected from the group consisting of halogen, cyano, nitro, hydroxy, amino, —OC$_{1-4}$-alkyl, —C(O)OC$_{1-4}$-alkyl, —OC(O)C$_{1-4}$-alkyl, —NHC(O)C$_{1-4}$-alkyl, and —C(O)NHC$_{1-4}$-alkyl, wherein C$_{1-4}$-alkyl is an unsubstituted branched or straight chain alkyl group; or a pharmaceutically acceptable salt In one embodiment of formula (VII), R$^1$ is —C(O)NH$_2$, —C(O)NHCH$_3$, —C(O)NHCH$_2$CH$_3$, —C(O)OCH$_3$, or —C(O)OCH$_2$CH$_3$.

In one embodiment of formula (VII), each R$^{1A}$ is H or —C$_{1-4}$-alkyl. In another embodiment of formula (VII), each R$^{1A}$ is H. In another embodiment of formula (VII), each R$^{1A}$ is —C$_{1-4}$-alkyl. In another embodiment of formula (VII), one R$^{1A}$ is —C$_{1-4}$-alkyl, and the other is H. In another embodiment of formula (VII), each R$^{1A}$ is —CH$_3$.

In one embodiment of formula (VII), X and Y are both H. In another embodiment of formula (VII), Y is H, and X is F, Cl, or Br. In another embodiment of formula (VII), Y is CH$_3$, and X is F, Cl, or Br. In another embodiment of formula (VII), Y is H, and X is F, Cl, Br, —NO$_2$, —CF$_3$, —C(O)NH$_2$, —CH$_3$, or, —OCH$_3$.

In one embodiment of formula (VII), A$^2$ is H. In another embodiment of formula (VII), A$^2$ is R$^2$ or R$^3$. In another embodiment of formula (VII), A$^2$ is R$^2$, and R$^2$ is —C$_{1-6}$-alkyl, —C$_{2-6}$-alkenyl, or —C$_{2-6}$-alkynyl, wherein R$^2$ is optionally substituted with 1, 2, 3, or 4 substituents selected from the group consisting of R$^4$, halogen, cyano, nitro, —OR$^b$, —C(O)R$^b$, —C(O)OR$^b$, —OC(O)R$^b$, —NR$^c$R$^d$, —NR$^c$C(O)R$^b$, —NHC(O)NHR$^c$, —C(O)NR$^c$R$^d$, NR$^c$SO$_2$R$^b$, —SR$^b$, —S(O)R$^b$, —SO$_2$R$^b$, —SO$_2$NR$^c$R$^d$, —CF$_3$, —CF$_2$CF$_3$, —OCF$_3$, and —OCF$_2$CF$_3$. In another embodiment of formula (VII), A$^2$ is R$^2$, and R$^2$ is —C$_{1-6}$-alkyl, wherein —C$_{1-6}$-alkyl is unsubstituted. In another embodiment of formula (VII), A$^2$ is R$^2$, and R$^2$ is —C$_{1-3}$-alkyl, wherein —C$_{1-3}$-alkyl is unsubstituted. In another embodiment of formula (VII), A$^2$ is —CH$_3$, —CH$_2$CH$_3$, or —CH(CH$_3$)$_2$. In another embodiment of formula (VII), A$^2$ is R$^2$, and R$^2$ is —C$_{1-6}$-alkyl, wherein R$^2$ is substituted with 1 or 2 substituents selected from the group consisting of R$^4$, —OR$^b$, —C(O)OR$^b$, —NR$^c$R$^d$, —C(O)NR$^c$R$^d$, —SO$_2$R$^b$, and —CF$_3$. In another embodiment of formula (VII), A$^2$ is R$^2$, and R$^2$ is —C$_{1-6}$-alkyl, wherein R$^2$ is substituted with 1 or 2 substituents selected from the group consisting of R$^4$, —OR$^b$, —C(O)OR$^b$, —NR$^c$R$^d$, —C(O)NR$^c$R$^d$, —SO$_2$R$^b$, and —CF$_3$, wherein R$^4$ is independently cycloalkyl, aryl, or heterocycloalkyl, R$^4$ is optionally substituted with 1 or 2 substituents selected from the group consisting of —C$_{1-6}$-alkyl, halogen, —OR$^e$, and —C(O)R$^e$, R$^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (VII), A$^2$ is —CH$_3$, —CH$_2$CH$_3$, —CH(CH$_3$)$_2$, —CH$_2$CF$_3$, —CH$_2$CH$_2$OH, —CH$_2$C(O)OH, —CH$_2$C(O)NH$_2$, —CH$_2$CH$_2$OCH$_3$, —CH$_2$CH(CH$_3$)OH, —CH$_2$CH(OH)CH$_2$CH$_3$, —CH$_2$CH$_2$SO$_2$CH$_3$, —CH$_2$C(O)NHCH$_3$, —CH$_2$CH$_2$N(CH$_3$)$_2$, —CH$_2$C(O)N(CH$_3$)$_2$, —CH$_2$CH$_2$CH(CH$_3$)$_2$, —CH$_2$C(O)OCH(CH$_3$)$_2$, —CH$_2$CH$_2$OCH$_2$CH$_2$OCH$_3$, or —CH$_2$CH$_2$N(CH$_3$)$_2$.

In one embodiment of formula (VII), R$^3$ is cycloalkyl, aryl, or heterocycloalkyl, optionally substituted with 1 or 2 substituents selected from the group consisting of —C$_{1-6}$-alkyl, halogen, —OR$^e$, and —C(O)R$^e$. In another embodiment of formula (VII), R$^3$ is —C$_{3-8}$-cycloalkyl. In another embodiment of formula (VII), R$^3$ is —C$_{3-6}$-cycloalkyl. In another embodiment of formula (II), R$^3$ is —C$_4$-cycloalkyl.

In another embodiment of formula (VII), R$^3$ is aryl. In another embodiment of formula (VII), R$^3$ is phenyl, which is unsubstituted. In another embodiment of formula (VII), R$^3$ is phenyl, which is optionally substituted with 1 or 2 substituents selected from the group consisting of —C$_{1-6}$-alkyl, halogen, —OR$^e$, and —C(O)R$^e$. In another embodiment of formula (VII), R$^3$ is phenyl, which is optionally substituted with 1 or 2 substituents selected from the group consisting of —C$_{1-6}$-alkyl, halogen, —OR$^e$, and —C(O)R$^e$, R$^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

In another embodiment of formula (VII), R$^3$ is heterocycloalkyl. In another embodiment of formula (VII), R$^3$ is heterocycloalkyl, which is unsubstituted. In another embodiment of formula (VII), R$^3$ is heterocycloalkyl, optionally substituted with 1 or 2 substituents selected from the group consisting of —C$_{1-6}$-alkyl, halogen, —OR$^e$, and —C(O)R$^e$. In another embodiment of formula (VII), R$^3$ is azetidinyl, pyrrolidinyl, morpholinyl, piperidinyl, tetrahydrofuranyl, or piperazinyl. In another embodiment of formula (VII), R$^3$ is azetidinyl, pyrrolidinyl, morpholinyl, piperidinyl, tetrahydrofuranyl, or piperazinyl, which are unsubstituted. In another embodiment of formula (VII), R$^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, halogen, —OR$^e$, and —C(O)R$^e$. In another embodiment of formula (VII), R$^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$. In another embodiment of formula (VII), $R^3$ is azetidinyl, pyrrolidinyl, piperidinyl, or tetrahydrofuranyl. In another embodiment of formula (VII), $R^3$ is azetidinyl, pyrrolidinyl, piperidinyl, or tetrahydrofuranyl, which are unsubstituted. In another embodiment of formula (VII), $R^3$ is azetidinyl, pyrrolidinyl, piperidinyl, or tetrahydrofuranyl, which are optionally substituted with 1 or 2 substituents selected from the group consisting of —$C_{1-6}$-alkyl, halogen, —$OR^e$, and —$C(O)R^e$. In another embodiment of formula (VII), $R^3$ is azetidinyl, pyrrolidinyl, piperidinyl, or tetrahydrofuranyl which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$.

In one embodiment of formula (VII), $A^3$ is H. In another embodiment of formula (VII), $A^3$ is —$C_{1-6}$-alkyl. In another embodiment of formula (VII), $A^3$ is methyl.

In one embodiment of formula (VII), $A^4$ is H. In another embodiment of formula (VII), $A^4$ is —$C_{1-6}$-alkyl. In another embodiment of formula (VII), $A^4$ is methyl.

In one embodiment of formula (VII), $A^3$ is H, and $A^4$ is H. In another embodiment of formula (VII), $A^3$ is H, and $A^4$ is methyl. In another embodiment of formula (VII), $A^3$ is methyl, and $A^4$ is H.

In one embodiment of formula (VII), Z is CH or O. In one embodiment of formula (VII), Z is CH. In one embodiment of formula (VII), Z is O.

Another aspect of the invention provides compounds of formula (VIIIa), (VIIIb), (VIIIc), and (VIIId), wherein $R^1$, X, Y, $A^2$, $A^3$, and $A^4$ are as defined generally and in subsets above.

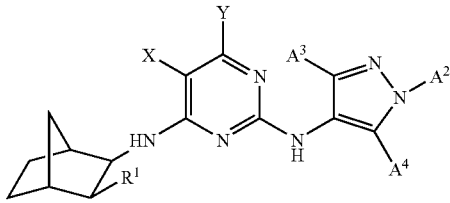

formula (VIIIa)

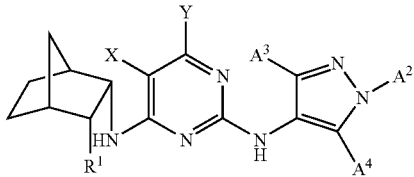

formula (VIIIb)

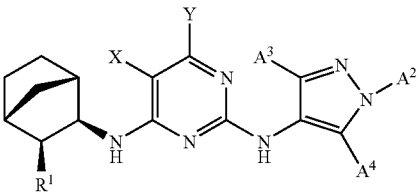

formula (VIIIc)

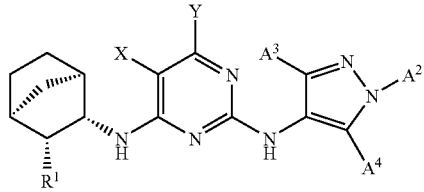

formula (VIIId)

In another aspect, the present invention provides compounds of formula (VIIIa), (VIIIb), (VIIIc), and (VIIId), wherein $R^1$, at each occurrence, is independently halogen, cyano, nitro, —$C_{1-4}$-alkyl, —$C_{3}$-$C_8$-cycloalkyl, —$C_{3-8}$-heterocycloalkyl, —OH, —$OC_{1-4}$-alkyl, —C(O)OH, —$C(O)OR^a$, —$C(O)NH_2$, —$C(O)NHR^a$, —$C(O)N(R^a)_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —$C(O)NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, —$N(C_{1-4}$-alkyl$)_2$, and —$C(O)NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group; or a pharmaceutically acceptable salt In one embodiment of formula (VIIIa), (VIIIb), (VIIIc), and (VIIId), $R^1$ is —$C(O)NH_2$, —$C(O)NHCH_3$, —$C(O)NHCH_2CH_3$, —$C(O)OCH_3$, or —$C(O)OCH_2CH_3$.

In one embodiment of formula (VIIIa), (VIIIb), (VIIIc), and (VIIId), X and Y are both H. In another embodiment of formula (VIIIa), (VIIIb), (VIIIc), and (VIIId), Y is H, and X is F, Cl, or Br. In another embodiment of formula (VIIIa), (VIIIb), (VIIIc), and (VIIId), Y is $CH_3$, and X is F, Cl, or Br. In another embodiment of formula (VIIIa), (VIIIb), (VIIIc), and (VIIId), Y is H, and X is F, Cl, Br, —$NO_2$, —$CF_3$, —$C(O)NH_2$, —$CH_3$, or, —$OCH_3$.

In one embodiment of formula (VIIIa), (VIIIb), (VIIIc), and (VIIId), $A^2$ is H. In another embodiment of formula (VIIIa), (VIIIb), (VIIIc), and (VIIId), $A^2$ is $R^2$ or $R^3$. In another embodiment of formula (VIIIa), (VIIIb), (VIIIc), and (VIIId), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$. In another embodiment of formula (VIIIa), (VIIIb), (VIIIc), and (VIIId), $A^2$ is $R^2$, and $R^2$ is —$C_{1-6}$-alkyl, wherein —$C_{1-6}$-alkyl is unsubstituted. In another embodiment of formula (VIIIa), (VIIIb), (VIIIc), and (VIIId), $A^2$ is $R^2$, and $R^2$ is —$C_{1-6}$-alkyl, wherein —$C_{1-3}$-alkyl is unsubstituted. In another embodiment of formula (VIIIa), (VIIIb), (VIIIc), and (VIIId), $A^2$ is —$CH_3$, —$CH_2CH_3$, or —$CH(CH_3)_2$. In another embodiment of formula (VIIIa), (VIIIb), (VIIIc), and (VIIId), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$. In another embodiment of formula (VIIIa), (VIIIb), (VIIIc), and (VIIId), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$, wherein $R^4$ is independently cycloalkyl, aryl, or heterocycloalkyl, $R^4$ is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (VIIIa), (VIIIb), (VIIIc), and (VIIId), $A^2$ is —$CH_3$, —$CH_2CH_3$, —$CH(CH_3)_2$, —$CH_2CF_3$, —$CH_2CH_2OH$, —$CH_2C(O)OH$, —$CH_2C(O)NH_2$, —$CH_2CH_2OCH_3$, —$CH_2CH(CH_3)OH$, —$CH_2CH(OH)CH_2CH_3$, —$CH_2CH_2SO_2CH_3$, —$CH_2C(O)NHCH_3$, —$CH_2CH_2N(CH_3)_2$, —$CH_2C(O)N(CH_3)_2$, —$CH_2CH_2CH(CH_3)_2$, —$CH_2C(O)OCH(CH_3)_2$, —$CH_2CH_2OCH_2CH_2OCH_3$, or —$CH_2CH_2N(CH_3)_2$.

In one embodiment of formula (VIIIa), (VIIIb), (VIIIc), and (VIIId), $R^3$ is cycloalkyl, aryl, or heterocycloalkyl, optionally substituted with 1 or 2 substituents selected from the group consisting of —$C_{1-6}$-alkyl, halogen, —$OR^e$, and —$C(O)R^e$. In another embodiment of formula (VIIIa), (VIIIb), (VIIIc), and (VIIId), $R^3$ is —$C_{3-8}$-cycloalkyl. In another embodiment of formula (VIIIa), (VIIIb), (VIIIc), and (VIIId), $R^3$ is —$C_{3-6}$-cycloalkyl. In another embodiment of formula (II), $R^3$ is —$C_4$-cycloalkyl.

In another embodiment of formula (VIIIa), (VIIIb), (VIIIc), and (VIIId), $R^3$ is aryl. In another embodiment of formula (VIIIa), (VIIIb), (VIIIc), and (VIIId), $R^3$ is phenyl, which is unsubstituted. In another embodiment of formula (VIIIa), (VIIIb), (VIIIc), and (VIIId), $R^3$ is phenyl, which is optionally substituted with 1 or 2 substituents selected from the group consisting of —$C_{1-6}$-alkyl, halogen, —$OR^e$, and —$C(O)R^e$. In another embodiment of formula (VIIIa), (VIIIb), (VIIIc), and (VIIId), $R^3$ is phenyl, which is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (VIIIa), (VIIIb), (VIIIc), and (VIIId), $R^3$ is heterocycloalkyl. In another embodiment of formula (VIIIa), (VIIIb), (VIIIc), and (VIIId), $R^3$ is heterocycloalkyl, which is unsubstituted. In another embodiment of formula (VIIIa), (VIIIb), (VIIIc), and (VIIId), $R^3$ is heterocycloalkyl, optionally substituted with 1 or 2 substituents selected from the group consisting of —$C_{1-6}$-alkyl, halogen, —$OR^e$, and —$C(O)R^e$. In another embodiment of formula (VIIIa), (VIIIb), (VIIIc), and (VIIId), $R^3$ is azetidinyl, pyrrolidinyl, morpholinyl, piperidinyl, tetrahydrofuranyl, or piperazinyl. In another embodiment of formula (VIIIa), (VIIIb), (VIIIc), and (VIIId), $R^3$ is azetidinyl, pyrrolidinyl, morpholinyl, piperidinyl, tetrahydrofuranyl, or piperazinyl, which are unsubstituted. In another embodiment of formula (VIIIa), (VIIIb), (VIIIc), and (VIIId), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, halogen, —$OR^e$, and —$C(O)R^e$. In another embodiment of formula (VIIIa), (VIIIb), (VIIIc), and (VIIId), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$. In another embodiment of formula (VIIIa), (VIIIb), (VIIIc), and (VIIId), $R^3$ is azetidinyl, pyrrolidinyl, piperidinyl, or tetrahydrofuranyl. In another embodiment of formula (VIIIa), (VIIIb), (VIIIc), and (VIIId), $R^3$ is azetidinyl, pyrrolidinyl, piperidinyl, or tetrahydrofuranyl, which are unsubstituted. In another embodiment of formula (VIIIa), (VIIIb), (VIIIc), and (VIIId), $R^3$ is azetidinyl, pyrrolidinyl, piperidinyl, or tetrahydrofuranyl, which are optionally substituted with 1 or 2 substituents selected from the group consisting of —$C_{1-6}$-alkyl, halogen, —$OR^e$, and —$C(O)R^e$. In another embodiment of formula (VIIIa), (VIIIb), (VIIIc), and (VIIId), $R^3$ is azetidinyl, pyrrolidinyl, piperidinyl, or tetrahydrofuranyl which are optionally substituted with 1 or 2 substituents selected from the group consisting of —$C_{1-6}$-alkyl, $C(O)CH_3$, $C(O)CH_2N(CH_3)_2$, and $C(O)CH_2NHC(O)CH_3$.

In one embodiment of formula (VIIIa), (VIIIb), (VIIIc), and (VIIId), $A^3$ is H. In another embodiment of formula (VIIIa), (VIIIb), (VIIIc), and (VIIId), $A^3$ is —$C_{1-6}$-alkyl. In another embodiment of formula (VIIIa), (VIIIb), (VIIIc), and (VIIId), $A^3$ is methyl.

In one embodiment of formula (VIIIa), (VIIIb), (VIIIc), and (VIIId), $A^4$ is H. In another embodiment of formula (VIIIa), (VIIIb), (VIIIc), and (VIIId), $A^4$ is —$C_{1-6}$-alkyl. In another embodiment of formula (VIIIa), (VIIIb), (VIIIc), and (VIIId), $A^4$ is methyl.

In one embodiment of formula (VIIIa), (VIIIb), (VIIIc), and (VIIId), $A^3$ is H, and $A^4$ is H. In another embodiment of formula (II), $A^3$ is H, and $A^4$ is methyl. In another embodiment of formula (VIIIa), (VIIIb), (VIIIc), and (VIIId), $A^3$ is methyl, and $A^4$ is H.

Another aspect of the invention provides compounds of formula (IXa), (IXb), (IXc), and (IXa), wherein $R^1$, X, Y, $A^2$, $A^3$, and $A^4$ are as defined generally and in subsets above.

formula (IXa)

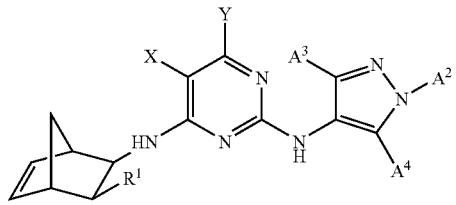

formula (IXb)

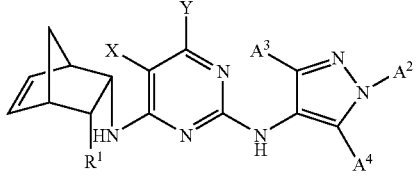

formula (IXc)

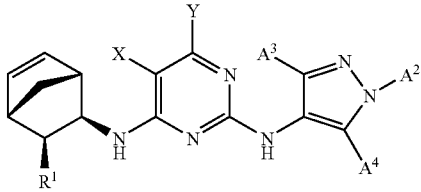

formula (IXd)

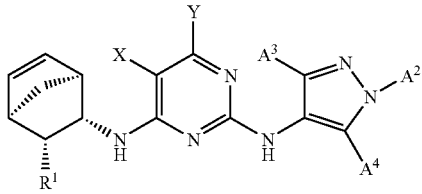

In another aspect, the present invention provides compounds of formula (IXa), (IXb), (IXc), and (IXa), wherein $R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —C(O)OH, —$C(O)OR^a$, —$C(O)NH_2$, —$C(O)NHR^a$, —$C(O)N(R^a)_2$, —$SO_2NH_2$, —$SO_2NR^a$, or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, $C_{1-4}$-haloalkyl, —$C_{1-4}$-alkylamino, and —$C_{1-4}$-alkylhydroxy;

X and Y are each independently H, F, Cl, Br, —$NO_2$, —$CF_3$, —$CF_2CF_3$, —$OCF_3$, —$OCF_2CF_3$, —$C(O)NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$R^5$ is cycloalkyl, cycloalkenyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —$C(O)R^e$, —$C(O)OR^e$, —$OC(O)R^e$, —$NR^fR^g$, —$NR^fC(O)R^e$, —$NHC(O)NHR^f$, —$C(O)NR^fR^g$, —$NR^fSO_2R^e$, —$SR^e$, —$S(O)R^e$, —$SO_2R^e$, —$OC(O)OR^e$, —$SO_2NR^fR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —$C(O)R^e$, —$C(O)OR^e$, —$OC(O)R^e$, —$NR^fR^g$, —$NR^fC(O)R^e$, —$NHC(O)NHR^f$ and —$C(O)NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, —$N(C_{1-4}$-alkyl$)_2$, and —$C(O)NHC_{1-4}$-alkyl, wherein $C_{1-4}$-alkyl is an unsubstituted branched or straight chain alkyl group; and $R^f$ and $R^g$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —$C(O)OC_{1-4}$-alkyl, —$OC(O)C_{1-4}$-alkyl, —$NHC(O)C_{1-4}$-alkyl, and —$C(O)NHC_{1-4}$-alkyl, wherein $C_{1-4}$-alkyl is an unsubstituted branched or straight chain alkyl group; or a pharmaceutically acceptable salt In one embodiment of formula (IXa), (IXb), (IXc), and (IXa), $R^1$ is —$C(O)NH_2$, —$C(O)NHCH_3$, —$C(O)NHCH_2CH_3$, —$C(O)OCH_3$, or —$C(O)OCH_2CH_3$.

In one embodiment of formula (IXa), (IXb), (IXc), and (IXa), X and Y are both H. In another embodiment of formula (IXa), (IXb), (IXc), and (IXa), Y is H, and X is F, Cl, or Br. In another embodiment of formula (IXa), (IXb), (IXc), and (IXa), Y is $CH_3$, and X is F, Cl, or Br. In another embodiment of formula (IXa), (IXb), (IXc), and (IXa), Y is H, and X is F, Cl, Br, —$NO_2$, —$CF_3$, —$C(O)NH_2$, —$CH_3$, or, —$OCH_3$.

In one embodiment of formula (IXa), (IXb), (IXc), and (IXa), $A^2$ is H. In another embodiment of formula (IXa), (IXb), (IXc), and (IXa), $A^2$ is $R^2$ or $R^3$. In another embodiment of formula (IXa), (IXb), (IXc), and (IXa), $A^2$ is $R^2$, and $R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —$C(O)R^b$, —$C(O)OR^b$, —$OC(O)R^b$, —$NR^cR^d$, —$NR^cC(O)R^b$, —$NHC(O)NHR^c$, —$C(O)NR^cR^d$, $NR^cSO_2R^b$, —$SR^b$, —$S(O)R^b$, —$SO_2R^b$, —$SO_2NR^cR^d$, —$CF_3$, —$CF_2CF_3$, —$OCF_3$, and —$OCF_2CF_3$. In another embodiment of formula (IXa), (IXb), (IXc), and (IXa), $A^2$ is $R^2$, and $R^2$ is —$C_{1-6}$-alkyl, wherein —$C_{1-6}$-alkyl is unsubstituted. In another embodiment of formula (IXa), (IXb), (IXc), and (IXa), $A^2$ is $R^2$, and $R^2$ is —$C_{1-3}$-alkyl, wherein —$C_{1-3}$-alkyl is unsubstituted. In another embodiment of formula (IXa), (IXb), (IXc), and (IXa), $A^2$ is —$CH_3$, —$CH_2CH_3$, or —$CH(CH_3)_2$. In another embodiment of formula (IXa), (IXb), (IXc), and (IXa), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$. In another embodiment of formula (IXa), (IXb), (IXc), and (IXa), $A^2$ is $R^2$, and $R^2$ is —$C_{1-6}$-alkyl, wherein $R^2$ is substituted with 1 or 2 substituents selected from the group consisting of $R^4$, —$OR^b$, —$C(O)OR^b$, —$NR^cR^d$, —$C(O)NR^cR^d$, —$SO_2R^b$, and —$CF_3$, wherein $R^4$ is independently cycloalkyl, aryl, or heterocycloalkyl, $R^4$ optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (IXa), (IXb), (IXc), and (IXa), $A^2$ is —$CH_3$, —$CH_2CH_3$, —$CH(CH_3)_2$, —$CH_2CF_3$, —$CH_2CH_2OH$, —$CH_2C(O)OH$, —$CH_2C(O)NH_2$, —$CH_2CH_2OCH_3$, —$CH_2CH(CH_3)OH$, —$CH_2CH(OH)CH_2CH_3$, —$CH_2CH_2SO_2CH_3$, —$CH_2C(O)NHCH_3$, —$CH_2CH_2N(CH_3)_2$, —$CH_2C(O)N(CH_3)_2$, —$CH_2CH_2CH(CH_3)_2$, —$CH_2C(O)OCH(CH_3)_2$, —$CH_2CH_2OCH_2CH_2OCH_3$, or —$CH_2CH_2N(CH_3)_2$.

In one embodiment of formula (IXa), (IXb), (IXc), and (IXa), $R^3$ is cycloalkyl, aryl, or heterocycloalkyl, optionally substituted with 1 or 2 substituents selected from the group consisting of —$C_{1-6}$-alkyl, halogen, —$OR^e$, and —$C(O)R^e$. In another embodiment of formula (IXa), (IXb), (IXc), and (IXa), $R^3$ is —$C_{3-8}$-cycloalkyl. In another embodiment of formula (IXa), (IXb), (IXc), and (IXa), $R^3$ is —$C_{3-6}$-cycloalkyl. In another embodiment of formula (Ix), $R^3$ is —$C_4$-cycloalkyl.

In another embodiment of formula (IXa), (IXb), (IXc), and (IXa), $R^3$ is aryl. In another embodiment of formula (IXa), (IXb), (IXc), and (IXa), $R^3$ is phenyl, which is unsubstituted. In another embodiment of formula (IXa), (IXb), (IXc), and (IXa), $R^3$ is phenyl, which is optionally substituted with 1 or 2 substituents selected from the group consisting of —$C_{1-6}$-alkyl, halogen, —$OR^e$, and —$C(O)R^e$. In another embodiment of formula (IXa), (IXb), (IXc), and (IXa), $R^3$ is phenyl, which is optionally substituted with 1 or 2 substituents selected from the group consisting of —$C_{1-6}$-alkyl, halogen, —$OR^e$, and —$C(O)R^e$, $R^e$ is $C_{1-6}$-alkyl, and wherein the $C_{1-6}$-alkyl is optionally substituted with one or more substituents selected from the group consisting of —$NHC(O)C_{1-4}$-alkyl, and —$N(C_{1-4}$-alkyl$)_2$.

In another embodiment of formula (IXa), (IXb), (IXc), and (IXa), $R^3$ is heterocycloalkyl. In another embodiment of formula (IXa), (IXb), (IXc), and (IXa), $R^3$ is heterocycloalkyl, which is unsubstituted. In another embodiment of formula (IXa), (IXb), (IXc), and (IXa), $R^3$ is heterocycloalkyl, optionally substituted with 1 or 2 substituents selected from the group consisting of —$C_{1-6}$-alkyl, halogen, —$OR^e$, and —$C(O)R^e$. In another embodiment of formula (IXa), (IXb), (IXc), and (IXa), $R^3$ is azetidinyl, pyrrolidinyl, morpholinyl, piperidinyl, tetrahydrofuranyl, or piperazinyl. In another embodiment of formula (IXa), (IXb), (IXc), and (IXa), $R^3$ is azetidinyl, pyrrolidinyl, morpholinyl, piperidinyl, tetrahydrofuranyl, or piperazinyl, which are unsubstituted. In another embodiment of formula (IXa), (IXb), (IXc), and (IXa), $R^3$ is azetidinyl, pyrrolidinyl, morpholinyl, piperidinyl, tetrahydrofuranyl, or piperazinyl, which are optionally substituted with 1 or 2 substituents selected from the group consisting of —$C_{1-6}$-alkyl, halogen, —$OR^e$, and —$C(O)R^e$. In another embodiment of formula (IXa), (IXb), (IXc), and (IXa), $R^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$. In another embodiment of formula (IXa), (IXb), (IXc), and (IXa), R$^3$ is azetidinyl, pyrrolidinyl, piperidinyl, or tetrahydrofuranyl. In another embodiment of formula (IXa), (IXb), (IXc), and (IXa), R$^3$ is azetidinyl, pyrrolidinyl, piperidinyl, or tetrahydrofuranyl, which are unsubstituted. In another embodiment of formula (IXa), (IXb), (IXc), and (IXa), R$^3$ is azetidinyl, pyrrolidinyl, piperidinyl, or tetrahydrofuranyl, which are optionally substituted with 1 or 2 substituents selected from the group consisting of —C$_{1-6}$-alkyl, halogen, —OR$^e$, and —C(O)R$^e$. In another embodiment of formula (IXa), (IXb), (IXc), and (IXa), R$^3$ is azetidinyl, pyrrolidinyl, piperidinyl, or tetrahydrofuranyl which are optionally substituted with 1 or 2 substituents selected from the group consisting of —C$_{1-6}$-alkyl, C(O)CH$_3$, C(O)CH$_2$N(CH$_3$)$_2$, and C(O)CH$_2$NHC(O)CH$_3$.

In one embodiment of formula (IXa), (IXb), (IXc), and (IXa), A$^3$ is H. In another embodiment of formula (IXa), (IXb), (IXc), and (IXa), A$^3$ is —C$_{1-6}$-alkyl. In another embodiment of formula (IXa), (IXb), (IXc), and (IXa), A$^3$ is methyl.

In one embodiment of formula (IXa), (IXb), (IXc), and (IXa), A$^4$ is H. In another embodiment of formula (IXa), (IXb), (IXc), and (IXa), A$^4$ is —C$_{1-6}$-alkyl. In another embodiment of formula (IXa), (IXb), (IXc), and (IXa), A$^4$ is methyl.

In one embodiment of formula (IXa), (IXb), (IXc), and (IXa), A$^3$ is H, and A$^4$ is H. In another embodiment of formula (II), A$^3$ is H, and A$^4$ is methyl. In another embodiment of formula (IXa), (IXb), (IXc), and (IXa), A$^3$ is methyl, and A$^4$ is H.

Specific embodiments contemplated as part of the invention include, but are not limited to, compounds of formula (I), for example:

(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxamide;
(1S,2S,3R,4R)-3-({2-[(1-methyl-1H-pyrazol-4-yl)amino]pyrimidin-4-yl}amino)bicyclo[2.2.1]hept-5-ene-2-carboxamide;
(1R,2R,3S,4S)-3-({2-[(1-methyl-1H-pyrazol-4-yl)amino]pyrimidin-4-yl}amino)bicyclo[2.2.1]hept-5-ene-2-carboxamide;
N$^4$-[(1S,2S,4R)-bicyclo[2.2.1]hept-2-yl]-5-fluoro-N$^2$-(1-methyl-1H-pyrazol-4-yl)pyrimidine-2,4-diamine;
N$^4$-[(1R,2R,4S)-bicyclo[2.2.1]hept-2-yl]-5-fluoro-N$^2$-(1-methyl-1H-pyrazol-4-yl)pyrimidine-2,4-diamine;
(1S,2R)-2-({5-fluoro-2-[(1-methyl-1H-pyrazol-4-yl)amino]pyrimidin-4-yl}amino)cyclopentanecarboxamide;
(1R,2S)-2-({5-fluoro-2-[(1-methyl-1H-pyrazol-4-yl)amino]pyrimidin-4-yl}amino)cyclopentanecarboxamide;
(1S,2S,3R,4R)-3-{[5-fluoro-2-(1H-pyrazol-4-ylamino)pyrimidin-4-yl]amino}bicyclo[2.2.1]hept-5-ene-2-carboxamide;
(1R,2R,3S,4S)-3-{[5-fluoro-2-(1H-pyrazol-4-ylamino)pyrimidin-4-yl]amino}bicyclo[2.2.1]hept-5-ene-2-carboxamide;
isopropyl{4-[(4-{[(1R,2R,3S,4S)-3-(aminocarbonyl)bicyclo[2.2.1]hept-5-ene-2-yl]amino}-5-fluoropyrimidin-2-yl)amino]-1H-pyrazol-1-yl}acetate;
isopropyl{4-[(4-{[(1S,2S,3R,4R)-3-(aminocarbonyl)bicyclo[2.2.1]hept-5-ene-2-yl]amino}-5-fluoropyrimidin-2-yl)amino]-1H-pyrazol-1-yl}acetate;
ethyl(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxylate;
ethyl(1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxylate;
(1S,2S,3R,4R)-3-({2-[(1-ethyl-1H-pyrazol-4-yl)amino]-5-fluoropyrimidin-4-yl}amino)bicyclo[2.2.1]hept-5-ene-2-carboxamide;
(1R,2R,3S,4S)-3-({2-[(1-ethyl-1H-pyrazol-4-yl)amino]-5-fluoropyrimidin-4-yl}amino)bicyclo[2.2.1]hept-5-ene-2-carboxamide;
(1S,2S,3R,4R)-3-({5-fluoro-2-[(1-methyl-1H-pyrazol-4-yl)amino]pyrimidin-4-yl}amino)-N-methylbicyclo[2.2.1]hept-5-ene-2-carboxamide;
(1R,2R,3S,4S)-3-({5-fluoro-2-[(1-methyl-1H-pyrazol-4-yl)amino]pyrimidin-4-yl}amino)-N-methylbicyclo[2.2.1]hept-5-ene-2-carboxamide;
(1S,2S,3R,4R)-3-{[2-[(1-methyl-1H-pyrazol-4-yl)amino]-5-(trifluoromethyl)pyrimidin-4-yl]amino}bicyclo[2.2.1]hept-5-ene-2-carboxamide;
(1R,2R,3S,4S)-3-{[2-[(1-methyl-1H-pyrazol-4-yl)amino]-5-(trifluoromethyl)pyrimidin-4-yl]amino}bicyclo[2.2.1]hept-5-ene-2-carboxamide;
(1S,2S,3R,4R)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide;
(1R,2R,3S,4S)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide;
(1R,2S,3R,4S)-3-({5-fluoro-2-[(1-methyl-1H-pyrazol-4-yl)amino]pyrimidin-4-yl}amino)bicyclo[2.2.1]heptane-2-carboxamide;
(1S,2R,3S,4R)-3-({5-fluoro-2-[(1-methyl-1H-pyrazol-4-yl)amino]pyrimidin-4-yl}amino)bicyclo[2.2.1]heptane-2-carboxamide;
(1R,2S,3R,4S)-3-({2-[(1-ethyl-1H-pyrazol-4-yl)amino]-5-fluoropyrimidin-4-yl}amino)bicyclo[2.2.1]heptane-2-carboxamide;
(1S,2R,3S,4R)-3-({2-[(1-ethyl-1H-pyrazol-4-yl)amino]-5-fluoropyrimidin-4-yl}amino)bicyclo[2.2.1]heptane-2-carboxamide;
(1R,2S,3R,4S)-3-[(5-fluoro-2-{[1-(2-hydroxyethyl)-1H-pyrazol-4-yl]amino}pyrimidin-4-yl)amino]bicyclo[2.2.1]heptane-2-carboxamide;
(1S,2R,3S,4R)-3-[(5-fluoro-2-{[1-(2-hydroxyethyl)-1H-pyrazol-4-yl]amino}pyrimidin-4-yl)amino]bicyclo[2.2.1]heptane-2-carboxamide;
(1R,2R,3S,4S)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide;
(1S,2S,3R,4R)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide;
(1S,2R,3S,4R)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide;
(1R,2S,3R,4S)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide;
(1S,2S,3R,4R)-3-({5-methyl-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-methyl-2-[(1-methyl-1H-pyrazol-4-yl)amino]pyrimidin-4-yl}amino)bicyclo[2.2.1]hept-5-ene-2-carboxamide;

(1S,2S,3R,4R)-3-[(2-{[1-(2-hydroxyethyl)-1H-pyrazol-4-yl]amino}-5-methylpyrimidin-4-yl)amino]bicyclo[2.2.1]hept-5-ene-2-carboxamide;

(1R,2R,3S,4S)-3-[(2-{[1-(2-hydroxyethyl)-1H-pyrazol-4-yl]amino}-5-methylpyrimidin-4-yl)amino]bicyclo[2.2.1]hept-5-ene-2-carboxamide;

(1R,2R,3S,4S)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;

(1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;

(1S,2S,3R,4R)-3-{[2-[(1-methyl-1H-pyrazol-4-yl)amino]-5-(trifluoromethyl)pyrimidin-4-yl]amino}bicyclo[2.2.1]heptane-2-carboxamide;

(1R,2R,3S,4S)-3-{[2-[(1-methyl-1H-pyrazol-4-yl)amino]-5-(trifluoromethyl)pyrimidin-4-yl]amino}bicyclo[2.2.1]heptane-2-carboxamide;

(1S,2R,3S,4R)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide;

(1R,2S,3R,4S)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide;

(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

$N^4$-[(1S,2S,4R)-bicyclo[2.2.1]hept-2-yl]-$N^2$-(1-methyl-1H-pyrazol-4-yl)-5-(trifluoromethyl)pyrimidine-2,4-diamine;

$N^4$-[(1R,2R,4S)-bicyclo[2.2.1]hept-2-yl]-$N^2$-(1-methyl-1H-pyrazol-4-yl)-5-(trifluoromethyl)pyrimidine-2,4-diamine;

(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide;

(1S,2R,3S,4R)-3-{[2-[(1-ethyl-1H-pyrazol-4-yl)amino]-5-(trifluoromethyl)pyrimidin-4-yl]amino}bicyclo[2.2.1]heptane-2-carboxamide;

(1S,2R)-2-{[2-[(1-methyl-1H-pyrazol-4-yl)amino]-5-(trifluoromethyl)pyrimidin-4-yl]amino}cyclopentanecarboxamide;

(1R,2S)-2-{[2-[(1-methyl-1H-pyrazol-4-yl)amino]-5-(trifluoromethyl)pyrimidin-4-yl]amino}cyclopentanecarboxamide;

(1S,6R)-6-{[2-[(1-methyl-1H-pyrazol-4-yl)amino]-5-(trifluoromethyl)pyrimidin-4-yl]amino}cyclohex-3-ene-1-carboxamide;

(1R,6S)-6-{[2-[(1-methyl-1H-pyrazol-4-yl)amino]-5-(trifluoromethyl)pyrimidin-4-yl]amino}cyclohex-3-ene-1-carboxamide;

(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-chloro-2-[(1-methyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-bromo-2-[(1-methyl-1H-pyrazol-4-yl)amino]pyrimidin-4-yl}amino)bicyclo[2.2.1]hept-5-ene-2-carboxamide;

(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;

(1R,2R,3S,4S)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-({5-chloro-2-[(1-ethyl-1H-pyrazol-4-yl)amino]pyrimidin-4-yl}amino)bicyclo[2.2.1]hept-5-ene-2-carboxamide;

(1R,2R,3S,4S)-3-({5-chloro-2-[(1-ethyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide;

(1R,2R,3S,4S)-3-({5-bromo-2-[(1-ethyl-1H-pyrazol-4-yl)amino]pyrimidin-4-yl}amino)bicyclo[2.2.1]hept-5-ene-2-carboxamide;

(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;

(1R,2R,3S,4S)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(2-piperidin-1-ylethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-piperidin-1-ylethyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(2-morpholin-4-ylethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-morpholin-4-ylethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide;

(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-ethyl-1H-pyrazol-4-yl)amino]pyrimidin-4-yl}amino)bicyclo[2.2.1]hept-5-ene-2-carboxamide;

(1S,2R)-2-({5-chloro-2-[(1-methyl-1H-pyrazol-4-yl)amino]pyrimidin-4-yl}amino)cyclopentanecarboxamide and (1R,2S)-2-({5-chloro-2-[(1-methyl-1H-pyrazol-4-yl)amino]pyrimidin-4-yl}amino)cyclopentanecarboxamide;

(1S,2S,3R,4R)-3-[(5-bromo-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1S,2S,3R,4R)-3-[(5-fluoro-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1R,2R,3S,4S)-3-[(5-fluoro-2-{[1-(2-pyrrolidin-1-ylethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-({5-bromo-2-[(1-methyl-1H-pyrazol-4-yl)amino]pyrimidin-4-yl}amino)-N-methylbicyclo[2.2.1]hept-5-ene-2-carboxamide;

(1R,2R,3S,4S)-3-({5-bromo-2-[(1-methyl-1H-pyrazol-4-yl)amino]pyrimidin-4-yl}amino)-N-methylbicyclo[2.2.1]hept-5-ene-2-carboxamide;

(1S,2S,3R,4R)-3-({5-bromo-2-[(1-ethyl-1H-pyrazol-4-yl)amino]pyrimidin-4-yl}amino)-N-methylbicyclo[2.2.1]hept-5-ene-2-carboxamide;

(1R,2R,3S,4S)-3-({5-bromo-2-[(1-ethyl-1H-pyrazol-4-yl)amino]pyrimidin-4-yl}amino)-N-methylbicyclo[2.2.1]hept-5-ene-2-carboxamide;

(1S,2S,3R,4R)-3-({5-chloro-2-[(1-methyl-1H-pyrazol-4-yl)amino]pyrimidin-4-yl}amino)-N-methylbicyclo[2.2.1]hept-5-ene-2-carboxamide;

(1R,2R,3S,4S)-3-({5-chloro-2-[(1-methyl-1H-pyrazol-4-yl)amino]pyrimidin-4-yl}amino)-N-methylbicyclo[2.2.1]hept-5-ene-2-carboxamide;

(1S,2S,3R,4R)-3-({5-chloro-2-[(1-ethyl-1H-pyrazol-4-yl)amino]pyrimidin-4-yl}amino)-N-methylbicyclo[2.2.1]hept-5-ene-2-carboxamide;

(1R,2R,3S,4S)-3-({5-chloro-2-[(1-ethyl-1H-pyrazol-4-yl)amino]pyrimidin-4-yl}amino)-N-methylbicyclo[2.2.1]hept-5-ene-2-carboxamide;

(1S,2S,3R,4R)-3-({5-methoxy-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-methoxy-2-[(1-methyl-1H-pyrazol-4-yl)amino]pyrimidin-4-yl}amino)bicyclo[2.2.1]hept-5-ene-2-carboxamide;

(1S,2S,3R,4R)-3-({2-[(1-ethyl-1H-pyrazol-4-yl)amino]-5-methoxypyrimidin-4-yl}amino)bicyclo[2.2.1]hept-5-ene-2-carboxamide;

(1R,2R,3S,4S)-3-({2-[(1-ethyl-1H-pyrazol-4-yl)amino]-5-methoxypyrimidin-4-yl}amino)bicyclo[2.2.1]hept-5-ene-2-carboxamide;

(1S,2S,3R,4R)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide;

isopropyl{4-[(4-{[(1S,2S,3R,4R)-3-(aminocarbonyl)bicyclo[2.2.1]hept-5-ene-2-yl]amino}-5-bromopyrimidin-2-yl)amino]-1H-pyrazol-1-yl}acetate;

isopropyl{4-[(4-{[(1R,2R,3S,4S)-3-(aminocarbonyl)bicyclo[2.2.1]hept-5-ene-2-yl]amino}-5-bromopyrimidin-2-yl)amino]-1H-pyrazol-1-yl}acetate;

(1R,2S,3R,4S)-3-({5-chloro-2-[(1-methyl-1H-pyrazol-4-yl)amino]pyrimidin-4-yl}amino)bicyclo[2.2.1]heptane-2-carboxamide;

(1S,2R,3S,4R)-3-({5-chloro-2-[(1-methyl-1H-pyrazol-4-yl)amino]pyrimidin-4-yl}amino)bicyclo[2.2.1]heptane-2-carboxamide;

(1R,2S,3R,4S)-3-({5-chloro-2-[(1-ethyl-1H-pyrazol-4-yl)amino]pyrimidin-4-yl}amino)bicyclo[2.2.1]heptane-2-carboxamide;

(1S,2R,3S,4R)-3-({5-chloro-2-[(1-ethyl-1H-pyrazol-4-yl)amino]pyrimidin-4-yl}amino)bicyclo[2.2.1]heptane-2-carboxamide;

(1R,2S,3R,4S)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide;

(1S,2R,3S,4R)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide;

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1S,2R,3S,4R)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1R,2S,3R,4S)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide;

(1S,2R,3S,4R)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide;

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2R,3S,4R)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-[(5-chloro-2-{[1-(2-hydroxyethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2,2,2-trifluoroethyl)-1H-pyrazol-4-yl]amino}pyrimidin-4-yl)amino]bicyclo[2.2.1]hept-5-ene-2-carboxamide;

(1S,2S,3R,4R)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide;

(1R,2R,3S,4S)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide;

(1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;

(1S,2S,3R,4R)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[5-chloro-2-({1-[(3S)-pyrrolidin-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3R)-pyrrolidin-3-yl]-1H-pyrazol-4-yl}amino)pyrimidin-4-yl]amino}bicyclo[2.2.1]hept-5-ene-2-carboxamide;

(1S,2S,3R,4R)-3-[(2-{[1-(2-amino-2-oxoethyl)-1H-pyrazol-4-yl]amino}-5-chloropyrimidin-4-yl)amino]bicyclo[2.2.1]hept-5-ene-2-carboxamide;

(1S,2S,3R,4R)-3-{[5-chloro-2-({1-[2-(methylamino)-2-oxoethyl]-1H-pyrazol-4-yl}amino)pyrimidin-4-yl]amino}bicyclo[2.2.1]hept-5-ene-2-carboxamide;

(1S,2S,3R,4R)-3-[(2-{[1-(2-amino-2-oxoethyl)-1H-pyrazol-4-yl]amino}-5-bromopyrimidin-4-yl)amino]bicyclo[2.2.1]hept-5-ene-2-carboxamide;

(1S,2S,3R,4R)-3-{[5-bromo-2-({1-[2-(methylamino)-2-oxoethyl]-1H-pyrazol-4-yl}amino)pyrimidin-4-yl]amino}bicyclo[2.2.1]hept-5-ene-2-carboxamide;

isopropyl{4-[(4-{[(1R,2R,3S,4S)-3-(aminocarbonyl)bicyclo[2.2.1]hept-5-ene-2-yl]amino}-5-chloropyrimidin-2-yl)amino]-1H-pyrazol-1-yl}acetate;

(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide;

(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide;

(1S,2S,3R,4R)-3-({2-[(1-azetidin-3-yl-1H-pyrazol-4-yl)amino]-5-chloropyrimidin-4-yl}amino)bicyclo[2.2.1]hept-5-ene-2-carboxamide;

(1S,2S,3R,4R)-3-({5-chloro-2-[(1-piperidin-4-yl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[(3S)-piperidin-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3R)-piperidin-3-yl]-1H-pyrazol-4-yl}amino)pyrimidin-4-yl]amino}bicyclo[2.2.1]hept-5-ene-2-carboxamide;

(1S,2S,3R,4R)-3-{[2-({1-[1-(N-acetylglycyl)piperidin-4-yl]-1H-pyrazol-4-yl}amino)-5-chloropyrimidin-4-yl]amino}bicyclo[2.2.1]hept-5-ene-2-carboxamide;

4-{[(1S,2S,3R,4R)-3-carbamoylbicyclo[2.2.1]hept-5-ene-2-yl]amino}-2-[(1-methyl-1H-pyrazol-4-yl)amino]pyrimidine-5-carboxamide;

4-{[(1R,2R,3S,4S)-3-carbamoylbicyclo[2.2.1]hept-5-ene-2-yl]amino}-2-[(1-methyl-1H-pyrazol-4-yl)amino]pyrimidine-5-carboxamide;

4-{[(1S,2S,3R,4R)-3-carbamoylbicyclo[2.2.1]hept-5-ene-2-yl]amino}-2-[(1-ethyl-1H-pyrazol-4-yl)amino]pyrimidine-5-carboxamide;

4-{[(1R,2R,3S,4S)-3-carbamoylbicyclo[2.2.1]hept-5-ene-2-yl]amino}-2-[(1-ethyl-1H-pyrazol-4-yl)amino]pyrimidine-5-carboxamide;

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[1-(N,N-dimethylglycyl)piperidin-4-yl]-1H-pyrazol-4-yl}amino)pyrimidin-4-yl]amino}bicyclo[2.2.1]hept-5-ene-2-carboxamide;

(1R,2S,3R,4S)-3-{[5-chloro-2-({1-[2-(4-methylpiperazin-1-yl)ethyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)-3-[(2-{[1-(1-acetylpiperidin-4-yl)-1H-pyrazol-4-yl]amino}-5-chloropyrimidin-4-yl)amino]bicyclo[2.2.1]hept-5-ene-2-carboxamide;

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1S,2S,3R,4R)-3-{[5-bromo-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(piperidin-4-yl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2-methoxyethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(1-methylpiperidin-4-yl)methyl]-1H-pyrazol-4-yl}amino)pyrimidin-4-yl]amino}bicyclo[2.2.1]hept-5-ene-2-carboxamide;

(1S,2S,3R,4R)-3-({5-chloro-2-[(1-isopropyl-1H-pyrazol-4-yl)amino]pyrimidin-4-yl}amino)bicyclo[2.2.1]hept-5-ene-2-carboxamide;

(1S,2S,3R,4R)-3-[(5-chloro-2-{[1-(3-methylbutyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(2-methoxyethoxy)ethyl]-1H-pyrazol-4-yl}amino)pyrimidin-4-yl]amino}bicyclo[2.2.1]hept-5-ene-2-carboxamide;

1-[2-({5-chloro-2-[(1-methyl-1H-pyrazol-4-yl)amino]pyrimidin-4-yl}amino)phenyl]cyclobutanol;

(1S,2S,3R,4R)-3-{[5-chloro-2-({1-[(2R)-pyrrolidin-2-ylmethyl]-1H-pyrazol-4-yl}amino)pyrimidin-4-yl]amino}bicyclo[2.2.1]hept-5-ene-2-carboxamide;

{4-[(4-{[(1R,2R,3S,4S)-3-carbamoylbicyclo[2.2.1]hept-5-ene-2-yl]amino}-5-chloropyrimidin-2-yl)amino]-1H-pyrazol-1-yl}acetic acid;

(1R,2S,3R,4S)-3-{[5-chloro-2-({1-[(2R)-2-hydroxypropyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[(2R)-2-hydroxypropyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(2-methoxyethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(3R)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3S)-tetrahydrofuran-3-yl]-1H-pyrazol-4-yl}amino)pyrimidin-4-yl]amino}bicyclo[2.2.1]hept-5-ene-2-carboxamide;

3-[2-({2-[(1-methyl-1H-pyrazol-4-yl)amino]-5-(trifluoromethyl)pyrimidin-4-yl}amino)phenyl]azetidin-3-ol;

(1S,2S,3R,4R)-3-{[5-bromo-2-({1-[2-(2-methoxyethoxy)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(3-methylbutyl)-1H-pyrazol-4-yl]amino}pyrimidin-4-yl)amino]bicyclo[2.2.1]hept-5-ene-2-carboxamide;

(1S,2S,3R,4R)-3-({5-bromo-2-[(1-isopropyl-1H-pyrazol-4-yl)amino]pyrimidin-4-yl}amino)bicyclo[2.2.1]hept-5-ene-2-carboxamide;

(1R,2R,3S,4S)-3-({5-chloro-2-[(1-methyl-1H-pyrazol-4-yl)amino]pyrimidin-4-yl}amino)bicyclo[2.2.1]heptane-2-carboxamide;

(1S,2S,3R,4R)-3-({5-chloro-2-[(1-methyl-1H-pyrazol-4-yl)amino]pyrimidin-4-yl}amino)bicyclo[2.2.1]heptane-2-carboxamide;

(1R,2R,3S,4S)-3-({5-chloro-2-[(1-ethyl-1H-pyrazol-4-yl)amino]pyrimidin-4-yl}amino)bicyclo[2.2.1]heptane-2-carboxamide;

(1S,2S,3R,4R)-3-({5-chloro-2-[(1-ethyl-1H-pyrazol-4-yl)amino]pyrimidin-4-yl}amino)bicyclo[2.2.1]heptane-2-carboxamide;

1-[2-({2-[(1-methyl-1H-pyrazol-4-yl)amino]-5-(trifluoromethyl)pyrimidin-4-yl}amino)phenyl]cyclobutanol;

(1S,2S,3R,4R)-3-{[5-bromo-2-({1-[(3R)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-{[5-bromo-2-({1-[(3S)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-({5-chloro-2-[(1-cyclobutyl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[2-(methylsulfonyl)ethyl]-1H-pyrazol-4-yl}amino)pyrimidin-4-yl]amino}bicyclo[2.2.1]hept-5-ene-2-carboxamide;

(1S,2R,3S,4R)-3-({5-chloro-2-[(1-methyl-1H-pyrazol-4-yl)amino]pyrimidin-4-yl}amino)bicyclo[2.2.1]hept-5-ene-2-carboxamide;

(1R,2S,3R,4S)-3-({5-chloro-2-[(1-methyl-1H-pyrazol-4-yl)amino]pyrimidin-4-yl}amino)bicyclo[2.2.1]hept-5-ene-2-carboxamide;

(1S,2R,3S,4R)-3-({5-chloro-2-[(1-ethyl-1H-pyrazol-4-yl)amino]pyrimidin-4-yl}amino)bicyclo[2.2.1]hept-5-ene-2-carboxamide;

(1R,2S,3R,4S)-3-({5-chloro-2-[(1-ethyl-1H-pyrazol-4-yl)amino]pyrimidin-4-yl}amino)bicyclo[2.2.1]hept-5-ene-2-carboxamide;

(1S,2S,3R,4R)-3-{[5-bromo-2-({1-[2-(methylsulfonyl)ethyl]-1H-pyrazol-4-yl}amino)pyrimidin-4-yl]amino}bicyclo[2.2.1]hept-5-ene-2-carboxamide;

(1S,2S,3R,4R)-3-({5-bromo-2-[(1-cyclobutyl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[(2S)-2,3-dihydroxypropyl]-1H-pyrazol-4-yl}amino)pyrimidin-4-yl]amino}bicyclo[2.2.1]hept-5-ene-2-carboxamide;

(1S,2S,3R,4R)-3-({5-chloro-6-methyl-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-chloro-6-methyl-2-[(1-methyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-ethyl-1H-pyrazol-4-yl)amino]-6-methylpyrimidin-4-yl}amino)bicyclo[2.2.1]hept-5-ene-2-carboxamide;

(1R,2R,3S,4S)-3-({5-chloro-2-[(1-ethyl-1H-pyrazol-4-yl)amino]-6-methylpyrimidin-4-yl}amino)bicyclo[2.2.1]hept-5-ene-2-carboxamide;

(1S,2S,3R,4R)-3-({5-chloro-2-[(1,3,5-trimethyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1,3,5-trimethyl-1H-pyrazol-4-yl)amino]pyrimidin-4-yl}amino)bicyclo[2.2.1]hept-5-ene-2-carboxamide;

(1S,2S,3R,4R)-3-[(5-chloro-2-{[1-(oxetan-2-ylmethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(2R)-2,3-dihydroxypropyl]-1H-pyrazol-4-yl}amino)pyrimidin-4-yl]amino}bicyclo[2.2.1]hept-5-ene-2-carboxamide;

(1S,2S,3R,4R)-3-{[5-bromo-2-({1-[(2S)-2,3-dihydroxypropyl]-1H-pyrazol-4-yl}amino)pyrimidin-4-yl]amino}bicyclo[2.2.1]hept-5-ene-2-carboxamide;

1-[2-({5-bromo-2-[(1-methyl-1H-pyrazol-4-yl)amino]pyrimidin-4-yl}amino)phenyl]cyclobutanol;

4-[2-({5-chloro-2-[(1-methyl-1H-pyrazol-4-yl)amino]pyrimidin-4-yl}amino)phenyl]tetrahydro-2H-pyran-4-ol;

(1S,2S,3R,4R)-3-({5-chloro-2-[(1,3-dimethyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1,3-dimethyl-1H-pyrazol-4-yl)amino]pyrimidin-4-yl}amino)bicyclo[2.2.1]hept-5-ene-2-carboxamide;

(1S,2R)-2-[(5-chloro-2-{[1-(piperidin-4-yl)-1H-pyrazol-4-yl]amino}pyrimidin-4-yl)amino]cyclopentanecarboxamide;

(1R,2S)-2-[(5-chloro-2-{[1-(piperidin-4-yl)-1H-pyrazol-4-yl]amino}pyrimidin-4-yl)amino]cyclopentanecarboxamide;

(1S,2R)-2-{[5-chloro-2-({1-[2-(morpholin-4-yl)ethyl]-1H-pyrazol-4-yl}amino)pyrimidin-4-yl]amino}cyclopentanecarboxamide;

(1R,2S)-2-{[5-chloro-2-({1-[2-(morpholin-4-yl)ethyl]-1H-pyrazol-4-yl}amino)pyrimidin-4-yl]amino}cyclopentanecarboxamide;

2-[2-({5-chloro-2-[(1-methyl-1H-pyrazol-4-yl)amino]pyrimidin-4-yl}amino)phenyl]propan-2-ol;

(1S,2S,3R,4R)-3-({2-[(1-methyl-1H-pyrazol-4-yl)amino]-5-nitropyrimidin-4-yl}amino)bicyclo[2.2.1]hept-5-ene-2-carboxamide;

(1S,2S,3R,4R)-3-({2-[(1-ethyl-1H-pyrazol-4-yl)amino]-5-nitropyrimidin-4-yl}amino)bicyclo[2.2.1]hept-5-ene-2-carboxamide;

(1S,2R,3S,4R)-3-({5-chloro-2-[(1-methyl-1H-pyrazol-4-yl)amino]pyrimidin-4-yl}amino)-7-oxabicyclo[2.2.1]heptane-2-carboxamide;

(1R,2S,3R,4S)-3-({5-chloro-2-[(1-methyl-1H-pyrazol-4-yl)amino]pyrimidin-4-yl}amino)-7-oxabicyclo[2.2.1]heptane-2-carboxamide;

(1S,2R,3S,4R)-3-({5-chloro-2-[(1-ethyl-1H-pyrazol-4-yl)amino]pyrimidin-4-yl}amino)-7-oxabicyclo[2.2.1]heptane-2-carboxamide;

(1R,2S,3R,4S)-3-({5-chloro-2-[(1-ethyl-1H-pyrazol-4-yl)amino]pyrimidin-4-yl}amino)-7-oxabicyclo[2.2.1]heptane-2-carboxamide;

(1S,2S,3R,4R)-3-[(5-chloro-2-{[1-(2-phenylethyl)-1H-pyrazol-4-yl]amino}pyrimidin-4-yl)amino]bicyclo[2.2.1]hept-5-ene-2-carboxamide;

(1S,2S,3R,4R)-3-({2-[(1-benzyl-1H-pyrazol-4-yl)amino]-5-chloropyrimidin-4-yl}amino)bicyclo[2.2.1]hept-5-ene-2-carboxamide;

[2-({5-chloro-2-[(1-methyl-1H-pyrazol-4-yl)amino]pyrimidin-4-yl}amino)phenyl]methanol;

(1S,6R)-6-({5-chloro-2-[(1-methyl-1H-pyrazol-4-yl)amino]pyrimidin-4-yl}amino)cyclohex-3-ene-1-carboxamide;

(1R,6S)-6-({5-chloro-2-[(1-methyl-1H-pyrazol-4-yl)amino]pyrimidin-4-(1S,2R)-2-({5-chloro-2-[(1-methyl-1H-pyrazol-4-yl)amino]pyrimidin-4-yl}amino)cyclohexanecarboxamide;

(1R,2S)-2-({5-chloro-2-[(1-methyl-1H-pyrazol-4-yl)amino]pyrimidin-4-yl}amino)cyclohexanecarboxamide;

(1S,2S,3R,4R)-3-[(5-bromo-2-{[1-(2-phenylethyl)-1H-pyrazol-4-yl]amino}pyrimidin-4-yl)amino]bicyclo[2.2.1]hept-5-ene-2-carboxamide;

(1S,2S,3R,4R)-3-({2-[(1-benzyl-1H-pyrazol-4-yl)amino]-5-bromopyrimidin-4-yl}amino)bicyclo[2.2.1]hept-5-ene-2-carboxamide;

3-({2-[(1-methyl-1H-pyrazol-4-yl)amino]-5-(trifluoromethyl)pyrimidin-4-yl}amino)thiophene-2-carboxamide;

(1S,2R)-2-({5-chloro-2-[(1-methyl-1H-pyrazol-4-yl)amino]pyrimidin-4-yl}amino)cyclobutanecarboxamide;

(1R,2S)-2-({5-chloro-2-[(1-methyl-1H-pyrazol-4-yl)amino]pyrimidin-4-yl}amino)cyclobutanecarboxamide;

2-({2-[(1-methyl-1H-pyrazol-4-yl)amino]-5-(trifluoromethyl)pyrimidin-4-yl}amino)thiophene-3-carboxamide;

1-methyl-4-({2-[(1-methyl-1H-pyrazol-4-yl)amino]-5-(trifluoromethyl)pyrimidin-4-yl}amino)-1H-pyrazole-3-carboxamide;

(1S,2S,3R,4R)-3-{[5-chloro-2-({1-[2-(3-methoxyphenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(3-methoxybenzyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(3-chlorobenzyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(3-chlorophenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(3-methoxybenzyl)-1H-pyrazol-4-yl]amino}pyrimidin-4-yl)amino]bicyclo[2.2.1]hept-5-ene-2-carboxamide;

(1S,2S,3R,4R)-3-{[5-bromo-2-({1-[2-(3-methoxyphenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(2-chlorobenzyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(4-chlorobenzyl)-1H-pyrazol-4-yl]amino}pyrimidin-4-yl)amino]bicyclo[2.2.1]hept-5-ene-2-carboxamide;

(1S,2R)-2-[(5-chloro-2-{[1-(piperidin-4-yl)-1H-pyrazol-4-yl]amino}pyrimidin-4-yl)amino]-N-isopropylcyclopentanecarboxamide;

(1R,2S)-2-[(5-chloro-2-{[1-(piperidin-4-yl)-1H-pyrazol-4-yl]amino}pyrimidin-4-yl)amino]-N-isopropylcyclopentanecarboxamide;

(1S,2R)-2-{[5-chloro-2-({1-[2-(morpholin-4-yl)ethyl]-1H-pyrazol-4-yl}amino)pyrimidin-4-yl]amino}-N-isopropylcyclopentanecarboxamide;

(1R,2R,3S,5R)-2-({5-chloro-2-[(1-methyl-1H-pyrazol-4-yl)amino]pyrimidin-4-yl}amino)-6,6-dimethylbicyclo[3.1.1]heptane-3-carboxamide;

(1R,2R,3S,5R)-2-({5-chloro-2-[(1-ethyl-1H-pyrazol-4-yl)amino]pyrimidin-4-yl}amino)-6,6-dimethylbicyclo[3.1.1]heptane-3-carboxamide;

(1R,2R,3S,5R)-6,6-dimethyl-2-({2-[(1-methyl-1H-pyrazol-4-yl)amino]-5-(trifluoromethyl)pyrimidin-4-yl}amino)bicyclo[3.1.1]heptane-3-carboxamide;

(1R,2R,3S,5R)-2-({2-[(1-ethyl-1H-pyrazol-4-yl)amino]-5-(trifluoromethyl)pyrimidin-4-yl}amino)-6,6-dimethylbicyclo[3.1.1]heptane-3-carboxamide;

(1S,2S,3R,4R)-3-({5-bromo-2-[(1,5-dimethyl-1H-pyrazol-4-yl)amino]pyrimidin-4-yl}amino)bicyclo[2.2.1]hept-5-ene-2-carboxamide;

(1S,2S,3R,4R)-3-[(5-bromo-2-{[1-(2-chlorobenzyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(4-chlorobenzyl)-1H-pyrazol-4-yl]amino}pyrimidin-4-yl)amino]bicyclo[2.2.1]hept-5-ene-2-carboxamide;

(1S,2S,3R,4R)-3-({5-bromo-2-[(1-phenyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-phenyl-1H-pyrazol-4-yl)amino]pyrimidin-4-yl}amino)bicyclo[2.2.1]hept-5-ene-2-carboxamide;

5-chloro-$N^4$-(1H-indazol-5-yl)-$N^2$-(1-methyl-1H-pyrazol-4-yl)pyrimidine-2,4-diamine;

5-chloro-$N^2$-(1-ethyl-1H-pyrazol-4-yl)-$N^4$-(1H-indazol-5-yl)pyrimidine-2,4-diamine;

5-chloro-$N^2$-(1H-indazol-5-yl)-$N^2$-{1-[2-(pyrrolidin-1-yl)ethyl]-1H-pyrazol-4-yl}pyrimidine-2,4-diamine;

(1S,2S,3R,4R)-3-[(5-chloro-2-{[1-(3-methylbenzyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2-naphthylmethyl)-1H-pyrazol-4-yl]amino}pyrimidin-4-yl)amino]bicyclo[2.2.1]hept-5-ene-2-carboxamide;

2-(4-{[5-chloro-4-(1H-indazol-5-ylamino)pyrimidin-2-yl]amino}-1H-pyrazol-1-yl)ethanol;

5-chloro-$N^2$-(1H-indazol-5-yl)-$N^2$-{1-[(3R)-pyrrolidin-3-yl]-1H-pyrazol-4-yl}pyrimidine-2,4-diamine;

(1R,2R,3S,5R)-2-({5-bromo-2-[(1-methyl-1H-pyrazol-4-yl)amino]pyrimidin-4-yl}amino)-6,6-dimethylbicyclo[3.1.1]heptane-3-carboxamide;

(1R,2R,3S,5R)-2-({5-bromo-2-[(1-ethyl-1H-pyrazol-4-yl)amino]pyrimidin-4-yl}amino)-6,6-dimethylbicyclo[3.1.1]heptane-3-carboxamide;

(1R,2R,3S,5R)-2-({5-chloro-2-[(1,5-dimethyl-1H-pyrazol-4-yl)amino]pyrimidin-4-yl}amino)-6,6-dimethylbicyclo[3.1.1]heptane-3-carboxamide;

(1R,2R,3S,5R)-2-({5-bromo-2-[(1,5-dimethyl-1H-pyrazol-4-yl)amino]pyrimidin-4-yl}amino)-6,6-dimethylbicyclo[3.1.1]heptane-3-carboxamide;

5-chloro-$N^2$-(1H-indazol-5-yl)-$N^2$-{1-[2-(4-methylpiperazin-1-yl)ethyl]-1H-pyrazol-4-yl}pyrimidine-2,4-diamine;

(1R,2R,3S,5R)-2-({2-[(1-benzyl-1H-pyrazol-4-yl)amino]-5-chloropyrimidin-4-yl}amino)-6,6-dimethylbicyclo[3.1.1]heptane-3-carboxamide;

(1R,2R,3S,5R)-2-[(5-chloro-2-{[1-(2-phenylethyl)-1H-pyrazol-4-yl]amino}pyrimidin-4-yl)amino]-6,6-dimethylbicyclo[3.1.1]heptane-3-carboxamide;

(1R,2R,3S,5R)-2-({5-chloro-2-[(1-phenyl-1H-pyrazol-4-yl)amino]pyrimidin-4-yl}amino)-6,6-dimethylbicyclo[3.1.1]heptane-3-carboxamide;

(1R,2R,3S,5R)-2-{[5-chloro-2-({1-[2-(4-methylpiperazin-1-yl)ethyl]-1H-pyrazol-4-yl}amino)pyrimidin-4-yl]amino}-6,6-dimethylbicyclo[3.1.1]heptane-3-carboxamide;

(1R,2R,3S,5R)-2-[(5-chloro-2-{[1-(piperidin-4-yl)-1H-pyrazol-4-yl]amino}pyrimidin-4-yl)amino]-6,6-dimethylbicyclo[3.1.1]heptane-3-carboxamide;

(1S,2S,3R,4R)-3-[(5-chloro-2-{[1-(3-fluoro-4-methoxybenzyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(3-fluoro-4-methoxybenzyl)-1H-pyrazol-4-yl]amino}pyrimidin-4-yl)amino]bicyclo[2.2.1]hept-5-ene-2-carboxamide; and 5-bromo-$N^2$-(1-ethyl-1H-pyrazol-4-yl)-$N^4$-(1H-indazol-5-yl)pyrimidine-2,4-diamine.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

in the literature, can be reacted with a compound of Formula (2), wherein X and Y are as described herein, in the presence of sodium bicarbonate, to provide compounds of Formula (3). The reaction is typically performed in a solvent such as methanol, water, or mixtures thereof. Compounds of Formula (3) can be reacted with compounds of Formula (4), wherein $A^2$, $A^3$, and $A^4$ are as described herein, which can be purchased commercially, prepared as described herein, or prepared as described in the literature, in the presence of HCl to provide compounds of Formula (I) which are representative of the compounds of this invention. The reaction is typically performed at an elevated temperature is a solvent such as but not limited to 2-propanol.

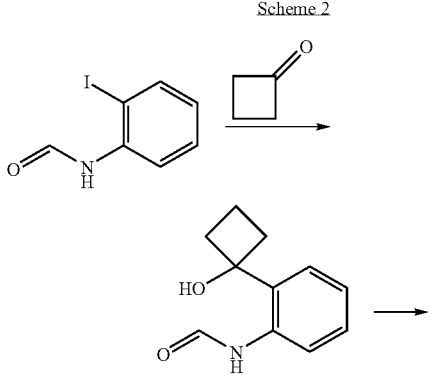

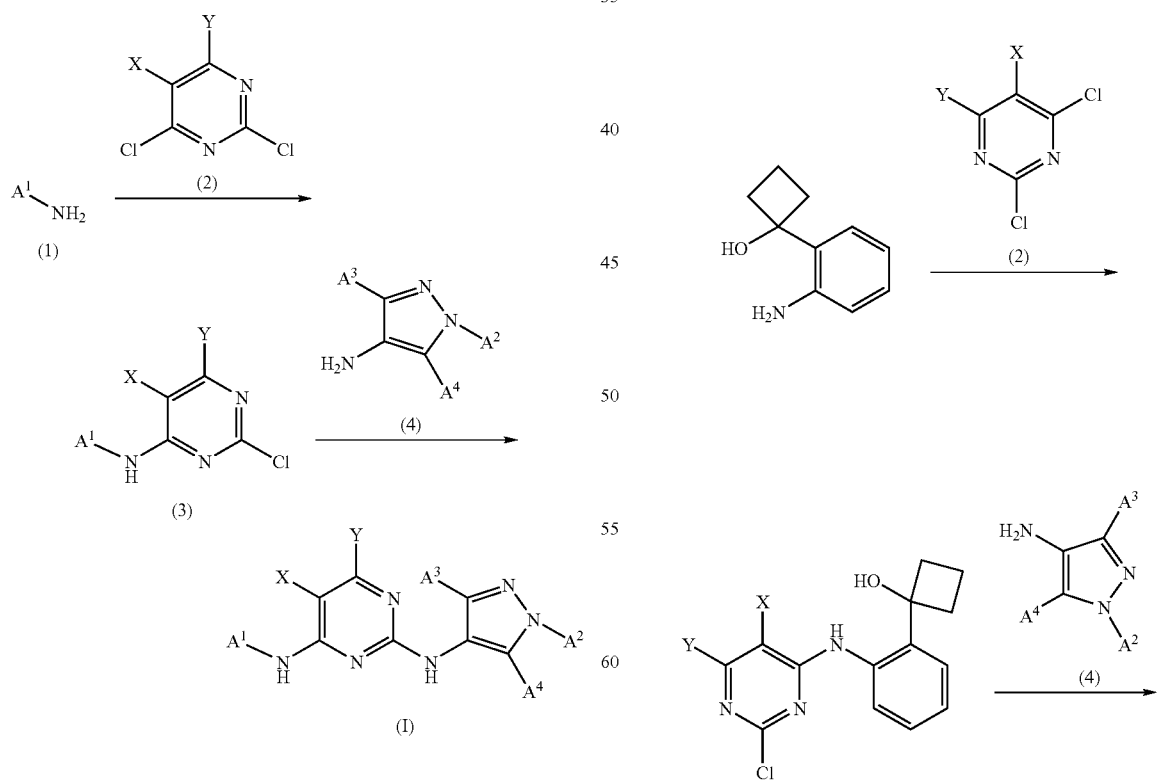

As shown in Scheme 1, amines of Formula (1), wherein $A^1$ is as described herein, and which can be purchased commercially, prepared as described herein, or prepared as described

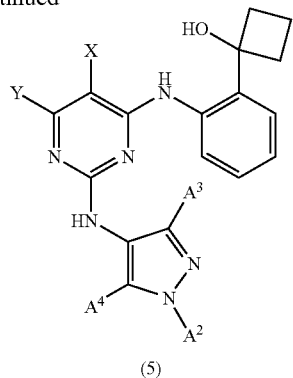

(5)

Compounds of formula (5), which are representative of compounds of this invention, can be prepared as shown in Scheme 2. N-(2-Iodophenyl)formamide can be treated with sodium hydride, followed by n-butyllithium in hexanes, and cyclobutanone to provide N-(2-(1-hydroxycyclobutyl)phenyl)formamide. The reaction is typically performed at low temperature in a solvent such as but not limited to tetrahydrofuran. N-(2-(1-hydroxycyclobutyl)phenyl)formamide can be reacted with a base such as but not limited to potassium hydroxide to provide 1-(2-aminophenyl)cyclobutanol. The reaction is typically performed at an elevated temperature in a solvent such as but not limited to methanol. 1-(2-Aminophenyl)cyclobutanol can be reacted with a compounds of formula (2), wherein X and Y are as described herein, in the presence of a base such as but not limited to N,N-diisopropylethylamine to provide compounds of formula (3). The reaction is typically performed at an elevated temperature in a solvent such as but not limited to 2-propanol. Compounds of formula 5, which are representative of compounds of formula (I), can be prepared by reacting compounds of formula (3) with compounds of formula (4), wherein $A^2$, $A^3$, and $A^4$ are as described herein, as described in Scheme 1.

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal. In particular, compounds of this invention are expected to have utility in treatment of diseases or conditions during which protein kinases such as any or all Aurora-kinase family members are expressed. In yet another aspect, compounds of this invention are expected to have utility in treatment of diseases or conditions during which protein kinases such as any or all KDR (VEGFR2) family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenström's macroglobulinemia, testicular tumors, uterine cancer and Wilms' tumor.

Involvement of Aurora Kinase in pancreatic carcinoma cells is reported in Zhu, J., et al., AURKA Amplification, Chromosome Instability, And Centrosome Abnormality in Human Pancreatic Carcinoma Cells. Cancer Genet. Cytogenet., 2005. 159(1): p. 10-17; and Li D., Zhu J., Firozi P. F., et al. Overexpression of Oncogenic STK15/BTAK/Aurora A Kinase in Human Pancreatic Cancer. Clin. Cancer Res. 2003; 9:991-7.

Involvement of Aurora Kinase in non-small cell lung carcinoma is reported in Smith, S. L., et al., Overexpression of Aurora B Kinase (AURKB) in Primary Non-Small Cell Lung Carcinoma is Frequent, Generally Driven from One Allele, and Correlates with the Level of Genetic Instability. Br. J. Cancer, 2005. 93(6): p. 719-729.

Involvement of Aurora Kinase in prostate cancer is reported in Chieffi, P., et al., Aurora B Expression Directly Correlates with Prostate Cancer Malignancy. Prostate, 2006. 66(3): p. 326-33; and Chieffi P., Cozzolino L., Kisslinger A., et al. Aurora B Expression Directly Correlates with Prostate Cancer Malignancy and Influences Prostate Cell Proliferation. Prostate 2006; 66:326-33.

Involvement of Aurora Kinase in head and neck squamous cell carcinoma is reported in Reiter, R., et al., Aurora Kinase A Messenger RNA Overexpression is Correlated with Tumor Progression and Shortened Survival in Head and Neck Squamous Cell Carcinoma. Clin Cancer Res, 2006. 12(17): p. 5136-41.

Involvement of Aurora Kinase in acute myeloid leukemia is reported in Walsby E., Walsh V., Pepper C., Burnett A., and Mills K. Haematologica. 2008 May; 93(5):662-9.

Involvement of Aurora Kinase in breast cancer is reported in Tanaka T., Kimura M., Matsunaga K., Fukada D., Mori H., Okano Y. Centrosomal Kinase AIK1 is Overexpressed in Invasive Ductal Carcinoma of The Breast. Cancer Res. 1999; 59:2041-4; Miyoshi Y., Iwao K., Egawa C., Noguchi S. Association of Centrosomal Kinase STK15/BTAK Mrna Expression with Chromosomal Instability in Human Breast Cancers. Int. J. Cancer 2001; 92:370-3; Hogue A., Carter J., Xia W., et al. Loss Of Aurora A/STK15/BTAK Overexpression Correlates with Transition of in Situ to Invasive Ductal Carcinoma of the Breast. Cancer Epidemiol. Biomarkers Prev. 2003; 12:1518-22; Royce M. E., Xia W., Sahin A. A., et al. STK15/Aurora-A Expression in Primary Breast Tumors is Correlated with Nuclear Grade But Not With Prognosis. Cancer 2004; 100:12-9; Bodvarsdottir S. K., Hilmarsdottir H., Birgisdottir V., Steinarsdottir M., Jonasson J. G., Eyfjord J. E., Aurora-A Amplification Associated with BRCA2 Mutation in Breast Tumours. Cancer Lett 2007; 248:96-102; Sen S., Zhou H., White R. A., A Putative Serine/Threonine Kinase Encoding Gene BTAK on Chromosome 20q13 is Amplified and Overexpressed in Human Breast Cancer Cell Lines. Oncogene 1997; 14:2195-200; Lo Y. L., Yu J. C., Chen S. T., et al. Breast Cancer Risk Associated with Genotypic Polymorphism of the Mitosisregulating Gene Aurora-A/STK15/BTAK. In. J. Cancer 2005; 115:276-83; Vidarsdottir L., Bodvarsdottir S. K., Hilmarsdottir H., Tryggvadottir L., Eyfjord J. E., Breast Cancer Risk Associated with AURKA 91T a Polymorphismin Relation to BRCA Mutations. Cancer Lett 2007; 250:206-12; Cox D. G., Hankinson S. E., Hunter D. J., Polymorphisms of the Aurka (STK15/Aurora Kinase) Gene and Breast Cancer Risk (United States). Cancer Causes Control 2006; 17:81-3; and Tchatchou S., Wirtenberger M., Hemminki K., et al. Aurora Kinases A and B and Familial Breast Cancer Risk. Cancer Lett 2007; 247:266-72.

Involvement of Aurora Kinase in lung cancer is reported in Smith S. L., Bowers N. L., Betticher D. C., et al. Overexpression Of Aurora B Kinase (AURKB) in Primary Non small Cell Lung Carcinoma is Frequent, Generally Driven Fromone Allele, and Correlates with the Level Of Genetic Instability. Br. J. Cancer 2005; 93:719-29; Xu H. T., Ma L., Qi F. J., et al. Expression of Serine Threonine Kinase15 is Associated with Poor Differentiation in Lung Squamous Cell Carcinoma and Adenocarcinoma. Pathol. Int. 2006; 56:375-80; Vischioni B., Oudejans J. J., Vos W., Rodriguez J. A., Giaccone G. Frequent Overexpression of Aurora B Kinase, a Novel Drug Target, in Non-Small Cell Lung Carcinoma Patients. Mol. Cancer Ther. 2006; 5:2905-13; and Gu J., Gong Y., Huang M., Lu C., Spitz M. R., Wu X. Polymorphisms Of STK15 (Aurora-A) Gene and Lung Cancer Risk in Caucasians. Carcinogenesis 2007; 28:350-5.

Involvement of Aurora Kinase in bladder cancer is reported in Comperat E., Camparo P., Haus R., et al. Aurora-A/STK-15 is a Predictive Factor for Recurrent Behaviour in Non-Invasive Bladder Carcinoma: A Study Of 128 Cases of Non-Invasive Neoplasms. Virchows Arch 2007; 450:419-24; Fraizer G. C., Diaz M. F., Lee I. L., Grossman H. B., Sen S. Aurora-A/STK15/BTAK Enhances Chromosomal Instability in Bladder Cancer Cells. Int. J. Oncol. 2004; 25:1631-9; and Sen S., Zhou H., Zhang R. D., et al. Amplification/Overexpression of A Mitotic Kinase Gene in Human Bladder cancer. J. Natl. Cancer Inst. 2002; 94:1320-9.

Involvement of Aurora Kinase in esophageal cancer is reported in Tong T., Zhong Y., Kong J., et al. Overexpression of Aurora-A Contributes to Malignant Development of Human Esophageal Squamous Cell Carcinoma. Clin. Cancer Res. 2004; 10:7304-10; Yang S. B., Zhou X. B., Zhu H. X., et al. Amplification and Overexpression of Aurora-A in Esophageal Squamous Cell Carcinoma. Oncol. Rep. 2007; 17:1083-8; and Kimura M. T., Mori T., Conroy J., et al. Two Functional Coding Single Nucleotide Polymorphisms in STK15 (Aurora-A) Coordinately Increase Esophageal Cancer Risk. Cancer Res 2005; 65:3548-54.

Involvement of Aurora Kinase in brain cancer is reported in Araki K., Nozaki K., Ueba T., Tatsuka M., Hashimoto N. High Expression of Aurora-B/Aurora and Ipll-Like Midbody-Associated Protein (AIM-1) in Astrocytomas. J. Neurooncol. 2004; 67:53-64; Zeng W. F., Navaratne K., Prayson R. A., Weil R. J. Aurora B Expression Correlates with Aggressive Behaviour in Glioblastoma Multiforme. J. Clin. Pathol. 2007; 60:218-21; Reichardt W., Jung V., Brunner C., et al. The Putative Serine/Threonine Kinase Gene STK15 on Chromosome 20q13.2 is Amplified In Human Gliomas. Oncol. Rep. 2003; 10:1275-9; Klein A., Reichardt W., Jung V., Zang K. D., Meese E., Urbschat S. Overexpression and Amplification of STK15 Inhuman Gliomas. Int. J. Oncol. 2004; 25:1789-94; and Neben K., Korshunov A., Benner A., et al. Microarray Based Screening for Molecular Markers Nmedulloblastoma Revealed STK15 as Independent Predictor for Survival. Cancer Res 2004; 64:3103-11.

Involvement of Aurora Kinase in liver cancer is reported in Jeng Y. M., Peng S. Y., Lin C. Y., Hsu H. C. Overexpression and Amplification of Aurora-A in Hepatocellular Carcinoma. Clin. Cancer Res. 2004; 10:2065-71.

Involvement of Aurora Kinase in head and neck cancer is reported in Zhao X., Li F. C., Li Y. H., et al. [Mutation of p53 and Overexpression Of STK15 in Laryngeal Squamous-Cell Carcinoma]. Zhonghua Zhong Liu Za Zhi 2005; 27:134-7; Li F. C., Li Y. H., Zhao X., et al. [Deletion of p15 and p16 Genes and Overexpression of STK15 Gene in Human Laryngeal Squamous Cell Carcinoma]. Zhonghua Yi Xue Za Zhi 2003; 83:316-9; Reiter R., Gais P., Jutting U., et al. Aurora Kinase A Messenger RNA Overexpression is Correlated with Tumor Progression and Shortened Survival in Head and Neck Squamous Cell Carcinoma. Clin. Cancer Res. 2006; 12:5136-41; Qi G., Ogawa I., Kudo Y., et al. Aurora-B Expression and Its Correlation with Cell Proliferation and Metastasis in Oral Cancer. Virchows Arch 2007; 450:297-302; and Tatsuka M., Sato S., Kitajima S., et al. Overexpression of Aurora-A Potentiates HRAS-mediated Oncogenic Transformation and is Implicated in Oral Carcinogenesis. Oncogene 2005; 4:1122-7.

Involvement of Aurora Kinase in thyroid cancer is reported in Sorrentino R., Libertini S., Pallante P. L., et al. Aurora B Overexpression Associates with the Thyroid Carcinoma Undifferentiated Phenotype and is Required for Thyroid Carcinoma Cell Proliferation. J. Clin. Endocrinol. Metab. 2005; 90:928-35.

Involvement of Aurora Kinase in ovarian cancer is reported in Lassmann S., Shen Y., Jutting U., et al. Predictive Value of Aurora-A/STK15 Expression for Late Stage Epithelial Ovarian Cancer Patients Treated By Adjuvant Chemotherapy. Clin Cancer Res 2007; 13:4083-91; and Landen C. N., Jr., Lin Y. G., Immaneni A., et al. Overexpression of the Centrosomal Protein Aurora-A Kinase is Associated with Poor Prognosis in Epithelial Ovarian Cancer Patients. Clin. Cancer Res. 2007; 13:4098-104.

Involvement of Aurora Kinase in renal cancer is reported in Kurahashi T., Miyake H., Hara I., Fujisawa M. Significance of Aurora-A Expression in Renal Cell Carcinoma. Urol. Oncol. 2007; 25:128-33.

Involvement of Aurora Kinase in endometrium cancer is reported in Moreno-Bueno G., Sanchez-Estevez C., Cassia R., et al. Differential Gene Expression Profile in Endometrioid and Nonendometrioid Endometrial Carcinoma: STK15 is Frequently Overexpressed and Amplified in Nonendometrioid Carcinomas. Cancer Res. 2003; 63:5697-702.

Involvement of Aurora Kinase in gastric cancer is reported in Ju H., Cho H., Kim Y. S., et al. Functional Polymorphism 57Val>Ile of Aurora Kinase A Associated with Increased Risk of Gastric Cancer Progression. Cancer Lett. 2006; 242:273-9.

Involvement of Aurora Kinase in colon cancer is reported in Nishida N., Nagasaka T., Kashiwagi K., Boland C. R., Goel A. High Copy Amplification of the Aurora-A Gene is Associated with Chromosomal Instability Phenotype in Human Colorectal Cancers. Cancer Biol. Ther. 2007; 6:525-33; Bischoff J. R., Anderson L., Zhu Y., et al. A Homologue of Drosophila Aurora Kinase is Oncogenic and Amplified In Human Colorectal Cancers. EMBO J 1998; 17:3052-65; Chen J., Sen S., Amos C. I., et al. Association Between Aurora-A Kinase Polymorphisms and Age of Onset of Hereditary Nonpolyposis Colorectal Cancer in a Caucasian Population. Mol. Carcinog. 2007; 46:249-56; Hienonen T., Salovaara R., Mecklin J. P., Jarvinen H., Karhu A., Aaltonen L. A. Preferential Amplification of AURKA 91A (Ile31) in Familial Colorectal Cancers. Int. J. Cancer 2006; 118:505-8; and Ewart-Toland A., Briassouli P., de Koning J. P., et al. Identification of Stk6/STK15 as a Candidate Low-Penetrance Tumor-Susceptibility Gene in Mouse and Human. Nat. Genet. 2003; 34:403-12.

Involvement of Aurora Kinase in cancer is reported in Lin, Y. S., et al., Gene Expression Profiles of the Aurora Family Kinases. Gene Expr., 2006. 13(1): p. 15-26; and Ewart-Toland A., Dai Q., Gao Y. T., et al. Aurora-A/STK15 T+91A is a General Low Penetrance Cancer Susceptibility Gene: A Meta-Analysis of Multiple Cancer Types. Carcinogenesis 2005; 26:1368-73.

Involvement of KDR (VEGFR2) in cancer and studies using VEGF-targeted therapy is reported in Ellis, Lee M., Hicklin, Daniel J. VEGF-Targeted Therapy: Mechanisms Of Anti-Tumor Activity. Nature Reviews Cancer 2008; 8:579-591.

Involvement of Aurora-kinases in bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer and thyroid cancer is reported in Nature Reviews/Cancer, Vol. 4 December, 2004.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like. Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-veMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxamide Example 1A (1S,2S,3R,4R)-3-(2-chloro-5-fluoropyrimidin-4-ylamino)bicyclo[2.2.1]hept-5-ene-2-carboxamide and (1R,2R,3S,4S)-3-(2-chloro-5-fluoropyrimidin-4-ylamino)bicyclo[2.2.1]hept-5-ene-2-carboxamide A light suspension of (+/−)-(1S,2S,3R,4R)-3-aminobicyclo[2.2.1]hept-5-ene-2-carboxamide trifluoroacetic acid salt (WO2005/118544, WO2006/055561 and WO2006/133426) (1.5 g, 5.63 mmol) and sodium bicarbonate (0.947 g, 11.27 mmol) in 21 ml of 2:1 methanol/water at room temperature was treated with 2,4-dichloro-5-fluoropyrimidine (1.129 g, 6.76 mmol). The resulting mixture, which thickened after 1 hour, was stirred at room temperature for 90 hours. The mixture was diluted with water (20 ml); and the suspension was saturated with NaCl and extracted with ethyl acetate (4×20 ml). The organic layers were dried with magnesium sulfate, filtered and concentrated; and the resulting solid was suspended in 10 ml of 5% methanol/methylene chloride and filtered with methylene chloride washes to afford the title compound.

Example 1B (1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxamide A suspension of (+/−)-(1S,2S,3R,4R)-3-(2-chloro-5-fluoropyrimidin-4-ylamino)bicyclo[2.2.1]hept-5-ene-2-carboxamide (100 mg, 0.354 mmol) and 1-methyl-1H-pyrazol-4-amine (41.2 mg, 0.424 mmol) in 2-propanol (1.5 ml) was treated with one drop of concentrated HCl and heated in a sealed tube at 85° C. for 10 hours. The mixture was cooled and diluted with ethyl acetate. This mixture was treated w/2M sodium bicarbonate (20 ml) and organic layer was dried with magnesium sulfate, filtered and concentrated. The crude product was flash chromatographed (30 mm; 7% methanol/$CH_2Cl_2$ to 9% methanol/$CH_2Cl_2$) to afford the title compound. $^1$H NMR (300 MHz, DMSO-$D_6$) ppm 1.41 (d, J=9.1 Hz, 1H), 2.11 (d, J=8.7 Hz, 1H), 2.43-2.61 (m, 1H), 2.79 (br s, 1H), 2.87 (brs, 1H), 2.79 (none, 1H), 2.87 (s, 1H), 3.77 (s, 3H), 4.10 (t, J=7.7 Hz, 1H), 6.17-6.46 (m, 2H), 7.21 (s, 1H), 7.30-7.56 (m, 2H), 7.73 (s, 2H), 7.83 (d, J=3.6 Hz, 1H), 8.89 (s, 1H); MS (ESI(+)) m/e 344 (M+H)$^+$.

Example 2

(1S,2S,3R,4R)-3-({2-[(1-methyl-1H-pyrazol-4-yl)amino]pyrimidin-4-yl}amino)bicyclo[2.2.1]hept-5-ene-2-carboxamide and (1R,2R,3S,4S)-3-({2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-pyrimidine for 2,4-dichloro-5-fluoropyrimidine in Example 1A. $^1$H NMR (300 MHz, DMSO-$D_6$) ppm 1.41 (d, J=8.8 Hz, 1H), 2.18 (d, J=8.8 Hz, 1H), 2.66 (s, 1H), 2.83 (s, 1H), 3.76 (s, 3H), 5.90 (d, J=5.8 Hz, 1H), 6.18-6.38 (m, 2H), 6.82 (br s, 1H), 6.94 (br s, 1H), 7.32 (br s, 1H), 7.44 (s, 1H), 7.75 (m, 2H), 8.75 (br s, 1H); MS (ESI(+)) m/e 326 (M+H)$^+$.

Example 3

$N^4$-[(1S,2S,4R)-bicyclo[2.2.1]hept-2-yl]-5-fluoro-$N^2$-(1-methyl-1H-pyrazol-4-yl)pyrimidine-2,4-diamine and $N^4$-[(1R,2R,4S)-bicyclo[2.2.1]hept-2-yl]-5-fluoro-$N^2$-(1-methyl-1H-pyrazol-4-yl)pyrimidine-2,4-diamine The title compound was prepared as described in Example 1, substituting (+/−)-bicyclo[2.2.1]heptan-2-amine for (+/−)-(1S,2S,3R,4R)-3-aminobicyclo[2.2.1]hept-5-ene-2-carboxamide in Example 1A. $^1$H NMR (300 MHz, DMSO-$D_6$) ppm 0.95-1.37 (m, 3H), 1.38-1.79 (m, 5H), 2.15-2.38 (m, 2H), 3.64-3.94 (m, 4H), 6.99 (d, J=6.4 Hz, 1H), 7.42 (s, 1H), 7.64-7.86 (m, 2H), 8.78 (s, 1H); MS (ESI(+)) m/e 303 (M+H)$^+$.

Example 4

(1S,2R)-2-({5-fluoro-2-[(1-methyl-1H-pyrazol-4-yl)amino]pyrimidin-4-yl}amino)cyclopentanecarboxamide and (1R,2S)-2-({5-fluoro-2-[(1-methyl-1H-pyrazol-4-yl)amino]pyrimidin-4-yl}amino)cyclopentanecarboxamide The title compound was prepared as described in Example 1, substituting (+/−)-(1S,2R)-2-aminocyclopentanecarboxamide for (+/−)-(1S,2S,3R,4R)-3-aminobicyclo[2.2.1]hept-5-ene-2-carboxamide in Example 1A. $^1$H NMR (300 MHz, DMSO-$D_6$) ppm 1.48-1.67 (m, 1H), 1.67-2.06 (m, 5H), 2.91 (q, J=7.7 Hz, 1H), 3.76 (s, 3H), 4.31-4.56 (m, 1H), 6.81 (d, J=6.7 Hz, 1H), 7.00 (s, 1H), 7.29-7.51 (m, 2H), 7.75 (s, 1H), 7.81 (d, J=3.6 Hz, 1H), 8.84 (s, 1H); MS (ESI(+)) m/e 320 (M+H)$^+$.

Example 5

(1S,2S,3R,4R)-3-{[5-fluoro-2-(1H-pyrazol-4-ylamino)pyrimidin-4-yl]amino}bicyclo[2.2.1]hept-5-ene-2-carboxamide and (1R,2R,3S,4S)-3-{[5-fluoro-2-(1H-pyrazol-4-ylamino)pyrimidin-4-yl]amino}bicyclo[2.2.1]hept-5-ene-2-carboxamide The title compound was prepared as described in Example 1, substituting 1H-pyrazol-4-amine for 1-methyl-1H-pyrazol-4-amine in Example 1B. $^1$H NMR (300 MHz, DMSO-$D_6$) ppm 1.41 (d, J=9.1 Hz, 1H), 2.10 (d, J=8.7 Hz, 1H), 2.82 (s, 1H), 2.88 (s, 1H), 6.18-6.48 (m, 2H), 7.22 (s, 1H), 7.30-7.58 (m, 2H), 7.74 (s, 1H), 7.69-7.87 (m, 2H), 8.90 (s, 1H), 12.37 (s, 1H); MS (ESI(+)) m/e 330 (M+H)$^+$.

Example 6 isopropyl{4-[(4-{[(1R,2R,3S,4S)-3-(aminocarbonyl)bicyclo[2.2.1]hept-5-ene-2-yl]amino}-5-fluoropyrimidin-2-yl)amino]-1H-pyrazol-1-yl}acetate and isopropyl{4-[(4-{[(1S,2S,3R,4R)-3-(aminocarbonyl)bicyclo[2.2.1]hept-5-ene-2-yl]amino}-5-fluoropyrimidin-2-yl)amino]-1H-pyrazol-1-yl}acetate The title compound was prepared as described in Example 1, substituting 2-(4-amino-1H-pyrazol-1-yl)acetic acid for 1-methyl-1H-pyrazol-4-amine in Example 1B. $^1$H NMR (300 MHz, DMSO-$D_6$) ppm 1.06-1.28 (m, 7H), 1.40 (d, J=8.7 Hz, 1H), 2.11 (d, J=8.7 Hz, 1H), 2.79 (s, 1H), 2.87 (s, 1H), 4.10 (t, J=7.3 Hz, 1H), 4.83-5.10 (m, 3H), 6.16-6.42 (m, 2H), 7.21 (s, 1H), 7.36-7.60 (m, 2H), 7.73 (s, 1H), 7.77-7.89 (m, 2H), 8.97 (s, 1H); MS (ESI(+)) m/e 430 (M+H)$^+$.

Example 7 ethyl(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxylate and ethyl(1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxylate The title compound was prepared as described in Example 1, substituting (+/−)-(1S,2S,3R,4R)-ethyl 3-aminobicyclo[2.2.1]hept-5-ene-2-carboxylate for (+/−)-(1S,2S,3R,4R)-3-aminobicyclo[2.2.1]hept-5-ene-2-carboxamide in Example 1A. $^1$H NMR (300 MHz, DMSO-$D_6$) ppm 0.86 (t, J=7.1 Hz, 3H), 1.50 (d, J=9.1 Hz, 1H), 2.25-2.35 (m, 1H), 2.65 (d, J=8.3 Hz, 1H), 2.81 (s, 1H), 2.95 (s, 1H), 3.70-3.78 (m, 3H), 3.78-3.93 (m, 2H) 4.39 (t, J=7.9 Hz, 1H), 6.19-6.40 (m, 2H), 6.91 (d, J=7.9 Hz, 1H), 7.44 (s, 1H), 7.73 (s, 1H), 7.81 (d, J=4.0 Hz, 1H), 8.81 (s, 1H); MS (ESI(+)) m/e 373 (M+H)$^+$.

Example 8

(1S,2S,3R,4R)-3-({2-[(1-ethyl-1H-pyrazol-4-yl)amino]-5-fluoropyrimidin-4-yl}amino)bicyclo[2.2.1]hept-5-ene-2-carboxamide and (1R,2R,3S,4S)-3-({2-[(1-ethyl-1H-pyrazol-4-yl)amino]-5-fluoropyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B. $^1$H NMR (300 MHz, DMSO-D$_6$) ppm 1.29-1.38 (m, 3H), 1.41 (d, J=8.8 Hz, 1H), 2.12 (d, J=8.8 Hz, 1H), 2.79 (s, 1H), 2.87 (s, 1H), 3.99-4.20 (m, 3H), 6.22-6.38 (m, 2H), 7.20 (s, 1H), 7.37 (s, 1H), 7.46 (s, 1H), 7.71 (s, 1H), 7.76 (s, 1H), 7.83 (d, J=3.7 Hz, 1H), 8.88 (s, 1H); MS (ESI(+)) m/e 358 (M+H)$^+$.

Example 9

(1S,2S,3R,4R)-3-({5-fluoro-2-[(1-methyl-1H-pyrazol-4-yl)amino]pyrimidin-4-yl}amino)-N-methylbicyclo[2.2.1]hept-5-ene-2-carboxamide and (1R,2R,3S,4S)-3-({5-fluoro-2-[(1-methyl-1H-pyrazol-4-yl)amino]pyrimidin-4-yl}amino)-N-methylbicyclo[2.2.1]hept-5-ene-2-carboxamide Example 9A (1S,2S,3R,4R)-3-amino-N-methylbicyclo[2.2.1]hept-5-ene-2-carboxamide and (1R,2R,3S,4S)-3-amino-N-methylbicyclo[2.2.1]hept-5-ene-2-carboxamide To a solution of (+/−)-exo-4-oxo-3-tert-butoxycarbonylaza-tricyclo[4.2.1.0(2,5)]non-7-ene (1 g, 4.25 mmol) (WO2005/118544, WO2006/055561 and WO2006/133426) in 71 ml ethyl acetate at room temperature was added methylamine (21.25 ml, 42.5 mmol) (2M in THF) dropwise by syringe. The solution was stirred for 17 hours after which the mixture was washed with brine (20 ml), dried with Mg$_2$SO$_4$, filtered, and concentrated. The resulting material was treated with 22 ml of 4:1 CH$_2$Cl$_2$/TFA, added dropwise to the solid by addition funnel. The mixture was stirred at room temperature for 3 hours and then concentrated under a stream of nitrogen. The resulting residue was triturated with diethyl ether and filtered and dried to afford the title compound.

Example 9B (1S,2S,3R,4R)-3-({5-fluoro-2-[(1-methyl-1H-pyrazol-4-yl)amino]pyrimidin-4-yl}amino)-N-methylbicyclo[2.2.1]hept-5-ene-2-carboxamide and (1R,2R,3S,4S)-3-({5-fluoro-2-[(1-methyl-1H-pyrazol-4-yl)amino]pyrimidin-4-yl}amino)-N-methylbicyclo[2.2.1]hept-5-ene-2-carboxamide The title compound was prepared as described in Example 1, substituting (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide in Example 1A. $^1$H NMR (300 MHz, DMSO-D$_6$) ppm 1.42 (d, J=8.8 Hz, 1H), 2.14 (d, J=8.5 Hz, 1H), 2.59 (d, J=4.8 Hz, 3H), 2.82 (d, J=10.9 Hz, 2H), 3.77 (s, 3H), 3.98-4.21 (m, 1H), 6.18-6.47 (m, 2H), 7.22-7.58 (m, 2H), 7.73 (s, 1H), 7.84 (d, J=3.7 Hz, 1H), 8.25 (d, J=4.4 Hz, 1H), 8.93 (s, 1H); MS (ESI(+)) m/e 358 (M+H)$^+$.

Example 10

(1S,2S,3R,4R)-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)-3-{[2-[(1-methyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting 2,4-dichloro-5-(trifluoromethyl)pyrimidine for 2,4-dichloro-5-fluoropyrimidine in Example 1A. $^1$H NMR (300 MHz, DMSO-D$_6$) ppm 1.41 (d, J=9.1 Hz, 1H), 2.03 (d, J=8.7 Hz, 1H), 2.87 (d, J=9.1 Hz, 2H), 3.80 (s, 3H), 4.15 (t, J=6.9 Hz, 1H), 6.16-6.46 (m, 2H), 7.32 (s, 1H), 7.57 (s, 1H), 7.71 (s, 1H), 7.82 (s, 1H), 8.02-8.28 (m, 2H), 9.61 (s, 1H); MS (ESI(+)) m/e 394 (M+H)$^+$.

Example 11

(1S,2S,3R,4R)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide and (1R,2R,3S,4S)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide Example 11A 2-(4-nitro-1H-pyrazol-1-yl)ethanol A solid mixture of 4-nitro-1H-pyrazole (1 g, 8.84 mmol), 1,3-dioxolan-2-one (3.89 g, 44.2 mmol) and cesium carbonate (2.88 g, 8.84 mmol) was suspended in 20 ml dimethylformamide and the resulting suspension was slowly heated to 100° C. overnight. The mixture was added to 100 ml water and 40 ml ethyl acetate; the separated aqueous layer was extracted with ethyl acetate (30 ml), and the combined organic layers were washed with brine (30 ml), dried with magnesium sulfate, filtered and concentrated. The residue was flash chromatographed (50 mm; 2% methanol/methylene chloride then 4% methanol/methylene chloride) to give the title compound with some residual DMF.

Example 11B 2-(4-amino-1H-pyrazol-1-yl)ethanol

A solution of 2-(4-nitro-1H-pyrazol-1-yl)ethanol (1.08 g, 6.87 mmol) in methanol (34 ml) was evacuated and purged with nitrogen and treated with palladium on carbon (0.1 g, 0.094 mmol). The resulting black suspension was evacuated and purged with a hydrogen balloon and stirred under hydrogen overnight. The mixture was filtered through celite with methanol washes, and concentrated. The residue was flash chromatographed (50 mm; 9% methanol/methylene chloride w/0.1% NH$_4$OH then 10% methanol/methylene chloride w/0.1% NH$_4$OH) to afford the title compound.

Example 11C (1S,2S,3R,4R)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide and (1R,2R,3S,4S)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide The title compound was prepared as described in Example 1, substituting 2-(4-amino-1H-pyrazol-1-yl)ethanol for 1-methyl-1H-pyrazol-4-amine in Example 1B. $^1$H NMR (300 MHz, DMSO-D$_6$) ppm 1.43 (d, J=9.1 Hz, 1H), 2.05 (d, J=9.1 Hz, 1H), 2.56 (d, J=7.9 Hz, 1H), 2.93 (d, J=8.3 Hz, 2H), 3.62-3.80 (m, 2H), 3.93-4.19 (m, 4H), 6.15-6.50 (m, 2H), 7.36 (s, 1H), 7.59 (s, 1H), 7.87 (s, 1H), 7.91 (s, 1H), 8.09 (s, 1H), 9.51 (br s, 1H), 10.22 (br s, 1H); MS (ESI(+)) m/e 374 (M+H)$^+$.

Example 12

(1R,2S,3R,4S)-3-({5-fluoro-2-[(1-methyl-1H-pyrazol-4-yl)amino]pyrimidin-4-yl}amino)bicyclo[2.2.1]heptane-2-carboxamide and (1S,2R,3S,4R)-3-({5-fluoro-2-[(1-methyl-1H-pyrazol-4-yl)amino]pyrimidin-4-yl}amino)bicyclo[2.2.1]heptane-2-carboxamide

Example 12A (+/−)-(1R,2S,3R,4S)-3-aminobicyclo[2.2.1]heptane-2-carboxamide

A solution of (+/−)-(1S,2S,3R,4R)-3-aminobicyclo[2.2.1]hept-5-ene-2-carboxamide (707 mg, 4.65 mmol) in methanol (23 ml) was evacuated and purged with nitrogen and treated with palladium on carbon (74.2 mg, 0.070 mmol). The resulting suspension was evacuated and purged with a hydrogen balloon and stirred under the hydrogen overnight. The mixture was filtered through celite, washed with methanol, and dried to afford the title compound.

Example 12B (1R,2S,3R,4S)-3-({5-fluoro-2-[(1-methyl-1H-pyrazol-4-yl)amino]pyrimidin-4-yl}amino)bicyclo[2.2.1]heptane-2-carboxamide and (1S,2R,3S,4R)-3-({5-fluoro-2-[(1-methyl-1H-pyrazol-4-yl)amino]pyrimidin-4-yl}amino)bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide in Example 1A. $^1$H NMR (300 MHz, DMSO-$D_6$) ppm 1.05-1.69 (m, 5H), 1.93 (d, J=10.2 Hz, 1H), 2.20-2.31 (m, 2H), 2.62 (d, J=8.5 Hz, 1H), 3.77 (s, 3H), 4.12 (t, J=7.6 Hz, 1H), 7.12 (s, 1H), 7.35-7.55 (m, 2H), 7.66 (s, 1H), 7.74-7.84 (m, 2H), 8.86 (s, 1H); MS (ESI(+)) m/e 346 (M+H)$^+$.

Example 13

(1R,2S,3R,4S)-3-({2-[(1-ethyl-1H-pyrazol-4-yl)amino]-5-fluoropyrimidin-4-yl}amino)bicyclo[2.2.1]heptane-2-carboxamide and (1S,2R,3S,4R)-3-({2-[(1-ethyl-1H-pyrazol-4-yl)amino]-5-fluoropyrimidin-4-yl}amino)bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide in Example 1A, and 1-ethyl-1H-pyrazol-4-amine for 1-methyl-1H-pyrazol-4-amine in Example 1B. $^1$H NMR (300 MHz, DMSO-$D_6$) ppm 1.06-1.30 (m, 3H), 1.34 (t, J=7.3 Hz, 3H), 1.43-1.73 (m, 2H), 1.93 (d, J=9.8 Hz, 1H), 2.21-2.32 (m, 2H), 2.62 (d, J=8.1 Hz, 1H), 3.94-4.27 (m, 3H), 7.12 (s, 1H), 7.32-7.54 (m, 2H), 7.65 (s, 1H), 7.71-7.88 (m, 2H), 8.86 (s, 1H); MS (ESI(+)) m/e 360 (M+H)$^+$.

Example 14

(1R,2S,3R,4S)-3-[(5-fluoro-2-{[1-(2-hydroxyethyl)-1H-pyrazol-4-yl]amino}pyrimidin-4-yl)amino]bicyclo[2.2.1]heptane-2-carboxamide and (1S,2R,3S,4R)-3-[(5-fluoro-2-{[1-(2-hydroxyethyl)-1H-pyrazol-4-yl]amino}pyrimidin-4-yl)amino]bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide in Example 1A, and 2-(4-amino-1H-pyrazol-1-yl)ethanol for 1-methyl-1H-pyrazol-4-amine in Example 1B. $^1$H NMR (300 MHz, DMSO-$D_6$) ppm 1.17 (t, J=10.1 Hz, 1H), 1.33 (t, J=6.9 Hz, 3H), 1.47-1.69 (m, 2H), 1.90 (d, J=9.9 Hz, 1H), 2.28-2.38 (m, 2H), 2.66 (d, J=8.3 Hz, 1H), 3.66-3.81 (m, 2H), 3.97-4.35 (m, 3H), 7.26 (s, 1H), 7.55-7.68 (m, 1H), 7.72-7.96 (m, 2H), 8.05 (d, J=4.4 Hz, 1H), 9.45 (s, 1H), 10.04 (s, 1H); MS (ESI(+)) m/e 376 (M+H)$^+$.

Example 15

(1R,2R,3S,4S)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide and (1S,2S,3R,4R)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide

Example 15A (R)-1-(4-nitro-1H-pyrazol-1-yl)propan-2-ol

The title compound was prepared by substituting (R)-4-methyl-1,3-dioxolan-2-one for 1,3-dioxolan-2-one in Example 11A.

Example 15B (1R,2R,3S,4S)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide and (1S,2S,3R,4R)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide The title compound was prepared by substituting (R)-1-(4-nitro-1H-pyrazol-1-yl)propan-2-ol for 1-methyl-1H-pyrazol-4-amine in Example 1B. $^1$H NMR (300 MHz, DMSO-$D_6$) ppm 1.01 (dd, J=5.6, 2.38 Hz, 2H), 1.41 (d, J=8.7 Hz, 1H), 2.12 (d, J=8.7 Hz, 1H), 2.79 (s, 1H), 2.87 (s, 1H), 3.83-4.02 (m, 3H), 4.01-4.20 (m, 1H), 4.87 (t, J=4.4 Hz, 1H), 6.21-6.43 (m, 2H), 7.21 (s, 1H), 7.37 (d, 1H), 7.47 (d, J=4.4 Hz, 1H), 7.71 (s, 1H), 7.77 (d, J=3.2 Hz, 1H), 7.83 (d, J=3.6 Hz, 1H), 8.90 (s, 1H); MS (ESI(+)) m/e 388 (M+H)$^+$.

Example 16

(1S,2R,3S,4R)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide and (1R,2S,3R,4S)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide The title compound was prepared as described in Example 1, substituting (+/−)-(1R,2S,3R,4S)-3-aminobicyclo[2.2.1]

heptane-2-carboxamide for (+/−)-(1S,2S,3R,4R)-3-aminobicyclo[2.2.1]hept-5-ene-2-carboxamide in Example 1A, and (R)-1-(4-nitro-1H-pyrazol-1-yl)propan-2-ol for 1-methyl-1H-pyrazol-4-amine in Example 1B. $^1$H NMR (300 MHz, DMSO-D$_6$) ppm 0.98-1.07 (m, 3H), 1.19 (d, J=9.8 Hz, 1H), 1.25-1.42 (m, 2H), 1.48-1.69 (m, 2H), 1.90 (d, J=9.8 Hz, 1H), 2.27-2.38 (m, 2H), 2.67 (d, J=8.1 Hz, 1H), 4.08-4.19 (m, 1H), 7.26 (s, 1H), 7.58 (s, 1H), 7.81 (s, 1H), 7.88 (d, J=3.0 Hz, 1H), 8.07 (s, 1H), 9.52 (s, 1H), 10.12 (s, 1H); MS (ESI(+)) m/e 390 (M+H)$^+$.

Example 17

(1S,2S,3R,4R)-3-({5-methyl-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-methyl-2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-5-methylpyrimidine for 2,4-dichloro-5-fluoropyrimidine in Example 1A. $^1$H NMR (300 MHz, DMSO-D$_6$) ppm 1.40 (d, J=8.8 Hz, 1H), 1.82 (s, 3H), 2.12 (d, J=8.8 Hz, 1H), 2.77 (s, 1H), 2.86 (s, 1H), 3.77 (s, 3H), 4.16 (t, J=7.8 Hz, 1H), 6.14-6.40 (m, 2H), 7.08 (s, 1H), 7.25 (s, 1H), 7.46 (s, 1H), 7.63 (s, 1H), 7.69-7.90 (m, 2H), 8.73 (s, 1H); MS (ESI(+)) m/e 340 (M+H)$^+$.

Example 18

(1S,2S,3R,4R)-3-[(2-{[1-(2-hydroxyethyl)-1H-pyrazol-4-yl]amino}-5-methylpyrimidin-4-yl)amino]bicyclo[2.2.1]hept-5-ene-2-carboxamide and (1R,2R,3S,4S)-3-[(2-{[1-(2-hydroxyethyl)-1H-pyrazol-4-yl]amino}-5-methylpyrimidin-4-yl)amino]bicyclo[2.2.1]hept-5-ene-2-carboxamide The title compound was prepared as described in Example 1, substituting 2,4-dichloro-5-methylpyrimidine for 2,4-dichloro-5-fluoropyrimidine in Example 1A, and 2-(4-amino-1H-pyrazol-1-yl)ethanol for 1-methyl-1H-pyrazol-4-amine in Example 1B. $^1$H NMR (300 MHz, DMSO-D$_6$) ppm 1.40 (d, J=8.7 Hz, 1H), 1.83 (s, 3H), 2.12 (d, J=8.7 Hz, 1H), 2.77 (s, 1H), 2.87 (s, 1H), 4.05 (t, J=5.6 Hz, 2H), 4.17 (t, J=7.5 Hz, 1H), 4.86 (t, J=5.2 Hz, 1H), 6.34 (s, 2H), 7.22 (s, 2H), 7.50 (s, 1H), 7.63 (s, 1H), 7.70-7.84 (m, 1H), 8.74 (s, 1H); MS (ESI(+)) m/e 370 (M+H)$^+$.

Example 19

(1R,2R,3S,4S)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide and (1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide The title compound was prepared as described in Example 1, substituting 2,4-dichloro-5-(trifluoromethyl)pyrimidine for 2,4-dichloro-5-fluoropyrimidine in Example 1A, and (R)-1-(4-nitro-1H-pyrazol-1-yl)propan-2-ol for 1-methyl-1H-pyrazol-4-amine in Example 1B. $^1$H NMR (300 MHz, DMSO-D$_6$) ppm 0.95-1.07 (m, 2H), 1.40 (d, J=8.7 Hz, 1H), 2.03 (d, J=8.3 Hz, 1H), 2.84 (s, 1H), 2.88 (s, 1H), 3.07-3.21 (m, 1H), 3.53-3.70 (m, 1H), 3.86-4.03 (m, 3H), 4.16 (s, 1H), 4.84-4.97 (m, 1H), 6.25-6.41 (m, 2H), 7.31 (s, 1H), 7.54-7.88 (m, 3H), 8.11 (s, 2H), 9.61 (s, 1H); MS (ESI(+)) m/e 438 (M+H)$^+$.

Example 20

(1S,2S,3R,4R)-3-{[2-[(1-methyl-1H-pyrazol-4-yl)amino]-5-(trifluoromethyl)pyrimidin-4-yl]amino}bicyclo[2.2.1]heptane-2-carboxamide and (1R,2R,3S,4S)-3-{[2-[(1-methyl-1H-pyrazol-4-yl)amino]-5-(trifluoromethyl)pyrimidin-4-yl]amino}bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide along with 2,4-dichloro-5-(trifluoromethyl)pyrimidine for 2,4-dichloro-5-fluoropyrimidine, both in Example 1A. $^1$H NMR (300 MHz, DMSO-D$_6$) ppm 1.08-1.73 (m, 3H), 1.85 (d, J=9.5 Hz, 1H), 2.23-2.35 (m, 2H), 2.62 (d, J=8.3 Hz, 1H), 3.21 (d, J=7.9 Hz, 1H), 3.80 (s, 3H), 4.20 (t, J=7.3 Hz, 1H), 7.20 (d, J=4.8 Hz, 1H), 7.51 (s, 1H), 7.61-7.88 (m, 3H), 8.00-8.26 (m, 2H), 9.57 (s, 1H); MS (ESI(+)) m/e 396 (M+H)$^+$.

Example 21

(1S,2R,3S,4R)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide and (1R,2S,3R,4S)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine, both in Example 1A and substitution of (R)-1-(4-nitro-1H-pyrazol-1-yl)propan-2-ol for 1-methyl-1H-pyrazol-4-amine in Example 1B. $^1$H NMR (300 MHz, DMSO-D$_6$) ppm 0.90-1.71 (m, 7H), 1.86 (d, J=9.8 Hz, 1H), 2.28 (s, 2H), 3.05-3.21 (m, 2H), 3.53-3.71 (m, 1H), 3.83-4.01 (m, 2H), 4.21 (t, J=7.1 Hz, 1H), 4.89 (s, 1H), 7.10-7.83 (m, 5H), 8.08 (s, 1H), 9.57 (s, 1H); MS (ESI(+)) m/e 440 (M+H)$^+$.

Example 22

(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide and (1R,2R,3S,4S)-3-{[2-[(1-ethyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting 2,4-dichloro-5-(trifluoromethyl)pyrimidine for 2,4-dichloro-5-fluoropyrimidine in Example 1A along with substitution of 1-ethyl-1H-pyrazol-4-amine for 1-methyl-1H-pyrazol-4-amine in Example 1B. $^1$H NMR (300 MHz, DMSO-D$_6$) ppm 1.31-1.48 (m, 5H), 2.03 (d, J=8.7 Hz, 1H), 2.84 (s, 1H), 2.88 (s, 1H), 4.01-4.13 (m, 2H), 4.17 (t, J=6.5 Hz, 1H), 6.15-6.54 (m, 2H), 7.31 (s, 1H), 7.59 (s, 1H), 7.73 (s, 1H), 7.81 (s, 1H), 7.99-8.26 (m, 2H), 9.60 (s, 1H); MS (ESI(+)) m/e 408 (M+H)$^+$.

Example 23

N⁴-[(1S,2S,4R)-bicyclo[2.2.1]hept-2-yl]-N²-(1-methyl-1H-pyrazol-4-yl)-5-(trifluoromethyl)pyrimidine-2,4-diamine and N⁴-[(1R,2R,4S)-bicyclo[2.2.1]hept-2-yl]-N²-(1-methyl-1H-pyrazol-4-yl)-5-(trifluoromethyl)pyrimidine-2,4-diamine The title compound was prepared as described in Example 1, substituting (+/−)-bicyclo[2.2.1]heptan-2-amine for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.02-1.79 (m, 8H), 2.26 (s, 1H), 2.30-2.37 (m, 1H), 3.79 (s, 3H), 3.84-4.00 (m, 1H), 5.69-6.15 (m, 1H), 7.51 (s, 1H), 7.83 (s, 1H), 8.11 (s, 1H), 9.56 (s, 1H); MS (ESI(+)) m/e 353 (M+H)⁺.

Example 24

(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide and (1S,2R,3S,4R)-3-{[2-[(1-ethyl-1H-pyrazol-4-yl)amino]-5-(trifluoromethyl)pyrimidin-4-yl]amino}bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine, both in Example 1A along with substitution of 1-ethyl-1H-pyrazol-4-amine for 1-methyl-1H-pyrazol-4-amine in Example 1B. $^1$H NMR (300 MHz, DMSO-D$_6$) ppm 1.05-1.72 (m, 6H), 1.86 (d, J=9.9 Hz, 1H), 2.28 (s, 2H), 2.62 (d, J=8.3 Hz, 1H), 4.08 (q, J=7.1 Hz, 2H), 4.21 (t, J=7.3 Hz, 1H), 7.21 (s, 1H), 7.54 (s, 1H), 7.73 (s, 1H), 7.84 (s, 1H), 8.03-8.26 (m, 2H), 9.57 (s, 1H); MS (ESI(+)) m/e 410 (M+H)⁺.

Example 25

(1S,2R)-2-{[2-[(1-methyl-1H-pyrazol-4-yl)amino]-5-(trifluoromethyl)pyrimidin-4-yl]amino}cyclopentanecarboxamide and (1R,2S)-2-{[2-[(1-methyl-1H-pyrazol-4-yl)amino]-5-(trifluoromethyl)pyrimidin-4-yl]amino}cyclopentanecarboxamide The title compound was prepared as described in Example 1, substituting (+/−)-(1S,2R)-2-aminocyclopentanecarboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.45-2.14 (m, 6H), 2.90 (d, J=7.1 Hz, 1H), 3.70-3.89 (m, 3H), 4.39-4.66 (m, 1H), 7.17 (s, 1H), 7.42-7.83 (m, 3H), 8.11 (s, 1H), 9.59 (s, 1H); MS (ESI(+)) m/e 370 (M+H)⁺.

Example 26

(1S,6R)-6-{[2-[(1-methyl-1H-pyrazol-4-yl)amino]-5-(trifluoromethyl)pyrimidin-4-yl]amino}cyclohex-3-ene-1-carboxamide and (1R,6S)-6-{[2-[(1-methyl-1H-pyrazol-4-yl)amino]-5-(trifluoromethyl)pyrimidin-4-yl]amino}cyclohex-3-ene-1-carboxamide The title compound was prepared as described in Example 1, substituting (+/−)-(1S,6R)-6-aminocyclohex-3-enecarboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 2.10-2.60 (m, 4H), 2.67-2.88 (m, 2H), 3.70-3.85 (m, 3H), 4.51 (s, 1H), 5.46-5.78 (m, 2H), 6.64-7.28 (m, 1H), 7.51 (s, 2H), 7.72 (s, 1H), 8.13 (s, 1H), 9.62 (s, 1H); MS (ESI(+)) m/e 382 (M+H)⁺.

Example 27

(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-chloro-2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4,5-trichloropyrimidine for 2,4-dichloro-5-fluoropyrimidine in Example 1A. $^1$H NMR (300 MHz, DMSO-D$_6$) ppm 1.41 (d, J=8.8 Hz, 1H), 2.10 (d, J=8.8 Hz, 1H), 2.54 (d, J=8.5 Hz, 1H), 2.79 (s, 1H), 2.88 (s, 1H), 3.78 (s, 3H), 4.10 (t, J=7.5 Hz, 1H), 6.21-6.48 (m, 2H), 7.25 (s, 1H), 7.48 (s, 1H), 7.72 (s, 1H), 7.78 (s, 1H), 7.88 (s, 1H), 9.09 (s, 1H); MS (ESI(+)) m/e 360 (M+H)⁺.

Example 28

(1S,2S,3R,4R)-3-({5-bromo-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-bromo-2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-5-bromopyrimidine for 2,4-dichloro-5-fluoropyrimidine in Example 1A. $^1$H NMR (300 MHz, DMSO-D$_6$) ppm 1.43 (d, J=9.1 Hz, 1H), 2.01 (d, J=8.7 Hz, 1H), 2.55 (d, J=7.5 Hz, 1H), 2.88 (s, 1H), 2.94 (s, 1H), 3.83 (s, 3H), 3.95-4.13 (m, 1H), 6.14-6.51 (m, 2H), 7.40 (s, 1H), 7.59 (s, 1H), 7.81 (s, 1H), 7.97 (s, 1H), 8.15 (s, 1H), 9.46 (s, 1H), 10.10 (s, 1H); MS (ESI(+)) m/e 404, 406 (M+H)⁺.

Example 29

(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide and (1R,2R,3S,4S)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide The title compound was prepared as described in Example 1, substituting 2,4-dichloro-5-(trifluoromethyl)pyrimidine for 2,4-dichloro-5-fluoropyrimidine in Example 1A along with substitution of 2-(4-amino-1H-pyrazol-1-yl)ethanol for 1-methyl-1H-pyrazol-4-amine in Example 1B. $^1$H NMR (300 MHz, DMSO-D$_6$) ppm 1.17-1.33 (m, 2H), 1.41 (d, J=8.7 Hz, 1H), 2.03 (d, J=8.7 Hz, 1H), 2.86 (d, J=11.9 Hz, 1H), 3.04-3.20 (m, 1H), 3.49-3.78 (m, 1H), 4.08 (t, J=5.6 Hz, 2H), 4.17 (t, J=6.7 Hz, 1H), 6.38 (s, 2H), 7.32 (s, 1H), 7.61 (s, 1H), 7.68-7.94 (m, 2H), 8.02-8.22 (m, 1H), 8.87 (s, 1H), 9.62 (s, 1H); MS (ESI(+)) m/e 424 (M+H)⁺.

Example 30

(1S,2S,3R,4R)-3-({5-chloro-2-[(1-ethyl-1H-pyrazol-4-yl)amino]pyrimidin-4-yl}amino)bicyclo[2.2.1]hept-5-ene-2-carboxamide and (1R,2R,3S,4S)-3-({5-chloro-2-[(1-ethyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-5-chloropyrimidine for 2,4-dichloro-5-fluoropyrimidine in Example 1A along with substitution of 1-ethyl-1H-pyrazol-4-amine for 1-methyl-1H-pyrazol-4-amine in Example 1B. $^1$H NMR (300 MHz, DMSO-$D_6$) ppm 1.34 (t, J=7.3 Hz, 3H), 1.41 (d, J=9.1 Hz, 1H), 2.11 (d, J=9.1 Hz, 1H), 2.54 (d, J=8.3 Hz, 1H), 2.78 (s, 1H), 2.88 (s, 1H), 3.97-4.19 (m, 3H), 6.20-6.43 (m, 2H), 7.26 (s, 1H), 7.50 (s, 1H), 7.75 (s, 1H), 7.79 (s, 1H), 7.89 (s, 1H), 9.10 (s, 1H); MS (ESI(+)) m/e 374 (M+H)$^+$.

Example 31

(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide and (1R,2R,3S,4S)-3-({5-bromo-2-[(1-ethyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-5-bromopyrimidine for 2,4-dichloro-5-fluoropyrimidine in Example 1A along with substitution of 1-ethyl-1H-pyrazol-4-amine for 1-methyl-1H-pyrazol-4-amine in Example 1B. $^1$H NMR (300 MHz, DMSO-$D_6$) ppm 1.34 (t, J=7.1 Hz, 3H), 1.41 (d, J=9.1 Hz, 1H), 2.11 (d, J=8.7 Hz, 1H), 2.77 (s, 1H), 2.88 (s, 1H), 3.96-4.20 (m, 3H), 6.09-6.52 (m, 2H), 7.25 (s, 1H), 7.50 (s, 1H), 7.58-7.84 (m, 3H), 7.95 (s, 1H), 9.10 (s, 1H); MS (ESI(+)) m/e 418, 420 (M+H)$^+$.

Example 32

(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide and (1R,2R,3S,4S)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide

Example 32A 1-(2,2,2-trifluoroethyl)-1H-pyrazol-4-amine

The title compound was prepared by substituting 4-nitro-1-(2,2,2-trifluoroethyl)-1H-pyrazole for 2-(4-nitro-1H-pyrazol-1-yl)ethanol in Example 11B.

Example 32B (1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide and (1R,2R,3S,4S)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide The title compound was prepared as described in Example 1, substituting 2,4-dichloro-5-(trifluoromethyl)pyrimidine for 2,4-dichloro-5-fluoropyrimidine in Example 1A along with substitution of 1-(2,2,2-trifluoroethyl)-1H-pyrazol-4-amine for 1-methyl-1H-pyrazol-4-amine in Example 1B. $^1$H NMR (300 MHz, DMSO-$D_6$) ppm 1.40 (d, J=8.8 Hz, 1H), 2.03 (d, J=8.5 Hz, 1H), 2.65-2.94 (m, 3H), 4.15 (s, 1H), 4.95-5.21 (m, 2H), 6.08-6.60 (m, 2H), 6.93-8.04 (m, 2H), 8.05-8.34 (m, 2H), 9.68 (s, 1H); MS (ESI(+)) m/e 462 (M+H)$^+$.

Example 33

(1S,2S,3R,4R)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide

Example 33A

N,N-dimethyl-2-(4-nitro-1H-pyrazol-1-yl)ethanamine

2-Dimethylaminoethyl chloride hydrochloride (955 mg, 6.63 mmol), potassium carbonate (1.83 g, 8.84 mmol) and 4-nitro-1H-pyrazole (750 mg, 6.63 mmol) were combined in acetone (30 ml) and the reaction was stirred overnight at reflux. After cooling to room temperature, the crude reaction mixture was filtered to remove inorganics, and the filtrate was concentrated to give the product.

Example 33B 1-(2-(dimethylamino)ethyl)-1H-pyrazol-4-amine

N,N-dimethyl-2-(4-nitro-1H-pyrazol-1-yl)ethanamine (1.19 g, 6.46 mmol) was dissolved in methanol (65 ml) and the flask was equipped with a hydrogenation stopcock apparatus. The flask was purged with $N_2$ and 10% Pd/C (100 mg) was added. The flask was again purged with $N_2$, then flushed with $H_2$ and left overnight stirring under $H_2$ (1 atm). The reaction was purged with $N_2$ and filtered through Celite, rinsing with methanol. The filtrate was concentrated in vacuo to give a viscous oil, which was dissolved in dioxane and treated with excess 4N HCl-dioxane, whereupon a thick and somewhat gummy precipitate formed. The mixture was concentrated to dryness and dried under vacuum.

Example 33C (1S,2S,3R,4R)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide The title compound was prepared as described in Example 1, substituting 1-(2-(dimethylamino)ethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-$D_6$) ppm 1.41 (d, J=8.8 Hz, 1H) 2.11 (d, J=8.8 Hz, 1H) 2.15 (s, 6H) 2.54 (d, J=8.3 Hz, 1H) 2.60 (t, J=6.7 Hz, 2H) 2.78 (s, 1H) 2.88 (s, 1H) 4.07-4.16 (m, 3H) 6.28-6.39 (m, 2H) 7.26 (s, 1H) 7.50 (s, 1H) 7.61-7.86 (m, 3H) 7.89 (s, 1H) 9.10 (s, 1H); MS (ESI(+)) m/e 417 (M+H)$^+$.

Example 34

(1S,2S,3R,4R)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide

Example 34A 1-(2-(pyrrolidine-1-yl)ethyl)-1H-pyrazol-4-amine

The title compound was prepared as described in Example 33 by substituting N-(2-chloroethyl)pyrrolidine hydrochloride for 2-(dimethylamino)ethyl chloride hydrochloride in Example 33A.

Example 34B (1S,2S,3R,4R)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-pyrrolidin-1-ylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-(pyrrolidine-1-yl)ethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 1.41 (d, J=8.7 Hz, 1H) 1.57-1.73 (m, 4H) 2.07-2.14 (m, 1H) 2.38-2.46 (m, 4H) 2.51-2.55 (m, 1H) 2.74-2.81 (m, 3H) 2.88 (br s, 1H) 3.99-4.21 (m, 3H) 6.20-6.44 (m, 2H) 7.26 (s, 1H) 7.50 (s, 1H) 7.66-7.85 (m, 3H) 7.89 (s, 1H) 9.10 (s, 1H); MS (ESI(+)) m/e 443 (M+H)$^+$.

Example 35

(1S,2S,3R,4R)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide

Example 35A 1-(2-(diethylamino)ethyl)-1H-pyrazol-4-amine

The title compound was prepared as described in Example 33 by substituting 2-(diethylamino)ethyl chloride hydrochloride for 2-(dimethylamino)ethyl chloride hydrochloride in Example 33A.

Example 35B (1S,2S,3R,4R)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide The title compound was prepared as described in Example 1, substituting 1-(2-(diethylamino)ethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 0.91 (t, J=7.1 Hz, 6H) 1.41 (d, J=9.1 Hz, 1H) 2.10 (d, J=8.7 Hz, 1H) 2.45 (q, J=7.1 Hz, 4H) 2.51-2.57 (m, 1H) 2.74 (t, J=6.7 Hz, 2H) 2.78 (s, 1H) 2.88 (s, 1H) 4.05 (t, J=6.7 Hz, 2H) 4.11 (t, J=7.7 Hz, 1H) 6.26-6.38 (m, 2H) 7.26 (s, 1H) 7.49 (s, 1H) 7.68-7.85 (m, 3H) 7.88 (s, 1H) 9.10 (s, 1H); MS (ESI(+)) m/e 445 (M+H)$^+$.

Example 36

(1S,2S,3R,4R)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide

Example 36A 1-(2-(piperidin-1-yl)ethyl)-1H-pyrazol-4-amine

The title compound was prepared as described in Example 33, substituting N-(2-chloroethyl)piperidine hydrochloride for 2-(dimethylamino)ethyl chloride hydrochloride in Example 33A.

Example 36B (1S,2S,3R,4R)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-piperidin-1-ylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-(piperidin-1-yl)ethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 1.32-1.51 (m, 7H) 2.10 (d, J=8.3 Hz, 1H) 2.31-2.39 (m, 4H) 2.52-2.56 (m, 1H) 2.62 (t, J=6.9 Hz, 2H) 2.78 (s, 1H) 2.88 (s, 1H) 4.07 (t, J=5.6 Hz, 1H) 4.12 (t, J=6.7 Hz, 2H) 6.28-6.42 (m, 2H) 7.26 (s, 1H) 7.50 (s, 1H) 7.69-7.85 (m, 3H) 7.89 (s, 1H) 9.10 (s, 1H); MS (ESI(+)) m/e 457 (M+H)$^+$.

Example 37

(1S,2S,3R,4R)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide

Example 37A 1-(2-morpholinoethyl)-1H-pyrazol-4-amine

The title compound was prepared as described in Example 33, substituting N-(2-chloroethyl)morpholine hydrochloride for 2-(dimethylamino)ethyl chloride hydrochloride in Example 33A.

Example 37B (1S,2S,3R,4R)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(2-morpholin-4-ylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-morpholinoethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 1.41 (d, J=8.3 Hz, 1H) 2.10 (d, J=8.3 Hz, 1H) 2.35-2.41 (m, 4H) 2.52-2.56 (m, 1H) 2.67 (t, J=6.5 Hz, 2H) 2.78 (s, 1H) 2.88 (s, 1H) 3.51-3.57 (m, 4H) 4.07-4.19 (m, 3H) 6.28-6.39 (m, 2H) 7.26 (s, 1H) 7.52 (s, 1H) 7.63-7.86 (m, 3H) 7.89 (s, 1H) 9.10 (s, 1H); MS (ESI(+)) m/e 459 (M+H)$^+$.

Example 38

(1S,2S,3R,4R)-3-[(5-bromo-2-{[1-(2-piperidin-1-ylethyl)-1H-pyrazol-4-yl]amino}pyrimidin-4-yl)amino]bicyclo[2.2.1]hept-5-ene-2-carboxamide and (1R,2R,3S,4S)-3-[(5-bromo-2-{[1-(2-piperidin-1-ylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-(piperidin-1-yl)ethyl)-1H-pyrazol-4-amine for 1-methyl-1H-pyrazol-4-amine in Example 1B along with substitution of 2,4-dichloro-5-bromopyrimidine for 2,4-dichloro-5-fluoropyrimidine in Example 1A. $^1$H NMR (300 MHz, DMSO-D$_6$) ppm 1.31-1.51 (m, 7H) 2.11 (d, J=8.7 Hz, 1H) 2.30-2.39 (m, 4H) 2.51-2.55 (m, 1H) 2.62 (t, J=6.7 Hz, 2H) 2.77 (s, 1H) 2.88 (s, 1H) 4.08-4.17 (m, 3H) 6.28-6.38 (m, 2H) 7.25 (s, 1H) 7.50 (s, 1H) 7.61-7.86 (m, 3H) 7.95 (s, 1H) 9.10 (s, 1H); MS (ESI(+)) m/e 501, 503 (M+H)$^+$.

Example 39

(1S,2S,3R,4R)-3-[(5-bromo-2-{[1-(2-morpholin-4-ylethyl)-1H-pyrazol-4-yl]amino}pyrimidin-4-yl)amino]bicyclo[2.2.1]hept-5-ene-2-carboxamide and (1R,2R,3S,4S)-3-[(5-bromo-2-{[1-(2-morpholin-4-ylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-morpholinoethyl)-1H-pyrazol-4-amine for 1-methyl-1H-pyrazol-4-amine in Example 1B along with substitution of 2,4-dichloro-5-bromopyrimidine for 2,4-dichloro-5-fluoropyrimidine in Example 1A. $^1$H NMR (300 MHz, DMSO-D$_6$) ppm 1.41 (d, J=9.1 Hz, 1H) 2.11 (d, J=8.7 Hz, 1H) 2.34-2.41 (m, 4H) 2.51-2.57 (m, 1H) 2.67 (t, J=6.5 Hz, 2H) 2.77 (s, 1H) 2.88 (s, 1H) 3.51-3.57 (m, 4H) 4.07-4.19 (m, 3H) 6.28-6.39 (m, 2H) 7.25 (s, 1H) 7.52 (s, 1H) 7.61-7.90 (m, 3H) 7.95 (s, 1H) 9.11 (s, 1H); MS (ESI(+)) m/e 503, 505 (M+H)$^+$.

Example 40

(1S,2S,3R,4R)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide

Example 40A 1-methyl-4-(4-nitro-1H-pyrazol-1-yl)piperidine

4-Nitro-1H-pyrazole (200 mg, 1.77 mmol), 1-methylpiperidin-4-ol (204 mg, 1.77 mmol) and triphenylphosphine (557 mg, 2.12 mmol) were combined in THF (6 mL) and di-tert-butyl azodicarboxylate (529 mg, 2.30 mmol) was added over about 1 minute. The resulting mixture was stirred at room temperature for 4 hours, and concentrated to dryness. The residue was purified by flash chromatography (Analogix, 12 g column, 0 to 7% methanol in CH$_2$Cl$_2$ over 25 minutes) to give 1-methyl-4-(4-nitro-1H-pyrazol-1-yl)piperidine.

Example 40B 1-(1-methylpiperidin-4-yl)-1H-pyrazol-4-amine

1-Methyl-4-(4-nitro-1H-pyrazol-1-yl)piperidine (132 mg, 0.628 mmol) was dissolved in methanol (6 mL) and the flask was purged with N$_2$. Pd/C (15 mg) was added and the flask was flushed with H$_2$ and stirred under 1 atm H$_2$ (balloon) for 3 hours. The reaction mixture was purged with N$_2$, and filtered through a pad of Celite. The filtrate was concentrated to dryness, yielding 1-(1-methylpiperidin-4-yl)-1H-pyrazol-4-amine.

Example 40C (1S,2S,3R,4R)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide and (1R,2R,3S,4S)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide The title compound was prepared as described in Example 1, substituting 1-(1-methylpiperidin-4-yl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 1.41 (d, J=8.72 Hz, 1H) 1.81-2.07 (m, 6H) 2.12 (d, J=8.73 Hz, 1H) 2.19 (s, 3H) 2.54 (d, J=8.72 Hz, 1H) 2.76 (s, 1H) 2.79-2.91 (m, 3H) 3.94-4.07 (m, 1H) 4.14 (t, J=7.54 Hz, 1H) 6.26-6.39 (m, 2H) 7.24 (s, 1H) 7.52 (s, 1H) 7.64 (br s, 1H) 7.77 (br s, 2H) 7.89 (s, 1H) 9.08 (s, 1H); MS (ESI(+)) m/e 443 (M+H)$^+$.

Example 41

(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide The title compound was prepared as described in Example 1, substituting (+)-(1S,2S,3R,4R)-3-aminobicyclo[2.2.1]hept-5-ene-2-carboxamide (WO2005/118544) for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-D$_6$, T=90° C.) ppm 1.42 (d, J=8.9 Hz, 1H) 2.11 (d, J=8.9 Hz, 1H) 2.55 (dd, J=8.2, 1.22 Hz, 1H) 2.79 (s, 1H) 2.88 (s, 1H) 3.77 (s, 3H) 4.04-4.22 (m, 1H) 6.20-6.39 (m, 2H) 6.73-7.03 (m, 1H) 7.48 (s, 1H) 7.54 (d, J=7.3 Hz, 1H) 7.68 (s, 1H) 7.83 (s, 1H) 8.66 (s, 1H); MS (ESI(+)) m/e 360 (M+H)$^+$.

Example 42

(1S,2S,3R,4R)-3-({5-chloro-2-[(1-ethyl-1H-pyrazol-4-yl)amino]pyrimidin-4-yl}amino)bicyclo[2.2.1] hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (501 MHz, DMSO-D$_6$, T=90° C.) ppm 1.36 (t, J=7.2 Hz, 3H) 1.42 (d, J=8.8 Hz, 1H) 2.12 (d, J=8.8 Hz, 1H) 2.55 (d, J=8.3 Hz, 1H) 2.79 (s, 1H) 2.88 (s, 1H) 4.05 (q, J=7.2 Hz, 2H) 4.15 (t, J=7.8 Hz, 1H) 6.23-6.38 (m, 2H) 6.81-7.02 (m, 1H) 7.50 (s, 1H) 7.52 (d, J=7.4 Hz, 1H) 7.71 (s, 1H) 7.84 (s, 1H) 8.70 (s, 1H); MS (ESI(+)) m/e 374 (M+H)$^+$.

Example 43

(1S,2R)-2-({5-chloro-2-[(1-methyl-1H-pyrazol-4-yl) amino]pyrimidin-4-yl}amino)cyclopentanecarboxamide and (1R,2S)-2-({5-chloro-2-[(1-methyl-1H-pyrazol-4-yl)amino]pyrimidin-4-yl}amino) cyclopentanecarboxamide The title compound was prepared as described in Example 1, substituting (+/−)-(1S,2R)-2-aminocyclopentanecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-D$_6$, T=90° C.) ppm 1.52-1.66 (m, 1H) 1.71-1.87 (m, 2H) 1.86-2.05 (m, 3H) 2.93 (q, J=7.53 Hz, 1H) 3.76 (s, 3H) 4.39-4.62 (m, 1H) 6.74 (d, J=6.71 Hz, 1H) 7.46 (s, 1H) 7.70 (s, 1H) 7.78-7.91 (m, 1H) 8.64 (s, 1H); MS (ESI(+)) m/e 336 (M+H)$^+$.

Example 44

(1S,2S,3R,4R)-3-[(5-bromo-2-{[1-(2-pyrrolidin-1-ylethyl)-1H-pyrazol-4-yl]amino}pyrimidin-4-yl) amino]bicyclo[2.2.1]hept-5-ene-2-carboxamide and (1R,2R,3S,4S)-3-[(5-bromo-2-{[1-(2-pyrrolidin-1-ylethyl)-1H-pyrazol-4-yl]amino}pyrimidin-4-yl) amino]bicyclo[2.2.1]hept-5-ene-2-carboxamide The title compound was prepared as described in Example 1, substituting 1-(2-(pyrrolidine-1-yl)ethyl)-1H-pyrazol-4-amine for 1-methyl-1H-pyrazol-4-amine in Example 1B along with substitution of 2,4-dichloro-5-bromopyrimidine for 2,4-dichloro-5-fluoropyrimidine in Example 1A. $^1$H NMR (300 MHz, DMSO-D$_6$) ppm 1.41 (d, J=9.12 Hz, 1H) 1.60-1.70 (m, 4H) 2.11 (d, J=8.7 Hz, 1H) 2.40-2.46 (m, 4H) 2.51-2.56 (m, 1H) 2.74-2.81 (m, 3H) 2.88 (s, 1H) 4.08-4.17 (m, 3H) 6.28-6.38 (m, 2H) 7.25 (s, 1H) 7.50 (s, 1H) 7.62-7.83 (m, 3H) 7.95 (s, 1H) 9.10 (s, 1H); MS (ESI(+)) m/e 486.9, 489 (M+H)$^+$.

Example 45

(1S,2S,3R,4R)-3-[(5-fluoro-2-{[1-(2-pyrrolidin-1-ylethyl)-1H-pyrazol-4-yl]amino}pyrimidin-4-yl) amino]bicyclo[2.2.1]hept-5-ene-2-carboxamide and (1R,2R,3S,4S)-3-[(5-fluoro-2-{[1-(2-pyrrolidin-1-ylethyl)-1H-pyrazol-4-yl]amino}pyrimidin-4-yl) amino]bicyclo[2.2.1]hept-5-ene-2-carboxamide The title compound was prepared as described in Example 1, substituting 1-(2-(pyrrolidine-1-yl)ethyl)-1H-pyrazol-4-amine for 1-methyl-1H-pyrazol-4-amine in Example 1B. $^1$H NMR (300 MHz, DMSO-D$_6$) ppm 1.41 (d, J=9.12 Hz, 1H) 1.61-1.69 (m, 4H) 2.12 (d, J=8.7 Hz, 1H) 2.40-2.46 (m, 4H) 2.51-2.56 (m, 1H) 2.74-2.81 (m, 3H) 2.87 (s, 1H) 4.07-4.16 (m, 3H) 6.28-6.38 (m, 2H) 7.21 (s, 1H) 7.36-7.45 (br, 1H) 7.46 (s, 1H) 7.72 (br s, 1H) 7.77 (s, 1H) 7.83 (d, J=3.6 Hz, 1H) 8.89 (s, 1H); MS (ESI(+)) m/e 427 (M+H)$^+$.

Example 46

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(4-methylpiperazin-1-yl)ethyl]-1H-pyrazol-4-yl}amino) pyrimidin-4-yl]amino}bicyclo[2.2.1]hept-5-ene-2-carboxamide

Example 46A 1-(2-(4-methylpiperazin-1-yl)ethyl)-1H-pyrazol-4-amine

The title compound was prepared as described in Example 40 substituting 2-(4-methylpiperazin-1-yl)ethanol for 1-methylpiperidin-4-ol in Example 40A.

Example 46B (1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(4-methylpiperazin-1-yl)ethyl]-1H-pyrazol-4-yl}amino) pyrimidin-4-yl]amino}bicyclo[2.2.1]hept-5-ene-2-carboxamide The title compound was prepared as described in Example 1, substituting 1-(2-(4-methylpiperazin-1-yl)ethyl)-1H-pyrazol-4-amine for 1-methyl-1H-pyrazol-4-amine in Example 1B along with substitution of 2,4,5-trichloropyrimidine for 2,4-dichloro-5-fluoropyrimidine in Example 1A. $^1$H NMR (300 MHz, DMSO-D$_6$) ppm 1.41 (d, J=9.1 Hz, 1H) 2.08-2.12 (m, 1H) 2.13 (s, 3H) 2.21-2.45 (br, 8H) 2.55 (s, 1H) 2.66 (t, J=6.5 Hz, 2H) 2.76-2.82 (m, 1H) 2.88 (s, 1H) 4.07-4.16 (m, 3H) 6.28-6.39 (m, 2H) 7.26 (s, 1H) 7.51 (s, 1H) 7.66-7.86 (m, 3H) 7.89 (s, 1H) 9.10 (s, 1H); MS (ESI(+)) m/e 472 (M+H)$^+$.

Example 47

(1S,2S,3R,4R)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.42 (d, J=8.8 Hz, 1H) 2.08 (d, J=8.8 Hz, 1H) 2.60 (s, 3H) 2.80-2.87 (m, 3H) 3.80 (s, 3H) 4.18 (s, 1H) 6.34 (d, J=22.4 Hz, 2H) 7.55-7.84 (m, 3H) 8.16-8.17 (m, 2H) 9.31-9.63 (m, 1H); MS (ESI(+)) m/e 408 (M+H)$^+$.

Example 48

(1S,2S,3R,4R)-3-({5-bromo-2-[(1-methyl-1H-pyrazol-4-yl)amino]pyrimidin-4-yl}amino)-N-methylbicyclo[2.2.1]hept-5-ene-2-carboxamide and (1R,2R,3S,4S)-3-({5-bromo-2-[(1-methyl-1H-pyrazol-4-yl)amino]pyrimidin-4-yl}amino)-N-methylbicyclo[2.2.1]hept-5-ene-2-carboxamide The title compound was prepared as described in Example 1, substituting (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-D$_6$) ppm 1.42 (d, J=8.7 Hz, 1H) 2.13 (d, J=8.7 Hz, 1H) 2.63 (s, 3H) 2.71-2.88 (m, 2H) 3.78 (s, 3H) 4.11 (t, J=7.3 Hz, 1H) 6.32 (d, J=17.1 Hz, 2H) 7.23-7.60 (m, 3H) 7.70 (s, 1H) 7.95 (s, 1H) 8.24 (s, 1H) 9.11 (s, 1H); MS (ESI(+)) m/e 418 (M+H)$^+$.

Example 49

(1S,2S,3R,4R)-3-({5-bromo-2-[(1-ethyl-1H-pyrazol-4-yl)amino]pyrimidin-4-yl}amino)-N-methylbicyclo[2.2.1]hept-5-ene-2-carboxamide and (1R,2R,3S,4S)-3-({5-bromo-2-[(1-ethyl-1H-pyrazol-4-yl)amino]pyrimidin-4-yl}amino)-N-methylbicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B and substitution of (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-D$_6$) ppm 1.34 (t, J=7.3 Hz, 3H) 1.43 (d, J=9.1 Hz, 1H) 2.14 (d, J=8.7 Hz, 1H) 2.62 (d, J=4.4 Hz, 3H) 2.81 (d, J=20.2 Hz, 2H) 3.90-4.22 (m, 3H) 6.06-6.52 (m, 3H) 7.50 (s, 2H) 7.73 (s, 1H) 7.95 (s, 1H) 8.23 (d, J=4.4 Hz, 1H) 9.10 (s, 1H); MS (ESI(+)) m/e 432 (M+H)$^+$.

Example 50

(1S,2S,3R,4R)-3-({5-chloro-2-[(1-methyl-1H-pyrazol-4-yl)amino]pyrimidin-4-yl}amino)-N-methylbicyclo[2.2.1]hept-5-ene-2-carboxamide and (1R,2R,3S,4S)-3-({5-chloro-2-[(1-methyl-1H-pyrazol-4-yl)amino]pyrimidin-4-yl}amino)-N-methylbicyclo[2.2.1]hept-5-ene-2-carboxamide The title compound was prepared as described in Example 1, substituting (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.42 (d, J=8.8 Hz, 1H) 2.13 (d, J=8.5 Hz, 1H) 2.58-2.68 (m, J=4.4 Hz, 3H) 2.85 (s, 2H) 3.78 (s, 3H) 3.95-4.20 (m, 1H) 6.12-6.47 (m, 2H) 7.35-7.79 (m, J=70.2 Hz, 4H) 7.89 (s, 1H) 8.26 (s, 1H) 9.09 (s, 1H); MS (ESI(+)) m/e 374 (M+H)$^+$.

Example 51

(1S,2S,3R,4R)-3-({5-chloro-2-[(1-ethyl-1H-pyrazol-4-yl)amino]pyrimidin-4-yl}amino)-N-methylbicyclo[2.2.1]hept-5-ene-2-carboxamide and (1R,2R,3S,4S)-3-({5-chloro-2-[(1-ethyl-1H-pyrazol-4-yl)amino]pyrimidin-4-yl}amino)-N-methylbicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B and substitution of (+/−)-(1S,2S,3R,4R)-3-amino-N-methylbicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.34 (t, J=7.1 Hz, 3H) 1.42 (d, J=8.8 Hz, 1H) 2.14 (d, J=8.5 Hz, 1H) 2.61 (d, J=4.4 Hz, 3H) 2.82 (d, J=17.6 Hz, 2H) 3.95-4.19 (m, 3H) 6.17-6.42 (m, 2H) 7.34-7.65 (m, 3H) 7.74 (s, 1H) 7.89 (s, 1H) 8.24 (d, J=4.1 Hz, 1H) 9.09 (s, 1H); MS (ESI(+)) m/e 388 (M+H)$^+$.

Example 52

(1S,2S,3R,4R)-3-({5-methoxy-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-methoxy-2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4-dichloro-5-methoxypyrimidine for 2,4-dichloro-5-fluoropyrimidine in Example 1A. $^1$H NMR (300 MHz, DMSO-D$_6$) ppm 1.39 (d, J=8.8 Hz, 1H) 2.12 (d, J=8.8 Hz, 1H) 2.73 (s, 1H) 2.84 (s, 1H) 3.70 (s, 3H) 3.76 (s, 3H) 4.13 (t, J=8.0 Hz, 1H) 6.16-6.41 (m, 2H) 7.05 (d, J=8.1 Hz, 1H) 7.15 (s, 1H) 7.43 (s, 1H) 7.54 (s, 1H) 7.59-7.79 (m, 3H) 8.53 (s, 1H); MS (ESI(+)) m/e 356 (M+H)$^+$.

Example 53

(1S,2S,3R,4R)-3-({2-[(1-ethyl-1H-pyrazol-4-yl)amino]-5-methoxypyrimidin-4-yl}amino)bicyclo[2.2.1]hept-5-ene-2-carboxamide and (1R,2R,3S,4S)-3-({2-[(1-ethyl-1H-pyrazol-4-yl)amino]-5-methoxypyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B and substitution of 2,4-dichloro-5-methoxypyrimidine for 2,4-dichloro-5-fluoropyrimidine in Example 1A. $^1$H NMR (300 MHz, DMSO-D$_6$) ppm 1.26-1.45 (m, 4H) 2.13 (d, J=8.7 Hz, 1H) 2.78 (d, J=37.7 Hz, 2H) 3.70 (s, 3H) 4.04 (q, J=7.4 Hz, 2H) 4.14 (t, J=8.1 Hz, 1H) 6.17-6.40 (m, 3H) 7.03 (d, J=8.3 Hz, 1H) 7.15 (s, 1H) 7.44 (s, 1H) 7.54 (s, 1H) 7.67 (s, 1H) 7.76 (s, 1H) 8.53 (s, 1H); MS (ESI(+)) m/e 370 (M+H)$^+$.

Example 54

(1S,2S,3R,4R)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide

Example 54A

N,N-dimethyl-2-(4-nitro-1H-pyrazol-1-yl)acetamide

A suspension of 4-nitro-1H-pyrazole (0.4 g, 3.54 mmol), 2-chloro-N,N-dimethylacetamide (0.546 ml, 5.31 mmol) and potassium carbonate (0.733 g, 5.31 mmol) in 18 ml acetone was refluxed for 6 hours. The cooled suspension was filtered with acetone washes and the concentrated residue was flash chromatographed (50 mm, 3% methanol in $CH_2Cl_2$) to afford the title compound.

Example 54B 2-(4-amino-1H-pyrazol-1-yl)-N,N-dimethylacetamide

A solution of N,N-dimethyl-2-(4-nitro-1H-pyrazol-1-yl)acetamide (870 mg, 4.39 mmol) in methanol (22 ml) was evacuated/purged with nitrogen and treated with Pd on carbon (87 mg, 0.082 mmol). The resulting black suspension was evacuated/purged with a hydrogen balloon and stirred under the hydrogen overnight when the mixture was filtered through celite with methanol washes. The filtrate was concentrated to give the product.

Example 54C (1S,2S,3R,4R)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide and (1R,2R,3S,4S)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide The title compound was prepared as described in Example 1, substituting 2-(4-amino-1H-pyrazol-1-yl)-N,N-dimethylacetamide for 1-methyl-1H-pyrazol-4-amine in Example 1B along with substitution of 2,4,5-trichloropyrimidine for 2,4-dichloro-5-fluoropyrimidine in Example 1A. $^1$H NMR (400 MHz, DMSO-$D_6$, T=90° C.) ppm 1.41 (d, J=8.5 Hz, 1H) 2.12 (d, J=8.9 Hz, 1H) 2.51-2.59 (m, 1H) 2.78 (s, 1H) 2.87 (s, 1H) 2.98 (s, 6H) 4.06-4.19 (m, 1H) 4.95 (s, 2H) 6.16-6.41 (m, 2H) 6.86 (br s, 1H) 7.31-7.62 (m, 3H) 7.62-7.77 (m, 1H) 7.84 (s, 1H) 8.72 (s, 1H); MS (ESI(+)) m/e 431 (M+H)$^+$.

Example 55 isopropyl{4-[(4-{[(1S,2S,3R,4R)-3-(aminocarbonyl)bicyclo[2.2.1]hept-5-ene-2-yl]amino}-5-bromopyrimidin-2-yl)amino]-1H-pyrazol-1-yl}acetate and isopropyl{4-[(4-{[(1R,2R,3S,4S)-3-(aminocarbonyl)bicyclo[2.2.1]hept-5-ene-2-yl]amino}-5-bromopyrimidin-2-yl)amino]-1H-pyrazol-1-yl}acetate The title compound was prepared as described in Example 1, substituting 2-(4-amino-1H-pyrazol-1-yl)acetic acid for 1-methyl-1H-pyrazol-4-amine in Example 1B and substitution of 2,4-dichloro-5-bromopyrimidine for 2,4-dichloro-5-fluoropyrimidine in Example 1A. $^1$H NMR (400 MHz, DMSO-$D_6$, T=90° C.) ppm 1.13-1.27 (m, 6H) 1.34-1.46 (m, 1H) 2.12 (d, J=8.61 Hz, 1H) 2.53 (d, J=8.14 Hz, 1H) 2.74-2.83 (m, 1H) 2.87 (s, 1H) 4.14 (t, J=7.09 Hz, 1H) 4.88 (s, 2H) 4.91-5.03 (m, 1H) 6.21-6.35 (m, 2H) 6.78-6.99 (br s, 1H) 7.49-7.55 (m, 1H) 7.56 (s, 1H) 7.76 (s, 1H) 7.92 (s, 1H) 8.78 (s, 1H); MS (ESI(+)) m/e 490, 492 (M+1)$^+$.

Example 56

(1R,2S,3R,4S)-3-({5-chloro-2-[(1-methyl-1H-pyrazol-4-yl)amino]pyrimidin-4-yl}amino)bicyclo[2.2.1]heptane-2-carboxamide and (1S,2R,3S,4R)-3-({5-chloro-2-[(1-methyl-1H-pyrazol-4-yl)amino]pyrimidin-4-yl}amino)bicyclo[2.2.1]heptane-2-carboxamide The title compound was prepared as described in Example 1, substituting (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$D_6$) ppm 1.15 (d, J=9.9 Hz, 1H) 1.29 (d, J=9.9 Hz, 2H) 1.50-1.71 (m, 2H) 1.91 (d, J=9.5 Hz, 1H) 2.13-2.35 (m, 2H) 2.62 (d, J=8.3 Hz, 1H) 3.78 (s, 3H) 4.13 (t, J=7.5 Hz, 1H) 7.17 (s, 1H) 7.45 (s, 1H) 7.58-7.91 (m, 4H) 9.07 (s, 1H); MS (ESI(+)) m/e 362 (M+1)$^+$.

Example 57

(1R,2S,3R,4S)-3-({5-chloro-2-[(1-ethyl-1H-pyrazol-4-yl)amino]pyrimidin-4-yl}amino)bicyclo[2.2.1]heptane-2-carboxamide and (1S,2R,3S,4R)-3-({5-chloro-2-[(1-ethyl-1H-pyrazol-4-yl)amino]pyrimidin-4-yl}amino)bicyclo[2.2.1]heptane-2-carboxamide The title compound was prepared as described in Example 1, substituting 1-ethyl-1H-pyrazol-4-amine for 1-methyl-1H-pyrazol-4-amine in Example 1B and substitution of (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$D_6$) ppm 1.15 (d, J=9.9 Hz, 1H) 1.24-1.40 (m, 5H) 1.49-1.71 (m, 2H) 1.92 (d, J=9.91 Hz, 1H) 2.18-2.32 (m, 2H) 2.63 (d, J=8.3 Hz, 1H) 4.09-4.25 (m, 3H) 7.16 (s, 1H) 7.47 (s, 1H) 7.66-7.93 (m, 4H) 9.07 (s, 1H); MS (ESI(+)) m/e 376 (M+H)$^+$.

Example 58

(1R,2S,3R,4S)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide and (1S,2R,3S,4R)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide The title compound was prepared as described in Example 1, substituting 2-(4-amino-1H-pyrazol-1-yl)-N,N-dimethylacetamide for 1-methyl-1H-pyrazol-4-amine in Example 1B and substitution of (+/−)-(1R,2S,3R,4S)-3-aminobicyclo[2.2.1]heptane-2-carboxamide for (+/−)-(1S,2S,3R,4R)-3- aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.14 (d, J=9.9 Hz, 1H) 1.20-1.33 (m, 3H) 1.42-1.65 (m, 2H) 1.92 (d, J=9.5 Hz, 1H) 2.24 (d, J=22.6 Hz, 2H) 2.61 (d, J=8.3 Hz, 1H) 2.84 (s, 3H) 3.01 (s, 3H) 4.13 (t, J=7.7 Hz, 1H) 4.86-5.14 (m, 2H) 7.15 (s, 1H) 7.50 (s, 1H) 7.65-7.89 (m, 3H) 9.13 (s, 1H); MS (ESI(+)) m/e 433 (M+H)$^+$.

Example 59

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide and (1S,2R,3S,4R)-3-[(5-chloro-2-{[1-(2-hydroxyethyl)-1H-pyrazol-4-yl]amino}pyrimidin-4-yl)amino]bicyclo[2.2.1]heptane-2-carboxamide The title compound was prepared as described in Example 1, substituting 2-(4-amino-1H-pyrazol-1-yl)ethanol for 1-methyl-1H-pyrazol-4-amine in Example 1B and substitution of (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.15 (d, J=9.9 Hz, 1H) 1.22-1.41 (m, 2H) 1.46-1.65 (m, 2H) 1.92 (d, J=10.3 Hz, 1H) 2.18-2.32 (m, 2H) 2.62 (d, J=7.9 Hz, 1H) 3.17 (d, J=5.2 Hz, 1H) 3.70 (q, J=5.6 Hz, 2H) 3.99-4.23 (m, 3H) 4.86 (t, J=5.4 Hz, 1H) 7.16 (s, 1H) 7.50 (s, 1H) 7.69 (s, 1H) 7.84 (d, J=11.1 Hz, 2H) 9.08 (s, 1H); MS (ESI(+)) m/e 392 (M+1)$^+$.

Example 60

(1R,2S,3R,4S)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide and (1S,2R,3S,4R)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide The title compound was prepared as described in Example 1, substituting 1-(2-morpholinoethyl)-1H-pyrazol-4-amine for 1-methyl-1H-pyrazol-4-amine in Example 1B and substitution of (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.15 (d, J=10.2 Hz, 1H) 1.20-1.39 (m, 2H) 1.45-1.67 (m, 2H) 1.92 (d, J=9.8 Hz, 1H) 2.16-2.32 (m, 2H) 2.33-2.41 (m, 4H) 2.58-2.71 (m, 3H) 3.49-3.58 (m, 4H) 4.14 (t, J=6.8 Hz, 3H) 7.15 (s, 1H) 7.50 (s, 1H) 7.63-7.77 (m, 2H) 7.84 (d, J=11.9 Hz, 2H) 9.06 (s, 1H); MS (ESI(+)) m/e 461 (M+1)$^+$.

Example 61

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide and (1S,2R,3S,4R)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide Example 61A 2-(4-amino-1H-pyrazol-1-yl)-N-methylacetamide The title compound was prepared as described in Example 55A substituting 2-chloro-N-methylacetamide for 2-chloro-N,N-dimethylacetamide.

Example 61B (1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide and (1S,2R,3S,4R)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide The title compound was prepared as described in Example 1, substituting 2-(4-amino-1H-pyrazol-1-yl)-N-methylacetamide for 1-methyl-1H-pyrazol-4-amine in Example 1B and substitution of (+/−)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.14 (d, J=8.5 Hz, 2H) 1.21-1.37 (m, 2H) 1.43-1.60 (m, 2H) 1.92 (d, J=7.5 Hz, 1H) 2.15-2.30 (m, 2H) 2.61 (t, J=4.6 Hz, 3H) 4.13 (t, J=7.6 Hz, 1H) 4.67 (d, J=2.4 Hz, 2H) 7.15 (s, 1H) 7.52 (s, 1H) 7.69 (s, 2H) 7.80-7.89 (m, 4H) 9.12 (bs, 1H); MS (ESI(+)) m/e 419 (M+1)$^+$.

Example 62

(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.28-1.47 (m, 4H) 2.03 (d, J=8.82 Hz, 1H) 2.86 (d, J=13.2 Hz, 2H) 4.08 (q, J=7.1 Hz, 2H) 4.17 (t, J=6.8 Hz, 1H) 6.28 (dd, J=5.6, 2.88 Hz, 1H) 6.38 (s, 1H) 7.30 (s, 1H) 7.59 (s, 1H) 7.77 (d, J=22.4 Hz, 3H) 8.11 (s, 2H) 9.20-9.66 (m, 1H); MS (ESI(+)) m/e 408 (M+1)$^+$.

Example 63

(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide The title compound was prepared as described in Example 1, substituting 2-(4-amino-1H-pyrazol-1-yl)ethanol for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.14-1.31 (m, 1H) 1.41 (d, J=8.8 Hz, 1H) 2.03 (d, J=8.8 Hz, 1H) 2.88 (s, 2H) 3.71 (q, J=5.4 Hz, 2H) 4.00-4.13 (m, 2H) 4.17 (t, J=7.1 Hz, 1H) 4.88 (t, J=4.9 Hz, 1H) 6.37 (s, 2H) 7.30 (s, 1H) 7.61 (s, 1H) 7.78 (d, J=18.7 Hz, 3H) 8.04-8.18 (m, 1H) 9.27-9.66 (m, 1H); MS (ESI(+)) m/e 424 (M+1)$^+$.

Example 64

(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide The title compound was prepared as described in Example 1, substituting 1-(2,2,2-trifluoroethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (501 MHz, DMSO-D$_6$) ppm 1.28 (d, J=5.7 Hz, 2H) 1.41 (d, J=8.5 Hz, 1H) 2.05 (d, J=9.0 Hz, 1H) 2.53 (d, J=8.3 Hz, 1H) 2.84 (d, J=35.1 Hz, 2H) 4.20 (t, J=7.5 Hz, 1H) 4.88-5.07 (m, 2H) 6.23-6.35 (m, 2H) 7.74 (s, 1H) 7.88 (d, J=19.7 Hz, 2H) 8.11 (s, 1H) 9.28 (s, 1H); MS (ESI(+)) m/e 462 (M+1)$^+$.

Example 65

(1S,2S,3R,4R)-3-[(5-chloro-2-{[1-(2-hydroxyethyl)-1H-pyrazol-4-yl]amino}pyrimidin-4-yl)amino]bicyclo[2.2.1]hept-5-ene-2-carboxamide The title compound was prepared as described in Example 1, substituting 2-(4-amino-1H-pyrazol-1-yl)ethanol for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.41 (d, J=8.7 Hz, 1H) 2.10 (d, J=8.7 Hz, 1H) 2.78 (s, 1H) 2.88 (s, 1H) 3.17 (d, J=5.2 Hz, 1H) 3.70 (q, J=5.6 Hz, 2H) 3.99-4.13 (m, 3H) 4.87 (t, J=5.4 Hz, 1H) 6.35 (s, 2H) 7.26 (s, 1H) 7.52 (s, 1H) 7.77 (s, 3H) 7.89 (s, 1H) 9.11 (s, 1H); MS (ESI(+)) m/e 390 (M+1)$^+$.

Example 66

(1S,2S,3R,4R)-3-[(5-chloro-2-{[1-(2,2,2-trifluoroethyl)-1H-pyrazol-4-yl]amino}pyrimidin-4-yl)amino]bicyclo[2.2.1]hept-5-ene-2-carboxamide The title compound was prepared as described in Example 1, substituting 1-(2,2,2-trifluoroethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.41 (d, J=8.7 Hz, 1H) 2.10 (d, J=8.7 Hz, 1H) 2.82 (d, J=31.7 Hz, 2H) 4.11 (t, J=7.5 Hz, 1H) 5.06 (q, J=9.4 Hz, 2H) 6.13-6.44 (m, 2H) 7.26 (s, 1H) 7.55-7.95 (m, 6H) 9.20 (s, 1H); MS (ESI(+)) m/e 428 (M+1)$^+$.

Example 67

(1S,2S,3R,4R)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide

Example 67A (+/−)-(1S,2S,3R,4R)-3-amino-N-(2-hydroxyethyl)bicyclo[2.2.1]hept-5-ene-2-carboxamide The title compound was prepared as described in Example 9A substituting ethanolamine for methylamine

Example 67B (1S,2S,3R,4R)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting (+/−)-(1S,2S,3R,4R)-3-amino-N-(2-hydroxyethyl)bicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.41 (d, J=8.5 Hz, 1H) 2.08 (d, J=8.5 Hz, 1H) 2.57 (d, J=8.1 Hz, 3H) 2.85 (s, 2H) 3.15 (d, J=4.4 Hz, 2H) 3.81 (s, 3H) 4.03-4.26 (m, 1H) 4.71 (t, J=5.3 Hz, 1H) 6.34 (d, J=24.1 Hz, 2H) 7.39-7.63 (m, 1H) 7.70 (s, 1H) 7.85 (d, J=6.1 Hz, 1H) 8.11 (s, 1H) 8.44 (s, 1H) 9.30-9.75 (m, 1H); MS (ESI(+)) m/e 438 (M+1)$^+$.

Example 68

(1S,2S,3R,4R)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide and (1R,2R,3S,4S)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+/−)-(1S,2S,3R,4R)-3-amino-N-(2-hydroxyethyl)bicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 1.13-1.37 (m, 4H) 1.37-1.46 (m, 1H) 2.09 (d, J=8.7 Hz, 1H) 2.57 (d, J=7.5 Hz, 1H) 2.84 (s, 2H) 3.03-3.19 (m, 2H) 3.33-3.46 (m, 1H) 3.89-4.23 (m, 3H) 4.67 (t, J=5.4 Hz, 1H) 6.13-6.50 (m, 2H) 7.59 (s, 1H) 7.66-7.85 (m, 2H) 8.11 (s, 1H) 8.39 (s, 1H) 9.21-9.75 (m, 1H); MS (ESI(+)) m/e 452 (M+1)$^+$.

Example 69

(1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide The title compound was prepared as described in Example 1, substituting (R)-1-(4-amino-1H-pyrazol-1-yl)propan-2-ol for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-D$_6$, T=90° C.) ppm 1.05 (d, J=5.8 Hz, 3H) 1.41 (d, J=9.2 Hz, 1H) 2.06 (d, J=8.9 Hz, 1H) 2.54 (d, J=7.9 Hz, 1H) 2.81 (s, 1H) 2.88 (s, 1H) 3.88-4.05 (m, 3H) 4.21 (t, J=7.5 Hz, 1H) 4.56 (d, J=4.3 Hz, 1H) 6.28-6.40 (m, 2H) 7.58 (s, 1H) 7.75 (s, 1H) 8.08 (s, 1H) 9.14 (s, 1H); MS (ESI(+)) m/e 438 (M+1)$^+$.

Example 70

(1S,2S,3R,4R)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide

Example 70A (+/−)-(1S,2S,3R,4R)-3-amino-N-cyclopropylbicyclo[2.2.1]hept-5-ene-2-carboxamide The title compound was prepared as described in Example 9A substituting cyclopropylamine for methylamine

Example 70B (1S,2S,3R,4R)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting (+/−)-(1S,2S,3R,4R)-3-amino-N-cyclopropylbicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 0.38 (d, J=2.37 Hz, 2H) 0.53-0.71 (m, 2H) 1.42 (d, J=8.81 Hz, 1H) 2.08 (d, J=8.48 Hz, 1H) 2.45 (d, J=7.80 Hz, 1H) 2.62 (s, 1H) 2.84 (s, 2H) 3.80 (s, 3H) 4.14 (t, J=6.95 Hz, 1H) 6.19-6.44 (m, 2H) 7.57 (s, 1H) 7.69 (s, 1H) 7.80 (d, J=6.10 Hz, 1H) 8.12 (s, 1H) 8.40 (s, 1H) 9.62 (s, 1H); MS (ESI(+)) m/e 434 (M+1)$^+$.

Example 71

(1S,2S,3R,4R)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide and (1R,2R,3S,4S)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+/−)-(1S,2S,3R,4R)-3-amino-N-cyclopropyl bicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (300 MHz, DMSO-D$_6$) ppm 0.37 (d, J=2.4 Hz, 2H) 0.63 (d, J=7.1 Hz, 2H) 1.35 (t, J=7.3 Hz, 3H) 1.42 (d, J=8.8 Hz, 1H) 2.09 (d, J=8.8 Hz, 1H) 2.45 (d, J=8.1 Hz, 1H) 2.56-2.68 (m, 1H) 2.84 (s, 2H) 4.08 (q, J=7.2 Hz, 2H) 4.17 (t, J=7.1 Hz, 1H) 6.18-6.32 (m, 1H) 6.37 (s, 1H) 7.59 (s, 1H) 7.66-7.81 (m, 2H) 8.12 (s, 1H) 8.39 (s, 1H) 9.62 (s, 1H); MS (ESI(+)) m/e 448 (M+1)$^+$.

Example 72

(1S,2S,3R,4R)-3-{[5-chloro-2-({1-[(3S)-pyrrolidin-3-yl]-1H-pyrazol-4-yl}amino)pyrimidin-4-yl]amino}bicyclo[2.2.1]hept-5-ene-2-carboxamide

Example 72A (S)-tert-butyl 3-(4-amino-1H-pyrazol-1-yl)pyrrolidine-1-carboxylate The title compound was prepared as described in Example 41A substituting (R)-tert-butyl 3-hydroxypyrrolidine-1-carboxylate for 1-methylpiperidin-4-ol.

Example 72B (1S,2S,3R,4R)-3-(2-chloro-5-chloropyrimidin-4-ylamino)bicyclo[2.2.1]hept-5-ene-2-carboxamide A light suspension of (+)-(1S,2S,3R,4R)-3-aminobicyclo[2.2.1]hept-5-ene-2-carboxamide, trifluoroacetic acid (3 g, 11.27 mmol) and sodium bicarbonate (1.893 g, 22.54 mmol) in 39 ml of 2:1 methanol/water at room temperature was treated with 2,4,5-trichloropyrimidine (1.550 ml, 13.52 mmol). The resulting mixture was stirred at room temperature for 2 days, diluted with water (20 ml) and ethyl acetate (30 ml); the separated aqueous phase was extracted with ethyl acetate (4×20 ml) and the combined organic layers were washed with brine (20 ml), dried w/Mg$_2$SO$_4$, filtered and concentrated. The crude product was flash chromatographed (50 mm; 0.5 L 2% methanol in CH$_2$Cl$_2$ to 4% methanol in CH$_2$Cl$_2$) to afford the desired product.

Example 72C (1S,2S,3R,4R)-3-{[5-chloro-2-({1-[(3S)-pyrrolidin-3-yl]-1H-pyrazol-4-yl}amino)pyrimidin-4-yl]amino}bicyclo[2.2.1]hept-5-ene-2-carboxamide (+)-(1S,2S,3R,4R)-3-(2,5-Dichloropyrimidin-4-ylamino)bicyclo[2.2.1]hept-5-ene-2-carboxamide (75 mg, 0.25 mmol) and (S)-tert-butyl 3-(4-amino-1H-pyrazol-1-yl)pyrrolidine-1-carboxylate (63 mg, 0.25 mmol) were combined with 2-propanol (2.4 ml) in a sealed tube and the mixture was heated to 85° C. for 4 hours. The reaction mixture was concentrated to dryness, then treated with 5 mL TFA and stirred for 15 minutes. The mixture was again concentrated to dryness, the residue was dissolved in $CH_2Cl_2$, and the mixture was treated with aqueous saturated $NaHCO_3$. The layers were separated and the aqueous layer was further extracted 3× with ethyl acetate. The extracts were dried ($Na_2SO_4$) and concentrated, then purified by flash chromatography yielding the desired product. $^1H$ NMR (300 MHz, DMSO-$D_6$) ppm 1.41 (d, J=7.8 Hz, 1H) 1.92-2.04 (m, 1H) 2.07-2.21 (m, 2H) 2.52-2.56 (m, 1H) 2.71-2.91 (m, 3H) 2.93 (d, J=5.4 Hz, 1H) 2.95-3.03 (m, 1H) 3.12 (dd, J=11.5, 7.12 Hz, 1H) 4.13 (t, J=7.5 Hz, 1H) 4.65-4.77 (m, 1H) 6.25-6.40 (m, 2H) 7.25 (s, 1H) 7.51 (s, 1H) 7.61-7.84 (m, 3H) 7.89 (s, 1H) 9.10 (s, 1H); MS (ESI(+)) m/e 415 (M+H)$^+$.

Example 73

(1S,2S,3R,4R)-3-{[5-chloro-2-({1-[(3R)-pyrrolidin-3-yl]-1H-pyrazol-4-yl}amino)pyrimidin-4-yl]amino}bicyclo[2.2.1]hept-5-ene-2-carboxamide

Example 73A (R)-tert-butyl 3-(4-amino-1H-pyrazol-1-yl)pyrrolidine-1-carboxylate The title compound was prepared as described in Example 41A substituting (S)-tert-butyl 3-hydroxypyrrolidine-1-carboxylate for 1-methylpiperidin-4-ol.

Example 73B (1S,2S,3R,4R)-3-{[5-chloro-2-({1-[(3R)-pyrrolidin-3-yl]-1H-pyrazol-4-yl}amino)pyrimidin-4-yl]amino}bicyclo[2.2.1]hept-5-ene-2-carboxamide The title compound was prepared as described in Example 73, substituting (R)-tert-butyl 3-(4-amino-1H-pyrazol-1-yl)pyrrolidine-1-carboxylate for (S)-tert-butyl 3-(4-amino-1H-pyrazol-1-yl)pyrrolidine-1-carboxylate in Example 73C. $^1H$ NMR (400 MHz, PYRIDINE-$D_5$, T=90° C.) ppm 1.55 (d, J=8.9 Hz, 1H) 2.12-2.31 (m, 2H) 2.51 (d, J=9.2 Hz, 1H) 2.77 (d, J=7.9 Hz, 1H) 2.95 (s, 1H) 3.00-3.05 (m, 1H) 3.06 (s, 1H) 3.22-3.34 (m, 2H) 3.42 (dd, J=11.60, 3.66 Hz, 1H) 4.44 (td, J=7.9, 1.22 Hz, 1H) 4.80-4.87 (m, 1H) 6.18 (dd, J=5.7, 2.90 Hz, 1H) 6.27 (dd, J=5.8, 3.1 Hz, 1H) 7.85-7.94 (m, 2H) 8.02 (s, 1H) 8.08 (s, 1H) 9.20 (s, 1H); MS (ESI(+)) m/e 415 (M+H)$^+$.

Example 74

(1S,2S,3R,4R)-3-[(2-{[1-(2-amino-2-oxoethyl)-1H-pyrazol-4-yl]amino}-5-chloropyrimidin-4-yl)amino]bicyclo[2.2.1]hept-5-ene-2-carboxamide

Example 74A 2-(4-amino-1H-pyrazol-1-yl)acetamide

The title compound was prepared as described in Example 54A substituting 2-chloroacetamide for 2-chloro-N,N-dimethylacetamide.

Example 74B (1S,2S,3R,4R)-3-[(2-{[1-(2-amino-2-oxoethyl)-1H-pyrazol-4-yl]amino}-5-chloropyrimidin-4-yl)amino]bicyclo[2.2.1]hept-5-ene-2-carboxamide The title compound was prepared as described in Example 1, substituting 2-(4-amino-1H-pyrazol-1-yl)acetamide for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1H$ NMR (400 MHz, DMSO-$D_6$, T=90° C.) ppm 1.41 (d, J=9.2 Hz, 1H) 2.12 (d, J=8.9 Hz, 1H) 2.55 (dd, J=8.2, 1.2 Hz, 1H) 2.79 (s, 1H) 2.87 (s, 1H) 4.05-4.21 (m, 1H) 4.65 (s, 2H) 6.25-6.34 (m, 2H) 6.74-7.03 (m, 3H) 7.36-7.59 (m, 3H) 7.76 (s, 1H) 8.74 (s, 1H); MS (ESI(+)) m/e 403.0 (M+H)$^+$.

Example 75

(1S,2S,3R,4R)-3-{[5-chloro-2-({1-[2-(methylamino)-2-oxoethyl]-1H-pyrazol-4-yl}amino)pyrimidin-4-yl]amino}bicyclo[2.2.1]hept-5-ene-2-carboxamide The title compound was prepared as described in Example 1, substituting 2-(4-amino-1H-pyrazol-1-yl)-N-methylacetamide for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1H$ NMR (400 MHz, DMSO-$D_6$, T=90° C.) ppm 1.41 (d, J=8.9 Hz, 1H) 2.11 (d, J=8.5 Hz, 1H) 2.55 (d, J=8.2 Hz, 1H) 2.63 (d, J=4.6 Hz, 3H) 2.79 (s, 1H) 2.87 (s, 1H) 3.19 (d, J=5.2 Hz, 1H) 4.14 (t, J=7.9 Hz, 1H) 4.65 (s, 2H) 6.23-6.35 (m, 2H) 6.76-7.01 (m, 1H) 7.37-7.62 (m, 3H) 7.76 (s, 1H) 7.85 (s, 1H) 8.75 (s, 1H); MS (ESI(+)) m/e 417 (M+H)$^+$.

Example 76

(1S,2S,3R,4R)-3-[(2-{[1-(2-amino-2-oxoethyl)-1H-pyrazol-4-yl]amino}-5-bromopyrimidin-4-yl)amino]bicyclo[2.2.1]hept-5-ene-2-carboxamide The title compound was prepared as described in Example 1, substituting 2-(4-amino-1H-pyrazol-1-yl)acetamide for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1H$ NMR (400 MHz, DMSO-$D_6$, T=90° C.) ppm 1.41 (d, J=8.9 Hz, 1H) 2.12 (d, J=8.5 Hz, 1H) 2.52-2.58 (m, 1H) 2.78 (s, 1H) 2.87 (s, 1H) 4.11-4.21 (m, 1H) 4.65 (s, 2H) 6.25-6.34 (m, 2H) 6.77-7.03 (m, 3H) 7.38-7.52 (m, J=7.6 Hz, 2H) 7.56 (s, 1H) 7.75 (s, 1H) 7.92 (s, 1H) 8.75 (s, 1H); MS (ESI(+)) m/e 447, 449 (M+H)$^+$.

Example 77

(1S,2S,3R,4R)-3-{[5-bromo-2-({1-[2-(methylamino)-2-oxoethyl]-1H-pyrazol-4-yl}amino)pyrimidin-4-yl]amino}bicyclo[2.2.1]hept-5-ene-2-carboxamide The title compound was prepared as described in Example 1, substituting 2-(4-amino-1H-pyrazol-1-yl)-N-methylacetamide for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-D$_6$, T=90° C.) ppm 1.42 (d, J=8.9 Hz, 1H) 2.12 (d, J=8.9 Hz, 1H) 2.54 (dd, J=8.2, 1.2 Hz, 1H) 2.63 (d, J=4.6 Hz, 3H) 2.77 (d, J=2.1 Hz, 1H) 2.87 (s, 1H) 4.06-4.22 (m, 1H) 4.65 (s, 2H) 6.24-6.36 (m, 2H) 6.72-6.99 (br s, 1H) 7.41-7.59 (m, 3H) 7.75 (s, 1H) 7.92 (s, 1H) 8.74 (s, 1H); MS (ESI(+)) m/e 461, 463 (M+H)$^+$.

Example 78 isopropyl{4-[(4-{[(1R,2R,3S,4S)-3-(aminocarbonyl)bicyclo[2.2.1]hept-5-ene-2-yl]amino}-5-chloropyrimidin-2-yl)amino]-1H-pyrazol-1-yl}acetate The title compound was prepared as described in Example 1, substituting 2-(4-amino-1H-pyrazol-1-yl)acetic acid for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-D$_6$, T=90° C.) ppm 1.14-1.25 (m, 7H) 1.42 (d, 1H) 2.11 (d, J=9.2 Hz, 1H) 2.54 (d, J=8.6 Hz, 1H) 2.79 (s, 1H) 2.88 (s, 1H) 4.13 (t, J=8.1 Hz, 1H) 4.87 (s, 2H) 4.90-5.07 (m, 1H) 6.21-6.36 (m, 2H) 7.51-7.62 (m, 2H) 7.77 (s, 1H) 7.85 (s, 1H) 8.76 (s, 1H); MS (ESI(+)) m/e 446.0 (M+H)$^+$.

Example 79

(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-D$_6$, T=90° C.) ppm 1.36 (t, J=7.32 Hz, 3H) 1.42 (d, J=8.54 Hz, 1H) 2.12 (d, J=8.85 Hz, 1H) 2.55 (d, J=7.93 Hz, 1H) 2.77 (s, 1H) 2.88 (s, 1H) 4.05 (q, J=7.32 Hz, 2H) 4.16 (t, J=7.93 Hz, 1H) 6.21-6.39 (m, 2H) 6.77-6.97 (m, 1H) 7.36-7.54 (m, 3H) 7.70 (s, 1H) 7.91 (s, 1H) 8.68 (s, 1H); MS (ESI(+)) m/e 420 (M+H)$^+$.

Example 80

(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide

Example 80A (+)-(1R,2S,3R,4S)-3-aminobicyclo[2.2.1]heptane-2-carboxamide

The title compound was prepared as described in Example 13A substituting (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide.

Example 80B (1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide The title compound was prepared as described in Example 1, substituting 1-ethyl-1H-pyrazol-4-amine for 1-methyl-1H-pyrazol-4-amine in Example 1B along with substitution of (+)-(1R,2S,3R,4S)-3-aminobicyclo[2.2.1]heptane-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-D$_6$) ppm 1.15 (d, J=9.77 Hz, 1H) 1.22-1.33 (m, 2H) 1.37 (t, J=7.17 Hz, 3H) 1.45-1.68 (m, 5H) 1.89 (d, J=10.07 Hz, 1H) 2.22-2.33 (m, 1H) 2.62 (d, J=8.24 Hz, 1H) 4.07 (q, J=7.22 Hz, 2H) 4.24 (t, J=7.48 Hz, 1H) 6.69-6.93 (m, 1H) 7.26-7.43 (m, 1H) 7.78 (s, 1H) 8.06 (s, 1H) 9.09 (s, 1H); MS (ESI(+)) m/e 410 (M+H)$^+$.

Example 81

(1S,2S,3R,4R)-3-({2-[(1-azetidin-3-yl-1H-pyrazol-4-yl)amino]-5-chloropyrimidin-4-yl}amino)bicyclo[2.2.1]hept-5-ene-2-carboxamide

Example 81A tert-butyl 3-(4-amino-1H-pyrazol-1-yl)azetidine-1-carboxylate

The title compound was prepared as described in Example 41A substituting tert-butyl 3-hydroxyazetidine-1-carboxylate for 1-methylpiperidin-4-ol.

Example 81B (1S,2S,3R,4R)-3-({2-[(1-azetidin-3-yl-1H-pyrazol-4-yl)amino]-5-chloropyrimidin-4-yl}amino)bicyclo[2.2.1]hept-5-ene-2-carboxamide The title compound was prepared as described in Example 72, substituting tert-butyl 3-(4-amino-1H-pyrazol-1-yl)azetidine-1-carboxylate for (S)-tert-butyl 3-(4-amino-1H-pyrazol-1-yl)pyrrolidine-1-carboxylate in Example 73C. $^1$H NMR (400 MHz, PYRIDINE-D$_5$, T=90° C.) ppm 1.55 (d, J=8.9 Hz, 1H) 2.49 (d, J=8.9 Hz, 1H) 2.77 (dd, J=8.2, 1.22 Hz, 1H) 2.95 (s, 1H) 3.07 (s, 1H) 4.39 (t, J=7.8 Hz, 1H) 4.64-4.72 (m, 4H) 5.51-5.59 (m, 1H) 6.19-6.27 (m, 2H) 8.03 (s, 1H) 8.09 (s, 1H) 8.11 (s, 1H) 8.14 (s, 1H) 9.29-9.67 (m, 1H); MS (ESI(+)) m/e 401 (M+H)$^+$.

Example 82

(1S,2S,3R,4R)-3-({5-chloro-2-[(1-piperidin-4-yl-1H-pyrazol-4-yl)amino]pyrimidin-4-yl}amino)bicyclo[2.2.1]hept-5-ene-2-carboxamide

Example 82A tert-butyl 4-(4-amino-1H-pyrazol-1-yl)piperidine-1-carboxylate

The title compound was prepared as described in Example 41A substituting tert-butyl 4-hydroxypiperidine-1-carboxylate for 1-methylpiperidin-4-ol.

Example 82B (1S,2S,3R,4R)-3-({5-chloro-2-[(1-piperidin-4-yl-1H-pyrazol-4-yl)amino]pyrimidin-4-yl}amino)bicyclo[2.2.1]hept-5-ene-2-carboxamide The title compound was prepared as described in Example 72, substituting tert-butyl 4-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (300 MHz, DMSO-D$_6$) ppm 1.41 (d, J=8.7 Hz, 1H) 1.64-1.79 (m, 2H) 1.87-1.96 (m, 2H) 2.12 (d, J=8.7 Hz, 1H) 2.51-2.62 (m, 3H) 2.76 (s, 1H) 2.87 (s, 1H) 2.98-3.08 (m, 2H) 3.96-4.18 (m, 2H) 6.29 (dd, J=5.6, 2.78 Hz, 1H) 6.37 (dd, J=5.6, 2.78 Hz, 1H) 7.24 (s, 1H) 7.52 (s, 1H) 7.58-7.70 (m, 1H) 7.76 (s, 2H) 7.89 (s, 1H) 9.07 (s, 1H); MS (ESI(+)) m/e 429 (M+H)$^+$.

Example 83

(1S,2S,3R,4R)-3-{[5-chloro-2-({1-[(3S)-piperidin-3-yl]-1H-pyrazol-4-yl}amino)pyrimidin-4-yl]amino}bicyclo[2.2.1]hept-5-ene-2-carboxamide

Example 83A (S)-tert-butyl 3-(4-amino-1H-pyrazol-1-yl)piperidine-1-carboxylate The title compound was prepared as described in Example 40A substituting (R)-tert-butyl 3-hydroxypiperidine-1-carboxylate for 1-methylpiperidin-4-ol.

Example 83B (1S,2S,3R,4R)-3-{[5-chloro-2-({1-[(3S)-piperidin-3-yl]-1H-pyrazol-4-yl}amino)pyrimidin-4-yl]amino}bicyclo[2.2.1]hept-5-ene-2-carboxamide The title compound was prepared as described in Example 72, substituting (S)-tert-butyl 3-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (400 MHz, PYRIDINE-D$_5$, T=90° C.) ppm 1.43-1.54 (m, 1H) 1.56 (dt, J=9.1, 1.56 Hz, 1H) 1.61-1.70 (m, 1H) 1.96-2.07 (m, 1H) 2.11-2.19 (m, 1H) 2.49-2.54 (m, 1H) 2.57 (ddd, J=12.5, 10.7, 3.1 Hz, 1H) 2.76 (d, J=8.2 Hz, 1H) 2.89 (dt, J=12.3, 3.93 Hz, 1H) 2.95 (s, 1H) 3.01-3.08 (m, 1H) 3.05 (s, 1H) 3.40 (dd, J=12.1, 3.5 Hz, 1H) 4.17-4.25 (m, 1H) 4.46 (td, J=7.9, 1.5 Hz, 1H) 6.18 (dd, J=5.6, 2.9 Hz, 1H) 6.29 (dd, J=5.5, 3.1 Hz, 1H) 7.87 (d, J=6.7 Hz, 1H) 7.93 (s, 1H) 8.03 (s, 1H) 8.08 (s, 1H) 9.19 (s, 1H); MS (ESI(+)) m/e 429 (M+H)$^+$.

Example 84

(1S,2S,3R,4R)-3-{[5-chloro-2-({1-[(3R)-piperidin-3-yl]-1H-pyrazol-4-yl}amino)pyrimidin-4-yl]amino}bicyclo[2.2.1]hept-5-ene-2-carboxamide

Example 84A (R)-tert-butyl 3-(4-amino-1H-pyrazol-1-yl)piperidine-1-carboxylate The title compound was prepared as described in Example 40A substituting (S)-tert-butyl 3-hydroxypiperidine-1-carboxylate for 1-methylpiperidin-4-ol.

Example 84

(1S,2S,3R,4R)-3-{[5-chloro-2-({1-[(3R)-piperidin-3-yl]-1H-pyrazol-4-yl}amino)pyrimidin-4-yl]amino}bicyclo[2.2.1]hept-5-ene-2-carboxamide The title compound was prepared as described in Example 72, substituting (R)-tert-butyl 3-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (400 MHz, PYRIDINE-D$_5$, T=90° C.) ppm 1.43-1.53 (m, 1H) 1.55 (d, J=10.1 Hz, 1H) 1.62-1.71 (m, 1H) 1.94-2.07 (m, 1H) 2.11-2.20 (m, 1H) 2.51 (d, J=8.9 Hz, 1H) 2.53-2.61 (m, 1H) 2.75 (d, J=7.9 Hz, 1H) 2.90 (dt, J=12.2, 3.8 Hz, 1H) 2.95 (s, 1H) 3.01-3.09 (m, 2H) 3.41 (dd, J=11.9, 3.4 Hz, 1H) 4.17-4.26 (m, 1H) 4.46 (t, J=7.9 Hz, 1H) 6.18 (dd, J=5.7, 2.90 Hz, 1H) 6.25-6.31 (m, 1H) 7.86 (d, J=7.6 Hz, 1H) 7.93 (s, 1H) 8.03 (s, 1H) 8.08 (s, 1H) 9.17 (s, 1H); MS (ESI(+)) m/e 429 (M+H)$^+$.

Example 85

(1S,2S,3R,4R)-3-{[2-({1-[1-(N-acetylglycyl)piperidin-4-yl]-1H-pyrazol-4-yl}amino)-5-chloropyrimidin-4-yl]amino}bicyclo[2.2.1]hept-5-ene-2-carboxamide (1S,2S,3R,4R)-3-(5-Chloro-2-(1-(piperidin-4-yl)-1H-pyrazol-4-ylamino)pyrimidin-4-ylamino)bicyclo[2.2.1]hept-5-ene-2-carboxamide (85 mg, 0.20 mmol), N-acetylglycine (26 mg, 0.22 mmol), 1-ethyl-3-[3-(dimethylamino)propyl]-carbodiimide hydrochloride (76 mg, 0.40 mmol) and 1-hydroxybenzotriazole hydrate (61 mg, 0.40 mmol) were taken up in N,N-dimethylformamide (1 mL), and N-methylmorpholine (0.11 mL, 1.0 mmol) was added. The reaction mixture was stirred at room temperature for 4 hours, then diluted with NaHCO$_3$ solution (30 mL). The mixture was extracted with ethyl acetate (3×20 mL), and the extracts were dried (Na$_2$SO$_4$) and concentrated. The residue was purified by flash chromatography, using a 12 g silica cartridge and eluting with a gradient from 0 to 8% methanol/CH$_2$Cl$_2$ over 30 minutes at a flow rate of 30 mL/minutes, yielding the desired product. $^1$H NMR (400 MHz, DMSO-D$_6$) ppm 1.42 (d, J=8.9 Hz, 1H) 1.73-1.86 (m, 2H) 1.88 (s, 3H) 2.01-2.08 (m, 2H) 2.13 (d, J=8.9 Hz, 1H) 2.55 (d, J=7.9 Hz, 1H) 2.76 (s, 1H) 2.87 (s, 1H) 2.93-3.14 (br m, 4H) 3.96 (d, J=5.2 Hz, 2H) 4.17 (t, J=7.9 Hz, 1H) 4.29-4.38 (m, 1H) 6.25 (dd, J=5.8, 3.1 Hz, 1H) 6.34 (dd, J=5.7, 2.9 Hz, 1H) 6.73-7.03 (br, 1H) 7.34-7.52 (br, 1H) 7.47 (d, J=7.6 Hz, 1H) 7.54 (s, 1H) 7.57-7.65 (br s, 1H) 7.75 (s, 1H) 7.84 (s, 1H) 8.69 (s, 1H); MS (ESI(+)) m/e 528 (M+H)$^+$.

Example 86

4-{[(1S,2S,3R,4R)-3-carbamoylbicyclo[2.2.1]hept-5-en-2-yl]amino}-2-[(1-methyl-1H-pyrazol-4-yl)amino]pyrimidine-5-carboxamide and 4-{[(1R,2R,3S,4S)-3-carbamoylbicyclo[2.2.1]hept-5-en-2-yl]amino}-2-[(1-methyl-1H-pyrazol-4-yl)amino]pyrimidine-5-carboxamide The title compound was prepared as described in Example 1, substituting 2,4-dichloro-5-carboxamidepyrimidine for 2,4-dichloro-5-fluoropyrimidine in Example 1A. $^1$H NMR (300 MHz, DMSO-d$_6$) ppm 1.44 (d, J=8.72 Hz, 1H) 2.16 (d, J=8.72 Hz, 1H) 2.68 (s, 1H) 2.82 (s, 1H) 3.76 (s, 3H) 4.39 (s, 1H) 6.31 (d, J=7.54 Hz, 2H) 6.85 (s, 2H) 7.26 (s, 2H) 7.54 (s, 1H) 7.70 (s, 1H) 8.41 (s, 1H) 8.94-9.29 (m, 1H) 9.38 (s, 1H) 9.50 (s, 1H); MS (ESI(+)) m/e 369 (M+H)$^+$.

Example 87

4-{[(1S,2S,3R,4R)-3-carbamoylbicyclo[2.2.1]hept-5-ene-2-yl]amino}-2-[(1-ethyl-1H-pyrazol-4-yl)amino]pyrimidine-5-carboxamide and 4-{[(1R,2R,3S,4S)-3-carbamoylbicyclo[2.2.1]hept-5-ene-2-yl]amino}-2-[(1-ethyl-1H-pyrazol-4-yl)amino]pyrimidine-5-carboxamide The title compound was prepared as described in Example 1, substituting 1-ethyl-1H-pyrazol-4-amine for 1-methyl-1H-pyrazol-4-amine in Example 1B along with substitution of 2,4-dichloro-5-carboxamidepyrimidine for 2,4-dichloro-5-fluoropyrimidine in Example 1A. $^1$H NMR (300 MHz, DMSO-d$_6$) ppm 1.28-1.37 (m, 3H) 1.44 (d, J=8.73 Hz, 1H) 2.17 (d, J=8.72 Hz, 1H) 2.67 (s, 1H) 2.82 (s, 1H) 4.07 (q, J=7.54 Hz, 2H) 4.44 (s, 1H) 6.21-6.36 (m, 2H) 6.83 (bs, 2H) 7.24 (bs, 2H) 7.54 (s, 1H) 7.76 (s, 1H) 8.41 (s, 1H) 9.20 (bs, 1H) 9.38 (s, 1H) 9.49 (s, 1H); MS (ESI(+)) m/e 383 (M+H)$^+$.

Example 88

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide The title compound was prepared as described in Example 1, substituting 2-(4-amino-1H-pyrazol-1-yl)-N-methylacetamide for 1-methyl-1H-pyrazol-4-amine in Example 1B along with substitution of (+)-(1S,2S,3R,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.14 (d, J=10.07 Hz, 1H) 1.20-1.40 (m, 2H) 1.44-1.66 (m, 2H) 1.95 (d, J=9.77 Hz, 1H) 2.23 (d, J=3.97 Hz, 1H) 2.31 (d, J=1.83 Hz, 1H) 2.58-2.73 (m, J=5.19, 5.19 Hz, 4H) 4.17 (t, J=7.78 Hz, 1H) 4.64 (s, 2H) 6.70 (br s, 1H) 7.30 (br s, 1H) 7.43-7.59 (m, 3H) 7.81 (s, 1H), 7.82 (s, 1H) 8.71 (s, 1H); MS (ESI(+)) m/e 419 (M+H)$^+$.

Example 89

(1S,2S,3R,4R)-3-{[5-chloro-2-({1-[1-(N,N-dimethylglycyl)piperidin-4-yl]-1H-pyrazol-4-yl}amino)pyrimidin-4-yl]amino}bicyclo[2.2.1]hept-5-ene-2-carboxamide The title compound was prepared as described in Example 86 substituting N,N-dimethylglycine for N-acetylglycine. $^1$H NMR (300 MHz, DMSO-d$_6$) ppm 1.41 (d, J=9.12 Hz, 1H) 1.58-1.76 (m, 1H) 1.76-1.92 (m, 1H) 2.02 (d, J=11.50 Hz, 2H) 2.12 (d, J=8.72 Hz, 1H) 2.21 (s, 6H) 2.51-2.58 (m, 1H) 2.65-2.80 (m, 2H) 2.88 (s, 1H) 3.08-3.20 (m, 3H) 4.11-4.16 (m, 2H) 4.27-4.40 (m, 1H) 4.40-4.47 (m, 1H) 6.27 (dd, J=5.35, 2.97 Hz, 1H) 6.36 (dd, J=5.55, 2.78 Hz, 1H) 7.24 (s, 1H) 7.54 (s, 1H) 7.58-7.71 (m, 1H) 7.77 (s, 2H) 7.89 (s, 1H) 9.10 (s, 1H); MS (ESI(+)) m/e 514 (M+H)$^+$.

Example 90

(1R,2S,3R,4S)-3-{[5-chloro-2-({1-[2-(4-methylpiperazin-1-yl)ethyl]-1H-pyrazol-4-yl}amino)pyrimidin-4-yl]amino}bicyclo[2.2.1]heptane-2-carboxamide The title compound was prepared as described in Example 1, substituting 1-(2-(4-methylpiperazin-1-yl)ethyl)-1H-pyrazol-4-amine for 1-methyl-1H-pyrazol-4-amine in Example 1B along with substitution of (+)-(1S,2S,3R,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) d ppm 1.15 (d, J=9.83 Hz, 1H) 1.20-1.40 (m, 2H) 1.45-1.68 (m, 2H) 1.92 (d, J=9.83 Hz, 1H) 2.14 (s, 3H) 2.19-2.34 (m, 6H) 2.35-2.45 (m, 4H) 2.59-2.71 (m, 3H) 4.09-4.17 (m, 3H) 7.15 (s, 1H) 7.49 (s, 1H) 7.69 (s, 1H) 7.70-7.88 (br s, 1H) 7.81 (s, 1H) 7.86 (s, 1H) 9.06 (s, 1H); MS (ESI(+)) m/e 474 (M+H)$^+$.

Example 91

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide The title compound was prepared as described in Example 1, substituting 1-(2-(4-methylpiperazin-1-yl)ethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) d ppm 1.41 (d, J=8.48 Hz, 1H) 2.06-2.13 (m, 1H) 2.12 (s, 3H) 2.20-2.33 (br m, 4H) 2.34-2.43 (br m, 4H) 2.51-2.58 (m, 1H) 2.66 (t, J=6.78 Hz, 2H) 2.78 (s, 1H) 2.88 (s, 1H) 4.07-4.16 (m, 3H) 6.27-6.39 (m, 2H) 7.25 (s, 1H) 7.51 (s, 1H) 7.70-7.82 (m, J=8.65, 8.65 Hz, 3H) 7.88 (s, 1H) 9.09 (s, 1H); MS (ESI(+)) m/e 472 (M+H)$^+$.

Example 92

(1S,2S,3R,4R)-3-[(2-{[1-(1-acetylpiperidin-4-yl)-1H-pyrazol-4-yl]amino}-5-chloropyrimidin-4-yl)amino]bicyclo[2.2.1]hept-5-ene-2-carboxamide The title compound was prepared as described in Example 86 substituting acetic acid for N-acetylglycine. $^1$H NMR (300 MHz, DMSO-d$_6$) d ppm 1.41 (d, J=8.48 Hz, 1H) 1.59-1.75 (m, 1H) 1.75-1.91 (m, 1H) 1.92-2.02 (m, 1H) 2.03 (s, 3H) 2.12 (d, J=8.48 Hz, 1H) 2.52-2.57 (m, 1H) 2.63-2.79 (m, 2H) 2.88 (s, 1H) 3.13-3.24 (m, 1H) 3.85-3.96 (m, 1H) 3.98-4.15 (br m, 1H) 4.14 (t, J=7.97 Hz, 1H) 4.28-4.40 (m, 1H) 4.40-4.51 (m, 1H) 6.24-6.29 (m, 1H) 6.36 (dd, J=5.59, 2.88 Hz, 1H) 7.24 (s, 1H) 7.54 (d, J=5.43 Hz, 1H) 7.60-7.72 (m, 1H) 7.77 (s, 2H) 7.89 (s, 1H) 9.11 (s, 1H); MS (ESI(+)) m/e 471 (M+H)$^+$.

Example 93

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide The title compound was prepared as described in Example 1, substituting 2-(4-amino-1H-pyrazol-1-yl)ethanol for 1-methyl-1H-pyrazol-4-amine in Example 1B along with substitution of (+)-(1S,2S,3R,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.15 (d, J=10.07 Hz, 1H) 1.21-1.42 (m, 2H) 1.44-1.69 (m, 2H) 2.23 (d, J=3.97 Hz, 1H) 2.31 (d, J=3.05 Hz, 1H) 2.64 (d, J=8.24 Hz, 1H) 3.74 (q, J=5.59 Hz, 2H) 4.07 (t, J=5.65 Hz, 2H) 4.17 (t, J=7.48 Hz, 1H) 4.54 (t, J=5.49 Hz, 1H) 6.75 (br s, 1H) 7.30 (br s, 1H) 7.44-7.59 (m, 2H) 7.79 (s, 1H), 7.81 (s, 1H) 8.63 (s, 1H).

Example 94

(1S,2S,3R,4R)-3-{[5-bromo-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide The title compound was prepared as described in Example 1, substituting 1-(2-(4-methylpiperazin-1-yl)ethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) δ ppm 1.41 (d, J=8.81 Hz, 1H) 2.10 (d, J=8.81 Hz, 1H) 2.18 (s, 3H) 2.28-2.47 (m, 8H) 2.52-2.56 (m, 1H) 2.67 (t, J=6.78 Hz, 2H) 2.77 (s, 1H) 2.88 (s, 1H) 4.08-4.16 (m, 3H) 6.25-6.41 (m, 2H) 7.25 (s, 1H) 7.51 (s, 1H) 7.67-7.83 (m, 3H) 7.95 (s, 1H) 9.11 (s, 1H); MS (ESI(+)) m/e 516, 518, Br pattern, (M+H)$^+$.

Example 95

(1S,2S,3R,4R)-3-[(5-bromo-2-{[1-(piperidin-4-yl)-1H-pyrazol-4-yl]amino}pyrimidin-4-yl)amino]bicyclo[2.2.1]hept-5-ene-2-carboxamide The title compound was prepared as described in Example 73, substituting 2,4-dichloro-5-bromopyrimidine for 2,4,5-trichloropyrimidine in Example 73B and tert-butyl 4-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (300 MHz, DMSO-d$_6$) d ppm 1.41 (d, J=9.15 Hz, 1H) 2.01-2.20 (m, 5H) 2.72-2.79 (m, 1H) 2.88 (s, 1H) 2.99-3.12 (m, 2H) 3.34-3.44 (m, 2H) 4.07-4.16 (m, 1H) 4.34-4.47 (m, 1H) 6.24-6.39 (m, 2H) 7.25 (s, 1H) 7.49-7.81 (m, 4H) 7.96 (s, 1H) 8.43-8.66 (m, 2H) 9.12 (s, 1H); MS (ESI(+)) m/e 473, 475, Br pattern (M+H)$^+$.

Example 96

(1S,2S,3R,4R)-3-[(5-chloro-2-{[1-(2-methoxyethyl)-1H-pyrazol-4-yl]amino}pyrimidin-4-yl)amino]bicyclo[2.2.1]hept-5-ene-2-carboxamide

Example 96A 1-(2-methoxyethyl)-1H-pyrazol-4-amine

The title compound was prepared as described in Example 41A substituting 2-methoxyethanol for 1-methylpiperidin-4-ol.

Example 96B (1S,2S,3R,4R)-3-[(5-chloro-2-{[1-(2-methoxyethyl)-1H-pyrazol-4-yl]amino}pyrimidin-4-yl)amino]bicyclo[2.2.1]hept-5-ene-2-carboxamide The title compound was prepared as described in Example 1, substituting 1-(2-methoxyethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=9.12 Hz, 1H) 2.10 (d, J=8.72 Hz, 1H) 2.55 (s, 1H) 2.78 (s, 1H) 2.88 (s, 1H) 3.21 (s, 3H) 3.64 (t, J=5.16 Hz, 2H) 4.11 (t, J=7.73 Hz, 1H) 4.17 (t, J=5.35 Hz, 2H) 6.34 (d, J=8.33 Hz, 2H) 7.26 (s, 1H) 7.51 (s, 1H) 7.70-7.83 (m, 3H) 7.89 (s, 1H) 9.11 (s, 1H); MS (ESI(+)) m/e 404 (M+H)$^+$.

Example 97

(1S,2S,3R,4R)-3-{[5-chloro-2-({1-[(1-methylpiperidin-4-yl)methyl]-1H-pyrazol-4-yl}amino)pyrimidin-4-yl]amino}bicyclo[2.2.1]hept-5-ene-2-carboxamide

Example 97A

1-[(1-methylpiperidin-4-yl)methyl]-1H-pyrazol-4-amine

The title compound was prepared as described in Example 41A substituting (1-methylpiperidin-4-yl)methanol for 1-methylpiperidin-4-ol.

Example 97B (1S,2S,3R,4R)-3-{[5-chloro-2-({1-[(1-methylpiperidin-4-yl)methyl]-1H-pyrazol-4-yl}amino)pyrimidin-4-yl]amino}bicyclo[2.2.1]hept-5-ene-2-carboxamide The title compound was prepared as described in Example 1, substituting 1-[(1-methylpiperidin-4-yl)methyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) δ ppm 1.17-1.35 (m, 2H) 1.41 (d, J=8.72 Hz, 1H) 1.45-1.57 (m, 2H) 1.70-1.87 (m, 1H) 1.99-2.38 (m, 6H) 2.51-2.56 (m, 1H) 2.78 (s, 1H) 2.83-3.00 (m, 3H) 3.93 (d, J=6.74 Hz, 2H) 4.11 (t, J=7.73 Hz, 1H) 6.25-6.41 (m, 2H) 7.26 (s, 1H) 7.52 (s, 1H) 7.64-7.85 (m, 3H) 7.89 (s, 1H) 9.11 (s, 1H); MS (ESI(+)) m/e 457 (M+H)+.

Example 98

(1S,2S,3R,4R)-3-({5-chloro-2-[(1-isopropyl-1H-pyrazol-4-yl)amino]pyrimidin-4-yl}amino)bicyclo[2.2.1]hept-5-ene-2-carboxamide

Example 98A 1-isopropyl-1H-pyrazol-4-amine

The title compound was prepared as described in Example 55A substituting 2-iodopropane for 2-chloro-N,N-dimethylacetamide.

Example 98B (1S,2S,3R,4R)-3-({5-chloro-2-[(1-isopropyl-1H-pyrazol-4-yl)amino]pyrimidin-4-yl}amino)bicyclo[2.2.1]hept-5-ene-2-carboxamide The title compound was prepared as described in Example 1, substituting 1-isopropyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-D$_6$) ppm 1.39 (d, J=6.74 Hz, 7H) 2.12 (d, J=8.33 Hz, 1H) 2.88 (s, 1H) 4.14 (t, J=7.54 Hz, 1H) 4.34-4.49 (m, 1H) 6.27 (d, J=3.17 Hz, 1H) 6.37 (d, J=5.16 Hz, 1H) 7.25 (s, 1H) 7.51 (s, 1H) 7.65 (s, 1H) 7.76 (d, J=5.95 Hz, 3H) 7.89 (s, 1H) 9.08 (s, 1H); MS (ESI(+)) m/e 388 (M+H)+.

Example 99

(1S,2S,3R,4R)-3-[(5-chloro-2-[1-(3-methylbutyl)-1H-pyrazol-4-yl]amino pyrimidin-4-yl)amino]bicyclo[2.2.1]hept-5-ene-2-carboxamide

Example 99A 1-isopentyl-1H-pyrazol-4-amine

The title compound was prepared as described in Example 55A substituting 1-iodo-3-methylbutane for 2-chloro-N,N-dimethylacetamide.

Example 99B (1S,2S,3R,4R)-3-[(5-chloro-2-[1-(3-methylbutyl)-1H-pyrazol-4-yl]amino pyrimidin-4-yl)amino]bicyclo[2.2.1]hept-5-ene-2-carboxamide The title compound was prepared as described in Example 1, substituting 1-isopentyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 0.89 (d, J=6.35 Hz, 7H) 1.37-1.55 (m, 2H) 1.58-1.69 (m, 2H) 2.11 (d, J=8.72 Hz, 1H) 2.78 (s, 1H) 2.88 (s, 1H) 4.04 (t, J=7.34 Hz, 2H) 4.12 (t, J=7.93 Hz, 1H) 6.23-6.33 (m, 1H) 6.36 (d, J=5.55 Hz, 1H) 7.26 (s, 1H) 7.48 (s, 1H) 7.67-7.83 (m, 3H) 7.89 (s, 1H) 9.10 (s, 1H); MS (ESI(+)) m/e 416 (M+H)+.

Example 100

(1S,2S,3R,4R)-3-{[5-chloro-2-({1-[2-(2-methoxyethoxy)ethyl]-1H-pyrazol-4-yl}amino)pyrimidin-4-yl]amino}bicyclo[2.2.1]hept-5-ene-2-carboxamide

Example 100A

1-[2-(2-methoxyethoxy)ethyl]-1H-pyrazol-4-amine

The title compound was prepared as described in Example 55A substituting 1-bromo-2-(2-methoxyethoxy)ethane for 2-chloro-N,N-dimethylacetamide.

Example 100B (1S,2S,3R,4R)-3-{[5-chloro-2-({1-[2-(2-methoxyethoxy)ethyl]-1H-pyrazol-4-yl}amino)pyrimidin-4-yl]amino}bicyclo[2.2.1]hept-5-ene-2-carboxamide The title compound was prepared as described in Example 1, substituting 1-[2-(2-methoxyethoxy)ethyl]-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=8.72 Hz, 1H) 2.10 (d, J=8.72 Hz, 1H) 2.78 (s, 1H) 2.88 (s, 1H) 3.20 (s, 3H) 3.36-3.42 (m, 2H) 3.48 (t, J=4.56 Hz, 2H) 3.73 (t, J=5.35 Hz, 2H) 4.06-4.13 (m, 1H) 4.17 (t, J=5.35 Hz, 2H) 6.35 (s, 2H) 7.26 (s, 1H) 7.53 (s, 1H) 7.78 (d, J=7.54 Hz, 3H) 7.89 (s, 1H) 9.10 (s, 1H); MS (ESI(+)) m/e 448 (M+H)+.

Example 101

1-[2-({5-chloro-2-[(1-methyl-1H-pyrazol-4-yl)amino]pyrimidin-4-yl}amino)phenyl]cyclobutanol

Example 101A

N-(2-(1-hydroxycyclobutyl)phenyl)formamide

Sodium hydride (65% dispersion in mineral oil, 71 mg, 1.775 mmol) was suspended in tetrahydrofuran (6 mL), and to this stirred slurry was added dropwise a solution of N-(2-iodophenyl)formamide (250 mg, 1.012 mmol) in tetrahydrofuran (4 mL). The mixture was stirred at room temperature for 20 minutes, then chilled to −78° C. To the cold suspension was added dropwise 2.5 M n-butyllithium in hexanes (0.506 ml, 1.265 mmol). The mixture was stirred at −78° C. for 30 minutes, then cyclobutanone (0.083 ml, 1.113 mmol) was added dropwise. The mixture was stirred at −78° C. for 2 hours and quenched with saturated NH$_4$Cl (20 mL) solution and warmed to room temperature. The mixture was extracted with ethyl acetate (3×30 mL), and the combined organic layers were dried (Na$_2$SO$_4$), filtered, and concentrated. The product was purified by flash chromatography (Analogix, 20 to 50% ethyl acetate-hexanes over 25 min, 4 g silica cartridge, 18 mL/min) to give the title compound as a 2:1 ratio of two rotational isomers.

Example 101B 1-(2-aminophenyl)cyclobutanol

N-(2-(1-hydroxycyclobutyl)phenyl)formamide (103 mg, 0.539 mmol) and potassium hydroxide (0.015 mL, 0.539 mmol) were combined in methanol (3 mL) and the mixture was heated to reflux for 3 hours. The reaction mixture was diluted with $H_2O$ (25 mL) and extracted with ethyl acetate (3×25 mL). The combined organic layers were dried ($Na_2SO_4$), filtered and concentrated. The product was purified by flash chromatography (Analogix, 0 to 40% ethyl acetate in hexanes over 25 minutes, 4 g silica, 18 mL/minutes) to give 1-(2-aminophenyl)cyclobutanol.

Example 101C 1-(2-(2,5-dichloropyrimidin-4-ylamino)phenyl)cyclobutanol 1-(2-Aminophenyl)cyclobutanol (56 mg, 0.343 mmol), 2,4,5-trichloropyrimidine (40 μl, 0.349 mmol) and N,N-diisopropylethylamine (120 μl, 0.694 mmol) were suspended in 2-propanol (1.5 mL) in a sealed tube, and the solution was heated to 85° C. for 4 hours. The reaction mixture was partitioned between $H_2O$ (15 mL) and $CH_2Cl_2$ (3×15 mL). The combined organic layers were dried ($Na_2SO_4$), filtered and concentrated. The product was purified by flash chromatography (Analogix, 0 to 25% ethyl acetate-hexanes over 25 minutes, 4 g silica, 18 mL/minute) to give the title compound.

Example 101D

1-[2-({5-chloro-2-[(1-methyl-1H-pyrazol-4-yl)amino]pyrimidin-4-yl}amino)phenyl]cyclobutanol The title compound was prepared as in Example 1, substituting 1-(2-(2,5-dichloropyrimidin-4-ylamino)phenyl)cyclobutanol for (+/−)-(1S,2S,3R,4R)-3-(2-chloro-5-fluoropyrimidin-4-ylamino)bicyclo[2.2.1]hept-5-ene-2-carboxamide in Example 1B. $^1$H NMR (300 MHz, DMSO-$d_6$) δ ppm 1.39-1.55 (m, 1H) 1.78-1.92 (m, 1H) 2.25-2.45 (m, 4H) 3.73 (s, 3H) 6.38 (s, 1H) 7.16 (t, J=7.12 Hz, 1H) 7.32-7.42 (m, 1H) 7.46 (d, J=7.80 Hz, 1H) 7.61-7.74 (m, 1H) 8.01-8.18 (m, 1H) 8.10 (s, 1H) 9.14-9.26 (m, 2H); MS (ESI(+)) m/e 371 (M+H)$^+$.

Example 102

(1S,2S,3R,4R)-3-{[5-chloro-2-({1-[(2R)-pyrrolidin-2-ylmethyl]-1H-pyrazol-4-yl}amino)pyrimidin-4-yl]amino}bicyclo[2.2.1]hept-5-ene-2-carboxamide

Example 102A (R)-tert butyl 2-((4-amino-1H-pyrazol-1-yl)methyl)pyrrolidine-1-carboxylate The title compound was prepared as in Example 41A substituting (R)-tert-butyl 2-(hydroxymethyl)pyrrolidine-1-carboxylate for 1-methylpiperidin-4-ol in Example 41A.

Example 102B (1S,2S,3R,4R)-3-{[5-chloro-2-({1-[(2R)-pyrrolidin-2-ylmethyl]-1H-pyrazol-4-yl}amino)pyrimidin-4-yl]amino}bicyclo[2.2.1]hept-5-ene-2-carboxamide (1S,2S,3R,4R)-3-(2,5-Dichloropyrimidin-4-ylamino)bicyclo[2.2.1]hept-5-ene-2-carboxamide (100 mg, 0.334 mmol) and (R)-tert-butyl 2-((4-amino-1H-pyrazol-1-yl)methyl)pyrrolidine-1-carboxylate (116 mg, 0.435 mmol) were combined with 2-propanol (2 ml) and 4N HCl in dioxane (0.084 ml, 0.334 mmol) in a sealed tube and the reaction was heated to 85° C. for 4 hours. The reaction mixture was concentrated to dryness, and the residue was treated with trifluoroacetic acid (3 mL). After stirring at room temperature for 30 minutes, the reaction mixture was again concentrated to dryness and the residue was suspended in saturated aqueous $NaHCO_3$ (5 mL). The resulting mixture was extracted with $CH_2Cl_2$ (2×10 mL) and ethyl acetate (2×10 mL). The organic extracts were combined, dried ($Na_2SO_4$) filtered, and concentrated. The residue was purified by flash chromotography (Analogix, 4 g column, 15 mL/minutes, 0 to 20% methanol (containing 5% $NH_4OH$)/$CH_2Cl_2$ over 25 minutes) to give the title compound. $^1$H NMR (300 MHz, DMSO-$d_6$) δ ppm 1.30-1.44 (m, 2H) 1.53-1.81 (m, 3H) 2.11 (d, J=8.82 Hz, 1H) 2.51-2.56 (m, 1H) 2.75-2.85 (m, 3H) 2.86-2.89 (m, 1H) 3.37-3.47 (m, 1H) 3.93-4.01 (m, 2H) 4.12 (t, J=7.12 Hz, 1H) 6.31-6.39 (m, 2H) 7.25 (s, 1H) 7.52 (s, 1H) 7.65-7.83 (m, 3H) 7.89 (s, 1H) 9.10 (s, 1H); MS (ESI(+)) m/e 429 (M+H)$^+$.

Example 103

{4-[(4-{[(1R,2R,3S,4S)-3-carbamoylbicyclo[2.2.1]hept-5-ene-2-yl]amino}-5-chloropyrimidin-2-yl)amino]-1H-pyrazol-1-yl}acetic acid The title compound was prepared as described in Example 1, substituting 2-(4-amino-1H-pyrazol-1-yl)acetic acid for 1-methyl-1H-pyrazol-4-amine and tert-butanol for 2-propanol in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$; T=90° C.) ppm 1.42 (d, J=8.85 Hz, 1H) 2.06 (d, J=9.16 Hz, 1H) 2.56 (d, J=7.93 Hz, 1H) 2.84 (s, 1H) 2.91 (s, 1H) 4.10 (t, J=7.32 Hz, 1H) 4.85 (s, 2H) 6.25 (dd, J=5.49, 3.05 Hz, 1H) 6.33 (dd, J=5.65, 2.90 Hz, 1H) 7.00 (br s, 1H) 7.45-7.66 (m, 2H) 7.80 (s, 1H) 7.96 (s, 1H) 8.52 (br s, 1H) 9.38 (br s, 1H); MS (ESI(+)) m/e 404 (M+H)$^+$.

Example 104

(1R,2S,3R,4S)-3-{[5-chloro-2-({1-[(2R)-2-hydroxypropyl]-1H-pyrazol-4-yl}amino)pyrimidin-4-yl]amino}bicyclo[2.2.1]heptane-2-carboxamide The title compound was prepared as described in Example 1, substituting 1-[(2R)-2-hydroxypropyl]-1H-pyrazol-4-amine for 1-methyl-1H-pyrazol-4-amine in Example 1B along with substitution of (+)-(1S,2S,3R,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 1.04 (d, J=5.80 Hz, 3H) 1.22-1.43 (m, 2H) 1.45-1.65 (m, 2H) 1.95 (d, J=9.77 Hz, 1H) 2.23 (d, J=4.27 Hz, 1H) 2.31 (d, J=2.44 Hz, 1H) 2.63 (d, J=8.24 Hz, 1H) 3.85-4.05 (m, 3H) 4.17 (t, J=7.78 Hz, 1H) 4.52 (d, J=4.58 Hz, 1H) 6.75 (br s, 1H) 7.29 (br s, 1H) 7.42-7.56 (m, 2H) 7.77 (s, 1H) 7.81 (s, 1H) 8.63 (s, 1H); MS (ESI(+)) m/e 406 (M+H)$^+$.

Example 105

(1S,2S,3R,4R)-3-{[5-chloro-2-({1-[(2R)-2-hydroxypropyl]-1H-pyrazol-4-yl}amino)pyrimidin-4-yl]amino}bicyclo[2.2.1]hept-5-ene-2-carboxamide The title compound was prepared as described in Example 1, substituting 1-[(2R)-2-hydroxypropyl]-1H-pyrazol-4- amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.05 (d, J=5.80 Hz, 3H) 1.43 (d, J=8.54 Hz, 1H) 2.13 (d, J=8.85 Hz, 1H) 2.56 (d, J=7.93 Hz, 1H) 2.79 (s, 1H) 2.89 (s, 1H) 3.81-4.05 (m, 3H) 4.16 (t, J=7.78 Hz, 1H) 4.45-4.63 (m, J=4.27 Hz, 1H) 6.23-6.39 (m, 2H) 6.85 (br s, 1H) 7.45 (m, 3H) 7.74 (s, 1H) 7.84 (s, 1H) 8.67 (s, 1H); MS (ESI(+)) m/e 404 (M+H)$^+$.

Example 106

(1S,2S,3R,4R)-3-[(5-bromo-2-{[1-(2-methoxyethyl)-1H-pyrazol-4-yl]amino}pyrimidin-4-yl)amino]bicyclo[2.2.1]hept-5-ene-2-carboxamide The title compound was prepared as described in Example 1, substituting 1-(2-methoxyethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) ppm 1.41 (d, J=8.81 Hz, 1H) 2.10 (d, J=9.15 Hz, 1H) 2.77 (s, 1H) 2.87 (s, 1H) 3.22 (s, 3H) 3.64 (t, J=5.26 Hz, 2H) 4.11 (t, J=7.80 Hz, 1H) 4.17 (t, J=5.26 Hz, 2H) 6.31-6.38 (m, 2H) 7.25 (s, 1H) 7.52 (s, 1H) 7.76 (d, J=12.54 Hz, 3H) 7.95 (s, 1H) 9.12 (s, 1H); MS (ESI(+)) m/e 449 (M+H)$^+$.

Example 107

(1S,2S,3R,4R)-3-{[5-chloro-2-({1-[(3R)-tetrahydrofuran-3-yl]-1H-pyrazol-4-yl}amino)pyrimidin-4-yl]amino}bicyclo[2.2.1]hept-5-ene-2-carboxamide Example 107A 1-[(3R)-tetrahydrofuran-3-yl]-1H-pyrazol-4-amine The title compound was prepared as described in Example 41A substituting (S)-tetrahydrofuran-3-ol for 1-methylpiperidin-4-ol.

Example 107B (1S,2S,3R,4R)-3-{[5-chloro-2-({1-[(3R)-tetrahydrofuran-3-yl]-1H-pyrazol-4-yl}amino)pyrimidin-4-yl]amino}bicyclo[2.2.1]hept-5-ene-2-carboxamide The title compound was prepared as described in Example 1, substituting 1-[(3R)-tetrahydrofuran-3-yl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=8.72 Hz, 1H) 2.04-2.28 (m, 2H) 2.28-2.40 (m, 1H) 2.76 (s, 1H) 2.88 (s, 1H) 3.73-3.99 (m, 4H) 4.13 (t, J=7.73 Hz, 1H) 4.87-5.02 (m, 1H) 6.25-6.31 (m, 1H) 6.36 (d, J=8.33 Hz, 1H) 7.25 (s, 1H) 7.56 (s, 1H) 7.68 (s, 1H) 7.78 (s, 2H) 7.89 (s, 1H) 9.11 (s, 1H); MS (ESI(+)) m/e 416 (M+H)$^+$.

Example 108

(1S,2S,3R,4R)-3-{[5-chloro-2-({1-[(3S)-tetrahydrofuran-3-yl]-1H-pyrazol-4-yl}amino)pyrimidin-4-yl]amino}bicyclo[2.2.1]hept-5-ene-2-carboxamide Example 108A 1-[(3S)-tetrahydrofuran-3-yl]-1H-pyrazol-4-amine The title compound was prepared as described in Example 41A substituting (R)-tetrahydrofuran-3-ol for 1-methylpiperidin-4-ol.

Example 108B (1S,2S,3R,4R)-3-{[5-chloro-2-({1-[(3S)-tetrahydrofuran-3-yl]-1H-pyrazol-4-yl}amino)pyrimidin-4-yl]amino}bicyclo[2.2.1]hept-5-ene-2-carboxamide The title compound was prepared as described in Example 1, substituting 1-[(3S)-tetrahydrofuran-3-yl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=8.72 Hz, 1H) 2.11 (d, J=8.73 Hz, 1H) 2.16-2.27 (m, 1H) 2.30-2.41 (m, 1H) 2.76 (s, 1H) 2.88 (s, 1H) 3.71-3.99 (m, 4H) 4.13 (t, J=7.73 Hz, 1H) 4.86-5.00 (m, 1H) 6.33 (d, J=16.26 Hz, 2H) 7.25 (s, 2H) 7.55 (s, 1H) 7.68 (s, 1H) 7.78 (s, 2H) 7.89 (s, 1H) 9.11 (s, 1H); MS (ESI(+)) m/e 416 (M+H)$^+$.

Example 109

3-[2-({2-[(1-methyl-1H-pyrazol-4-yl)amino]-5-(trifluoromethyl)pyrimidin-4-yl}amino)phenyl]azetidin-3-ol The title compound was prepared as described in Example 101 substituting tert-butyl 3-oxoazetidine-1-carboxylate for cyclobutanone in Example 101A and 2,4-dichloro-5-(trifluoromethyl)pyrimidine for 2,4,5-trichloropyrimidine in 101C. $^1$H NMR (400 MHz, DMSO-d$_6$, T=90° C.) δ ppm 3.63 (s, 3H) 4.05 (d, J=11.60 Hz, 2H) 4.37 (d, J=11.90 Hz, 2H) 6.77 (s, 1H) 7.23-7.32 (m, 1H) 7.37 (t, J=7.32 Hz, 1H) 7.46-7.53 (m, 2H) 7.67-7.77 (m, 1H) 8.10 (s, 1H) 8.32 (s, 1H) 8.37-9.11 (br m, 2H) 9.39 (s, 1H); MS (ESI(+)) m/e 406 (M+H)$^+$.

Example 110

(1S,2S,3R,4R)-3-{[5-bromo-2-({1-[2-(2-methoxyethoxy)ethyl]-1H-pyrazol-4-yl}amino)pyrimidin-4-yl]amino}bicyclo[2.2.1]hept-5-ene-2-carboxamide The title compound was prepared as described in Example 1, substituting 1-[2-(2-methoxyethoxy)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) ppm 1.41 (d, J=9.16 Hz, 1H) 2.10 (d, J=8.82 Hz, 1H) 2.77 (s, 1H) 2.87 (s, 1H) 3.20 (s, 3H) 3.35-3.42 (m, 2H) 3.44-3.51 (m, 2H) 3.73 (t, J=5.43 Hz, 3H) 4.07-4.13 (m, 1H) 4.17 (t, J=5.43

Hz, 2H) 6.35 (s, 2H) 7.24 (s, 1H) 7.53 (s, 1H) 7.76 (d, J=4.41 Hz, 3H) 7.95 (s, 1H) 9.10 (s, 1H); MS (ESI(+)) m/e 492 (M+H)⁺.

Example 111

(1S,2S,3R,4R)-3-[(5-bromo-2-{[1-(3-methylbutyl)-1H-pyrazol-4-yl]amino}pyrimidin-4-yl)amino]bicyclo[2.2.1]hept-5-ene-2-carboxamide The title compound was prepared as described in Example 1, substituting 1-isopentyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. ¹H NMR (300 MHz, DMSO-d₆) ppm 0.89 (d, J=6.78 Hz, 6H) 1.36-1.55 (m, 2H) 1.58-1.70 (m, 2H) 2.11 (d, J=8.82 Hz, 1H) 2.77 (s, 1H) 2.88 (s, 1H) 3.98-4.08 (m, 2H) 4.12 (t, J=7.80 Hz, 1H) 6.29 (d, J=2.71 Hz, 1H) 6.32-6.39 (m, 1H) 7.24 (s, 1H) 7.48 (s, 1H) 7.67 (s, 1H) 7.71-7.80 (m, 2H) 7.95 (s, 1H) 9.11 (s, 1H); MS (ESI(+)) m/e 461 (M+H)⁺.

Example 112

(1S,2S,3R,4R)-3-({5-bromo-2-[(1-isopropyl-1H-pyrazol-4-yl)amino]pyrimidin-4-yl}amino)bicyclo[2.2.1]hept-5-ene-2-carboxamide The title compound was prepared as described in Example 1, substituting 1-isopropyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. ¹H NMR (300 MHz, DMSO-d₆) ppm 1.39 (d, J=6.78 Hz, 6H) 2.12 (d, J=8.82 Hz, 1H) 2.75 (s, 1H) 2.75 (s, 1H) 2.87 (s, 1H) 2.87 (s, 1H) 4.15 (t, J=7.97 Hz, 1H) 4.31-4.49 (m, 1H) 6.28 (s, 1H) 6.38 (s, 1H) 7.23 (s, 1H) 7.51 (s, 1H) 7.58 (s, 1H) 7.74 (s, 2H) 7.95 (s, 1H) 9.07 (s, 1H); MS (ESI(+)) m/e 432 (M+H)⁺.

Example 113

(1R,2R,3S,4S)-3-({5-chloro-2-[(1-methyl-1H-pyrazol-4-yl)amino]pyrimidin-4-yl}amino)bicyclo[2.2.1]heptane-2-carboxamide and (1S,2S,3R,4R)-3-({5-chloro-2-[(1-methyl-1H-pyrazol-4-yl)amino]pyrimidin-4-yl}amino)bicyclo[2.2.1]heptane-2-carboxamide The title compound was prepared as described in Example 1, substituting (+/−)-(1S,2R,3S,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. ¹H NMR (400 MHz, DMSO-d₆, T=90° C.) ppm 1.20-1.39 (m, 2H) 1.39-1.46 (m, 1H) 1.47-1.57 (m, 1H) 1.62-1.73 (m, 1H) 2.52 (s, 1H) 2.60-2.68 (m, 1H) 2.87-2.94 (m, 1H) 4.22-4.41 (m, 2H) 6.75 (br s, 1H) 7.25 (br s, 1H) 7.43 (s, 1H) 7.70 (s, 1H) 7.80 (s, 1H) 8.57 (s, 1H) 8.69 (d, J=6.10 Hz, 1H); MS (ESI(+)) m/e 362 (M+H)⁺.

Example 114

(1R,2R,3S,4S)-3-({5-chloro-2-[(1-ethyl-1H-pyrazol-4-yl)amino]pyrimidin-4-yl}amino)bicyclo[2.2.1]heptane-2-carboxamide and (1S,2S,3R,4R)-3-({5-chloro-2-[(1-ethyl-1H-pyrazol-4-yl)amino]pyrimidin-4-yl}amino)bicyclo[2.2.1]heptane-2-carboxamide The title compound was prepared as described in Example 1, substituting 1-ethyl-1H-pyrazol-4-amine for 1-methyl-1H-pyrazol-4-amine in Example 1B along with substitution of (+/−)-(1S,2R,3S,4R)-3-aminobicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. ¹H NMR (400 MHz, DMSO-d₆, T=90° C.) ppm 1.23-1.32 (m, 2H) 1.36 (t, J=7.32 Hz, 3H) 1.42 (d, J=9.77 Hz, 1H) 1.49-1.58 (m, 2H) 1.63-1.73 (m, 1H) 2.50-2.54 (m, 1H) 2.64 (s, 1H) 2.86-2.94 (m, 1H) 4.05 (q, J=7.32 Hz, 2H) 4.26-4.45 (m, 1H) 6.74-6.92 (m, 1H) 7.20-7.38 (m, 1H) 7.43 (s, 1H) 7.76 (s, 1H) 7.80 (s, 1H) 8.58 (s, 1H) 8.70 (d, J=6.41 Hz, 1H); MS (ESI(+)) m/e 376 (M+H)⁺.

Example 115

1-[2-({2-[(1-methyl-1H-pyrazol-4-yl)amino]-5-(trifluoromethyl)pyrimidin-4-yl}amino)phenyl]cyclobutanol The title compound was prepared as in Example 101 substituting 2,4-dichloro-5-(trifluoromethyl)pyrimidine for 2,4,5-trichloropyrimidine in Example 101C. ¹H NMR (400 MHz, DMSO-d₆, T=90° C.) d ppm 1.44-1.56 (m, 1H) 1.82-1.92 (m, 1H) 2.25-2.34 (m, 2H) 2.40-2.47 (m, 2H) 3.69 (s, 3H) 5.96 (s, 1H) 7.19 (t, J=7.48 Hz, 1H) 7.32-7.39 (m, 2H) 7.46 (dd, J=7.78, 1.37 Hz, 1H) 7.56 (s, 1H) 7.91 (s, 1H) 8.29 (s, 1H) 8.91 (s, 1H) 9.28 (s, 1H); MS (ESI(+)) m/e 405 (M+H)⁺.

Example 116

(1S,2S,3R,4R)-3-{[5-bromo-2-({1-[(3R)-tetrahydrofuran-3-yl]-1H-pyrazol-4-yl}amino)pyrimidin-4-yl]amino}bicyclo[2.2.1]hept-5-ene-2-carboxamide The title compound was prepared as described in Example 1, substituting 1-[(3R)-tetrahydrofuran-3-yl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. ¹H NMR (300 MHz, DMSO-d₆) ppm 1.41 (d, J=8.82 Hz, 1H) 2.11 (d, J=8.82 Hz, 1H) 2.17-2.27 (m, 1H) 2.30-2.43 (m, 1H) 2.74 (s, 1H) 2.87 (s, 1H) 3.71-3.85 (m, 2H) 3.88-3.99 (m, 2H) 4.14 (t, J=7.97 Hz, 1H) 4.87-4.99 (m, 1H) 6.28 (d, J=8.48 Hz, 1H) 6.33-6.39 (m, 1H) 7.23 (s, 1H) 7.56 (s, 1H) 7.62 (s, 1H) 7.76 (s, 2H) 7.96 (s, 1H) 9.11 (s, 1H); (ESI(+)) m/e 461 (M+H)⁺.

Example 117

(1S,2S,3R,4R)-3-{[5-bromo-2-({1-[(3S)-tetrahydrofuran-3-yl]-1H-pyrazol-4-yl}amino)pyrimidin-4-yl]amino}bicyclo[2.2.1]hept-5-ene-2-carboxamide The title compound was prepared as described in Example 1, substituting 1-[(3S)-tetrahydrofuran-3-yl]-1H-pyrazol-4- amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-$d_6$) ppm 1.41 (d, J=8.81 Hz, 1H) 2.11 (d, J=8.81 Hz, 1H) 2.18-2.26 (m, 1H) 2.28-2.40 (m, 1H) 2.75 (s, 1H) 2.87 (s, 1H) 3.74-3.87 (m, 2H) 3.91-3.99 (m, 2H) 4.14 (t, J=7.46 Hz, 1H) 4.87-4.99 (m, 1H) 6.30 (d, J=3.05 Hz, 1H) 6.32-6.40 (m, 1H) 7.24 (s, 1H) 7.56 (s, 1H) 7.64 (s, 1H) 7.76 (s, 2H) 7.96 (s, 1H) 9.12 (s, 1H); (ESI(+)) m/e 461 (M+H)$^+$.

Example 118

(1S,2S,3R,4R)-3-({5-chloro-2-[(1-cyclobutyl-1H-pyrazol-4-yl)amino]pyrimidin-4-yl}amino)bicyclo[2.2.1]hept-5-ene-2-carboxamide

Example 118A 1-cyclobutyl-1H-pyrazol-4-yl-amine

The title compound was prepared as described in Example 41A substituting cyclobutanol for 1-methylpiperidin-4-ol.

Example 118B (1S,2S,3R,4R)-3-({5-chloro-2-[(1-cyclobutyl-1H-pyrazol-4-yl)amino]pyrimidin-4-yl}amino)bicyclo[2.2.1]hept-5-ene-2-carboxamide The title compound was prepared as described in Example 1, substituting 1-cyclobutyl-1H-pyrazol-4-yl-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.42 (d, J=8.82 Hz, 1H) 1.71-1.83 (m, 2H) 2.11 (d, J=8.82 Hz, 1H) 2.29-2.46 (m, 4H) 2.77 (s, 1H) 2.88 (s, 1H) 4.14 (t, J=7.97 Hz, 1H) 4.65-4.81 (m, 1H) 6.28 (d, J=8.48 Hz, 1H) 6.38 (d, J=8.14 Hz, 1H) 7.24 (s, 1H) 7.53 (s, 1H) 7.68 (s, 1H) 7.79 (s, 2H) 7.89 (s, 1H) 9.09 (s, 1H); MS (ESI(+)) m/e 400 (M+H)$^+$.

Example 119

(1S,2S,3R,4R)-3-{[5-chloro-2-({1-[2-(methylsulfonyl)ethyl]-1H-pyrazol-4-yl}amino)pyrimidin-4-yl]amino}bicyclo[2.2.1]hept-5-ene-2-carboxamide

Example 119A 2-(methylsulfonyl)ethyl]-1H-pyrazol-4-amine

The title compound was prepared as described in Example 41A substituting 2-(methylsulfonyl)ethanol for 1-methylpiperidin-4-ol.

Example 119B (1S,2S,3R,4R)-3-{[5-chloro-2-({1-[2-(methylsulfonyl)ethyl]-1H-pyrazol-4-yl}amino)pyrimidin-4-yl]amino}bicyclo[2.2.1]hept-5-ene-2-carboxamide The title compound was prepared as described in Example 1, substituting 2-(methylsulfonyl)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.41 (d, J=8.82 Hz, 1H) 2.10 (d, J=8.48 Hz, 1H) 2.54 (d, J=8.14 Hz, 1H) 2.78 (s, 1H) 2.83 (s, 3H) 2.88 (s, 1H) 3.66 (t, J=6.78 Hz, 2H) 4.12 (t, J=7.63 Hz, 1H) 4.47 (t, J=6.78 Hz, 2H) 6.35 (d, J=2.71 Hz, 2H) 7.25 (s, 1H) 7.61 (s, 1H) 7.81 (d, J=14.58 Hz, 2H) 7.90 (s, 1H) 9.16 (s, 1H); MS (ESI(+)) m/e 452 (M+H)$^+$.

Example 120

(1S,2R,3S,4R)-3-({5-chloro-2-[(1-methyl-1H-pyrazol-4-yl)amino]pyrimidin-4-yl}amino)bicyclo[2.2.1]hept-5-ene-2-carboxamide and (1R,2S,3R,4S)-3-({5-chloro-2-[(1-methyl-1H-pyrazol-4-yl)amino]pyrimidin-4-yl}amino)bicyclo[2.2.1]hept-5-ene-2-carboxamide The title compound was prepared as described in Example 1, substituting (+/−)-(1S,2R,3S,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.31-1.49 (m, 2H) 3.08-3.20 (m, 1H) 3.23-3.38 (m, 2H) 3.77 (s, 3H) 4.70 (s, 1H) 6.04 (dd, J=5.76, 3.05 Hz, 1H) 6.21 (dd, J=5.43, 2.37 Hz, 1H) 7.06 (s, 1H) 7.45 (s, 1H) 7.68 (s, 1H) 7.79 (s, 1H) 7.83 (s, 1H) 8.04 (s, 1H) 9.03 (s, 1H); MS (ESI(+)) m/e 360 (M+H)$^+$.

Example 121

(1S,2R,3S,4R)-3-({5-chloro-2-[(1-ethyl-1H-pyrazol-4-yl)amino]pyrimidin-4-yl}amino)bicyclo[2.2.1]hept-5-ene-2-carboxamide and (1R,2S,3R,4S)-3-({5-chloro-2-[(1-ethyl-1H-pyrazol-4-yl)amino]pyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+/−)-(1S,2R,3S,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.26-1.54 (m, 5H) 3.05-3.24 (m, 2H) 3.24-3.39 (m, 1H) 4.06 (q, J=7.35 Hz, 2H) 4.71 (s, 1H) 6.04 (dd, J=5.59, 2.88 Hz, 1H) 6.21 (dd, J=5.43, 2.37 Hz, 1H) 7.06 (s, 1H) 7.45 (s, 1H) 7.68 (s, 1H) 7.83 (s, 1H) 7.85 (s, 1H) 8.06 (s, 1H) 9.04 (s, 1H); MS (ESI(+)) m/e 374 (M+H)$^+$.

Example 122

(1S,2S,3R,4R)-3-{[5-bromo-2-({1-[2-(methylsulfonyl)ethyl]-1H-pyrazol-4-yl}amino)pyrimidin-4-yl]amino}bicyclo[2.2.1]hept-5-ene-2-carboxamide The title compound was prepared as described in Example 1, substituting 2-(methylsulfonyl)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-$d_6$) ppm 1.41 (d, J=8.82 Hz, 1H) 2.10 (d, J=8.82 Hz, 1H) 2.76 (s, 1H) 2.83 (s, 3H) 2.87 (s, 1H) 3.66 (t, J=6.78 Hz, 2H) 4.12 (t, J=7.63 Hz, 1H) 4.46 (t, J=6.78 Hz, 2H) 6.35 (d, J=2.71 Hz, 2H) 7.24 (s, 1H) 7.61 (s, 1H) 7.79 (d, J=14.58 Hz, 3H) 7.96 (s, 1H) 9.16 (s, 1H); MS (ESI(+)) m/e 497 (M+H)$^+$.

Example 123

(1S,2S,3R,4R)-3-({5-bromo-2-[(1-cyclobutyl-1H-pyrazol-4-yl)amino]pyrimidin-4-yl}amino)bicyclo[2.2.1]hept-5-ene-2-carboxamide The title compound was prepared as described in Example 1, substituting 1-cyclobutyl-1H-pyrazol-4-yl-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-$d_6$) ppm 1.41 (d, J=8.82 Hz, 1H) 1.69-1.83 (m, 2H) 2.11 (d, J=8.82 Hz, 2H) 2.30-2.43 (m, 4H) 2.76 (s, 1H) 2.88 (s, 1H) 4.14 (t, J=7.46 Hz, 1H) 4.62-4.80 (m, 1H) 6.28 (d, J=5.76 Hz, 1H) 6.37 (d, J=5.09 Hz, 1H) 7.23 (s, 1H) 7.54 (s, 1H) 7.63 (s, 1H) 7.77 (s, 2H) 7.95 (s, 1H) 9.10 (s, 1H); MS (ESI(+)) m/e 445 (M+H)$^+$.

Example 124

(1S,2S,3R,4R)-3-{[5-chloro-2-({1-[(2S)-2,3-dihydroxypropyl]-1H-pyrazol-4-yl}amino)pyrimidin-4-yl]amino}bicyclo[2.2.1]hept-5-ene-2-carboxamide Example 124A 1-[(2S)-2,3-dihydroxypropyl]-1H-pyrazol-4-amine The title compound was prepared as described in Example 41A substituting (S)-(2,2-dimethyl-1,3-dioxolan-4-yl)methanol for 1-methylpiperidin-4-ol followed by treatment with 4N HCl in dioxane.

Example 124B (1S,2S,3R,4R)-3-{[5-chloro-2-({1-[(2S)-2,3-dihydroxypropyl]-1H-pyrazol-4-yl}amino)pyrimidin-4-yl]amino}bicyclo[2.2.1]hept-5-ene-2-carboxamide The title compound was prepared as described in Example 1, substituting 1-[(2S)-2,3-dihydroxypropyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.41 (d, J=8.48 Hz, 1H) 2.10 (d, J=8.82 Hz, 1H) 2.78 (s, 1H) 2.87 (s, 1H) 3.68-3.81 (m, 1H) 3.82-3.92 (m, 1H) 4.13 (d, J=4.07 Hz, 1H) 4.17 (d, J=3.73 Hz, 1H) 4.68 (t, J=5.59 Hz, 1H) 4.94 (d, J=5.09 Hz, 3H) 6.36 (d, J=2.37 Hz, 2H) 7.25 (s, 1H) 7.51 (s, 1H) 7.76 (s, 3H) 7.88 (s, 1H) 9.10 (s, 1H); MS (ESI(+)) m/e 420 (M+H)$^+$.

Example 125

(1S,2S,3R,4R)-3-({5-chloro-6-methyl-2-[(1-methyl-1H-pyrazol-4-yl)amino]pyrimidin-4-yl}amino)bicyclo[2.2.1]hept-5-ene-2-carboxamide and (1R,2R,3S,4S)-3-({5-chloro-6-methyl-2-[(1-methyl-1H-pyrazol-4-yl)amino]pyrimidin-4-yl}amino)bicyclo[2.2.1]hept-5-ene-2-carboxamide The title compound was prepared as described in Example 1, substituting 2,4,5-trichloro-6-methylpyrimidine for 2,4-dichloro-5-fluoropyrimidine in Example 1A. $^1$H NMR (400 MHz, DMSO-$d_6$, T=90° C.) ppm 1.41 (dd, J=7.17, 1.68 Hz, 1H) 2.12 (d, J=8.85 Hz, 1H) 2.24 (s, 3H) 2.52-2.59 (m, 1H) 2.77 (s, 1H) 2.87 (s, 1H) 3.76 (s, 3H) 4.03-4.20 (m, 1H) 6.25-6.30 (m, 1H) 6.33 (dd, J=5.65, 2.90 Hz, 1H) 6.78-6.92 (m, 1H) 7.36-7.53 (m, 3H) 7.68 (s, 1H) 8.59 (s, 1H) MS (ESI(+)) m/e 374 (M+H)$^+$.

Example 126

(1S,2S,3R,4R)-3-({5-chloro-2-[(1-ethyl-1H-pyrazol-4-yl)amino]-6-methylpyrimidin-4-yl}amino)bicyclo[2.2.1]hept-5-ene-2-carboxamide and (1R,2R,3S,4S)-3-({5-chloro-2-[(1-ethyl-1H-pyrazol-4-yl)amino]-6-methylpyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of 2,4,5-trichloro-6-methylpyrimidine for 2,4-dichloro-5-fluoropyrimidine in Example 1A. $^1$H NMR (300 MHz, DMSO-$d_6$) ppm 1.32-1.47 (m, 4H) 2.01 (d, J=9.16 Hz, 1H) 2.35 (s, 3H) 2.55 (d, J=8.14 Hz, 1H) 2.80-2.88 (m, 1H) 2.93 (s, 1H) 3.96-4.19 (m, 3H) 6.23 (dd, J=5.59, 3.22 Hz, 1H) 6.40 (dd, J=5.59, 3.22 Hz, 1H) 7.38 (s, 1H) 7.60 (s, 1H) 7.84 (s, 1H) 7.94 (s, 1H) 9.66 (s, 1H); MS (ESI(+)) m/e 388 (M+H)$^+$.

Example 127

(1S,2S,3R,4R)-3-({5-chloro-2-[(1,3,5-trimethyl-1H-pyrazol-4-yl)amino]pyrimidin-4-yl}amino)bicyclo[2.2.1]hept-5-ene-2-carboxamide The title compound was prepared as described in Example 1, substituting 1,3,5-trimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.36 (d, J=8.48 Hz, 1H) 1.95 (s, 3H) 1.99-2.14 (m, 3H) 2.43 (d, J=8.14 Hz, 1H) 2.61 (s, 1H) 2.82 (s, 1H) 3.52-3.71 (m, 3H) 3.95 (s, 1H) 6.11 (br s, 1H) 6.28 (dd, J=5.43, 2.71 Hz, 1H) 7.19 (s, 1H) 7.34 (d, J=7.80 Hz, 1H) 7.68 (s, 1H) 7.76 (s, 1H) 7.95 (s, 1H); MS (ESI(+)) m/e 388 (M+H)$^+$.

Example 128

(1S,2S,3R,4R)-3-({5-bromo-2-[(1,3,5-trimethyl-1H-pyrazol-4-yl)amino]pyrimidin-4-yl}amino)bicyclo[2.2.1]hept-5-ene-2-carboxamide The title compound was prepared as described in Example 1, substituting 1,3,5-trimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) ppm 1.35 (d, J=8.82 Hz, 1H) 1.95 (s, 3H) 1.99-2.12 (m, 4H) 2.42 (d, J=8.82 Hz, 1H) 2.54-2.63 (m, 1H) 2.81 (s, 1H) 3.62 (s, 3H) 6.07 (br s, 1H) 6.27 (dd, J=5.59, 2.88 Hz, 1H) 7.18 (s, 1H) 7.29 (d, J=7.80 Hz, 1H) 7.67 (s, 1H) 7.83 (s, 1H) 7.96 (s, 1H); MS (ESI(+)) m/e 432, 434 (M+H)$^+$.

Example 129

(1S,2S,3R,4R)-3-[(5-chloro-2-{[1-(oxetan-2-ylmethyl)-1H-pyrazol-4-yl]amino}pyrimidin-4-yl)amino]bicyclo[2.2.1]hept-5-ene-2-carboxamide Example 129A 1-(oxetan-2-ylmethyl)-1H-pyrazol-4-amine The title compound was prepared as described in Example 41A substituting oxetan-2-ylmethanol for 1-methylpiperidin-4-ol.

Example 129B (1S,2S,3R,4R)-3-[(5-chloro-2-{[1-(oxetan-2-ylmethyl)-1H-pyrazol-4-yl]amino}pyrimidin-4-yl)amino]bicyclo[2.2.1]hept-5-ene-2-carboxamide The title compound was prepared as described in Example 1, substituting 1-(oxetan-2-ylmethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=8.82 Hz, 1H) 1.64-1.77 (m, 1H) 2.07-2.14 (m, 1H) 2.78 (s, 1H) 2.88 (s, 1H) 3.63-3.74 (m, 2H) 3.86-3.97 (m, 2H) 3.97-4.04 (m, 2H) 4.11 (t, J=7.80 Hz, 1H) 5.13 (t, J=5.26 Hz, 1H) 6.36 (s, 2H) 7.25 (s, 1H) 7.54 (d, J=3.39 Hz, 1H) 7.77 (d, J=4.75 Hz, 3H) 7.89 (s, 1H) 9.10 (s, 1H); MS (ESI(+)) m/e 416 (M+H)$^+$.

Example 130

(1S,2S,3R,4R)-3-{[5-chloro-2-({1-[(2R)-2,3-dihydroxypropyl]-1H-pyrazol-4-yl}amino)pyrimidin-4-yl]amino}bicyclo[2.2.1]hept-5-ene-2-carboxamide Example 130A 1-[(2R)-2,3-dihydroxypropyl]-1H-pyrazol-4-amine The title compound was prepared as described in Example 41A substituting (R)-(2,2-dimethyl-1,3-dioxolan-4-yl)methanol for 1-methylpiperidin-4-ol followed by treatment with 4N HCl in dioxane.

Example 130B (1S,2S,3R,4R)-3-{[5-chloro-2-({1-[(2R)-2,3-dihydroxypropyl]-1H-pyrazol-4-yl}amino)pyrimidin-4-yl]amino}bicyclo[2.2.1]hept-5-ene-2-carboxamide The title compound was prepared as described in Example 1, substituting 1-[(2R)-2,3-dihydroxypropyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.41 (d, J=8.72 Hz, 1H) 2.10 (d, J=8.72 Hz, 1H) 2.78 (s, 1H) 2.87 (s, 1H) 3.72-3.81 (m, 1H) 3.85-3.94 (m, 1H) 4.05-4.14 (m, 1H) 4.16 (d, J=4.36 Hz, 1H) 4.67 (t, J=5.55 Hz, 1H) 4.92 (d, J=5.55 Hz, 1H) 6.35 (s, 2H) 7.25 (s, 1H) 7.53 (s, 1H) 7.76 (d, J=8.73 Hz, 3H) 7.89 (s, 1H) 9.10 (s, 1H); MS (ESI(+)) m/e 420 (M+H)$^+$.

Example 131

(1S,2S,3R,4R)-3-{[5-bromo-2-({1-[(2S)-2,3-dihydroxypropyl]-1H-pyrazol-4-yl}amino)pyrimidin-4-yl]amino}bicyclo[2.2.1]hept-5-ene-2-carboxamide The title compound was prepared as described in Example 1, substituting 1-[(2S)-2,3-dihydroxypropyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-D$_6$) ppm 1.41 (d, J=8.14 Hz, 1H) 2.10 (d, J=8.82 Hz, 1H) 2.77 (s, 1H) 2.87 (s, 1H) 3.17 (d, J=5.43 Hz, 2H) 3.78 (d, J=4.07 Hz, 1H) 3.82-3.92 (m, 1H) 4.01-4.15 (m, 2H) 4.17 (d, J=3.73 Hz, 1H) 4.68 (t, J=5.59 Hz, 1H) 4.94 (d, J=5.09 Hz, 1H) 6.36 (s, 2H) 7.24 (s, 1H) 7.52 (s, 1H) 7.75 (s, 3H) 7.95 (s, 1H) 9.10 (s, 1H); MS (ESI(+)) m/e 465 (M+H)$^+$.

Example 132

1-[2-({5-bromo-2-[(1-methyl-1H-pyrazol-4-yl)amino]pyrimidin-4-yl}amino)phenyl]cyclobutanol The title compound was prepared as described in Example 1, substituting 1-(2-aminophenyl)cyclobutanol for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) d ppm 1.48 (s, 1H) 1.79-1.91 (m, 1H) 2.25-2.46 (m, 4H) 3.72 (s, 3H) 6.36 (s, 1H) 7.10-7.21 (m, 1H) 7.31-7.42 (m, 2H) 7.46 (d, J=7.80 Hz, 1H) 7.55-7.74 (m, 1H) 7.83-8.10 (m, 1H) 8.17 (s, 1H) 9.07 (s, 1H) 9.21 (s, 1H); MS (ESI(+)) m/e 415, 417, Br pattern (M+H)$^+$.

Example 133

4-[2-({5-chloro-2-[(1-methyl-1H-pyrazol-4-yl)amino]pyrimidin-4-yl}amino)phenyl]tetrahydro-2H-pyran-4-ol Example 133A 4-(2-(2,5-dichloropyrimidin-4-ylamino)phenyl)tetrahydro-2H-pyran-4-ol The title compound was prepared as in Example 101 substituting tetrahydro-4H-pyran-4-one for cyclobutanone in Example 101A.

Example 133B

4-[2-({5-chloro-2-[(1-methyl-1H-pyrazol-4-yl)amino]pyrimidin-4-yl}amino)phenyl]tetrahydro-2H-pyran-4-ol 4-(2-(2,5-Dichloropyrimidin-4-ylamino)phenyl)tetrahydro-2H-pyran-4-ol (40 mg, 0.118 mmol) and 1-methyl-1H-pyrazol-4-amine, 2HCl (20 mg, 0.118 mmol) were combined in acetonitrile (0.5 mL) and water (0.050 mL) in a sealed tube and the solution was heated to 85° C. for 2.5 hours. The reaction was diluted with $H_2O$ (5 mL) and neutralized by the addition of saturated $NaHCO_3$ (5 mL). The mixture was extracted with $CH_2Cl_2$ (3×10 mL), dried ($Na_2SO_4$), filtered, and concentrated. The product was purified by chromatography (Analogix, 4 g column, 0 to 5% methanol in dichloromethane over 25 minutes, 15 mL/minute) to give the title compound. $^1$H NMR (300 MHz, DMSO-$d_6$) d ppm 1.79-1.90 (m, 2H) 1.98 (td, J=12.39, 4.16 Hz, 2H) 3.66-3.77 (m, 5H) 3.83 (t, J=10.71 Hz, 2H) 6.17 (s, 1H) 7.14 (t, J=7.54 Hz, 1H) 7.31-7.43 (m, 3H) 7.71 (s, 1H) 8.00-8.35 (m, 1H) 8.10 (s, 1H) 9.20 (s, 1H) 10.12 (s, 1H); MS (ESI(+)) m/e 401 (M+H)$^+$.

Example 134

(1S,2S,3R,4R)-3-({5-chloro-2-[(1,3-dimethyl-1H-pyrazol-4-yl)amino]pyrimidin-4-yl}amino)bicyclo[2.2.1]hept-5-ene-2-carboxamide The title compound was prepared as described in Example 1, substituting 1,3-dimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 1.34-1.47 (m, 1H) 2.06-2.16 (m, 4H) 2.73 (s, 1H) 2.87 (s, 1H) 3.71 (s, 3H) 4.03-4.15 (m, 1H) 6.21 (dd, J=5.49, 3.05 Hz, 1H) 6.31 (dd, J=5.65, 2.90 Hz, 1H) 7.42 (d, J=7.63 Hz, 1H) 7.65 (s, 1H) 7.81 (s, 1H) 7.87 (s, 1H); MS (ESI(+)) m/e 374 (M+H)$^+$.

Example 135

(1S,2S,3R,4R)-3-({5-bromo-2-[(1,3-dimethyl-1H-pyrazol-4-yl)amino]pyrimidin-4-yl}amino)bicyclo[2.2.1]hept-5-ene-2-carboxamide The title compound was prepared as described in Example 1, substituting 1,3-dimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.37-1.43 (m, 1H) 2.05-2.17 (m, 4H) 2.49-2.53 (m, 1H) 2.72 (s, 1H) 2.86 (s, 1H) 3.70 (s, 3H) 4.03-4.14 (m, 1H) 6.20 (dd, J=5.80, 3.05 Hz, 1H) 6.30 (dd, J=5.65, 2.90 Hz, 1H) 7.38 (d, J=7.93 Hz, 1H) 7.64 (s, 1H) 7.88 (s, 1H) 7.91 (s, 1H); MS (ESI(+)) m/e 418, 420 (M+H)$^+$.

Example 136

(1S,2R)-2-[(5-chloro-2-{[1-(piperidin-4-yl)-1H-pyrazol-4-yl]amino}pyrimidin-4-yl)amino]cyclopentanecarboxamide and (1R,2S)-2-[(5-chloro-2-{[1-(piperidin-4-yl)-1H-pyrazol-4-yl]amino}pyrimidin-4-yl)amino]cyclopentanecarboxamide The title compound was prepared as described in Example 73, substituting (+/−)-(1S,2R)-2-aminocyclopentanecarboxamide for (+)-(1S,2S,3R,4R)-3-aminobicyclo[2.2.1]hept-5-ene-2-carboxamide in Example 73B and tert-butyl 4-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (300 MHz, DMSO-$d_6$) d ppm 1.50-2.03 (m, 10H) 2.57 (td, J=12.39, 2.58 Hz, 2H) 2.92 (q, J=7.54 Hz, 1H) 2.98-3.06 (m, 2H) 4.04-4.15 (m, 1H) 4.41-4.52 (m, 1H) 6.89 (d, J=5.16 Hz, 1H) 7.09 (s, 1H) 7.46 (s, 1H) 7.57 (s, 1H) 7.83 (s, 1H) 7.88 (s, 1H) 9.07 (s, 1H); MS (ESI(+)) m/e 405 (M+H)$^+$.

Example 137

(1S,2R)-2-{[5-chloro-2-({1-[2-(morpholin-4-yl)ethyl]-1H-pyrazol-4-yl}amino)pyrimidin-4-yl]amino}cyclopentanecarboxamide and (1R,2S)-2-{[5-chloro-2-({1-[2-(morpholin-4-yl)ethyl]-1H-pyrazol-4-yl}amino)pyrimidin-4-yl]amino}cyclopentanecarboxamide The title compound was prepared as described in Example 1, substituting (+/−)-(1S,2R)-2-aminocyclopentanecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) d ppm 1.53-1.66 (m, 1H) 1.68-1.87 (m, 2H) 1.87-2.05 (m, 3H) 2.35-2.43 (m, 4H) 2.67 (t, J=6.27 Hz, 2H) 2.90 (q, J=7.80 Hz, 1H) 3.51-3.59 (m, 4H) 4.15 (t, J=6.27 Hz, 2H) 4.42-4.52 (m, 1H) 6.88-6.97 (m, 1H) 7.09 (s, 1H) 7.48 (s, 1H) 7.57 (s, 1H) 7.81 (s, 1H) 7.88 (s, 1H) 9.06 (s, 1H); MS (ESI(+)) m/e 436 (M+H)$^+$.

Example 138

2-[2-({5-chloro-2-[(1-methyl-1H-pyrazol-4-yl)amino]pyrimidin-4-yl}amino)phenyl]propan-2-ol The title compound was prepared as described in Example 1, substituting 2-(2-aminophenyl)propan-2-ol for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) δ ppm 1.53 (s, 6H) 3.73 (s, 3H) 6.13 (s, 1H) 7.09 (t, J=7.46 Hz, 1H) 7.28-7.40 (m, 3H) 7.65-7.78 (m, 1H) 7.98-8.34 (m, 1H) 8.10 (s, 1H) 9.18 (s, 1H) 10.31 (s, 1H); MS (ESI(+)) m/e 359 (M+H)$^+$.

Example 139

(1S,2S,3R,4R)-3-({2-[(1-methyl-1H-pyrazol-4-yl)amino]-5-nitropyrimidin-4-yl}amino)bicyclo[2.2.1]hept-5-ene-2-carboxamide The title compound was prepared as described in Example 1, substituting (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4- dichloro-5-nitropyrimidine for 2,4-dichloro-5-fluoropyrimidine in Example 1A. $^1$H NMR (400 MHz, DMSO-d$_6$) ppm 1.40-1.50 (m, 1H) 2.19 (d, J=8.85 Hz, 1H) 2.58 (d, J=8.24 Hz, 1H) 2.85 (s, 1H) 2.91 (s, 1H) 3.81 (s, 3H) 4.35 (s, 1H) 6.30 (dd, J=5.80, 3.05 Hz, 1H) 6.38 (dd, J=5.34, 2.90 Hz, 1H) 6.82 (br s, 1H) 7.33 (br s, 1H) 7.62 (s, 1H) 7.76 (s, 1H) 8.89 (s, 1H) 9.70 (brs, 1H) 9.98 (br s, 1H); MS (ESI(+)) m/e 371 (M+H)$^+$.

Example 140

(1S,2S,3R,4R)-3-({2-[(1-ethyl-1H-pyrazol-4-yl)amino]-5-nitropyrimidin-4-yl}amino)bicyclo[2.2.1]hept-5-ene-2-carboxamide The title compound was prepared as described in Example 1, substituting 1-ethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-nitropyrimidine for 2,4-dichloro-5-fluoropyrimidine in Example 1A. $^1$H NMR (400 MHz, DMSO-d$_6$) ppm 1.38 (t, J=7.32 Hz, 3H) 1.42-1.50 (m, 1H) 2.19 (d, J=8.85 Hz, 1H) 2.58 (d, J=7.93 Hz, 1H) 2.84 (s, 1H) 2.91 (s, 1H) 4.10 (q, J=7.32 Hz, 2H) 4.38 (s, 1H) 6.29 (dd, J=5.49, 3.05 Hz, 1H) 6.37 (dd, J=5.65, 2.90 Hz, 1H) 6.80 (br s, 1H) 7.31 (br s, 1H) 7.63 (s, 1H) 7.79 (s, 1H) 8.89 (s, 1H) 9.68 (br s, 1H) 9.98 (br s, 1H); MS (ESI(+)) m/e 385 (M+H)$^+$.

Example 141

(1S,2R,3S,4R)-3-({5-chloro-2-[(1-methyl-1H-pyrazol-4-yl)amino]pyrimidin-4-yl}amino)-7-oxabicyclo[2.2.1]heptane-2-carboxamide and (1R,2S,3R,4S)-3-({5-chloro-2-[(1-methyl-1H-pyrazol-4-yl)amino]pyrimidin-4-yl}amino)-7-oxabicyclo[2.2.1]heptane-2-carboxamide The title compound was prepared as described in Example 1, substituting (+/−)-(1S,2R,3S,4R)-3-amino-7-oxabicyclo[2.2.1]heptane-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.48-1.78 (m, 4H) 2.89 (d, J=8.24 Hz, 1H) 3.77 (s, 3H) 4.34 (d, J=5.49 Hz, 1H) 4.44 (t, J=7.93 Hz, 1H) 4.56 (d, J=3.97 Hz, 1H) 7.35-7.51 (m, 2H) 7.70 (s, 1H) 7.84 (s, 1H) 8.64 (s, 1H); MS (ESI(+)) m/e 364 (M+H)$^+$.

Example 142

(1S,2R,3S,4R)-3-({5-chloro-2-[(1-ethyl-1H-pyrazol-4-yl)amino]pyrimidin-4-yl}amino)-7-oxabicyclo[2.2.1]heptane-2-carboxamide and (1R,2S,3R,4S)-3-({5-chloro-2-[(1-ethyl-1H-pyrazol-4-yl)amino]pyrimidin-4-yl}amino)-7-oxabicyclo[2.2.1]heptane-2-carboxamide The title compound was prepared as described in Example 1, substituting 1-ethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.36 (t, J=7.32 Hz, 3H) 1.50-1.73 (m, 4H) 2.89 (d, J=8.24 Hz, 1H) 4.06 (q, J=7.32 Hz, 2H) 4.33 (d, J=5.49 Hz, 1H) 4.45 (t, J=7.78 Hz, 1H) 4.56 (d, J=3.66 Hz, 1H) 7.39 (d, J=7.32 Hz, 1H) 7.47 (s, 1H) 7.73 (s, 1H) 7.84 (s, 1H) 8.64 (s, 1H); MS (ESI(+)) m/e 378 (M+H)$^+$.

Example 143

(1S,2S,3R,4R)-3-[(5-chloro-2-{[1-(2-phenylethyl)-1H-pyrazol-4-yl]amino}pyrimidin-4-yl)amino]bicyclo[2.2.1]hept-5-ene-2-carboxamide Example 143A 1-(2-phenylethyl)-1H-pyrazol-4-amine The title compound was prepared as described in Example 55A substituting 2-(bromoethyl)benzene for 2-chloro-N,N-dimethylacetamide.

Example 143B (1S,2S,3R,4R)-3-[(5-chloro-2-{[1-(2-phenylethyl)-1H-pyrazol-4-yl]amino}pyrimidin-4-yl)amino]bicyclo[2.2.1]hept-5-ene-2-carboxamide The title compound was prepared as described in Example 1, substituting 1-(2-phenylethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.40 (d, J=8.72 Hz, 1H) 2.09 (d, J=8.72 Hz, 1H) 2.74 (s, 1H) 2.88 (s, 1H) 3.06 (t, J=7.34 Hz, 2H) 4.00-4.11 (m, 1H) 4.26 (t, J=7.34 Hz, 2H) 6.25 (d, J=5.55 Hz, 1H) 6.36 (d, J=5.55 Hz, 1H) 7.06-7.33 (m, 6H) 7.52 (s, 1H) 7.65 (s, 1H) 7.80 (s, 1H) 7.88 (s, 1H) 9.09 (s, 1H); MS (ESI(+)) m/e 450 (M+H)$^+$.

Example 144

(1S,2S,3R,4R)-3-({2-[(1-benzyl-1H-pyrazol-4-yl)amino]-5-chloropyrimidin-4-yl}amino)bicyclo[2.2.1]hept-5-ene-2-carboxamide Example 144A 1-benzyl-1H-pyrazol-4-amine The title compound was prepared as described in Example 55A substituting benzyl bromide for 2-chloro-N,N-dimethylacetamide.

Example 144B (1S,2S,3R,4R)-3-({2-[(1-benzyl-1H-pyrazol-4-yl)amino]-5-chloropyrimidin-4-yl}amino)bicyclo[2.2.1]hept-5-ene-2-carboxamide The title compound was prepared as described in Example 1, substituting 1-benzyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.38 (d, J=8.72 Hz, 1H)

2.08 (d, J=8.72 Hz, 1H) 2.73 (s, 1H) 2.86 (s, 1H) 4.02-4.10 (m, 1H) 5.27 (s, 2H) 6.13 (s, 1H) 6.31 (dd, J=5.55, 2.78 Hz, 1H) 7.19 (d, J=7.93 Hz, 2H) 7.23-7.39 (m, 4H) 7.56 (s, 1H) 7.78 (s, 3H) 7.88 (s, 1H) 9.14 (s, 1H); MS (ESI(+)) m/e 436 (M+H)$^+$.

Example 145

[2-({5-chloro-2-[(1-methyl-1H-pyrazol-4-yl)amino]pyrimidin-4-yl}amino)phenyl]methanol The title compound was prepared as described in Example 1, substituting 2-(aminophenyl)methanol for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) δ ppm 3.62 (s, 3H) 4.52 (d, J=5.16 Hz, 2H) 5.51 (s, 1H) 7.15-7.30 (m, 2H) 7.37 (t, J=7.34 Hz, 1H) 7.41-7.50 (m, 1H) 7.51-7.82 (m, 1H) 8.07 (s, 1H) 8.95 (s, 1H) 9.17 (s, 1H); MS (ESI(+)) m/e 331 (M+H)$^+$.

Example 146

(1S,6R)-6-({5-chloro-2-[(1-methyl-1H-pyrazol-4-yl)amino]pyrimidin-4-yl}amino)cyclohex-3-ene-1-carboxamide and (1R,6S)-6-({5-chloro-2-[(1-methyl-1H-pyrazol-4-yl)amino]pyrimidin-4-yl}amino)cyclohex-3-ene-1-carboxamide The title compound was prepared as described in Example 1, substituting (+/−)-(1S,6R)-6-aminocyclohex-3-enecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 2.23-2.42 (m, 5H) 2.74-2.88 (m, 1H) 4.38-4.55 (m, 1H) 5.57-5.68 (m, 1H) 5.68-5.79 (m, 1H) 6.43 (d, J=7.32 Hz, 1H) 6.91 (br s, 2H) 7.44 (s, 1H) 7.69 (s, 1H) 7.86 (s, 1H) 8.67 (s, 1H); MS (ESI(+)) m/e 348 (M+H)$^+$.

Example 147

(1S,2R)-2-({5-chloro-2-[(1-methyl-1H-pyrazol-4-yl)amino]pyrimidin-4-yl}amino)cyclohexanecarboxamide and (1R,2S)-2-({5-chloro-2-[(1-methyl-1H-pyrazol-4-yl)amino]pyrimidin-4-yl}amino)cyclohexanecarboxamide The title compound was prepared as described in Example 1, substituting (+/−)-(1S,2R)-2-aminocyclohexanecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-d$_6$) ppm 1.42 (s, 3H) 1.60 (s, 3H) 1.89-2.19 (m, 2H) 2.66-2.81 (m, 1H) 3.78 (s, 3H) 4.12-4.28 (m, 1H) 6.70 (d, J=7.12 Hz, 1H) 7.03 (s, 1H) 7.40-7.54 (m, 2H) 7.73 (s, 1H) 7.89 (s, 1H) 9.05 (s, 1H); MS (ESI(+)) m/e 350 (M+H)$^+$.

Example 148

(1S,2S,3R,4R)-3-[(5-bromo-2-{[1-(2-phenyl ethyl)-1H-pyrazol-4-yl]amino}pyrimidin-4-yl)amino]bicyclo[2.2.1]hept-5-ene-2-carboxamide The title compound was prepared as described in Example 1, substituting 1-(2-phenylethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) ppm 1.40 (d, J=8.82 Hz, 1H) 2.10 (d, J=8.48 Hz, 1H) 2.73 (s, 1H) 2.87 (s, 1H) 3.06 (t, J=7.29 Hz, 2H) 3.99-4.12 (m, 1H) 4.26 (t, J=7.29 Hz, 2H) 6.25 (d, J=8.48 Hz, 1H) 6.31-6.40 (m, 1H) 7.15 (d, J=6.78 Hz, 2H) 7.20-7.30 (m, 4H) 7.53 (s, 1H) 7.64 (s, 2H) 7.78 (s, 1H) 7.94 (s, 1H) 9.09 (s, 1H); MS (ESI(+)) m/e 494 (M+H)$^+$.

Example 149

(1S,2S,3R,4R)-3-({2-[(1-benzyl-1H-pyrazol-4-yl)amino]-5-bromopyrimidin-4-yl}amino)bicyclo[2.2.1]hept-5-ene-2-carboxamide The title compound was prepared as described in Example 1, substituting 1-benzyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-d$_6$) ppm 1.38 (d, J=8.82 Hz, 1H) 2.08 (d, J=8.82 Hz, 1H) 2.72 (s, 1H) 2.85 (s, 1H) 3.97-4.13 (m, 1H) 5.27 (s, 3H) 6.12 (s, 1H) 6.30 (d, J=8.48 Hz, 1H) 7.15-7.23 (m, 2H) 7.25-7.37 (m, 4H) 7.56 (s, 1H) 7.67 (s, 1H) 7.77 (d, J=7.46 Hz, 2H) 7.94 (s, 1H) 9.14 (s, 1H); MS (ESI(+)) m/e 480 (M+H)$^+$.

Example 150

3-({2-[(1-methyl-1H-pyrazol-4-yl)amino]-5-(trifluoromethyl)pyrimidin-4-yl}amino)thiophene-2-carboxamide The title compound was prepared as described in Example 1, substituting 3-aminothiophene-2-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-d$_6$) ppm 3.80 (s, 3H) 7.30 (s, 2H) 7.46 (s, 1H) 7.66 (d, J=5.49 Hz, 1H) 7.77 (s, 1H) 8.26 (s, 1H) 8.34 (s, 1H) 9.36 (s, 1H) 11.40 (s, 1H); MS (ESI(+)) m/e 384 (M+H)$^+$.

Example 151

(1S,2R)-2-({5-chloro-2-[(1-methyl-1H-pyrazol-4-yl)amino]pyrimidin-4-yl}amino)cyclobutanecarboxamide and (1R,2S)-2-({5-chloro-2-[(1-methyl-1H-pyrazol-4-yl)amino]pyrimidin-4-yl}amino)cyclobutanecarboxamide The title compound was prepared as described in Example 1, substituting (+/−)-(1S,2R)-2-aminocyclobutanecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) ppm 1.96-2.09 (m, 2H) 2.11-2.27 (m, 1H) 2.30-2.44 (m, 1H) 3.27-3.44 (m, 1H) 3.77 (s, 3H) 4.67-4.88 (m, 1H) 7.18 (d, J=7.63 Hz, 1H) 7.45 (s, 1H) 7.70 (s, 1H) 7.85 (s, 1H) 8.64 (s, 1H); MS (ESI(+)) m/e 322 (M+H)$^+$.

Example 152

2-({2-[(1-methyl-1H-pyrazol-4-yl)amino]-5-(trifluoromethyl)pyrimidin-4-yl}amino)thiophene-3-carboxamide The title compound was prepared as described in Example 1, substituting 2-aminothiophene-3-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-$d_6$) ppm 3.82 (s, 3H) 6.93 (d, J=5.80 Hz, 1H) 7.42 (d, J=5.80 Hz, 3H) 7.53 (s, 1H) 7.83 (s, 1H) 8.39 (s, 1H) 9.26 (s, 1H) 12.79 (s, 1H); MS (ESI(+)) m/e 384 (M+H)$^+$.

Example 153

1-methyl-4-({2-[(1-methyl-1H-pyrazol-4-yl)amino]-5-(trifluoromethyl)pyrimidin-4-yl}amino)-1H-pyrazole-3-carboxamide The title compound was prepared as described in Example 1, substituting 4-amino-1-methyl-1H-pyrazole-3-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-$d_6$) ppm 3.84 (s, 3H) 3.88 (s, 3H) 7.23 (s, 2H) 7.49 (s, 1H) 7.81 (s, 1H) 8.29 (s, 1H) 8.40 (s, 1H) 9.21 (s, 1H) 9.99 (s, 1H); MS (ESI(+)) m/e 382 (M+H)$^+$.

Example 154

(1S,2S,3R,4R)-3-{[5-chloro-2-({1-[2-(3-methoxyphenyl)ethyl]-1H-pyrazol-4-yl}amino)pyrimidin-4-yl]amino}bicyclo[2.2.1]hept-5-ene-2-carboxamide

Example 154A

1-[2-(3-methoxyphenyl)ethyl]-1H-pyrazol-4-amine

The title compound was prepared as described in Example 55A substituting 1-(2-bromoethyl)-3-methoxybenzene for 2-chloro-N,N-dimethylacetamide.

Example 154B

(1S,2S,3R,4R)-3-{[5-chloro-2-({1-[2-(3-methoxyphenyl)ethyl]-1H-pyrazol-4-yl}amino)pyrimidin-4-yl]amino}bicyclo[2.2.1]hept-5-ene-2-carboxamide The title compound was prepared as described in Example 1, substituting 1-[2-(3-methoxyphenyl)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.40 (d, J=8.72 Hz, 1H) 2.09 (d, J=8.72 Hz, 1H) 2.74 (s, 1H) 2.87 (s, 1H) 3.04 (t, J=7.34 Hz, 2H) 3.68 (s, 3H) 4.06 (t, J=7.34 Hz, 1H) 4.25 (t, J=7.34 Hz, 2H) 6.24 (d, J=8.33 Hz, 1H) 6.35 (d, J=8.72 Hz, 1H) 6.71 (d, J=11.10 Hz, 1H) 6.73-6.78 (m, 2H) 7.18 (t, J=7.73 Hz, 1H) 7.26 (s, 1H) 7.54 (s, 1H) 7.73 (d, J=37.68 Hz, 3H) 7.88 (s, 1H) 9.10 (s, 1H); MS (ESI(+)) m/e 480 (M+H)$^+$.

Example 155

(1S,2S,3R,4R)-3-[(5-chloro-2-{[1-(3-methoxybenzyl)-1H-pyrazol-4-yl]amino}pyrimidin-4-yl)amino]bicyclo[2.2.1]hept-5-ene-2-carboxamide

Example 155A

1-(3-methoxybenzyl)-1H-pyrazol-4-amine

The title compound was prepared as described in Example 55A substituting 3-methoxybenzyl bromide for 2-chloro-N,N-dimethylacetamide.

Example 155B

1S,2S,3R,4R)-3-[(5-chloro-2-{[1-(3-methoxybenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-methoxybenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) ppm 1.38 (d, J=9.16 Hz, 1H) 2.08 (d, J=8.82 Hz, 1H) 2.73 (s, 1H) 2.86 (s, 1H) 3.72 (s, 3H) 4.06 (t, J=5.43 Hz, 1H) 5.24 (s, 2H) 6.12 (s, 1H) 6.30 (d, J=8.48 Hz, 1H) 6.67-6.78 (m, 2H) 6.84 (d, J=7.46 Hz, 1H) 7.25 (t, J=7.97 Hz, 2H) 7.57 (s, 1H) 7.77 (s, 2H) 7.88 (s, 1H) 9.13 (s, 1H); MS (ESI(+)) m/e 466 (M+H)$^+$.

Example 156

(1S,2R)-2-({5-chloro-2-[(1-methyl-1H-pyrazol-4-yl)amino]pyrimidin-4-yl}amino)-N-isopropylcyclopentanecarboxamide and (1R,2S)-2-({5-chloro-2-[(1-methyl-1H-pyrazol-4-yl)amino]pyrimidin-4-yl}amino)-N-isopropylcyclopentanecarboxamide The title compound was prepared as described in Example 1, substituting (+/−)-(1S,2R)-2-amino-N-isopropylcyclopentanecarboxamide (US2007/0032514) for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 0.97 (d, J=6.71 Hz, 3H) 1.03 (d, J=6.71 Hz, 3H) 1.51-1.63 (m, 1H) 1.72-2.04 (m, 5H) 2.90 (q, J=7.63 Hz, 1H) 3.76 (s, 3H) 3.83 (dd, J=14.04, 6.71 Hz, 1H) 4.51 (q, J=6.71 Hz, 1H) 6.53 (d, J=7.02 Hz, 1H) 7.46 (s, 2H) 7.70 (s, 1H) 7.83 (s, 1H) 8.63 (s, 1H); MS (ESI(+)) m/e 378 (M+H)$^+$.

Example 157

(1S,2S,3R,4R)-3-[(5-chloro-2-{[1-(3-chlorobenzyl)-1H-pyrazol-4-yl]amino}pyrimidin-4-yl)amino]bicyclo[2.2.1]hept-5-ene-2-carboxamide

Example 157A

1-(3-chlorobenzyl)-1H-pyrazol-4-amine

The title compound was prepared as described in Example 55A substituting 3-chlorobenzyl bromide for 2-chloro-N,N-dimethylacetamide.

Example 157B (1S,2S,3R,4R)-3-[(5-chloro-2-{[1-(3-chlorobenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-chlorobenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 1.40 (d, J=12.21 Hz, 1H) 2.11 (d, J=8.85 Hz, 1H) 2.76 (s, 1H) 2.87 (s, 1H) 4.11 (t, J=7.93 Hz, 1H) 5.27 (s, 2H) 6.15 (d, J=8.85 Hz, 1H) 6.29 (d, J=8.54 Hz, 1H) 6.87 (s, 1H) 7.16 (d, J=7.32 Hz, 1H) 7.23 (s, 1H) 7.28-7.38 (m, 2H) 7.44 (s, 1H) 7.55 (d, J=7.63 Hz, 2H) 7.60 (s, 1H) 7.80 (s, 1H) 7.85 (s, 1H) 8.74 (s, 1H); MS (ESI(+)) m/e 470 (M+H)$^+$.

Example 158

(1S,2S,3R,4R)-3-{[5-chloro-2-({1-[2-(3-chlorophenyl)ethyl]-1H-pyrazol-4-yl}amino)pyrimidin-4-yl]amino}bicyclo[2.2.1]hept-5-ene-2-carboxamide

Example 158A 2-(3-chlorophenyl)ethyl]-1H-pyrazol-4-amine

The title compound was prepared as described in Example 55A substituting 1-(2-bromoethyl)-3-chlorobenzene for 2-chloro-N,N-dimethylacetamide.

Example 158B (1S,2S,3R,4R)-3-{[5-chloro-2-({1-[2-(3-chlorophenyl)ethyl]-1H-pyrazol-4-yl}amino)pyrimidin-4-yl]amino}bicyclo[2.2.1]hept-5-ene-2-carboxamide The title compound was prepared as described in Example 1, substituting 2-(3-chlorophenyl)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 2.12 (d, J=8.85 Hz, 1H) 2.55 (d, J=8.24 Hz, 1H) 2.77 (s, 1H) 2.89 (s, 1H) 3.11 (t, J=7.17 Hz, 2H) 4.12 (t, J=7.93 Hz, 1H) 4.28 (t, J=7.17 Hz, 2H) 6.23 (d, J=5.80 Hz, 1H) 6.33 (d, J=8.54 Hz, 1H) 6.88 (s, 1H) 7.10 (d, J=7.32 Hz, 1H) 7.17-7.30 (m, 3H) 7.44 (s, 1H) 7.55 (s, 2H) 7.65 (s, 1H) 7.83 (s, 1H) 8.67 (s, 1H); MS (ESI(+)) m/e 484 (M+H)$^+$.

Example 159

(1S,2S,3R,4R)-3-[(5-bromo-2-{[1-(3-methoxybenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-methoxybenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (300 MHz, DMSO-$D_6$) ppm 1.38 (d, J=8.48 Hz, 1H) 2.08 (d, J=9.16 Hz, 1H) 2.72 (s, 1H) 2.85 (s, 1H) 3.71 (s, 3H) 3.94-4.16 (m, 1H) 5.23 (s, 2H) 6.12 (s, 1H) 6.30 (d, J=8.48 Hz, 1H) 6.68-6.79 (m, 2H) 6.79-6.89 (m, 1H) 7.25 (t, J=7.97 Hz, 2H) 7.57 (s, 1H) 7.76 (s, 3H) 7.95 (s, 1H) 9.14 (s, 1H); MS (ESI(+)) m/e 510 (M+H)$^+$.

Example 160

(1S,2S,3R,4R)-3-{[5-bromo-2-({1-[2-(3-methoxyphenyl)ethyl]-1H-pyrazol-4-yl}amino)pyrimidin-4-yl]amino}bicyclo[2.2.1]hept-5-ene-2-carboxamide The title compound was prepared as described in Example 1, substituting 1-[2-(3-methoxyphenyl)ethyl]-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 2.11 (d, J=8.85 Hz, 1H) 2.54 (d, J=9.46 Hz, 1H) 2.75 (s, 1H) 2.87 (s, 1H) 3.06 (t, J=7.32 Hz, 2H) 3.70 (s, 3H) 4.12 (t, J=7.93 Hz, 1H) 4.20-4.31 (m, 2H) 6.23 (d, J=8.85 Hz, 1H) 6.32 (d, J=8.54 Hz, 1H) 6.65-6.78 (m, 3H) 6.85 (s, 1H) 7.08-7.20 (m, 1H) 7.48 (d, J=7.63 Hz, 1H) 7.54 (s, 3H) 7.63 (s, 1H) 7.90 (s, 1H) 8.68 (s, 1H); MS (ESI(+)) m/e 524 (M+H)$^+$.

Example 161

(1S,2S,3R,4R)-3-[(5-chloro-2-{[1-(2-chlorobenzyl)-1H-pyrazol-4-yl]amino}pyrimidin-4-yl)amino]bicyclo[2.2.1]hept-5-ene-2-carboxamide

Example 161A 1-(2-chlorobenzyl)-1H-pyrazol-4-amine

The title compound was prepared as described in Example 55A substituting 2-chlorobenzyl bromide for 2-chloro-N,N-dimethylacetamide.

Example 161B (1S,2S,3R,4R)-3-[(5-chloro-2-{[1-(2-chlorobenzyl)-1H-pyrazol-4-yl]amino}pyrimidin-4-yl)amino]bicyclo[2.2.1]hept-5-ene-2-carboxamide The title compound was prepared as described in Example 1, substituting 1-(2-chlorobenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 1.39 (d, J=8.85 Hz, 1H) 2.10 (d, J=8.85 Hz, 1H) 2.75 (s, 1H) 2.86 (s, 1H) 4.10 (t, J=7.48 Hz, 1H) 5.36 (s, 2H) 6.14 (d, J=2.14 Hz, 1H) 6.28 (d, J=8.54 Hz, 1H) 6.88 (s, 1H) 7.04 (d, J=9.16 Hz, 1H) 7.24-7.35 (m, 2H) 7.45 (d, J=9.16 Hz, 2H) 7.56 (d, J=8.85 Hz, 1H) 7.60 (s, 1H) 7.82 (d, J=16.17 Hz, 2H) 8.77 (s, 1H); MS (ESI(+)) m/e 470 (M+H)$^+$.

Example 162

(1S,2S,3R,4R)-3-[(5-chloro-2-{[1-(4-chlorobenzyl)-1H-pyrazol-4-yl]amino}pyrimidin-4-yl)amino]bicyclo[2.2.1]hept-5-ene-2-carboxamide

Example 162A 1-(4-chlorobenzyl)-1H-pyrazol-4-amine

The title compound was prepared as described in Example 55A substituting 4-chlorobenzyl bromide for 2-chloro-N,N-dimethylacetamide.

Example 162B (1S,2S,3R,4R)-3-[(5-chloro-2-{[1-(4-chlorobenzyl)-1H-pyrazol-4-yl]amino}pyrimidin-4-yl)amino]bicyclo[2.2.1]hept-5-ene-2-carboxamide The title compound was prepared as described in Example 1, substituting 1-(4-chlorobenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 1.40 (d, J=9.16 Hz, 1H) 2.10 (d, J=8.85 Hz, 1H) 2.75 (s, 1H) 2.87 (s, 1H) 4.10 (t, J=8.70 Hz, 1H) 5.24 (s, 2H) 6.14 (d, J=8.85 Hz, 1H) 6.29 (d, J=8.54 Hz, 1H) 6.87 (s, 1H) 7.21 (d, J=8.54 Hz, 2H) 7.32-7.40 (m, 2H) 7.45 (s, 1H) 7.54 (d, J=7.32 Hz, 1H) 7.58 (s, 2H) 7.77 (s, 1H) 7.84 (s, 1H) 8.75 (s, 1H); MS (ESI(+)) m/e 470 (M+H)$^+$.

Example 163

(1S,2R)-2-[(5-chloro-2-{[1-(piperidin-4-yl)-1H-pyrazol-4-yl]amino}pyrimidin-4-yl)amino]-N-isopropylcyclopentanecarboxamide and (1R,2S)-2-[(5-chloro-2-{[1-(piperidin-4-yl)-1H-pyrazol-4-yl]amino}pyrimidin-4-yl)amino]-N-isopropylcyclopentanecarboxamide The title compound was prepared as described in Example 73, substituting (+/−)-(1S,2R)-2-amino-N-isopropylcyclopentanecarboxamide for (+)-(1S,2S,3R,4R)-3-aminobicyclo[2.2.1]hept-5-ene-2-carboxamide in Example 73B and tert-butyl 4-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (400 MHz, DMSO-$d_6$, T=90° C.) δ ppm 0.97 (d, J=6.71 Hz, 3H) 1.03 (d, J=6.71 Hz, 3H) 1.51-1.61 (m, 1H) 1.74-2.05 (m, 11H) 2.74 (td, J=12.44, 2.29 Hz, 2H) 2.86-2.94 (m, 2H) 3.10-3.16 (m, 2H) 3.77-3.89 (m, 1H) 4.12-4.23 (m, 1H) 7.44-7.51 (m, 2H) 7.79 (s, 1H) 7.83 (s, 1H) 8.66 (s, 1H); MS (ESI(+)) m/e 447 (M+H)$^+$.

Example 164

(1S,2R)-2-{[5-chloro-2-({1-[2-(morpholin-4-yl)ethyl]-1H-pyrazol-4-yl}amino)pyrimidin-4-yl]amino}-N-isopropylcyclopentanecarboxamide The title compound was prepared as described in Example 1, substituting 1-[2-(morpholin-4-yl)ethyl]-1H-pyrazol-4-amine for 1-methyl-1H-pyrazol-4-amine in Example 1B along with substitution of (+/−)-(1S,2R)-2-amino-N-isopropylcyclopentanecarboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (300 MHz, DMSO-$d_6$) δ ppm 0.96 (d, J=6.78 Hz, 3H) 1.02 (d, J=6.44 Hz, 3H) 1.58 (s, 1H) 1.68-2.02 (m, 5H) 2.34-2.42 (m, 4H) 2.67 (t, J=6.78 Hz, 2H) 2.88 (q, J=8.02 Hz, 1H) 3.50-3.59 (m, 4H) 3.75-3.88 (m, 1H) 4.15 (t, J=6.78 Hz, 2H) 4.41-4.56 (m, 1H) 6.71 (s, 1H) 7.48 (s, 1H) 7.81 (s, 1H) 7.83-7.90 (m, 2H) 9.05 (s, 1H); MS (ESI(+)) m/e 477 (M+H)$^+$.

Example 165

(1R,2R,3S,5R)-2-({5-chloro-2-[(1-methyl-1H-pyrazol-4-yl)amino]pyrimidin-4-yl}amino)-6,6-dimethylbicyclo[3.1.1]heptane-3-carboxamide The title compound was prepared as described in Example 1, substituting (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 1.04 (s, 3H) 1.24 (s, 3H) 1.74 (d, J=9.77 Hz, 1H) 1.87-2.21 (m, 5H) 3.26-3.38 (m, 1H) 3.76 (s, 3H) 4.79-4.97 (m, 1H) 6.74 (br s, 1H) 6.91 (d, J=8.54 Hz, 1H) 7.23 (br s, 1H) 7.47 (s, 1H) 7.63 (s, 1H) 7.81 (s, 1H) 8.62 (s, 1H); MS (ESI(+)) m/e 390 (M+H)$^+$.

Example 166

(1R,2R,3S,5R)-2-({5-chloro-2-[(1-ethyl-1H-pyrazol-4-yl)amino]pyrimidin-4-yl}amino)-6,6-dimethylbicyclo[3.1.1]heptane-3-carboxamide The title compound was prepared as described in Example 1, substituting 1-ethyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 0.97-1.11 (m, 3H) 1.17-1.29 (m, 3H) 1.36 (t, J=7.17 Hz, 3H) 1.74 (d, J=9.77 Hz, 1H) 1.87-2.21 (m, 5H) 3.26-3.43 (m, 1H) 4.05 (q, J=7.22 Hz, 2H) 4.78-4.99 (m, 1H) 6.74 (s, 1H) 6.88 (d, J=8.54 Hz, 1H) 7.25 (s, 1H) 7.49 (s, 1H) 7.66 (s, 1H) 7.81 (s, 1H) 8.60 (s, 1H); MS (ESI(+)) m/e 404 (M+H)$^+$.

Example 167

(1R,2R,3S,5R)-6,6-dimethyl-2-({2-[(1-methyl-1H-pyrazol-4-yl)amino]-5-(trifluoromethyl)pyrimidin-4-yl}amino)bicyclo[3.1.1]heptane-3-carboxamide The title compound was prepared as described in Example 1, substituting (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-$d_6$, T=90° C.) ppm 1.04 (s, 3H) 1.24 (s, 3H) 1.69 (d, J=9.46 Hz, 1H) 1.89-2.00 (m, 2H) 2.03-2.20 (m, 3H) 3.23-3.48 (m, 1H) 3.78 (s, 3H) 4.88-5.12 (m, 1H) 6.75 (br s, 1H) 7.04 (d, J=7.32 Hz, 1H) 7.29 (br s, 1H) 7.52 (s, 1H) 7.65 (s, 1H) 8.05 (s, 1H) 9.08 (s, 1H); MS (ESI(+)) m/e 424 (M+H)$^+$.

Example 168

(1R,2R,3S,5R)-2-({2-[(1-ethyl-1H-pyrazol-4-yl) amino]-5-(trifluoromethyl)pyrimidin-4-yl}amino)-6, 6-dimethylbicyclo[3.1.1]heptane-3-carboxamide The title compound was prepared as described in Example 1, substituting 1-ethyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4-dichloro-5-(trifluoromethyl)pyrimidine for 2,4-dichloro-5-fluoropyrimidine in Example 1A. $^1$H NMR (400 MHz, DMSO-$d_6$, T=90° C.) ppm 0.99-1.05 (m, 3H) 1.23 (s, 3H) 1.37 (t, J=7.17 Hz, 3H) 1.69 (d, J=9.46 Hz, 1H) 1.86-2.02 (m, 2H) 2.02-2.20 (m, 3H) 3.26-3.42 (m, 1H) 4.06 (q, J=7.22 Hz, 2H) 4.81-5.08 (m, 1H) 6.73 (s, 1H) 7.01 (s, 1H) 7.26 (s, 1H) 7.55 (s, 1H) 7.67 (s, 1H) 8.06 (s, 1H); MS (ESI(+)) m/e 438 (M+H)$^+$.

Example 169

(1S,2S,3R,4R)-3-({5-chloro-2-[(1,5-dimethyl-1H-pyrazol-4-yl)amino]pyrimidin-4-yl}amino)bicyclo [2.2.1]hept-5-ene-2-carboxamide The title compound was prepared as described in Example 1, substituting 1,5-dimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 1.38 (d, J=8.85 Hz, 1H) 2.08 (d, J=8.85 Hz, 1H) 2.15 (s, 3H) 2.71 (s, 1H) 2.85 (s, 1H) 3.65-3.71 (m, 3H) 3.97-4.10 (m, 1H) 6.17 (dd, J=5.49, 3.05 Hz, 1H) 6.28 (dd, J=5.65, 2.90 Hz, 1H) 6.84 (br s, 1H) 7.39 (d, J=7.93 Hz, 1H) 7.47 (s, 1H) 7.78 (s, 1H) 7.89 (s, 1H); MS (ESI(+)) m/e 374 (M+H)$^+$.

Example 170

(1S,2S,3R,4R)-3-({5-bromo-2-[(1,5-dimethyl-1H-pyrazol-4-yl)amino]pyrimidin-4-yl}amino)bicyclo [2.2.1]hept-5-ene-2-carboxamide The title compound was prepared as described in Example 1, substituting 1,5-dimethyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.38 (d, J=8.85 Hz, 1H) 2.08 (d, J=8.85 Hz, 1H) 2.15 (s, 3H) 2.70 (s, 1H) 2.85 (s, 1H) 3.68 (s, 3H) 3.71 (q, J=5.19 Hz, 1H) 3.96-4.13 (m, 1H) 6.16 (dd, J=5.49, 3.05 Hz, 1H) 6.27 (dd, J=5.65, 2.90 Hz, 1H) 6.82 (s, 1H) 7.22-7.42 (m, J=7.63 Hz, 2H) 7.47 (s, 1H) 7.85 (s, 1H) 7.91 (s, 1H); MS (ESI(+)) m/e 418, 420 (M+H)$^+$.

Example 171

(1S,2S,3R,4R)-3-[(5-bromo-2-{[1-(2-chlorobenzyl)-1H-pyrazol-4-yl]amino}pyrimidin-4-yl)amino]bicyclo[2.2.1]hept-5-ene-2-carboxamide The title compound was prepared as described in Example 1, substituting 1-(2-chlorobenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.40 (d, J=8.85 Hz, 1H) 2.11 (d, J=8.85 Hz, 1H) 2.74 (s, 1H) 2.86 (s, 1H) 4.11 (t, J=7.93 Hz, 1H) 5.36 (s, 2H) 6.14 (d, J=5.49 Hz, 1H) 6.27 (d, J=8.54 Hz, 1H) 6.86 (s, 1H) 7.05 (d, J=9.16 Hz, 1H) 7.24-7.35 (m, 2H) 7.45 (d, J=9.46 Hz, 1H) 7.50 (d, J=7.32 Hz, 2H) 7.60 (s, 1H) 7.79 (s, 1H) 7.91 (s, 1H) 8.76 (s, 1H); MS (ESI(+)) m/e 516 (M+H)$^+$.

Example 172

(1S,2S,3R,4R)-3-[(5-bromo-2-{[1-(4-chlorobenzyl)-1H-pyrazol-4-yl]amino}pyrimidin-4-yl)amino]bicyclo[2.2.1]hept-5-ene-2-carboxamide The title compound was prepared as described in Example 1, substituting 1-(4-chlorobenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.40 (d, J=8.85 Hz, 1H) 2.11 (d, J=8.85 Hz, 1H) 2.52 (d, J=8.24 Hz, 1H) 2.74 (s, 1H) 2.86 (s, 1H) 4.11 (t, J=8.70 Hz, 1H) 5.24 (s, 2H) 6.13 (d, J=8.54 Hz, 1H) 6.29 (d, J=8.54 Hz, 1H) 6.85 (s, 1H) 7.21 (d, J=8.24 Hz, 2H) 7.30-7.41 (m, 3H) 7.47 (d, J=7.63 Hz, 1H) 7.58 (s, 1H) 7.76 (s, 1H) 8.73 (s, 1H); MS (ESI(+)) m/e 516 (M+H)$^+$.

Example 173

(1S,2S,3R,4R)-3-({5-bromo-2-[(1-phenyl-1H-pyrazol-4-yl)amino]pyrimidin-4-yl}amino)bicyclo[2.2.1] hept-5-ene-2-carboxamide

Example 173A 4-nitro-1-phenyl-1H-pyrazole

4-Nitro-1H-pyrazole (1 g, 8.84 mmol), phenylboronic acid (2.223 g, 17.69 mmol), copper (II) acetate (2.409 g, 13.27 mmol) and pyridine (2.86 ml, 35.4 mmol) were combined in dichloromethane (40 ml) and the mixture stirred at ambient temperature open to the air with a drying tube. The mixture was filtered through a diatomaceous earth pad washing with dichloromethane; and the filtrate washed with water and brine, dried over MgSO$_4$, filtered and concentrated to give the title compound.

Example 173B 1-phenyl-1H-pyrazol-4-amine

The title compound was prepared as in Example 55B substituting 4-nitro-1-phenyl-1H-pyrazole for N,N-dimethyl-2-(4-nitro-1H-pyrazol-1-yl)acetamide.

Example 173C 1S,2S,3R,4R)-3-({5-bromo-2-[(1-phenyl-1H-pyrazol-4-yl)amino]pyrimidin-4-yl}amino)bicyclo[2.2.1] hept-5-ene-2-carboxamide The title compound was prepared as described in Example 1, substituting 1-phenyl-1H-pyrazol-4-amine for 1-methyl- 1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-d$_6$) ppm 1.32 (d, J=8.85 Hz, 1H) 2.04 (d, J=8.85 Hz, 1H) 2.48 (d, J=7.93 Hz, 1H) 2.68 (s, 1H) 2.77 (s, 1H) 4.13 (t, J=7.48 Hz, 1H) 6.08 (d, J=8.54 Hz, 1H) 6.22 (d, J=5.49 Hz, 1H) 6.76 (s, 1H) 7.13 (s, 1H) 7.35 (t, J=8.09 Hz, 2H) 7.33-7.44 (m, 2H) 7.58 (d, J=7.63 Hz, 2H) 7.72 (s, 1H) 7.87 (s, 1H) 8.24 (s, 1H) 8.83 (s, 1H); MS (ESI(+)) m/e 468 (M+H)$^+$.

Example 174

(1S,2S,3R,4R)-3-({5-chloro-2-[(1-phenyl-1H-pyrazol-4-yl)amino]pyrimidin-4-yl}amino)bicyclo[2.2.1]hept-5-ene-2-carboxamide The title compound was prepared as described in Example 1, substituting 1-phenyl-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 1.43 (d, J=10.38 Hz, 1H) 2.15 (d, J=8.85 Hz, 1H) 2.59 (d, J=8.24 Hz, 1H) 2.80 (s, 1H) 2.89 (s, 1H) 4.13-4.32 (m, 1H) 6.20 (d, J=8.85 Hz, 1H) 6.33 (d, J=8.85 Hz, 1H) 6.88 (s, 1H) 7.26 (t, J=7.32 Hz, 1H) 7.41-7.49 (m, 2H) 7.56 (d, J=7.93 Hz, 1H) 7.69 (d, J=7.63 Hz, 2H) 7.83 (s, 1H) 7.90 (s, 1H) 8.36 (s, 1H) 8.94 (s, 1H); MS (ESI(+)) m/e 422 (M+H)$^+$.

Example 175

5-chloro-N$^4$-(1H-indazol-5-yl)-N$^2$-(1-methyl-1H-pyrazol-4-yl)pyrimidine-2,4-diamine The title compound was prepared as described in Example 1, substituting 1H-indazol-5-amine for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 3.43 (s, 3H) 6.99-7.31 (m, 2H) 7.44 (d, J=8.85 Hz, 1H) 7.55 (d, J=8.85 Hz, 1H) 7.88 (s, 1H) 7.95-8.11 (m, 2H) 8.51 (s, 1H) 8.71 (s, 1H) 12.81 (s, 1H); MS (ESI(+)) m/e 341 (M+H)$^+$.

Example 176

5-chloro-N$^2$-(1-ethyl-1H-pyrazol-4-yl)-N$^4$-(1H-indazol-5-yl)pyrimidine-2,4-diamine The title compound was prepared as described in Example 1, substituting 1-ethyl-1H-pyrazol-4-amine for 1-methyl-1H-pyrazol-4-amine in Example 1B along with substitution of 1H-indazol-5-amine for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 1.11 (t, J=7.17 Hz, 3H) 3.70 (q, J=7.12 Hz, 2H) 7.06-7.35 (m, 2H) 7.47 (d, J=8.85 Hz, 1H) 7.58 (d, J=8.85 Hz, 1H) 7.89 (s, 1H) 7.97-8.12 (m, 2H) 8.54 (s, 1H) 8.74 (s, 1H) 12.84 (s, 1H); MS (ESI(+)) m/e 355 (M+H)$^+$.

Example 177

5-chloro-N$^2$-(1H-indazol-5-yl)-N$^2$-{1-[2-(pyrrolidin-1-yl)ethyl]-1H-pyrazol-4-yl}pyrimidine-2,4-diamine The title compound was prepared as described in Example 1, substituting 1-[2-(pyrrolidin-1-yl)ethyl]-1H-pyrazol-4-amine for 1-methyl-1H-pyrazol-4-amine in Example 1B along with substitution of 1H-indazol-5-amine for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 1.53-1.69 (m, 3H) 2.44-2.52 (m, 4H) 2.57 (t, J=6.56 Hz, 4H) 3.79 (t, J=6.56 Hz, 2H) 7.28 (s, 1H) 7.39 (s, 1H) 7.41-7.47 (m, 1H) 7.49-7.56 (m, 1H) 7.88 (s, 1H) 7.96-8.04 (m, 1H) 8.48 (s, 1H) 8.72 (s, 1H) 12.82 (s, 1H); MS (ESI(+)) m/e 424 (M+H)$^+$.

Example 178

(1S,2S,3R,4R)-3-[(5-chloro-2-{[1-(3-methylbenzyl)-1H-pyrazol-4-yl]amino}pyrimidin-4-yl)amino]bicyclo[2.2.1]hept-5-ene-2-carboxamide Example 178A 1-(3-methylbenzyl)-1H-pyrazol-4-amine The title compound was prepared as described in Example 55A substituting 3-methylbenzyl bromide for 2-chloro-N,N-dimethylacetamide.

Example 178B (1S,2S,3R,4R)-3-[(5-chloro-2-{[1-(3-methylbenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-methylbenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 1.40 (d, J=8.85 Hz, 1H) 2.10 (d, J=8.54 Hz, 1H) 2.27 (s, 3H) 2.52 (d, J=8.24 Hz, 1H) 2.75 (s, 1H) 2.87 (s, 1H) 4.05-4.19 (m, 1H) 5.19 (s, 2H) 6.15 (d, J=8.54 Hz, 1H) 6.28 (d, J=5.49 Hz, 1H) 6.86 (s, 1H) 6.99 (d, J=7.63 Hz, 1H) 7.03 (s, 1H) 7.08 (d, J=7.63 Hz, 1H) 7.20 (t, J=7.63 Hz, 1H) 7.44 (s, 1H) 7.54 (d, J=7.63 Hz, 1H) 7.56 (s, 1H) 7.74 (s, 1H) 7.83 (s, 1H) 8.71 (s, 1H); MS (ESI(+)) m/e 450 (M+H)$^+$.

Example 179

(1S,2S,3R,4R)-3-[(5-chloro-2-{[1-(2-naphthylmethyl)-1H-pyrazol-4-yl]amino}pyrimidin-4-yl)amino]bicyclo[2.2.1]hept-5-ene-2-carboxamide Example 179A 1-(2-naphthylmethyl)-1H-pyrazol-4-amine The title compound was prepared as described in Example 55A substituting 2-(bromomethyl)naphthalene for 2-chloro-N,N-dimethylacetamide.

Example 179B (1S,2S,3R,4R)-3-[(5-chloro-2-{[1-(3-methylbenzyl)-1H-pyrazol-4-yl]amino}pyrimidin-4-yl)amino]bicyclo[2.2.1]hept-5-ene-2-carboxamide The title compound was prepared as described in Example 1, substituting 1-(2-naphthylmethyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 1.37 (d, J=8.85 Hz, 1H) 2.09 (d, J=8.85 Hz, 1H) 2.74 (s, 1H) 2.84 (s, 1H) 5.41 (s, 2H) 6.11 (d, J=8.85 Hz, 1H) 6.21 (d, J=8.54 Hz, 1H) 6.87 (s, 1H) 7.35 (dd, J=8.39, 1.68 Hz, 2H) 7.45-7.50 (m, 2H) 7.49-7.53 (m, 3H) 7.61 (s, 1H) 7.73 (s, 1H) 7.79-7.89 (m, 4H) 8.73 (s, 1H); MS (ESI(+)) m/e 486 (M+H)$^+$.

Example 180

2-(4-{[5-chloro-4-(1H-indazol-5-ylamino)pyrimidin-2-yl]amino}-1H-pyrazol-1-yl)ethanol The title compound was prepared as described in Example 1, substituting 2-(4-amino-1H-pyrazol-1-yl)ethanol for 1-methyl-1H-pyrazol-4-amine in Example 1B along with substitution of 1H-indazol-5-amine for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 3.58 (s, 2H) 3.81 (s, 2H) 4.37 (d, J=10.99 Hz, 1H) 7.31 (s, 1H) 7.39-7.57 (m, 4H) 7.90 (s, 1H) 8.01 (s, 1H) 8.46 (s, 1H) 8.71 (s, 1H) 12.78 (s, 1H); MS (ESI(+)) m/e 371 (M+H)$^+$.

Example 181

5-chloro-N$^2$-(1H-indazol-5-yl)-N$^2$-{1-[(3R)-pyrrolidin-3-yl]-1H-pyrazol-4-yl}pyrimidine-2,4-diamine The title compound was prepared as described in Example 73, substituting 1H-indazol-5-amine for (+)-(1S,2S,3R,4R)-3-aminobicyclo[2.2.1]hept-5-ene-2-carboxamide in 73B and (R)-tert-butyl 3-(4-amino-1H-pyrazol-1-yl)pyrrolidine-1-carboxylate for (S)-tert-butyl 3-(4-amino-1H-pyrazol-1-yl)pyrrolidine-1-carboxylate in Example 73C. $^1$H NMR (400 MHz, DMSO-$d_6$) ppm 1.87-2.01 (m, 1H) 2.07-2.18 (m, 1H) 2.48 (s, 1H) 2.85-3.94 (m, 6H) 4.48 (s, 1H) 7.28-7.50 (m, 2H) 7.57 (s, 1H) 7.87 (s, 1H) 8.01 (s, 1H) 8.54 (s, 1H) 8.80 (s, 1H) 12.85 (s, 1H); MS (ESI(+)) m/e 396 (M+H)$^+$.

Example 182

(1R,2R,3S,5R)-2-({5-bromo-2-[(1-methyl-1H-pyrazol-4-yl)amino]pyrimidin-4-yl}amino)-6,6-dimethylbicyclo[3.1.1]heptane-3-carboxamide The title compound was prepared as described in Example 1, substituting (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4-dichloro-5-bromo-pyrimidine for 2,4-dichloro-5-fluoropyrimidine in Example 1A. $^1$H NMR (500 MHz, DMSO-$d_6$, T=90° C.) ppm 1.04 (s, 3H) 1.24 (s, 3H) 1.73 (d, J=9.53 Hz, 1H) 1.89-2.05 (m, 3H) 2.06-2.18 (m, 2H) 3.25-3.41 (m, 1H) 3.77 (s, 3H) 4.88 (t, J=9.16 Hz, 1H) 6.89 (m, 2H) 7.29 (s, 1H) 7.47 (br s, 1H) 7.63 (s, 1H) 7.89 (s, 1H) 8.69 (s, 1H); MS (ESI(+)) m/e 434, 436 (M+H)$^+$.

Example 183

(1R,2R,3S,5R)-2-({5-bromo-2-[(1-ethyl-1H-pyrazol-4-yl)amino]pyrimidin-4-yl}amino)-6,6-dimethylbicyclo[3.1.1]heptane-3-carboxamide The title compound was prepared as described in Example 1, substituting 1-ethyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (500 MHz, DMSO-$d_6$, T=90° C.) ppm 1.03 (s, 3H) 1.24 (s, 3H) 1.36 (t, J=7.33 Hz, 3H) 1.73 (d, J=9.89 Hz, 1H) 1.90-2.05 (m, 3H) 2.05-2.17 (m, 2H) 3.22-3.43 (m, 1H) 4.05 (q, J=7.33 Hz, 2H) 4.88 (t, J=9.53 Hz, 1H) 6.65-6.92 (m, J=8.43 Hz, 2H) 7.28 (s, 1H) 7.49 (s, 1H) 7.65 (s, 1H) 7.89 (s, 1H) 8.67 (s, 1H); MS (ESI(+)) m/e 448, 450 (M+H)$^+$.

Example 184

(1R,2R,3S,5R)-2-({5-chloro-2-[(1,5-dimethyl-1H-pyrazol-4-yl)amino]pyrimidin-4-yl}amino)-6,6-dimethylbicyclo[3.1.1]heptane-3-carboxamide The title compound was prepared as described in Example 1, substituting 1,5-dimethyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$, T=90° C.) ppm 0.93 (s, 3H) 1.21 (s, 3H) 1.72 (d, J=9.77 Hz, 1H) 1.82-1.99 (m, 3H) 2.01-2.12 (m, 2H) 2.13 (s, 3H) 3.20-3.28 (m, 1H) 3.67 (s, 3H) 4.60-4.95 (m, 1H) 6.56-6.93 (m, J=8.85 Hz, 2H) 7.18 (br s, 1H) 7.42 (s, 1H) 7.69-7.81 (m, 1H) 7.86 (s, 1H); MS (ESI(+)) m/e 404 (M+H)$^+$.

Example 185

(1R,2R,3S,5R)-2-({5-bromo-2-[(1,5-dimethyl-1H-pyrazol-4-yl)amino]pyrimidin-4-yl}amino)-6,6-dimethylbicyclo[3.1.1]heptane-3-carboxamide The title compound was prepared as described in Example 1, substituting 1,5-dimethyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$, T=90° C.) ppm 0.92 (s, 3H) 1.21 (s, 3H) 1.72 (d, J=9.77 Hz, 1H) 1.85-1.98 (m, 3H) 2.03-2.11 (m, 2H) 2.13 (s, 3H) 3.15-3.28 (m, 1H) 3.67 (s, 3H) 4.71-4.82 (m, 1H) 6.53-6.91 (m, J=8.85 Hz, 1H) 7.18 (br s, 1H) 7.41 (s, 1H) 7.83 (s, 1H) 7.87 (s, 1H); MS (ESI(+)) m/e 448, 450 (M+H)$^+$.

Example 186

5-chloro-N²-(1H-indazol-5-yl)-N²-{1-[2-(4-methylpiperazin-1-yl)ethyl]-1H-pyrazol-4-yl}pyrimidine-2,4-diamine 2-(4-{[5-chloro-4-(1H-indazol-5-ylamino)pyrimidin-2-yl]amino}-1H-pyrazol-1-yl)ethanol The title compound was prepared as described in Example 1, substituting 1-[2-(4-methylpiperazin-1-yl)ethyl]-1H-pyrazol-4-amine for 1-methyl-1H-pyrazol-4-amine in Example 1B along with substitution of 1H-indazol-5-amine for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 2.12 (s, 3H) 2.24 (d, J=4.58 Hz, 4H) 2.41-2.53 (m, 5H) 3.78 (t, J=6.56 Hz, 3H) 7.28 (s, 1H) 7.32-7.40 (m, 1H) 7.42-7.46 (m, 1H) 7.54-7.59 (m, 1H) 7.83-7.90 (m, 1H) 7.95-8.04 (m, 1H) 8.42-8.53 (m, 1H) 8.75 (s, 1H) 12.82 (s, 1H); MS (ESI(−)) m/e 451 (M−H)⁺.

Example 187

(1R,2R,3S,5R)-2-({2-[(1-benzyl-1H-pyrazol-4-yl)amino]-5-chloropyrimidin-4-yl}amino)-6,6-dimethylbicyclo[3.1.1]heptane-3-carboxamide The title compound was prepared as described in Example 1, substituting 1-benzyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 0.97 (s, 3H) 1.19 (s, 3H) 1.73 (d, J=9.77 Hz, 1H) 1.88-2.04 (m, 5H) 2.11 (t, J=10.53 Hz, 3H) 3.23-3.35 (m, 1H) 4.86 (t, J=9.31 Hz, 1H) 5.24 (s, 2H) 6.74 (s, 1H) 6.89 (d, J=8.24 Hz, 1H) 7.18 (d, J=6.71 Hz, 2H) 7.23-7.29 (m, 2H) 7.32 (t, J=7.02 Hz, 2H) 7.59 (s, 1H) 7.71 (s, 1H) 7.81 (s, 1H) 8.66 (s, 1H); MS (ESI(+)) m/e 466 (M+H)⁺.

Example 188

(1R,2R,3S,5R)-2-[(5-chloro-2-{[1-(2-phenylethyl)-1H-pyrazol-4-yl]amino}pyrimidin-4-yl)amino]-6,6-dimethylbicyclo[3.1.1]heptane-3-carboxamide The title compound was prepared as described in Example 1, substituting 1-(2-phenylethyl)-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 1.03 (s, 3H) 1.24 (s, 3H) 1.75 (d, J=9.77 Hz, 1H) 1.89-2.06 (m, 3H) 2.07-2.19 (m, 2H) 3.11 (t, J=7.32 Hz, 2H) 3.31 (t, J=10.38 Hz, 1H) 4.26 (t, J=7.32 Hz, 2H) 4.87 (t, J=9.16 Hz, 1H) 6.76 (s, 1H) 6.90 (d, J=8.54 Hz, 1H) 7.11-7.22 (m, 3H) 7.22-7.33 (m, 2H) 7.54 (s, 1H) 7.60 (s, 1H) 7.81 (s, 1H) 8.62 (s, 1H); MS (ESI(+)) m/e 480 (M+H)⁺.

Example 189

(1R,2R,3S,5R)-2-({5-chloro-2-[(1-phenyl-1H-pyrazol-4-yl)amino]pyrimidin-4-yl}amino)-6,6-dimethylbicyclo[3.1.1]heptane-3-carboxamide The title compound was prepared as described in Example 1, substituting 1-phenyl-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$) ppm 0.95 (s, 3H) 1.20 (s, 3H) 1.74 (d, J=9.77 Hz, 1H) 1.85-1.95 (m, 1H) 1.95-2.07 (m, 2H) 2.07-2.17 (m, 2H) 3.27-3.40 (m, 1H) 4.83-4.95 (m, 1H) 6.74 (s, 1H) 6.91 (d, J=8.54 Hz, 1H) 7.26 (t, J=6.87 Hz, 2H) 7.40-7.49 (m, 2H) 7.70 (d, J=9.77 Hz, 2H) 7.83 (s, 1H) 7.88 (s, 1H) 8.28 (s, 1H) 8.83 (s, 1H); MS (ESI(+)) m/e 452 (M+H)⁺.

Example 190

(1R,2R,3S,5R)-2-{[5-chloro-2-({1-[2-(4-methylpiperazin-1-yl)ethyl]-1H-pyrazol-4-yl}amino)pyrimidin-4-yl]amino}-6,6-dimethylbicyclo[3.1.1]heptane-3-carboxamide The title compound was prepared as described in Example 1, substituting 1-(2-(4-methylpiperazin-1-yl)ethyl)-1H-pyrazol-4-amine for 1-methyl-1H-pyrazol-4-amine in Example 1B along with substitution of (1R,2R,3S,5R)-2-amino-6,6-dimethylbicyclo[3.1.1]heptane-3-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-d$_6$, T=90° C.) δ ppm 1.06 (s, 3H) 1.20 (s, 3H) 1.28 (dd, J=9.31, 6.26 Hz, 1H) 1.61 (d, J=10.38 Hz, 1H) 1.86-1.98 (m, 3H) 2.04-2.11 (m, 2H) 2.14 (s, 3H) 2.27-2.31 (m, 4H) 2.41-2.44 (m, 4H) 2.72 (td, J=6.87, 1.53 Hz, 2H) 2.85-2.94 (m, 1H) 4.10 (td, J=6.87, 1.83 Hz, 2H) 4.94 (t, J=8.70 Hz, 1H) 5.99 (d, J=8.54 Hz, 1H) 6.57-6.75 (m, 1H) 7.50 (s, 1H) 7.80 (s, 1H) 7.81 (s, 1H) 8.57 (s, 1H); MS (ESI(+)) m/e 502 (M+H)⁺.

Example 191

(1R,2R,3S,5R)-2-[(5-chloro-2-{[1-(piperidin-4-yl)-1H-pyrazol-4-yl]amino}pyrimidin-4-yl)amino]-6,6-dimethylbicyclo[3.1.1]heptane-3-carboxamide The title compound was prepared as described in Example 73, substituting (1R,2R,3S,5R)-2-amino-6,6-dimethylbicyclo[3.1.1]heptane-3-carboxamide for (+)-(1S,2S,3R,4R)-3-aminobicyclo[2.2.1]hept-5-ene-2-carboxamide in 73B and tert-butyl 4-(4-amino-1H-pyrazol-1-yl)piperidine-1-carboxylate for (S)-tert-butyl 3-(4-amino-1H-pyrazol-1-yl)pyrrolidine-1-carboxylate in Example 73C. $^1$H NMR (400 MHz, DMSO-d$_6$, T=90° C.) d ppm 1.03 (s, 3H) 1.22-1.26 (m, 1H) 1.24 (s, 3H) 1.74 (d, J=10.07 Hz, 1H) 1.84-1.95 (m, 3H) 1.97-2.05 (m, 4H) 2.10 (s, 2H) 2.71-2.80 (m, 2H) 3.14-3.21 (m, 2H) 3.31 (td, J=10.38, 4.27 Hz, 1H) 4.13-4.22 (m, 1H) 4.83-4.90 (m, 1H) 6.63-6.86 (m, 1H) 6.88 (d, J=8.54 Hz, 1H) 7.11-7.36 (m, 1H) 7.56 (s, 1H) 7.67 (s, 1H) 7.81 (s, 1H) 8.59 (s, 1H); MS (ESI(+)) m/e 460 (M+H)⁺.

Example 192

(1S,2S,3R,4R)-3-[(5-chloro-2-{[1-(3-fluoro-4-methoxybenzyl)-1H-pyrazol-4-yl]amino}pyrimidin-4-yl)amino]bicyclo[2.2.1]hept-5-ene-2-carboxamide

Example 192A 1-(3-fluoro-4-methoxybenzyl)-1H-pyrazol-4-amine

The title compound was prepared as described in Example 55A substituting 3-fluoro-4-methoxybenzyl bromide for 2-chloro-N,N-dimethylacetamide.

Example 192B (1S,2S,3R,4R)-3-[(5-chloro-2-{[1-(3-fluoro-4-methoxybenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-fluoro-4-methoxybenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4,5-trichloropyrimidine for 2,4-dichloro-5-fluoropyrimidine in Example 1A. $^1$H NMR (400 MHz, DMSO-$d_6$) ppm 1.40 (d, J=8.85 Hz, 1H) 2.11 (d, J=8.85 Hz, 1H) 2.51 (d, J=7.02 Hz, 1H) 2.74 (s, 1H) 2.86 (s, 1H) 3.81 (s, 3H) 4.11 (t, J=8.70 Hz, 1H) 5.17 (s, 2H) 6.15 (d, J=8.54 Hz, 1H) 6.29 (d, J=8.54 Hz, 1H) 6.86 (s, 1H) 6.96-7.05 (m, 2H) 7.09 (t, J=8.54 Hz, 1H) 7.48 (d, J=7.63 Hz, 2H) 7.58 (s, 1H) 7.74 (s, 1H) 7.91 (s, 1H) 8.72 (s, 1H); MS (ESI(+)) m/e 528 (M+H)$^+$.

Example 193

(1S,2S,3R,4R)-3-[(5-bromo-2-{[1-(3-fluoro-4-methoxybenzyl)-1H-pyrazol-4-yl]amino}pyrimidin-4-yl)amino]bicyclo[2.2.1]hept-5-ene-2-carboxamide The title compound was prepared as described in Example 1, substituting 1-(3-fluoro-4-methoxybenzyl)-1H-pyrazol-4-amine for 1-methyl-1H-pyrazol-4-amine in Example 1B along with substitution of (+)-(1S,2S,3R,4R)-3-aminobicyclo[2.2.1]hept-5-ene-2-carboxamide for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.40 (d, J=12.21 Hz, 1H) 2.11 (d, J=8.85 Hz, 1H) 2.75 (s, 1H) 2.87 (s, 1H) 3.81 (s, 3H) 4.11 (t, J=8.70 Hz, 1H) 5.17 (s, 2H) 6.15 (d, J=5.80 Hz, 1H) 6.29 (d, J=8.54 Hz, 1H) 6.86 (s, 1H) 6.96-7.04 (m, 2H) 7.09 (t, J=7.93 Hz, 2H) 7.42 (s, 1H) 7.53 (d, J=7.63 Hz, 1H) 7.53-7.59 (m, 1H) 7.75 (s, 1H) 7.84 (s, 1H) 8.71 (s, 1H); MS (ESI(+)) m/e 484 (M+H)$^+$.

Example 194

5-bromo-$N^2$-(1-ethyl-1H-pyrazol-4-yl)-$N^2$-(1H-indazol-5-yl)pyrimidine-2,4-diamine The title compound was prepared as described in Example 1, substituting 1-ethyl-1H-pyrazol-4-amine for 1-methyl-1H-pyrazol-4-amine in Example 1B along with substitution of 1H-indazol-5-amine for (+/−)-(1S,2S,3R,4R)-3-aminobicyclo[2.2.1]hept-5-ene-2-carboxamide and 2,4-dichloro-5-bromopyrimidine for 2,4-dichloro-5-fluoropyrimidine in Example 1A. $^1$H NMR (400 MHz, DMSO-$d_6$) ppm 1.06 (t, J=7.32 Hz, 3H) 3.64 (q, J=7.02 Hz, 2H) 7.23 (s, 2H) 7.41 (d, J=8.85 Hz, 1H) 7.55 (d, J=8.85 Hz, 1H) 7.84 (s, 1H) 8.02 (s, 1H) 8.07 (s, 1H) 8.28 (s, 1H) 8.74 (s, 1H); MS (ESI(+)) m/e 399 (M+H)$^+$.

Example 195

Enzyme Inhibition Data

This example describes the assays that may be used to identify compounds having kinase activity.

To determine Aurora B activity of representative compounds of the invention, Active Aurora B enzyme (recombinant residues 1-344) and INCENP (recombinant GST fusion protein (Upstate)) were incubated in wells of a 384 well plate with biotinylated histone H3 peptide residues 1-21 (Upstate), 1 mM ATP, and various concentrations of inhibitors in a HEPES buffer, pH 7.4 containing $MgCl_2$, sodium othrovanadate, and Triton X-100. After 1 hour, the reaction was stopped with EDTA and anti-phospho-histone H3 Europium Cryptate (Cis-Bio) and SA-APC (Phycolink, Prozyme) were added to detect the phosphopeptide. The amount of phosphorylation was determined by the time-resolved fluorescence ratio of signals at 665 nm and 615 nm. The $IC_{50}$'s were calculated by an exponential fit of the inhibition values with the inhibitor concentrations using Assay Explorer software.

To determine Aurora A and C activity of representative compounds of the invention, Active Aurora A or C enzyme was incubated in wells of a 384 well plate with biotinylated STK substrate-2 (Upstate), 1 mM ATP, and various concentrations of inhibitors in a Hepes buffer, pH 7.4 containing $MgCl_2$, sodium othrovanadate, and Triton X-100. After 1 hour, the reaction was stopped with EDTA and anti-phospho-STK antibody Europium Cryptate (Upstate) and SA-XL665 (Upstate) were added to detect the phosphopeptide. The amount of phosphorylation was determined by the time-resolved fluorescence ratio of signals at 665 nm and 615 nm. The $IC_{50}$s were calculated by an exponential fit of the inhibition values with the inhibitor concentrations using Assay Explorer software.

To determine the activity of the various kinases, a homogenous time-resolved fluorescence (HTRF) in vitro kinase assay was used. (Mathis, G., HTRF® Technology. J Biomol Screen, 1999. 4(6): p. 309-314; Alfred J. Kolb, Paul V. Kaplita, David J. Hayes, Young-Whan Park, Christine Pernell, John S. Major and Gerard Mathis, Drug Discovery Today, 1998, 3, 333-342.)

For example for KDR, 7 ng/well of purified enzyme (His6-KDR 789-1354, MW 63 kD) was mixed with 0.5 μM N-biotinylated substrate (Biotin-Ahx-AEEEYFFLA-amide (SEQ. ID. 1)), various concentrations of inhibitor in reaction buffer (50 mM HEPES, pH 7.1, 10 mM $MgCl_2$, 2 mM $MnCl_2$, 0.1% BSA and 1 mM DTT, 40 L final volume), ATP (1 mM final conc.) in a black 384-well plate. After 60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hours and was then read in a time-resolved fluorescence detector (InVision, Perkin-Elmer) at 620 nm and 665 nm sequentially with excitation. The ratio between the signal of 620 nm and 665 nm was used in the calculation of the $IC_{50}$.

Table 1 depicts enzyme inhibition data ($K_i$) for exemplary compounds. In Table 1, "A" represents a $K_i$ of less than 0.1 µM, "B" represents a $K_i$ of between 0.1 µM and 1 µM, "C" represents a $K_i$ of between 1 µM and 5 µM, and "D" represents a $K_i$ of greater than 5 µM for the indicated enzyme.

TABLE 1

| Example | Aurora B | Aurora A | KDR |
| --- | --- | --- | --- |
| 1 | A | A | B |
| 2 | B | C | D |
| 3 | B | C | C |
| 4 | B | D | D |
| 5 | A | B | B |
| 6 | B | B | B |
| 7 | B | D | D |
| 8 | A | A | B |
| 9 | A | B | D |
| 10 | A | A | A |
| 11 | A | A | B |
| 12 | A | B | B |
| 13 | A | A | B |
| 14 | A | B | C |
| 15 | A | B | C |
| 16 | B | B | C |
| 17 | A | B | B |
| 18 | B | B | B |
| 19 | A | A | A |
| 20 | A | A | A |
| 21 | B | A | B |
| 22 | A | A | A |
| 23 | A | B | B |
| 24 | A | A | A |
| 25 | A | B | B |
| 26 | A | C | C |
| 27 | A | A | A |
| 28 | A | A | A |
| 29 | B | A | A |
| 30 | A | A | A |
| 31 | A | A | A |
| 32 | A | A | A |
| 33 | A | A | A |
| 34 | A | A | A |
| 35 | A | A | A |
| 36 | A | A | A |
| 37 | A | A | A |
| 38 | A | A | A |
| 39 | A | A | A |
| 40 | A | A | A |
| 41 | A | A | A |
| 42 | A | A | A |
| 43 | A | A | A |
| 44 | A | A | A |
| 45 | A | A | A |
| 46 | A | A | A |
| 47 | A | A | A |
| 48 | A | A | A |
| 49 | A | A | A |
| 50 | A | A | A |
| 51 | A | A | A |
| 52 | A | A | A |
| 53 | A | A | A |
| 54 | A | A | A |
| 55 | A | A | A |
| 56 | A | A | A |
| 57 | A | A | A |
| 58 | A | A | A |
| 59 | A | A | A |
| 60 | A | A | A |
| 61 | A | A | A |
| 62 | A | A | A |
| 63 | A | A | A |
| 64 | A | A | A |
| 65 | A | A | A |
| 66 | A | A | A |
| 67 | A | A | A |
| 68 | A | A | A |
| 69 | A | A | A |
| 70 | A | A | A |
| 71 | A | A | A |
| 72 | A | A | A |
| 73 | A | A | A |
| 74 | A | A | A |
| 75 | A | A | A |
| 76 | A | A | A |
| 77 | A | A | A |
| 78 | A | A | A |
| 79 | A | A | A |
| 80 | A | A | A |
| 81 | A | A | A |
| 82 | A | A | A |
| 83 | A | A | A |
| 84 | A | A | A |
| 85 | A | A | A |
| 86 | A | A | B |
| 87 | A | A | A |
| 88 | A | A | A |
| 89 | A | A | A |
| 90 | A | A | A |
| 91 | A | A | A |
| 92 | A | A | A |
| 93 | A | A | A |
| 94 | A | A | A |
| 95 | A | A | A |
| 96 | A | A | A |
| 97 | A | A | A |
| 98 | A | A | A |
| 99 | A | A | A |
| 100 | A | A | A |
| 101 | A | A | A |
| 102 | A | A | A |
| 103 | A | A | A |
| 104 | A | A | A |
| 105 | A | A | A |
| 106 | A | A | A |
| 107 | A | A | A |
| 108 | A | A | A |
| 109 | A | A | A |
| 110 | A | A | A |
| 111 | A | A | A |
| 112 | A | A | A |
| 113 | A | A | A |
| 114 | A | A | A |
| 115 | A | A | A |
| 116 | A | A | A |
| 117 | A | A | A |
| 118 | A | A | A |
| 119 | A | A | A |
| 120 | A | A | A |
| 121 | A | A | A |
| 122 | A | A | A |
| 123 | A | A | A |
| 124 | A | A | A |
| 125 | A | B | B |
| 126 | A | A | B |
| 127 | B | B | B |
| 128 | B | B | B |
| 129 | A | A | A |
| 130 | A | A | A |
| 131 | A | A | A |
| 132 | A | A | A |
| 133 | A | A | B |
| 134 | A | A | A |
| 135 | A | A | A |
| 136 | A | A | B |
| 137 | A | A | A |
| 138 | A | A | A |
| 139 | A | A | A |
| 140 | A | A | A |
| 141 | A | A | A |
| 142 | A | A | A |
| 143 | A | A | A |
| 144 | A | A | A |
| 145 | A | A | A |
| 146 | A | A | B |
| 147 | A | A | A |
| 148 | A | A | A |

TABLE 1-continued

| Example | Aurora B | Aurora A | KDR |
|---|---|---|---|
| 149 | A | A | A |
| 150 | A | A | A |
| 151 | A | A | A |
| 152 | A | A | B |
| 153 | A | A | B |
| 154 | A | A | A |
| 155 | A | A | A |
| 156 | A | A | B |
| 157 | A | A | A |
| 158 | A | A | A |
| 159 | A | A | A |
| 160 | A | A | A |
| 161 | A | A | A |
| 162 | A | A | A |
| 163 | A | A | B |
| 164 | A | A | B |
| 165 | A | A | A |
| 166 | A | A | A |
| 167 | A | A | A |
| 168 | A | A | A |
| 169 | A | A | A |
| 170 | A | A | A |
| 171 | A | A | A |
| 172 | A | A | A |
| 173 | A | A | A |
| 174 | A | A | A |
| 175 | A | A | A |
| 177 | A | A | A |
| 178 | A | A | A |
| 179 | A | A | A |
| 180 | A | A | A |
| 181 | A | A | A |
| 182 | A | A | A |
| 183 | A | A | A |
| 184 | A | A | A |
| 185 | A | A | A |
| 187 | A | A | A |
| 188 | A | A | A |
| 189 | A | A | A |
| 190 | A | B | B |
| 191 | A | A | A |
| 192 | A | A | A |
| 193 | A | A | A |

Example 196

KDR Cellular Assay

The ability of compounds to inhibit KDR receptor phosphorylation in cells was measured by ELISA following the protocol outlined below.

Day 1 Protocol

KDR transfected 3T3 (embryonic mouse) cells added to 96-well tissue culture plates at 20,000 cells/well.

Plates were covered and placed in a 37° C. humidified incubator with 5% CO2 overnight, to allow cells to adhere.

Coating solution was prepared: 500 l/vial PBS was added to 2 vials of anti-KDR antibody, then 1 ml solubilized anti-KDR antibody into 29.0 ml bicarbonate buffer. Coating solution was added to all wells at 150 l/well (final amount anti-KDR=1 g/well) and placed at 4° C. overnight.

Day 2 Protocol

Blocking solution (2.1 g dry milk+42 ml PBS=5% milk in PBS) was placed on a stir plate for 30 min.

Assay plates were washed twice with PBST, and 200 l/well blocking solution was added to all wells. Assay plates were covered with plate sealers and placed in a 37° C. microplate chamber until just before cell lysate transfer.

Compound stocks were thawed or prepared in DMSO as 5 mM stocks.

Dilution medium (DM, 1% DMSO in DMEM) and compounds were diluted by half-log increments for concentration response analysis.

Conditioned media was dumped from the tissue culture plates, and plates were blotted dry.

Standard solution in DM, compound dilutions in DM, or DM (for high control, negative control, and reference wells) were added to the tissue culture plates, 25 l/well. Each pair of tissue culture plates was prepared with the same compounds, solutions, and layout; and will be combined later; Tissue culture plates were covered and placed in the 37° C. microplate chamber for 20 min.

VEGF solution was prepared: 110 l VEGF stock+10.89 ml DM=100 ng/ml VEGF

VEGF solution or DM (for reference wells) was added to the tissue culture plates, 25 μl/well.

Tissue culture plates were covered and placed in the 37° C. microplate chamber for 10 min.

RIPA buffer was prepared (240 l NaVO3 stock+240 l PIC stock+24 l NaF stock+23.496 ml RIPA base) and added to the tissue culture plates, 50 l/well.

Tissue culture plates were covered and placed on a Labline plate shaker for 10 min (speed about 5).

Assay plates were washed twice with PBST.

Cell lysates from matching wells of each pair of tissue culture plates were combined to =200 l/well, and were pipetted up and down to mix. Cell lysates were transferred to the assay plates using the same layouts, 170 l/well.

Assay plates were covered with plate sealers and placed on a Labline plate shaker for 2 hr (speed about 5).

Assay plates were washed 5 times with PBST.

Biotin antibody solution was prepared (16 l biotin antibody stock+32 ml PBST=2000× dilution) and added to the assay plates, 150 l/well.

Assay plates were covered with plate sealers and placed on a Labline plate shaker for 90 min Assay plates were washed 5 times with PBST.

Streptavidin-HRP solution was prepared (16 l streptavidin-HRP stock+32 ml PBST=2000× dilution) and added to the assay plates, 150 l/well.

Assay plates were covered with plate sealers and placed on a Labline plate shaker for 60 min Assay plates were washed 5 times with PBST.

Substrate was added to the assay plates, 100 l/well.

As assay plates developed, the plates were each monitored on a Molecular Devices Spectramax set to 650 nm, until the signal in the high control wells was around 0.6 OD and the signal in the negative control wells was around 0.1-0.15 OD.

Stop solution was added to the assay plates, 100 l/well.

The plates were read on a Molecular Devices Spectramax set to 450 nm.

Data was calculated by Assay Explorer, using same-plate high control wells as 0% and reference standard wells as 100% inhibition of KDR phosphorylation. IC50 values were calculated by non-linear regression analysis of the concentration response data.

Reagents & Materials 96-well tissue culture plate: flat bottom tissue culture-treated, Costar 3599

PBS: 1× phosphate-buffered saline, pH 7.4, without calcium chloride, without magnesium chloride; Invitrogen/Gibco 10010 lot 1187052+1201198

Anti-KDR antibody: anti-human VEGF R2 (KDR) antibody, R&D Systems AF357 lot CUE02405A, 5 mg per vial at 2.630 mg/ml; divided into 38 l aliquots; stored at −30° C.

Bicarbonate buffer: 1 packet BupH carbonate-bicarbonate buffer pack (Pierce 28382 lot DH58189B)+500 ml nH2O, stored at room temperature
96-well assay plate: EIA/RIA Easywash plate, high binding; Costar 3369
Dry milk: Biorad 170-6404 lot 175026B
PBST: 1 ml tween+1 L PBS=1% tween in PBS, stored at room temperature
Tween: Tween 20, Sigma P-1379 lot 033K0711
DMEM 11965: Dulbecco's modified Eagle medium, high glucose, with L-glutamine, with pyroxidine hydrochloride, without sodium pyruvate; Invitrogen/Gibco 11965 lot 1212380
VEGF stock: 1 ml PBS/BSA (PBS+0.1% BSA, prepared by Keith Glaser and stored at room temperature, catalog and lot numbers unknown) added to 1 vial VEGF (recombinant human VEGF, R&D Systems 293-VE lot II16311, 10 g per vial)=10 g/ml; divided into 55 l aliquots; stored at −80° C.
NaVO3 stock: 12.19 mg/ml sodium metavanadate (Sigma S-6383 lot 092K0853, FW 121.9) in $nH_2O$=100 mM, heated at 37° C. to solubilize, then divided into 120 l aliquots; stored at −20° C.; final concentration 1 mM in RIPA buffer
PIC stock: protease inhibitor cocktail (Sigma P-8340 lot 044K4106); divided into 120 l aliquots; stored at −20° C.; final dilution 100× in RIPA buffer
NaF stock: 41.99 mg/ml sodium fluoride (Sigma S-7920 lot 070K0120, FW 41.99) in nH2O=1 M, divided into 12 l aliquots; stored at −20° C.; final concentration 1 mM in RIPA buffer
RIPA base: prepared in $nH_2O$ to 500 ml final volume with components below, pH'd to 7.4; stored at 4° C.
   3.94 g Trizma hydrochloride (Sigma T-3253 lot 108H5406, FW 157.6)=50 mM
   5.0 ml Igepal CA-630 (Sigma I-3021 lot 122K0040)=1%
   1.25 g deoxycholic acid, sodium salt (Sigma D-6750 lot 44F-0504, FW 414.5)=0.25%
   4.383 g NaCl (Fisher S271-3 lot 005493, FW 58.44)=150 mM
   226.1 mg EDTA (Sigma E-5391 lot 33H0478, FW 452.2)=1 mM
Biotin antibody stock: anti-phosphotyrosine, biotin-conjugate, mouse monoclonal IgG2b, clone 4G10; Upstate Biotechnology 16-103 lot 23957
Streptavidin-HRP stock: streptavidin, horseradish peroxidase conjugate; Upstate Biotechnology 18-152 lot 26275, bottle opened Jul. 1, 2004
Substrate: Enhanced K-blue substrate (TMB), Neogen 308177 lot 040405
Stop solution: 14.5 ml phosphoric acid (Sigma P-5811 lot 051K3451, FW 98.00, 17.245 M)+235.5 ml $nH_2O$=1 M; stored at room temperature.

Table 2 depicts inhibition data for exemplary compounds. In Table 2, "A" represents an $IC_{50}$ of less than 0.1 μM and "B" represents an $IC_{50}$ of between 0.1 μM and 1 μM.

TABLE 2

| Example | $IC_{50}$ |
|---|---|
| 10 | A |
| 19 | A |
| 20 | A |
| 21 | B |
| 22 | A |
| 24 | A |
| 27 | A |
| 28 | A |
| 29 | B |
| 30 | A |
| 31 | A |
| 32 | A |
| 86 | B |
| 87 | B |
| 88 | B |
| 89 | A |
| 90 | A |
| 91 | A |
| 92 | B |
| 93 | B |
| 94 | A |
| 95 | A |
| 96 | A |
| 97 | A |
| 98 | A |
| 99 | A |
| 100 | A |
| 101 | B |
| 102 | A |
| 103 | B |
| 104 | B |
| 105 | A |
| 106 | A |
| 107 | A |
| 108 | A |
| 109 | B |
| 110 | A |
| 111 | A |
| 112 | A |
| 113 | B |
| 114 | B |
| 115 | B |
| 116 | A |
| 117 | A |
| 118 | A |
| 119 | B |
| 121 | B |
| 122 | A |
| 123 | A |
| 124 | B |
| 125 | B |
| 126 | B |
| 127 | B |
| 128 | B |
| 129 | A |
| 130 | B |
| 131 | B |
| 132 | B |
| 133 | B |
| 134 | B |
| 135 | A |
| 136 | B |
| 137 | B |
| 138 | B |
| 139 | B |
| 140 | B |
| 141 | B |
| 142 | B |
| 143 | A |
| 144 | A |
| 145 | B |
| 146 | B |
| 147 | B |
| 148 | A |
| 149 | A |
| 150 | B |
| 151 | B |
| 152 | B |
| 153 | B |
| 154 | B |
| 155 | A |
| 156 | B |
| 157 | A |
| 158 | B |
| 159 | A |
| 160 | A |
| 161 | A |

TABLE 2-continued

| Example | IC$_{50}$ |
|---|---|
| 162 | A |
| 163 | B |
| 164 | B |
| 165 | B |
| 166 | B |
| 167 | B |
| 168 | B |
| 169 | A |
| 170 | A |
| 171 | A |
| 172 | A |
| 173 | A |
| 174 | A |
| 175 | B |
| 176 | B |
| 178 | A |
| 179 | A |
| 180 | B |
| 181 | B |
| 182 | B |
| 183 | B |
| 184 | B |
| 185 | B |
| 187 | B |
| 188 | B |
| 189 | B |
| 190 | B |
| 191 | B |
| 192 | A |
| 193 | A |

Example 197

Induction of Polyploidy in H1299

Human Non-Small Cell Lung Carcinoma

To determine the induction of polyploidy in H1299 cells, NCI-H1299 were seeded (4K/well) into 96-well culture plates (tissue culture grade, black, flat-clear bottom) and incubated overnight to produce cell-to-plate adherence. Inhibitors at varying concentrations were added into duplicate wells containing cells and culture media (RPMI 1640, 10% fetal calf serum) and incubated at 37 C for 48 hours. The plates were then washed with PBS and the adherent cells fixed by incubating with 3% formalin for 1 hour. After washing four times with PBS, the cells were then stained with Hoechst and subjected to fluorescent (360 i/460e) microscopic high content analysis to determine the effect of inhibitors on nuclear size. Polyploid cells ($\geq$4N) were defined as those having nuclear area>750$\mu^2$. Potency was expressed as the concentration of inhibitor necessary to induce polyploidy in 15% of cells (EC15) and was calculated from least squares analysis of the log dose-response.

Table 3 depicts potency for exemplary compounds. In Table 3, "A" represents an EC15 of less than 0.1 µM and "B" represents an EC15 of between 0.1 µM and 1 µM.

TABLE 3

| Example | EC15 |
|---|---|
| 1 | B |
| 2 | A |
| 5 | B |
| 8 | A |
| 9 | A |
| 10 | A |
| 11 | A |
| 12 | B |
| 13 | B |
| 14 | B |
| 17 | A |
| 18 | A |
| 19 | A |
| 20 | A |
| 21 | A |
| 22 | A |
| 23 | B |
| 24 | A |
| 25 | A |
| 26 | A |
| 30 | A |
| 31 | A |
| 88 | B |
| 89 | A |
| 90 | B |
| 91 | A |
| 92 | A |
| 93 | A |
| 94 | A |
| 95 | B |
| 96 | B |
| 97 | B |
| 98 | A |
| 99 | A |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | B |
| 121 | A |
| 122 | A |
| 123 | A |
| 124 | A |
| 129 | A |
| 130 | A |
| 131 | A |
| 132 | B |
| 134 | A |
| 135 | A |
| 136 | A |
| 137 | B |
| 139 | A |
| 140 | A |
| 141 | B |
| 142 | B |
| 143 | A |
| 144 | A |
| 148 | A |
| 149 | A |
| 150 | A |
| 151 | A |
| 154 | A |
| 155 | A |
| 157 | A |

TABLE 3-continued

| Example | EC15 |
|---|---|
| 158 | A |
| 159 | A |
| 160 | A |
| 161 | A |
| 162 | A |
| 163 | A |
| 165 | A |
| 167 | A |
| 168 | A |
| 169 | A |
| 170 | A |
| 171 | A |
| 172 | A |
| 173 | A |
| 174 | A |
| 178 | A |
| 179 | A |
| 192 | A |
| 193 | |

Compounds of the present invention assessed by the above-described assays were found to have kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

$A^1$ is selected from the group consisting of;

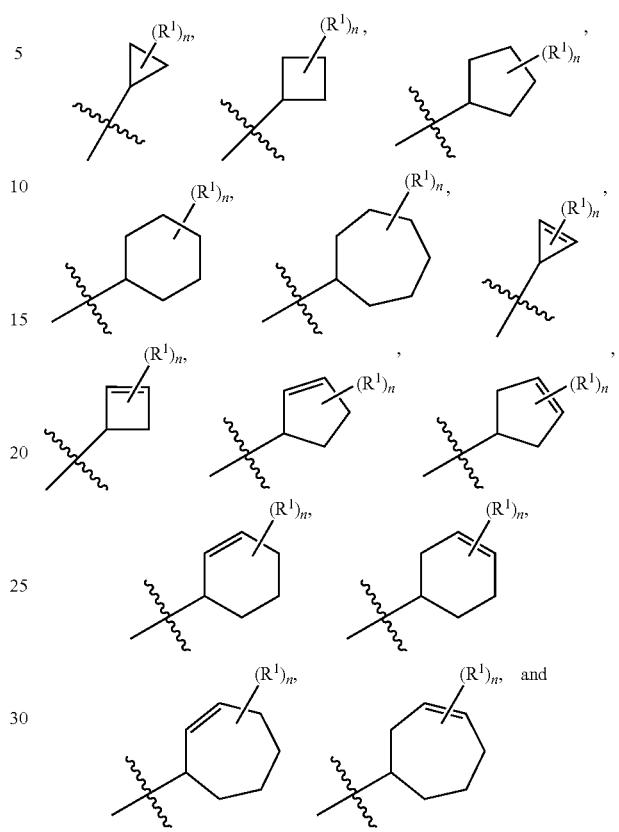

We claim:

1. A compound having formula (I)

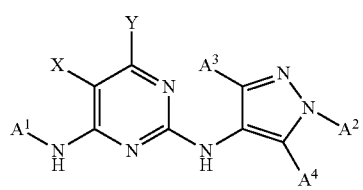

formula (I)

-continued

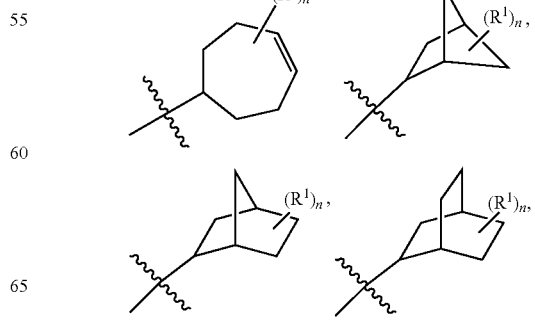

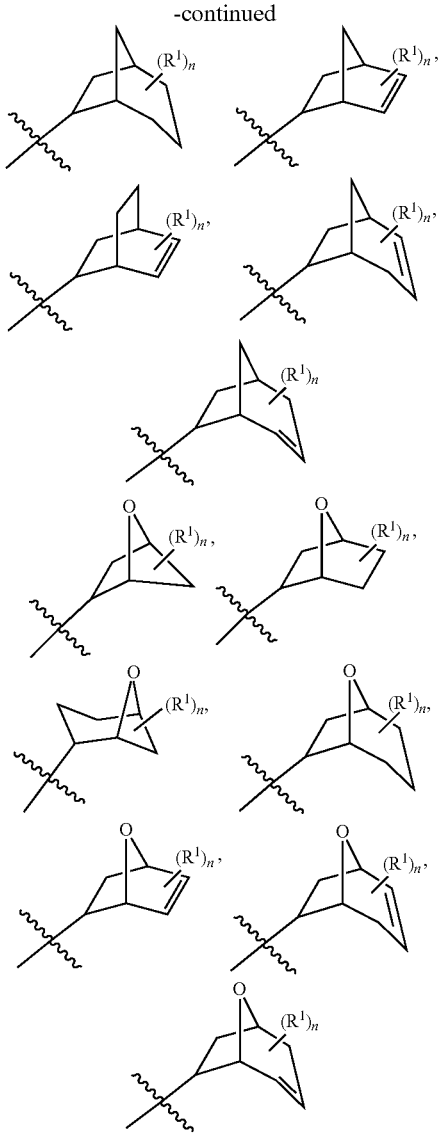

wherein n is 0, 1, or 2;

$R^1$, at each occurrence, is independently halogen, cyano, nitro, —$C_{1-4}$-alkyl, —$C_3$-$C_8$-cycloalkyl, —$C_{3-8}$-heterocycloalkyl, —OH, —$OC_{1-4}$-alkyl, —$OC_{1-4}$-haloalkyl, —C(O)OH, —C(O)$OR^a$, —C(O)$NH_2$, —C(O)$NHR^a$, —C(O)N($R^a$)$_2$, —$SO_2NH_2$, —$SO_2NHR^a$ or —$SO_2N(R^a)_2$, wherein the $R^1$—$C_{1-4}$-alkyl is optionally substituted with halogen, —OH, —$OC_{1-4}$-alkyl, or —$C_{3-8}$-heterocycloalkyl, and wherein the $R^1$—$C_3$-$C_8$-cycloalkyl and —$C_{3-8}$-heterocycloalkyl are each independently optionally substituted with halogen, —OH, or —$C_{1-4}$-alkyl;

$R^a$, at each occurrence, is independently selected from the group consisting of —$C_{1-4}$-alkyl, —$C_{3-8}$-cycloalkyl, —$C_{3-8}$-heterocycloalkyl, —$C_{1-4}$-alkylamino, and —$C_{1-4}$-alkylhydroxy;

X and Y are each independently H, F, Cl, Br, nitro, —$CF_3$, —$CF_2CF_3$, —$OCF_3$, —$OCF_2CF_3$, —C(O)$NH_2$, —$CH_3$, —$CH_2CH_3$, —$OCH_3$, or —$OCH_2CH_3$;

$A^2$ is H, $R^2$, or $R^3$;

$R^2$ is —$C_{1-6}$-alkyl, —$C_{2-6}$-alkenyl, or —$C_{2-6}$-alkynyl, wherein $R^2$ is optionally substituted with 1, 2, 3, or 4 substituents selected from the group consisting of $R^4$, halogen, cyano, nitro, —$OR^b$, —C(O)$R^b$, —C(O)$OR^b$, —OC(O)$R^b$, —$NR^cR^d$, —$NR^cC(O)R^b$, —NHC(O)$NHR^b$, —C(O)$NR^cR^d$, $NR^cSO_2R^b$, —$SR^b$, —S(O)$R^b$, —$SO_2R^b$, —$SO_2NR^cR^d$, —$CF_3$, —$CF_2CF_3$, —$OCF_3$, and —$OCF_2CF_3$;

$R^3$ and $R^4$, at each occurrence, is independently cycloalkyl, cycloalkenyl, aryl, heteroaryl, heterocycloalkyl, or heterocycloalkenyl, wherein $R^3$ and $R^4$ are optionally substituted with 1, 2, 3, or 4 substituents selected from the group consisting of $R^5$, —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$R^5$ is cycloalkenyl, cycloalkyl, aryl, heteroaryl, heterocycloalkyl, or heterocycloalkenyl, wherein $R^5$ is optionally substituted with 1, 2, 3, or 4 substituents selected from the group consisting of —$C_{1-6}$-alkyl, —$C_{2-6}$-alkenyl, —$C_{2-6}$-alkynyl, halogen, cyano, nitro, —$OR^e$, —C(O)$R^e$, —C(O)$OR^e$, —OC(O)$R^e$, —$NR^fR^g$, —$NR^fC(O)R^e$, —NHC(O)$NHR^f$, —C(O)$NR^fR^g$, —$NR^fSO_2R^e$, —$SR^e$, —S(O)$R^e$, —$SO_2R^e$, —OC(O)$OR^e$, —$SO_2NR^fNR^g$, —$CF_3$, —$CF_2CF_3$, —$OCF_3$, and —$OCF_2CF_3$, wherein the alkyl, alkenyl, and alkynyl substituents are optionally substituted with one or more substituents selected from the group consisting of aryl, heterocyclyl, cycloalkyl, halogen, cyano, —$OR^e$, —C(O)$R^e$, —C(O)$OR^e$, —OC(O)$R^e$, —$NR^fR^g$, —$NR^fC(O)R^e$, —NHC(O)$NHR^f$ and —C(O)$NR^fR^g$;

$A^3$ and $A^4$ are each independently H or —$C_{1-6}$-alkyl;

$R^b$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^c$ and $R^d$, at each occurrence, are independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, and —C(O)$NHC_{1-4}$-alkyl, wherein $C_{1-4}$-alkyl is an unsubstituted branched or straight chain alkyl group;

$R^e$, at each occurrence, is independently selected from the group consisting of hydrogen, $C_{1-6}$ alkyl, $C_{3-8}$ cycloalkyl, phenyl, and benzyl, wherein the $C_{1-6}$ alkyl, $C_{3-8}$ cycloalkyl, phenyl, or benzyl are optionally substituted with one or more substituents selected from the group consisting of halogen, cyano, nitro, hydroxy, amino, —$OC_{1-4}$-alkyl, —C(O)$OC_{1-4}$-alkyl, —OC(O)$C_{1-4}$-alkyl, —NHC(O)$C_{1-4}$-alkyl, —N($C_{1-4}$-alkyl)$_2$, and —C(O)NHC$_{1-4}$-alkyl, wherein C$_{1-4}$-alkyl is an unsubstituted branched or straight chain alkyl group; and R$^f$ and R$^g$, at each occurrence, are independently selected from the group consisting of hydrogen, C$_{1-6}$ alkyl, C$_{3-8}$ cycloalkyl, phenyl, and benzyl, wherein the C$_{1-6}$ alkyl, C$_{3-8}$ cycloalkyl, phenyl, or benzyl are optionally substituted with one or more substituents selected from the group consisting of halogen, cyano, nitro, hydroxy, amino, —OC$_{1-4}$-alkyl, —C(O)OC$_{1-4}$-alkyl, —OC(O)C$_{1-4}$-alkyl, —NHC(O)C$_{1-4}$-alkyl, and —C(O)NHC$_{1-4}$-alkyl, wherein C$_{1-4}$-alkyl is an unsubstituted branched or straight chain alkyl group; or a pharmaceutically acceptable salt thereof.

2. The compound according to claim 1, wherein n is 1 or 2, and wherein R$^1$ is selected from the group consisting of —C(O)OH, —C(O)OC$_{1-4}$-alkyl, —C(O)NH$_2$, —C(O)NHC$_{1-4}$-alkyl, F, Cl, and Br.

3. The compound according to claim 2, wherein n is 0 or 1, and wherein R$^1$ is selected from the group consisting of —C(O)OCH$_3$, —C(O)OCH$_2$CH$_3$, —C(O)NH$_2$, —C(O)NHCH$_3$, and —C(O)NHCH$_2$CH$_3$.

4. The compound according to claim 1, wherein X and Y are both H.

5. The compound according to claim 1, wherein one of X and Y is H, and the other is —CF$_3$, —CF$_2$CF$_3$, —CH$_3$, or —CH$_2$CH$_3$.

6. The compound according to claim 1, wherein one of X and Y is H, and the other is F, Cl, or Br.

7. The compound according to claim 1, wherein X is F, —CF$_3$, or Cl, and Y is H.

8. The compound according to claim 1, wherein A$^3$ and A$^4$ are H.

9. The compound according to claim 1, wherein A$^2$ is H.

10. The compound according to claim 1, wherein A$^2$ is R$^2$, wherein R$^2$ is —C$_{1-6}$-alkyl, wherein R$^2$ is optionally substituted with 1 or 2 substituents selected from the group consisting of R$^4$, —OR$^b$, —C(O)OR$^b$, —NR$^c$R$^d$, —C(O)NR$^c$R$^d$, —SO$_2$R$^b$, and —CF$_3$, wherein R$^4$ is independently cycloalkyl, aryl, or heterocycloalkyl, R$^4$ is optionally substituted with 1 or 2 substituents selected from the group consisting of —C$_{1-6}$-alkyl, halogen, —OR$^e$, and —C(O)R$^e$, R$^e$ is C$_{1-6}$-alkyl, and wherein the C$_{1-6}$-alkyl is optionally substituted with one or more substituents selected from the group consisting of —NHC(O)C$_{1-4}$-alkyl, and —N(C$_{1-4}$-alkyl)$_2$.

11. The compound according to claim 10, wherein R$^2$ is methyl, ethyl, n-propyl, iso-propyl, n-butyl, sec-butyl, or n-pentyl.

12. The compound according to claim 1, wherein A$^2$ is R$^3$, wherein R$^3$ is azetidinyl, pyrrolidinyl, morpholinyl, piperidinyl, tetrahydrofuranyl, or piperazinyl, which are optionally substituted with 1 or 2 substituents selected from the group consisting of —C$_{1-6}$-alkyl, halogen, —OR$^e$, and —C(O)R$^e$.

13. The compound of claim 1 which is
(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxamide;
(1S,2S,3R,4R)-3-({2-[(1-methyl-1H-pyrazol-4-yl)amino]pyrimidin-4-yl}amino)bicyclo[2.2.1]hept-5-ene-2-carboxamide;
(1R,2R,3S,4S)-3-({2-[(1-methyl-1H-pyrazol-4-yl)amino]pyrimidin-4-yl}amino)bicyclo[2.2.1]hept-5-ene-2-carboxamide;
N$^4$-[(1S,2S,4R)-bicyclo[2.2.1]hept-2-yl]-5-fluoro-N$^2$-(1-methyl-1H-pyrazol-4-yl)pyrimidine-2,4-diamine;
N$^4$-[(1R,2R,4S)-bicyclo[2.2.1]hept-2-yl]-5-fluoro-N$^2$-(1-methyl-1H-pyrazol-4-yl)pyrimidine-2,4-diamine;
(1S,2R)-2-({5-fluoro-2-[(1-methyl-1H-pyrazol-4-yl)amino]pyrimidin-4-yl}amino)cyclopentanecarboxamide;
(1R,2S)-2-({5-fluoro-2-[(1-methyl-1H-pyrazol-4-yl)amino]pyrimidin-4-yl}amino)cyclopentanecarboxamide;
(1S,2S,3R,4R)-3-{[5-fluoro-2-(1H-pyrazol-4-ylamino)pyrimidin-4-yl]amino}bicyclo[2.2.1]hept-5-ene-2-carboxamide;
(1R,2R,3S,4S)-3-{[5-fluoro-2-(1H-pyrazol-4-ylamino)pyrimidin-4-yl]amino}bicyclo[2.2.1]hept-5-ene-2-carboxamide;
isopropyl{4-[(4-{[(1R,2R,3S,4S)-3-(aminocarbonyl)bicyclo[2.2.1]hept-5-en-2-yl]amino}-5-fluoropyrimidin-2-yl)amino]-1H-pyrazol-1-yl}acetate;
isopropyl{4-[(4-{[(1S,2S,3R,4R)-3-(aminocarbonyl)bicyclo[2.2.1]hept-5-en-2-yl]amino}-5-fluoropyrimidin-2-yl)amino]-1H-pyrazol-1-yl}acetate;
ethyl(1S,2S,3R,4R)-3-({5-fluoro-2-[(1-methyl-1H-pyrazol-4-yl)amino]pyrimidin-4-yl}amino)bicyclo[2.2.1]hept-5-ene-2-carboxylate;
ethyl(1R,2R,3S,4S)-3-({5-fluoro-2-[(1-methyl-1H-pyrazol-4-yl)amino]pyrimidin-4-yl}amino)bicyclo[2.2.1]hept-5-ene-2-carboxylate;
(1S,2S,3R,4R)-3-({2-[(1-ethyl-1H-pyrazol-4-yl)amino]-5-fluoropyrimidin-4-yl}amino)bicyclo[2.2.1]hept-5-ene-2-carboxamide;
(1R,2R,3S,4S)-3-({2-[(1-ethyl-1H-pyrazol-4-yl)amino]-5-fluoropyrimidin-4-yl}amino)bicyclo[2.2.1]hept-5-ene-2-carboxamide;
(1S,2S,3R,4R)-3-({5-fluoro-2-[(1-methyl-1H-pyrazol-4-yl)amino]pyrimidin-4-yl}amino)-N-methylbicyclo[2.2.1]hept-5-ene-2-carboxamide;
(1R,2R,3S,4S)-3-({5-fluoro-2-[(1-methyl-1H-pyrazol-4-yl)amino]pyrimidin-4-yl}amino)-N-methylbicyclo[2.2.1]hept-5-ene-2-carboxamide;
(1S,2S,3R,4R)-3-{[2-[(1-methyl-1H-pyrazol-4-yl)amino]-5-(trifluoromethyl)pyrimidin-4-yl]amino}bicyclo[2.2.1]hept-5-ene-2-carboxamide;
(1R,2R,3S,4S)-3-{[2-[(1-methyl-1H-pyrazol-4-yl)amino]-5-(trifluoromethyl)pyrimidin-4-yl]amino}bicyclo[2.2.1]hept-5-ene-2-carboxamide;
(1S,2S,3R,4R)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide;
(1R,2R,3S,4S)-3-[(5-fluoro-2-{[1-(2-hydroxyethyl)-1H-pyrazol-4-yl]amino}pyrimidin-4-yl)amino]bicyclo[2.2.1]hept-5-ene-2-carboxamide;
(1R,2S,3R,4S)-3-({5-fluoro-2-[(1-methyl-1H-pyrazol-4-yl)amino]pyrimidin-4-yl}amino)bicyclo[2.2.1]heptane-2-carboxamide;
(1S,2R,3S,4R)-3-({5-fluoro-2-[(1-methyl-1H-pyrazol-4-yl)amino]pyrimidin-4-yl}amino)bicyclo[2.2.1]heptane-2-carboxamide;
(1R,2S,3R,4S)-3-({2-[(1-ethyl-1H-pyrazol-4-yl)amino]-5-fluoropyrimidin-4-yl}amino)bicyclo[2.2.1]heptane-2-carboxamide;
(1S,2R,3S,4R)-3-({2-[(1-ethyl-1H-pyrazol-4-yl)amino]-5-fluoropyrimidin-4-yl}amino)bicyclo[2.2.1]heptane-2-carboxamide;
(1R,2S,3R,4S)-3-[(5-fluoro-2-{[1-(2-hydroxyethyl)-1H-pyrazol-4-yl]amino}pyrimidin-4-yl)amino]bicyclo[2.2.1]heptane-2-carboxamide;

(1S,2R,3S,4R)-3-[(5-fluoro-2-{[1-(2-hydroxyethyl)-1H-pyrazol-4-yl]amino}pyrimidin-4-yl)amino]bicyclo[2.2.1]heptane-2-carboxamide;
(1R,2R,3S,4S)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide;
(1S,2S,3R,4R)-3-{[5-fluoro-2-({1-[(2R)-2-hydroxypropyl]-1H-pyrazol-4-yl}amino)pyrimidin-4-yl]amino}bicyclo[2.2.1]hept-5-ene-2-carboxamide;
(1S,2R,3S,4R)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide;
(1R,2S,3R,4S)-3-{[5-fluoro-2-({1-[(2R)-2-hydroxypropyl]-1H-pyrazol-4-yl}amino)pyrimidin-4-yl]amino}bicyclo[2.2.1]heptane-2-carboxamide;
(1S,2S,3R,4R)-3-({5-methyl-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-methyl-2-[(1-methyl-1H-pyrazol-4-yl)amino]pyrimidin-4-yl}amino)bicyclo[2.2.1]hept-5-ene-2-carboxamide;
(1S,2S,3R,4R)-3-[(2-{[1-(2-hydroxyethyl)-1H-pyrazol-4-yl]amino}-5-methylpyrimidin-4-yl)amino]bicyclo[2.2.1]hept-5-ene-2-carboxamide;
(1R,2R,3S,4S)-3-[(2-{[1-(2-hydroxyethyl)-1H-pyrazol-4-yl]amino}-5-methylpyrimidin-4-yl)amino]bicyclo[2.2.1]hept-5-ene-2-carboxamide;
(1R,2R,3S,4S)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;
(1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;
(1S,2S,3R,4R)-3-{[2-[(1-methyl-1H-pyrazol-4-yl)amino]-5-(trifluoromethyl)pyrimidin-4-yl]amino}bicyclo[2.2.1]heptane-2-carboxamide;
(1R,2R,3S,4S)-3-{[2-[(1-methyl-1H-pyrazol-4-yl)amino]-5-(trifluoromethyl)pyrimidin-4-yl]amino}bicyclo[2.2.1]heptane-2-carboxamide;
(1S,2R,3S,4R)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide;
(1R,2S,3R,4S)-3-{[2-({1-[(2R)-2-hydroxypropyl]-1H-pyrazol-4-yl}amino)-5-(trifluoromethyl)pyrimidin-4-yl]amino}bicyclo[2.2.1]heptane-2-carboxamide;
(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;
(1R,2R,3S,4S)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;
$N^4$-[(1S,2S,4R)-bicyclo[2.2.1]hept-2-yl]-$N^2$-(1-methyl-1H-pyrazol-4-yl)-5-(trifluoromethyl)pyrimidine-2,4-diamine;
$N^4$-[(1R,2R,4S)-bicyclo[2.2.1]hept-2-yl]-$N^2$-(1-methyl-1H-pyrazol-4-yl)-5-(trifluoromethyl)pyrimidine-2,4-diamine;
(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide;
(1S,2R,3S,4R)-3-{[2-[(1-ethyl-1H-pyrazol-4-yl)amino]-5-(trifluoromethyl)pyrimidin-4-yl]amino}bicyclo[2.2.1]heptane-2-carboxamide;
(1S,2R)-2-{[2-[(1-methyl-1H-pyrazol-4-yl)amino]-5-(trifluoromethyl)pyrimidin-4-yl]amino}cyclopentanecarboxamide;
(1R,2S)-2-{[2-[(1-methyl-1H-pyrazol-4-yl)amino]-5-(trifluoromethyl)pyrimidin-4-yl]amino}cyclopentanecarboxamide;
(1S,6R)-6-{[2-[(1-methyl-1H-pyrazol-4-yl)amino]-5-(trifluoromethyl)pyrimidin-4-yl]amino}cyclohex-3-ene-1-carboxamide;
(1R,6S)-6-{[2-[(1-methyl-1H-pyrazol-4-yl)amino]-5-(trifluoromethyl)pyrimidin-4-yl]amino}cyclohex-3-ene-1-carboxamide;
(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-chloro-2-[(1-methyl-1H-pyrazol-4-yl)amino]pyrimidin-4-yl}amino)bicyclo[2.2.1]hept-5-ene-2-carboxamide;
(1S,2S,3R,4R)-3-({5-bromo-2-[(1-methyl-1H-pyrazol-4-yl)amino]pyrimidin-4-yl}amino)bicyclo[2.2.1]hept-5-ene-2-carboxamide;
(1R,2R,3S,4S)-3-({5-bromo-2-[(1-methyl-1H-pyrazol-4-yl)amino]pyrimidin-4-yl}amino)bicyclo[2.2.1]hept-5-ene-2-carboxamide;
(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;
(1R,2R,3S,4S)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;
(1S,2S,3R,4R)-3-({5-chloro-2-[(1-ethyl-1H-pyrazol-4-yl)amino]pyrimidin-4-yl}amino)bicyclo[2.2.1]hept-5-ene-2-carboxamide;
(1R,2R,3S,4S)-3-({5-chloro-2-[(1-ethyl-1H-pyrazol-4-yl)amino]pyrimidin-4-yl}amino)bicyclo[2.2.1]hept-5-ene-2-carboxamide;
(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide;
(1R,2R,3S,4S)-3-({5-bromo-2-[(1-ethyl-1H-pyrazol-4-yl)amino]pyrimidin-4-yl}amino)bicyclo[2.2.1]hept-5-ene-2-carboxamide;
(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;
(1R,2R,3S,4S)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;
(1S,2S,3R,4R)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide;
(1R,2R,3S,4S)-3-{[5-chloro-2-({1-[2-(dimethylamino)ethyl]-1H-pyrazol-4-yl}amino)pyrimidin-4-yl]amino}bicyclo[2.2.1]hept-5-ene-2-carboxamide;
(1S,2S,3R,4R)-3-[(5-chloro-2-{[1-(2-pyrrolidin-1-yl-ethyl)-1H-pyrazol-4-yl]amino}pyrimidin-4-yl)amino]bicyclo[2.2.1]hept-5-ene-2-carboxamide;
(1R,2R,3S,4S)-3-[(5-chloro-2-{[1-(2-pyrrolidin-1-yl-ethyl)-1H-pyrazol-4-yl]amino}pyrimidin-4-yl)amino]bicyclo[2.2.1]hept-5-ene-2-carboxamide;
(1S,2S,3R,4R)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide;
(1R,2R,3S,4S)-3-{[5-chloro-2-({1-[2-(diethylamino)ethyl]-1H-pyrazol-4-yl}amino)pyrimidin-4-yl]amino}bicyclo[2.2.1]hept-5-ene-2-carboxamide;
(1S,2S,3R,4R)-3-[(5-chloro-2-{[1-(2-piperidin-1-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(2-piperidin-1-yl-ethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2-morpholin-4-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(2-morpholin-4-yl-ethyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(2-piperidin-1-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-piperidin-1-yl-ethyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(2-morpholin-4-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-morpholin-4-yl-ethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide;

(1R,2R,3S,4S)-3-[(5-chloro-2-{[1-(1-methylpiperidin-4-yl)-1H-pyrazol-4-yl]amino}pyrimidin-4-yl)amino]bicyclo[2.2.1]hept-5-ene-2-carboxamide;

(1S,2S,3R,4R)-3-({5-chloro-2-[(1-methyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-ethyl-1H-pyrazol-4-yl)amino]pyrimidin-4-yl}amino)bicyclo[2.2.1]hept-5-ene-2-carboxamide;

(1S,2R)-2-({5-chloro-2-[(1-methyl-1H-pyrazol-4-yl)amino]pyrimidin-4-yl}amino)cyclopentanecarboxamide;

(1R,2S)-2-({5-chloro-2-[(1-methyl-1H-pyrazol-4-yl)amino]pyrimidin-4-yl}amino)cyclopentanecarboxamide;

(1S,2S,3R,4R)-3-[(5-bromo-2-{[1-(2-pyrrolidin-1-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-bromo-2-{[1-(2-pyrrolidin-1-yl-ethyl)-1H-pyrazol-4-yl]amino}pyrimidin-4-yl)amino]bicyclo[2.2.1]hept-5-ene-2-carboxamide;

(1S,2S,3R,4R)-3-[(5-fluoro-2-{[1-(2-pyrrolidin-1-yl-ethyl)-1H-pyrazol-4-yl]amino}pyrimidin-4-yl)amino]bicyclo[2.2.1]hept-5-ene-2-carboxamide;

(1R,2R,3S,4S)-3-[(5-fluoro-2-{[1-(2-pyrrolidin-1-yl-ethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-methyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-({5-bromo-2-[(1-methyl-1H-pyrazol-4-yl)amino]pyrimidin-4-yl}amino)-N-methylbicyclo[2.2.1]hept-5-ene-2-carboxamide;

(1R,2R,3S,4S)-3-({5-bromo-2-[(1-methyl-1H-pyrazol-4-yl)amino]pyrimidin-4-yl}amino)-N-methylbicyclo[2.2.1]hept-5-ene-2-carboxamide;

(1S,2S,3R,4R)-3-({5-bromo-2-[(1-ethyl-1H-pyrazol-4-yl)amino]pyrimidin-4-yl}amino)-N-methylbicyclo[2.2.1]hept-5-ene-2-carboxamide;

(1R,2R,3S,4S)-3-({5-bromo-2-[(1-ethyl-1H-pyrazol-4-yl)amino]pyrimidin-4-yl}amino)-N-methylbicyclo[2.2.1]hept-5-ene-2-carboxamide;

(1S,2S,3R,4R)-3-({5-chloro-2-[(1-methyl-1H-pyrazol-4-yl)amino]pyrimidin-4-yl}amino)-N-methylbicyclo[2.2.1]hept-5-ene-2-carboxamide;

(1R,2R,3S,4S)-3-({5-chloro-2-[(1-methyl-1H-pyrazol-4-yl)amino]pyrimidin-4-yl}amino)-N-methylbicyclo[2.2.1]hept-5-ene-2-carboxamide;

(1S,2S,3R,4R)-3-({5-chloro-2-[(1-ethyl-1H-pyrazol-4-yl)amino]pyrimidin-4-yl}amino)-N-methylbicyclo[2.2.1]hept-5-ene-2-carboxamide;

(1R,2R,3S,4S)-3-({5-chloro-2-[(1-ethyl-1H-pyrazol-4-yl)amino]pyrimidin-4-yl}amino)-N-methylbicyclo[2.2.1]hept-5-ene-2-carboxamide;

(1S,2S,3R,4R)-3-({5-methoxy-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-methoxy-2-[(1-methyl-1H-pyrazol-4-yl)amino]pyrimidin-4-yl}amino)bicyclo[2.2.1]hept-5-ene-2-carboxamide;

(1S,2S,3R,4R)-3-({2-[(1-ethyl-1H-pyrazol-4-yl)amino]-5-methoxypyrimidin-4-yl}amino)bicyclo[2.2.1]hept-5-ene-2-carboxamide;

(1R,2R,3S,4S)-3-({2-[(1-ethyl-1H-pyrazol-4-yl)amino]-5-methoxypyrimidin-4-yl}amino)bicyclo[2.2.1]hept-5-ene-2-carboxamide;

(1S,2S,3R,4R)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide;

(1R,2R,3S,4S)-3-{[5-chloro-2-({1-[2-(dimethylamino)-2-oxoethyl]-1H-pyrazol-4-yl}amino)pyrimidin-4-yl]amino}bicyclo[2.2.1]hept-5-ene-2-carboxamide;

isopropyl{4-[(4-{[(1S,2S,3R,4R)-3-(aminocarbonyl)bicyclo[2.2.1]hept-5-en-2-yl]amino}-5-bromopyrimidin-2-yl)amino]-1H-pyrazol-1-yl}acetate;

isopropyl{4-[(4-{[(1R,2R,3S,4S)-3-(aminocarbonyl)bicyclo[2.2.1]hept-5-en-2-yl]amino}-5-bromopyrimidin-2-yl)amino]-1H-pyrazol-1-yl}acetate;

(1R,2S,3R,4S)-3-({5-chloro-2-[(1-methyl-1H-pyrazol-4-yl)amino]pyrimidin-4-yl}amino)bicyclo[2.2.1]heptane-2-carboxamide;

(1S,2R,3S,4R)-3-({5-chloro-2-[(1-methyl-1H-pyrazol-4-yl)amino]pyrimidin-4-yl}amino)bicyclo[2.2.1]heptane-2-carboxamide;

(1R,2S,3R,4S)-3-({5-chloro-2-[(1-ethyl-1H-pyrazol-4-yl)amino]pyrimidin-4-yl}amino)bicyclo[2.2.1]heptane-2-carboxamide;

(1S,2R,3S,4R)-3-({5-chloro-2-[(1-ethyl-1H-pyrazol-4-yl)amino]pyrimidin-4-yl}amino)bicyclo[2.2.1]heptane-2-carboxamide;

(1R,2S,3R,4S)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide;

(1S,2R,3S,4R)-3-{[5-chloro-2-({1-[2-(dimethylamino)-2-oxoethyl]-1H-pyrazol-4-yl}amino)pyrimidin-4-yl]amino}bicyclo[2.2.1]heptane-2-carboxamide;

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1S,2R,3S,4R)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1R,2S,3R,4S)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide;

(1S,2R,3S,4R)-3-[(5-chloro-2-{[1-(2-morpholin-4-ylethyl)-1H-pyrazol-4-yl]amino}pyrimidin-4-yl)amino]bicyclo[2.2.1]heptane-2-carboxamide;

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2R,3S,4R)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2S,3R,4R)-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[2-{[1-(2-hydroxyethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-{[2-{[1-(2,2,2-trifluoroethyl)-1H-pyrazol-4-yl]amino}-5-(trifluoromethyl)pyrimidin-4-yl]amino}bicyclo[2.2.1]hept-5-ene-2-carboxamide;

(1S,2S,3R,4R)-3-[(5-chloro-2-{[1-(2-hydroxyethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2,2,2-trifluoroethyl)-1H-pyrazol-4-yl]amino}pyrimidin-4-yl)amino]bicyclo[2.2.1]hept-5-ene-2-carboxamide;

(1S,2S,3R,4R)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-(2-hydroxyethyl)-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide;

(1R,2R,3S,4S)-3-{[2-[(1-ethyl-1H-pyrazol-4-yl)amino]-5-(trifluoromethyl)pyrimidin-4-yl]amino}-N-(2-hydroxyethyl)bicyclo[2.2.1]hept-5-ene-2-carboxamide;

(1S,2S,3R,4R)-3-{[2-({1-[(2R)-2-hydroxypropyl]-1H-pyrazol-4-yl}amino)-5-(trifluoromethyl)pyrimidin-4-yl]amino}bicyclo[2.2.1]hept-5-ene-2-carboxamide;

(1S,2S,3R,4R)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-cyclopropyl-3-{[2-[(1-methyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1R,2R,3S,4S)—N-cyclopropyl-3-{[2-[(1-ethyl-1H-pyrazol-4-yl)amino]-5-(trifluoromethyl)pyrimidin-4-yl]amino}bicyclo[2.2.1]hept-5-ene-2-carboxamide;

(1S,2S,3R,4R)-3-{[5-chloro-2-({1-[(3S)-pyrrolidin-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3R)-pyrrolidin-3-yl]-1H-pyrazol-4-yl}amino)pyrimidin-4-yl]amino}bicyclo[2.2.1]hept-5-ene-2-carboxamide;

(1S,2S,3R,4R)-3-[(2-{[1-(2-amino-2-oxoethyl)-1H-pyrazol-4-yl]amino}-5-chloropyrimidin-4-yl)amino]bicyclo[2.2.1]hept-5-ene-2-carboxamide;

(1S,2S,3R,4R)-3-{[5-chloro-2-({1-[2-(methylamino)-2-oxoethyl]-1H-pyrazol-4-yl}amino)pyrimidin-4-yl]amino}bicyclo[2.2.1]hept-5-ene-2-carboxamide;

(1S,2S,3R,4R)-3-[(2-{[1-(2-amino-2-oxoethyl)-1H-pyrazol-4-yl]amino}-5-bromopyrimidin-4-yl)amino]bicyclo[2.2.1]hept-5-ene-2-carboxamide;

(1S,2S,3R,4R)-3-{[5-bromo-2-({1-[2-(methylamino)-2-oxoethyl]-1H-pyrazol-4-yl}amino)pyrimidin-4-yl]amino}bicyclo[2.2.1]hept-5-ene-2-carboxamide;

isopropyl{4-[(4-{[(1R,2R,3S,4S)-3-(aminocarbonyl)bicyclo[2.2.1]hept-5-en-2-yl]amino}-5-chloropyrimidin-2-yl)amino]-1H-pyrazol-1-yl}acetate;

(1S,2S,3R,4R)-3-({5-bromo-2-[(1-ethyl-1H-pyrazol-4-yl)amino]pyrimidin-4-yl}amino)bicyclo[2.2.1]hept-5-ene-2-carboxamide;

(1R,2S,3R,4S)-3-{[2-[(1-ethyl-1H-pyrazol-4-yl)amino]-5-(trifluoromethyl)pyrimidin-4-yl]amino}bicyclo[2.2.1]heptane-2-carboxamide;

(1S,2S,3R,4R)-3-({2-[(1-azetidin-3-yl-1H-pyrazol-4-yl)amino]-5-chloropyrimidin-4-yl}amino)bicyclo[2.2.1]hept-5-ene-2-carboxamide;

(1S,2S,3R,4R)-3-({5-chloro-2-[(1-piperidin-4-yl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[(3S)-piperidin-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3R)-piperidin-3-yl]-1H-pyrazol-4-yl}amino)pyrimidin-4-yl]amino}bicyclo[2.2.1]hept-5-ene-2-carboxamide;

(1S,2S,3R,4R)-3-{[2-({1-[1-(N-acetylglycyl)piperidin-4-yl]-1H-pyrazol-4-yl}amino)-5-chloropyrimidin-4-yl]amino}bicyclo[2.2.1]hept-5-ene-2-carboxamide;

4-{[(1S,2S,3R,4R)-3-carbamoylbicyclo[2.2.1]hept-5-en-2-yl]amino}-2-[(1-methyl-1H-pyrazol-4-yl)amino]pyrimidine-5-carboxamide;

4-{[(1R,2R,3S,4S)-3-carbamoylbicyclo[2.2.1]hept-5-en-2-yl]amino}-2-[(1-methyl-1H-pyrazol-4-yl)amino]pyrimidine-5-carboxamide;

4-{[(1S,2S,3R,4R)-3-carbamoylbicyclo[2.2.1]hept-5-en-2-yl]amino}-2-[(1-ethyl-1H-pyrazol-4-yl)amino]pyrimidine-5-carboxamide;

4-{[(1R,2R,3S,4S)-3-carbamoylbicyclo[2.2.1]hept-5-en-2-yl]amino}-2-[(1-ethyl-1H-pyrazol-4-yl)amino]pyrimidine-5-carboxamide;

(1R,2S,3R,4S)-3-{[5-chloro-2-({1-[2-(methylamino)-2-oxoethyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[1-(N,N-dimethylglycyl)piperidin-4-yl]-1H-pyrazol-4-yl}amino)pyrimidin-4-yl]amino}bicyclo[2.2.1]hept-5-ene-2-carboxamide;

(1R,2S,3R,4S)-3-{[5-chloro-2-({1-[2-(4-methylpiperazin-1-yl)ethyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)-3-[(2-{[1-(1-acetylpiperidin-4-yl)-1H-pyrazol-4-yl]amino}-5-chloropyrimidin-4-yl)amino]bicyclo[2.2.1]hept-5-ene-2-carboxamide;

(1R,2S,3R,4S)-3-[(5-chloro-2-{[1-(2-hydroxyethyl)-1H-pyrazol-4-yl]amino}pyrimidin-4-yl)amino]bicyclo[2.2.1]heptane-2-carboxamide;

(1S,2S,3R,4R)-3-{[5-bromo-2-({1-[2-(4-methylpiperazin-1-yl)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(piperidin-4-yl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(2-methoxyethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(1-methylpiperidin-4-yl)methyl]-1H-pyrazol-4-yl}amino)pyrimidin-4-yl]amino}bicyclo[2.2.1]hept-5-ene-2-carboxamide;

(1S,2S,3R,4R)-3-({5-chloro-2-[(1-isopropyl-1H-pyrazol-4-yl)amino]pyrimidin-4-yl}amino)bicyclo[2.2.1]hept-5-ene-2-carboxamide;

(1S,2S,3R,4R)-3-[(5-chloro-2-{[1-(3-methylbutyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(2-methoxyethoxy)ethyl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(2R)-pyrrolidin-2-ylmethyl]-1H-pyrazol-4-yl}amino)pyrimidin-4-yl]amino}bicyclo[2.2.1]hept-5-ene-2-carboxamide;

{4-[(4-{[(1R,2R,3S,4S)-3-carbamoylbicyclo[2.2.1]hept-5-en-2-yl]amino}-5-chloropyrimidin-2-yl)amino]-1H-pyrazol-1-yl}acetic acid;

(1R,2S,3R,4S)-3-{[5-chloro-2-({1-[(2R)-2-hydroxypropyl]-1H-pyrazol-4-yl}amino)pyrimidin-4-yl]amino}bicyclo[2.2.1]heptane-2-carboxamide;

(1S,2S,3R,4R)-3-{[5-chloro-2-({1-[(2R)-2-hydroxypropyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(2-methoxyethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(3R)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-{[5-chloro-2-({1-[(3S)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-{[5-bromo-2-({1-[2-(2-methoxyethoxy)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(3-methylbutyl)-1H-pyrazol-4-yl]amino}pyrimidin-4-yl)amino]bicyclo[2.2.1]hept-5-ene-2-carboxamide;

(1S,2S,3R,4R)-3-({5-bromo-2-[(1-isopropyl-1H-pyrazol-4-yl)amino]pyrimidin-4-yl}amino)bicyclo[2.2.1]hept-5-ene-2-carboxamide;

(1R,2R,3S,4S)-3-({5-chloro-2-[(1-methyl-1H-pyrazol-4-yl)amino]pyrimidin-4-yl}amino)bicyclo[2.2.1]heptane-2-carboxamide;

(1S,2S,3R,4R)-3-({5-chloro-2-[(1-methyl-1H-pyrazol-4-yl)amino]pyrimidin-4-yl}amino)bicyclo[2.2.1]heptane-2-carboxamide;

(1R,2R,3S,4S)-3-({5-chloro-2-[(1-ethyl-1H-pyrazol-4-yl)amino]pyrimidin-4-yl}amino)bicyclo[2.2.1]heptane-2-carboxamide;

(1S,2S,3R,4R)-3-({5-chloro-2-[(1-ethyl-1H-pyrazol-4-yl)amino]pyrimidin-4-yl}amino)bicyclo[2.2.1]heptane-2-carboxamide;

(1S,2S,3R,4R)-3-{[5-bromo-2-({1-[(3R)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-{[5-bromo-2-({1-[(3S)-tetrahydrofuran-3-yl]-1H-pyrazol-4-yl}amino)pyrimidin-4-yl]amino}bicyclo[2.2.1]hept-5-ene-2-carboxamide;

(1S,2S,3R,4R)-3-({5-chloro-2-[(1-cyclobutyl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[2-(methylsulfonyl)ethyl]-1H-pyrazol-4-yl}amino)pyrimidin-4-yl]amino}bicyclo[2.2.1]hept-5-ene-2-carboxamide;

(1S,2R,3S,4R)-3-({5-chloro-2-[(1-methyl-1H-pyrazol-4-yl)amino]pyrimidin-4-yl}amino)bicyclo[2.2.1]hept-5-ene-2-carboxamide;

(1R,2S,3R,4S)-3-({5-chloro-2-[(1-methyl-1H-pyrazol-4-yl)amino]pyrimidin-4-yl}amino)bicyclo[2.2.1]hept-5-ene-2-carboxamide;

(1S,2R,3S,4R)-3-({5-chloro-2-[(1-ethyl-1H-pyrazol-4-yl)amino]pyrimidin-4-yl}amino)bicyclo[2.2.1]hept-5-ene-2-carboxamide;

(1R,2S,3R,4S)-3-({5-chloro-2-[(1-ethyl-1H-pyrazol-4-yl)amino]pyrimidin-4-yl}amino)bicyclo[2.2.1]hept-5-ene-2-carboxamide;

(1S,2S,3R,4R)-3-{[5-bromo-2-({1-[2-(methylsulfonyl)ethyl]-1H-pyrazol-4-yl}amino)pyrimidin-4-yl]amino}bicyclo[2.2.1]hept-5-ene-2-carboxamide;

(1S,2S,3R,4R)-3-({5-bromo-2-[(1-cyclobutyl-1H-pyrazol-4-yl)amino]pyrimidin-4-yl}amino)bicyclo[2.2.1]hept-5-ene-2-carboxamide;

(1S,2S,3R,4R)-3-{[5-chloro-2-({1-[(2S)-2,3-dihydroxypropyl]-1H-pyrazol-4-yl}amino)pyrimidin-4-yl]amino}bicyclo[2.2.1]hept-5-ene-2-carboxamide;

(1S,2S,3R,4R)-3-({5-chloro-6-methyl-2-[(1-methyl-1H-pyrazol-4-yl)amino]pyrimidin-4-yl}amino)bicyclo[2.2.1]hept-5-ene-2-carboxamide;

(1R,2R,3S,4S)-3-({5-chloro-6-methyl-2-[(1-methyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-ethyl-1H-pyrazol-4-yl)amino]-6-methylpyrimidin-4-yl}amino)bicyclo[2.2.1]hept-5-ene-2-carboxamide;

(1R,2R,3S,4S)-3-({5-chloro-2-[(1-ethyl-1H-pyrazol-4-yl)amino]-6-methylpyrimidin-4-yl}amino)bicyclo[2.2.1]hept-5-ene-2-carboxamide;

(1S,2S,3R,4R)-3-({5-chloro-2-[(1,3,5-trimethyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1,3,5-trimethyl-1H-pyrazol-4-yl)amino]pyrimidin-4-yl}amino)bicyclo[2.2.1]hept-5-ene-2-carboxamide;

(1S,2S,3R,4R)-3-[(5-chloro-2-{[1-(oxetan-2-ylmethyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[(2R)-2,3-dihydroxypropyl]-1H-pyrazol-4-yl}amino)pyrimidin-4-yl]amino}bicyclo[2.2.1]hept-5-ene-2-carboxamide;

(1S,2S,3R,4R)-3-{[5-bromo-2-({1-[(2S)-2,3-dihydroxypropyl]-1H-pyrazol-4-yl}amino)pyrimidin-4-yl]amino}bicyclo[2.2.1]hept-5-ene-2-carboxamide;

(1S,2S,3R,4R)-3-({5-chloro-2-[(1,3-dimethyl-1H-pyrazol-4-yl)amino]pyrimidin-4-yl}amino)bicyclo[2.2.1]hept-5-ene-2-carboxamide;

(1S,2S,3R,4R)-3-({5-bromo-2-[(1,3-dimethyl-1H-pyrazol-4-yl)amino]pyrimidin-4-yl}amino)bicyclo[2.2.1]hept-5-ene-2-carboxamide;

(1S,2R)-2-[(5-chloro-2-{[1-(piperidin-4-yl)-1H-pyrazol-4-yl]amino}pyrimidin-4-yl)amino]cyclopentanecarboxamide;

(1R,2S)-2-[(5-chloro-2-{[1-(piperidin-4-yl)-1H-pyrazol-4-yl]amino}pyrimidin-4-yl)amino]cyclopentanecarboxamide;

(1S,2R)-2-{[5-chloro-2-({1-[2-(morpholin-4-yl)ethyl]-1H-pyrazol-4-yl}amino)pyrimidin-4-yl]amino}cyclopentanecarboxamide;

(1R,2S)-2-{[5-chloro-2-({1-[2-(morpholin-4-yl)ethyl]-1H-pyrazol-4-yl}amino)pyrimidin-4-yl]amino}cyclopentanecarboxamide;

(1S,2S,3R,4R)-3-({2-[(1-methyl-1H-pyrazol-4-yl)amino]-5-nitropyrimidin-4-yl}amino)bicyclo[2.2.1]hept-5-ene-2-carboxamide;

(1S,2S,3R,4R)-3-({2-[(1-ethyl-1H-pyrazol-4-yl)amino]-5-nitropyrimidin-4-yl}amino)bicyclo[2.2.1]hept-5-ene-2-carboxamide;

(1S,2R,3S,4R)-3-({5-chloro-2-[(1-methyl-1H-pyrazol-4-yl)amino]pyrimidin-4-yl}amino)-7-oxabicyclo[2.2.1]heptane-2-carboxamide;

(1R,2S,3R,4S)-3-({5-chloro-2-[(1-methyl-1H-pyrazol-4-yl)amino]pyrimidin-4-yl}amino)-7-oxabicyclo[2.2.1]heptane-2-carboxamide;

(1S,2R,3S,4R)-3-({5-chloro-2-[(1-ethyl-1H-pyrazol-4-yl)amino]pyrimidin-4-yl}amino)-7-oxabicyclo[2.2.1]heptane-2-carboxamide;

(1R,2S,3R,4S)-3-({5-chloro-2-[(1-ethyl-1H-pyrazol-4-yl)amino]pyrimidin-4-yl}amino)-7-oxabicyclo[2.2.1]heptane-2-carboxamide;

(1S,2S,3R,4R)-3-[(5-chloro-2-{[1-(2-phenylethyl)-1H-pyrazol-4-yl]amino}pyrimidin-4-yl)amino]bicyclo[2.2.1]hept-5-ene-2-carboxamide;

(1S,2S,3R,4R)-3-({2-[(1-benzyl-1H-pyrazol-4-yl)amino]-5-chloropyrimidin-4-yl}amino)bicyclo[2.2.1]hept-5-ene-2-carboxamide;

(1S,6R)-6-({5-chloro-2-[(1-methyl-1H-pyrazol-4-yl)amino]pyrimidin-4-yl}amino)cyclohex-3-ene-1-carboxamide;

(1R,6S)-6-({5-chloro-2-[(1-methyl-1H-pyrazol-4-yl)amino]pyrimidin-4-(1S,2R)-2-({5-chloro-2-[(1-methyl-1H-pyrazol-4-yl)amino]pyrimidin-4-yl}amino)cyclohexanecarboxamide;

(1R,2S)-2-({5-chloro-2-[(1-methyl-1H-pyrazol-4-yl)amino]pyrimidin-4-yl}amino)cyclohexanecarboxamide;

(1S,2S,3R,4R)-3-[(5-bromo-2-{[1-(2-phenylethyl)-1H-pyrazol-4-yl]amino}pyrimidin-4-yl)amino]bicyclo[2.2.1]hept-5-ene-2-carboxamide;

(1S,2S,3R,4R)-3-({2-[(1-benzyl-1H-pyrazol-4-yl)amino]-5-bromopyrimidin-4-yl}amino)bicyclo[2.2.1]hept-5-ene-2-carboxamide;

(1S,2R)-2-({5-chloro-2-[(1-methyl-1H-pyrazol-4-yl)amino]pyrimidin-4-yl}amino)cyclobutanecarboxamide;

(1R,2S)-2-({5-chloro-2-[(1-methyl-1H-pyrazol-4-yl)amino]pyrimidin-4-yl}amino)cyclobutanecarboxamide;

(1S,2S,3R,4R)-3-{[5-chloro-2-({1-[2-(3-methoxyphenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(3-methoxybenzyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(3-chlorobenzyl)-1H-pyrazol-4-yl]amino}pyrimidin-4-yl)amino]bicyclo[2.2.1]hept-5-ene-2-carboxamide;

(1S,2S,3R,4R)-3-{[5-chloro-2-({1-[2-(3-chlorophenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-bromo-2-{[1-(3-methoxybenzyl)-1H-pyrazol-4-yl]amino}pyrimidin-4-yl)amino]bicyclo[2.2.1]hept-5-ene-2-carboxamide;

(1S,2S,3R,4R)-3-{[5-bromo-2-({1-[2-(3-methoxyphenyl)ethyl]-1H-pyrazol-4-yl}amino)pyrimidin-4-yl]amino}bicyclo[2.2.1]hept-5-ene-2-carboxamide;

(1S,2S,3R,4R)-3-[(5-chloro-2-{[1-(2-chlorobenzyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(4-chlorobenzyl)-1H-pyrazol-4-yl]amino}pyrimidin-4-yl)amino]bicyclo[2.2.1]hept-5-ene-2-carboxamide;

(1S,2R)-2-[(5-chloro-2-{[1-(piperidin-4-yl)-1H-pyrazol-4-yl]amino}pyrimidin-4-yl)amino]-N-isopropylcyclopentanecarboxamide;

(1R,2S)-2-[(5-chloro-2-{[1-(piperidin-4-yl)-1H-pyrazol-4-yl]amino}pyrimidin-4-yl)amino]-N-isopropylcyclopentanecarboxamide;

(1S,2R)-2-{[5-chloro-2-({1-[2-(morpholin-4-yl)ethyl]-1H-pyrazol-4-yl}amino)pyrimidin-4-yl]amino}-N-isopropylcyclopentanecarboxamide;

(1R,2R,3S,5R)-2-({2-[(1-ethyl-1H-pyrazol-4-yl)amino]-5-(trifluoromethyl)pyrimidin-4-yl}amino)-6,6-dimethylbicyclo[3.1.1]heptane-3-carboxamide;

(1S,2S,3R,4R)-3-({5-bromo-2-[(1,5-dimethyl-1H-pyrazol-4-yl)amino]pyrimidin-4-yl}amino)bicyclo[2.2.1]hept-5-ene-2-carboxamide;

(1S,2S,3R,4R)-3-[(5-bromo-2-{[1-(2-chlorobenzyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(4-chlorobenzyl)-1H-pyrazol-4-yl]amino}pyrimidin-4-yl)amino]bicyclo[2.2.1]hept-5-ene-2-carboxamide;

(1S,2S,3R,4R)-3-({5-bromo-2-[(1-phenyl-1H-pyrazol-4-yl)amino]pyrimidin-4-yl}amino)bicyclo[2.2.1]hept-5-ene-2-carboxamide;

(1S,2S,3R,4R)-3-({5-chloro-2-[(1-phenyl-1H-pyrazol-4-yl)amino]pyrimidin-4-yl}amino)bicyclo[2.2.1]hept-5-ene-2-carboxamide;

(1S,2S,3R,4R)-3-[(5-chloro-2-{[1-(2-naphthylmethyl)-1H-pyrazol-4-yl]amino}pyrimidin-4-yl)amino]bicyclo[2.2.1]hept-5-ene-2-carboxamide;

(1S,2S,3R,4R)-3-[(5-chloro-2-{[1-(3-fluoro-4-methoxybenzyl)-1H-pyrazol-4-yl]amino}pyrimidin-4-yl)amino]bicyclo[2.2.1]hept-5-ene-2-carboxamide;

(1S,2S,3R,4R)-3-[(5-bromo-2-{[1-(3-fluoro-4-methoxybenzyl)-1H-pyrazol-4-yl]amino}pyrimidin-4-yl)amino]bicyclo[2.2.1]hept-5-ene-2-carboxamide.

14. A pharmaceutical composition comprising a compound or pharmaceutically acceptable salt of claim 1 and pharmaceutically acceptable excipient.

* * * * *

SEQUENCE LISTING

```
<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Ala Glu Glu Glu Tyr Phe Phe Leu Ala
1               5
```